(12) United States Patent
Naganuma et al.

(10) Patent No.: US 9,008,742 B2
(45) Date of Patent: Apr. 14, 2015

(54) CONSTITUENT CONCENTRATION MEASURING APPARATUS AND CONSTITUENT CONCENTRATION MEASURING APPARATUS CONTROLLING METHOD

(71) Applicant: Nippon Telegraph and Telephone Corporation, Tokyo (JP)

(72) Inventors: Kazunori Naganuma, Tokyo (JP); Takuro Tajima, Tokyo (JP); Yuichi Okabe, Tokyo (JP); Shoichi Sudo, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 234 days.

(21) Appl. No.: 13/669,262

(22) Filed: Nov. 5, 2012

(65) Prior Publication Data
US 2013/0123591 A1  May 16, 2013

Related U.S. Application Data

(62) Division of application No. 11/568,110, filed as application No. PCT/JP2005/008309 on May 2, 2005, now Pat. No. 8,332,006.

(30) Foreign Application Priority Data

| May 6, 2004 | (JP) | 2004-137770 |
| May 17, 2004 | (JP) | 2004-145926 |
| May 26, 2004 | (JP) | 2004-155886 |
| May 27, 2004 | (JP) | 2004-157341 |
| Oct. 8, 2004 | (JP) | 2004-295619 |
| Oct. 12, 2004 | (JP) | 2004-297076 |
| Oct. 20, 2004 | (JP) | 2004-305671 |
| Oct. 28, 2004 | (JP) | 2004-314666 |

(51) Int. Cl.
*A61B 5/1455* (2006.01)
*A61B 5/00* (2006.01)
(Continued)

(52) U.S. Cl.
CPC ........... *A61B 5/0095* (2013.01); *A61B 5/14532* (2013.01); *A61B 5/1455* (2013.01);
(Continued)

(58) Field of Classification Search
CPC ............ A61B 5/0095; A61B 5/14532; A61B 5/14546; A61B 5/1455; A61B 5/1495; A61B 2562/0204
USPC .......................................... 600/310, 322, 323
See application file for complete search history.

(56) References Cited

U.S. PATENT DOCUMENTS

5,068,864 A    11/1991 Javan .............................. 372/32
5,348,002 A *  9/1994 Caro ............................ 600/310
(Continued)

FOREIGN PATENT DOCUMENTS

| CN | 1445526 | 10/2003 |
| CN | 1493252 | 5/2004 |

(Continued)

OTHER PUBLICATIONS

"Pulse photoacoustic techniques and glucose determination in human blood and tissue", University of Oulu, Finland, 2002.
(Continued)

*Primary Examiner* — Eric Winakur
(74) *Attorney, Agent, or Firm* — DLA Piper LLP (US)

(57) ABSTRACT

An object of the present invention is to provide a noninvasive constituent concentration measuring apparatus and constituent concentration measuring apparatus controlling method, in which accurate measurement can be performed by superimposing two photoacoustic signals having the same frequency and reverse phases to nullify the effect from the other constituent occupying large part of the object to be measured. The constituent concentration measuring apparatus according to the invention includes light generating means for generating two light beams having different wavelengths, modulation means for electrically intensity-modulating each of the two light beams having different wavelengths using signals having the same frequency and reverse phases, light outgoing means for outputting the two intensity-modulated light beams having different wavelengths toward a test subject, and acoustic wave detection means for detecting an acoustic wave generated in the test subject by the outputted light.

20 Claims, 61 Drawing Sheets

(51) Int. Cl.
*A61B 5/145* (2006.01)
*G01N 21/17* (2006.01)
*G01N 29/24* (2006.01)
*G01N 29/44* (2006.01)
*A61B 5/1495* (2006.01)

(52) U.S. Cl.
CPC ............ *A61B5/6826* (2013.01); *A61B 5/6838* (2013.01); *G01N 21/1702* (2013.01); *G01N 29/2425* (2013.01); *G01N 29/449* (2013.01); *G01N 29/2418* (2013.01); *A61B 5/1495* (2013.01)

(56) References Cited

U.S. PATENT DOCUMENTS

| | | | |
|---|---|---|---|
| 5,713,356 | A | 2/1998 | Kruger |
| 5,941,821 | A | 8/1999 | Chou ............... 600/316 |
| 6,102,857 | A | 8/2000 | Kruger |
| 6,212,421 | B1 | 4/2001 | Vo-Dinh et al. |
| 6,292,682 | B1 | 9/2001 | Kruger |
| 6,403,944 | B1 | 6/2002 | MacKenzie et al. |
| 6,846,288 | B2 | 1/2005 | Nagar et al. |
| 6,921,366 | B2 | 7/2005 | Jeon et al. |
| 7,515,948 | B1 * | 4/2009 | Balberg et al. ............ 600/323 |
| 2002/0035327 | A1 | 3/2002 | Kruger |
| 2003/0167002 | A1 | 9/2003 | Nagar et al. |
| 2003/0225320 | A1 | 12/2003 | Jeon et al. |
| 2007/0015978 | A1 | 1/2007 | Kanayama et al. |

FOREIGN PATENT DOCUMENTS

| | | |
|---|---|---|
| DE | 4446390 | 7/1996 |
| DE | 19516974 | 10/1996 |
| EP | 1346684 | 9/2003 |
| JP | 55-047434 | 4/1980 |
| JP | 06-317566 | 11/1994 |
| JP | 07-136150 | 5/1995 |
| JP | 08-224228 | 9/1996 |
| JP | 09-133654 | 5/1997 |
| JP | 09-145683 | 6/1997 |
| JP | 09-173323 | 7/1997 |
| JP | 10-000189 | 1/1998 |
| JP | 10-160711 | 6/1998 |
| JP | 11-514549 | 12/1999 |
| JP | 2000-023947 | 1/2000 |
| JP | 2001-507952 | 6/2001 |
| JP | 2001-526557 | 12/2001 |
| JP | 2002257793 A | 9/2002 |
| JP | 2003-265477 | 9/2003 |
| JP | 2004-506477 | 3/2004 |
| WO | 9727801 | 8/1997 |
| WO | WO 97/33514 | 9/1997 |
| WO | 9814118 | 4/1998 |
| WO | WO 98/38904 | 9/1998 |
| WO | 0117424 | 3/2001 |
| WO | 0215776 | 2/2002 |
| WO | 0215820 | 2/2002 |
| WO | 03042690 A2 | 5/2003 |

OTHER PUBLICATIONS

Chinese language office action and it's partial English translation for corresponding Chinese application 2005800102377.
Barbieri Stefano et al., "Gas detection with quantum cascade lasers: An adapted photoacoustic sensor based on Helmholtz resonance", Review of Scientific Instruments, AIP, vol. 73, No. 6, pp. 2458-2461, Jun. 1, 2002.
European Search Report for Corresponding European application 05737063.7.
Chinese language office action dated May 12, 2010 and it's partial English translation for corresponding Chinese application 200810125416.0.
Extended European Search Report dated Jun. 6, 2011 for corresponding European application 11002585.5.
Extended European Search Report dated Jun. 6, 2011 for corresponding European application 11002586.3.
Japanese language office action dated Dec. 6, 2011 for corresponding Japanese application 2010-035143.
Japanese language office action dated Apr. 24, 2012 for corresponding Japanese application 2010-035208.
European office action dated Sep. 3, 2013 issued in corresponding European application 11002585.5 cites the foreign patent documents listed above.

* cited by examiner

CONSTITUENT CONCENTRATION MEASURING APPARATUS AND CONSTITUENT CONCENTRATION MEASURING APPARATUS CONTROLLING METHOD

TECHNICAL FIELD

The present invention relates to a noninvasive constituent concentration measuring apparatus and constituent concentration measuring apparatus controlling method, particularly to the noninvasive apparatus and method in which glucose of a blood constituent is set as a measuring object to measure a concentration of the glucose, i.e., a blood sugar level in a noninvasive manner.

BACKGROUND ART

Various methods are proposed to date as the noninvasive constituent concentration measuring method based on percutaneous irradiation of electromagnetic wave and/or observation of radiation. In these methods, an interaction between the objective blood constituent, for example, a glucose molecule in the case of a blood sugar level, and the electromagnetic waves having a particular wavelength, i.e., absorption or scattering is utilized.

However, the interaction between the glucose and the electromagnetic wave is weak, there is a limitation to intensity of the electromagnetic wave with which a living body can safely be irradiated, and the living body is a scatterer for the electromagnetic wave. Therefore, satisfactory result is not obtained so far in the blood sugar level measurement of the living body.

An photoacoustic method of irradiating the living body with the electromagnetic wave to observe an acoustic wave generated in the living body deserves attention among the conventional techniques of utilizing the interaction between the glucose and the electromagnetic wave.

The photoacoustic method is a method of measuring an amount of molecule in the living body by measuring pressure of the acoustic wave. That is, when the living body is irradiated with a certain amount of electromagnetic wave, the electromagnetic wave is absorbed in the molecule contained in the living body, the acoustic wave is generated by a local heating of the region irradiated with the electromagnetic wave followed by thermal expansion, and the pressure of the acoustic wave depends on the amount of molecule absorbing the electromagnetic wave. Furthermore among the photoacoustic method, a method in which heat is generated in a local area irradiated with the light, and the thermal expansion occurs locally without thermal diffusion to generate the propagating and finally utilized acoustic wave, is called the direct photoacoustic method.

The acoustic wave is a pressure wave propagating in the living body, and the acoustic wave has a feature that it is less prone to scattering effect as compared with the electromagnetic wave. Therefore, the photoacoustic method is a noteworthy technique in the blood constituent measurement of the living body.

FIGS. 49 and 50 show, configuration examples of the prior art for constituent concentration measuring apparatus in which the photoacoustic method is utilized.

FIG. 49 shows an example for the first prior art example in which a light pulse is used as the electromagnetic wave (for example, see Non-Patent Document 1). In this example, blood sugar, i.e., glucose is set as a measuring object in the blood constituent. In FIG. 49, a drive power supply 604 supplies a pulse-shaped excitation current to a pulse light source 616, the pulse light source 616 generates a light pulse having a duration of sub-microsecond, and a living body test region 610 is irradiated with the light pulse. The light pulse generates the pulse-shaped acoustic wave called a photoacoustic signal in the living body test region 610, and an ultrasonic detector 613 detects the photoacoustic signal to convert it into an electric signal proportional to the acoustic pressure.

A waveform of the electric signal is observed by a waveform observing apparatus 620. Since the apparatus 620 is triggered by a signal synchronized with the excitation current, the electric signal proportional to the acoustic pressure is displayed at a predetermined position on a screen of the waveform observing apparatus 620, and the signals can be integrated and averaged.

Amplitude of the obtained electric signal proportional to the acoustic pressure is analyzed to measure the amount of blood sugar level, i.e., the amount of glucose in the living body test region 610. In the example shown in FIG. 49, the sub-microsecond light pulses are generated in a repetition up to 1 kHz, averaged measurement for 1024 light pulses provides the electric signal proportional to the acoustic pressure. However, the sufficient accuracy is not obtained.

Therefore, an example of the second prior art in which a continuously intensity-modulated light source is used is disclosed to increase the accuracy. FIG. 50 shows a configuration of an apparatus of the second conventional example (for example, see Patent Document 1). In this example, the blood sugar is set as the main measuring object, and multiple light sources having different wavelengths are used to attempt a measurement with the high accuracy.

To avoid explanation from becoming complicated, the operation with the two light sources will be exemplified with reference to FIG. 50. In FIG. 50, the light sources having the different wavelengths, i.e., a first light source 601 and a second light source 605 are driven to emit continuous light beams by a drive power supply 604 and a drive power supply 608 respectively.

The light beams output from the first light source 601 and the second light source 605 are modulated by a chopper plate 617 which is driven by a motor 618 and rotated at the constant number of revolutions. The chopper plate 617 is made of an opaque material, a shaft of the motor 618 is positioned at the center of concentric circles, of which circumferences where the light beams of the first light source 601 and the second light source 605 pass respectively have mutually-indivisible numbers of apertures.

The light beams output from the first light source 601 and the second light source 605 are intensity-modulated by a mutually indivisible modulation frequency $f_1$ and a modulation frequency $f_2$, the light beams are combined by a coupler 609, and the living body test region 610 is irradiated by the combined light beam.

In the living body test region 610, the photoacoustic signal having the frequency $f_1$ is generated by the light of the first light source 601, and the photoacoustic signal having the frequency $f_2$ is generated by the light of the second light source 605. The photoacoustic signals are detected by an acoustic sensor 619 and converted into the electric signals proportional to the acoustic pressures, and frequency spectrum is observed by a frequency analyzer 621.

In the example, all the wavelengths of the multiple light sources are set at absorption wavelengths of glucose, and photoacoustic signal intensity at each wavelength is measured as the electric signal corresponding to the amount of glucose contained in the blood.

In this configuration, a relationship between the measured intensity of the photoacoustic signal and the glucose concentration measured from the separately collected blood are previously stored to measure the glucose amount from the observed value of the photoacoustic signal.

On the other hand, in health management and treatment, it is important to continuously perform the measurement while the constituent concentration measuring apparatus is carried around. Therefore, a portable type or wearable constituent concentration measuring apparatus is also developed. The following examples for the third and fourth prior arts are disclosed as the portable type constituent concentration measuring apparatus.

The third example shown in FIG. 51 is an example mounted on a eyeglasses handle that comes into contact with the back of an ear (for example, see Patent Document 2). In FIG. 51, both a light source 500 and an acoustic wave detector 541 are embedded in a contact surface of an apparatus body 540 with a living body 499. In the acoustic wave generated in the living body 499 by the irradiation light emitted from the light source 500, a part of the acoustic wave propagating backward is detected by the acoustic wave detector 541.

The fourth example shown in FIG. 52 is an example mounted on an erring (for example, see Patent Document 2). In FIG. 52, the apparatus body 540 comes into contact with the living body 499 from both sides, the light source 500 is embedded in one of the contact surfaces of the apparatus body 540, and the acoustic wave detector 541 is embedded in the other contact surface. In the acoustic wave generated in the living body 499 by the irradiated light emitted from the light source 500, a part of the acoustic wave propagating forward is detected by the acoustic wave detector 541.

[Patent Document 1] Japanese Patent Application Laid-Open (JP-A) No. 10-189
[Patent Document 2] JP-A No. 8-224228
[Non-Patent Document 1] Thesis (University of Oulu, Finland) "Pulse photoacoustic techniques and glucose determination in human blood and tissue", (IBS951-42-6690-0, http://herkules.oulu.fi/isbn9514266900/, 2002)

DISCLOSURE OF THE INVENTION

Problem to be Solved by the Invention

In the above examples, there are the following problems. In the first prior art, because the measurement is repeated using the pulse light source, there is a problem that a long time is required to perform the measurement.

About two-thirds of a human body or an animal body is made of water, and water occupies near 80% in the blood constituent, while a water molecule exhibits significant absorption of lights having wavelength longer than 1 μm. On the other hand, a glucose molecule exhibits the absorption characteristics in the light wavelength bands near 1.6 μm and 2.1 μm. In a concentration ranging from 50 to 100 mg/dl (2.8 to 5.6 mM) which is the blood sugar level of a healthy subject, water has the absorption 1000 times larger than glucose. Accordingly, in order to measure the blood sugar level, it is necessary that the measurement is performed with an accuracy higher than 0.1%. Usually the accuracy of 5 mg/dl (0.28 mM) is required for the blood sugar level measurement, so the necessary accuracy is estimated to be ca. 0.003%. Thus, the extremely high measurement accuracy is required in order to measure the blood constituent concentration, particularly in order to measure the blood sugar level, i.e., the glucose amount.

In the above prior art, when other constituents in the blood or the constituent in a non-blood tissue also exhibits the absorption in the wavelength in which the objective blood constituent exhibits absorption, in the generated photoacoustic signal, the other blood constituents or the constituent in a non-blood tissue also constibute. Since the photoacoustic signal which might be generated in a non-blood tissue, is also added, measurement is highly prone to the ambient disturbances. Accordingly, in order to measure the blood constituent with higher accuracy, the photoacoustic signal generated in the blood needs to be separated from the other photoacoustic signals.

When the higher accuracy is to be achieved by repeating and averaging the signals by the pulse light source, the necessary number of measurements must be increased, which lengthens a measuring time. For example, even if the signal is obtained with accuracy of 1% per pulse using the pulse light source, it is necessary to measure for 110,000 pulses in order to improve the accuracy up to 0.003% by averaging. In the case where the pulse light source has a repetition of 1 kHz, 110 seconds are required for the measurement.

During the blood sugar level measurement, it is necessary that a subject is kept motionless, which imposes physical stress to the subject. In the case where a test subject is an animal, it is extremely difficult to keep the animal motionless for a long time. In the photoacoustic method measurement, the living body test region 610 is irradiated with the light to generate the acoustic wave, and the acoustic wave propagating in the living body is detected by the ultrasonic detector 613 shown in FIG. 49 or the acoustic sensor 619 shown in FIG. 50. The ultrasonic detector 613 and the acoustic sensor 619 are in contact with the living body test region 610. In order to improve acoustic wave measuring efficiency, it is necessary to apply a gel containing a large amount of moisture to the contact surface between a skin of the living body test region 610 and the ultrasonic detector 613 or the acoustic sensor 619 to establish a good acoustic coupling. In this case, fine air bubbles evaporated from the living body test region 610 are mixed in the gel to result in an error.

When a change in relative position happens between the detector such as the ultrasonic detector 613 or the acoustic sensor 619 and the living body test region 610, the acoustic coupling is influenced. Therefore, it is necessary for the subject to be motionless during the measurement.

The acoustic pressure measured by the ultrasonic detector 613 or the acoustic sensor 619 is reversely proportional to a distance between the detection portion where the ultrasonic detector 613 or the acoustic sensor 619 comes into contact and the irradiation portion where the living body test region 610 is irradiated by the light. However, the distance between the detection portion and the irradiation portion is easily changed depending on how the ultrasonic detector 613 or the acoustic sensor 619 is pressed against the living body test region 610. Accordingly, in order to keep the distance between the detection portion and the irradiation portion constant, it is necessary that the living body test region is contacted with the ultrasonic detector 613 or the acoustic sensor 619 at a constant pressure and without relative motion as well.

As described later, the photoacoustic signal of the living body test region 610 is dependent on specific heat, thermal expansion coefficient, sound velocity, and the like. The specific heat, the thermal expansion coefficient, and the sound velocity are quantities which are changeable by a temperature (body temperature), and above all the thermal expansion coefficient is as sensitive as about 3%/° C. The sound velocity is also changed by the frequency of the acoustic wave, and it is also reported that all of the specific heat, the thermal expansion coefficient, and the sound velocity are changed depending on the blood sugar level itself.

Therefore, in the first prior art, it is necessary to measure at least the body temperature to correct the measured value of the photoacoustic signal. Compilation of high-accuracy basic data for the correction is not an easy task. Even if such correction data is successfully collected, it takes a long time to verify the reliability of the blood sugar calculated using such complicated correction.

On the other hand, in the second prior art, since the photoacoustic signals for the multiple different wavelengths are simultaneously measured, there is a possibility that all of the changeable factors, such as the acoustic coupling condition, the distance between the detection portion and the irradiation portion, the specific heat, the thermal expansion coefficient, and the sound velocity are eliminated as an unknown multiplier.

That is, in the case where absorption coefficients $\alpha_1^{(b)}$ and $\alpha_2^{(b)}$ of the background (water) for the light beams having a wavelength $\lambda_1$ and a wavelength $\lambda_2$ and molar absorption coefficients $\alpha_1^{(O)}$ and $\alpha_2^{(O)}$ of the objective blood constituent (glucose) are already known, simultaneous equations for measured values $S_1$ and $S_2$ of the photoacoustic signal for the wavelengths are expressed as follows:

$$C(\alpha_1^{(b)}+M\alpha_1^{(O)})=s_1 \qquad \text{[Formula 1]}$$

$$C(\alpha_2^{(b)}+M\alpha_2^{(O)})=s_2$$

The formula (1) is solved to compute an unknown blood constituent concentration (blood sugar level) M where C is an unknown multiplier containing the above changeable factors.

M can be computed from the formula (1) even if C is unknown. At this point, in the case where the measurements with third and fourth wavelengths are added, the number of equations becomes excessive as compared with the number of unknown numbers. However, even in this case, it is known that M is obtained as the best solution in the sense of the least-square method.

However, the photoacoustic signal is not exactly linear to the absorption coefficient. As a result, the unknown multipliers C are not equal to one another between measurements for the wavelength $\lambda_1$ and wavelength $\lambda_2$ experiencing different absorption coefficients of the water.

In the second prior art, the photoacoustic signal depends also on a modulation frequency f. Accordingly, the unknown multipliers C are not equal in the photoacoustic signals generated in the different modulation frequencies.

Thus, because C in the first line differs from C in the second line in the formula (1), usually it is impossible to solve the formula (1) to determine M. When a functional form of the unknown multipliers C for the absorption coefficient $\alpha$, and the modulation frequency f is completely determined, the formula (1) would possibly be solved. However, as described later, it is found that the functional form itself is possibly changed by the amount of scattering.

In the second prior art, because the photoacoustic signal is not exactly linear to the absorption coefficient, it is necessary to perform the complicated correction to the measurements for the wavelength $\lambda_1$ and wavelength $\lambda_2$ experiencing different absorption coefficients of the water.

In the second prior art, the photoacoustic signal also depends on the modulation frequency f. Accordingly, it is necessary to perform the even more complicated correction to the measured values of the photoacoustic signals generated for the different modulation frequencies.

In the second conventional example, there is also the problem arising from uneven frequency characteristics of the acoustic sensor 619 between the frequencies $f_1$ and $f_2$.

The unevenness of the frequency characteristics also results from the following cause. The acoustic wave is reflected unavoidably by acoustic impedance mismatch at the boundary between the examined region of the living body and a surrounding substance (air in this case). As a result, the detected photoacoustic signal is influenced by the boundary reflection according to the shape of the living body test region, and the frequency of a standing wave of the photoacoustic signal varies, so that it is difficult that the constituent concentration is computed from the detected photoacoustic signal evenly across individuals.

In the photoacoustic method, in order to obtain information on the absorption coefficient $\alpha$, it is necessary that the acoustic wave wavelength is shorter than the absorption length of about $\alpha^{-1} \times 2\pi$. In a glucose molecule absorption band near a light wavelength of 1.6 μm, since the water absorption coefficient is about $\alpha=0.6$ mm$^{-1}$, it is desirable that the acoustic wave wavelength is 10 mm or less. At this point, because the sound velocity c is about 1.5 km/s in water, it is necessary to use the modulation frequency of 150 kHz or higher. Similarly for a glucose absorption band near the light wavelength of 2.1 μm, the water absorption coefficient becomes about four times of that for glucose, the desirable acoustic wave wavelength is 2.5 mm or less, and the desirable modulation frequency is 0.6 MHz or higher.

In a view of practicality, there is also the problem that the intensity modulation at such a high frequency is realized using the chopper plate 617 rotated by the motor as described in the second prior art. For an ultrasonic wave having the wavelength of 10 mm or the wavelength 2.5 mm or less, the wavelength of the ultrasonic wave is close to a device size of a normally utilized ultrasonic detector. Therefore, the standing wave is easily generated and it is very difficult to realize the detector having flat frequency characteristics. The detector in which resonant phenomenon is suppressed by a damper material is available, however, even in this case, unevenness of about ±2 dB still remains in the sensitivity.

If the frequency dependence of the detector sensitivity is flat, in the second prior art, a difference in sensitivity between the different modulation frequencies can be corrected. However, the frequency dependence of the detector sensitivity changes by the temperature, and the frequency dependence of the detector sensitivity is also changed by the contact condition between the detector and the living body. The former is attributable to the change in mechanical coefficient such as Young's modulus and the size change caused by the thermal expansion, and the latter is attributable to a fluctuation in resonant Q value (Quality Factor) due to the change in degree of the scattering of elastic energy by the contact. Accordingly, since certain means or a jig for stabilizing acoustic coupling is required in addition to a thermometer, it is very difficult to exactly correct the difference in detector sensitivity for different modulation frequencies.

FIG. 53 shows an example of the change in Q value of the resonance characteristics in the photoacoustic signal detector. In FIG. 53, the photoacoustic signal detection sensitivity characteristics indicated by a solid line is changed to the detection sensitivity characteristics indicated by a broken line by the change in pressing force between the living body test region and the photoacoustic signal detector. In the example shown in FIG. 53, a peak value of the photoacoustic signal detection sensitivity indicated by the solid line decreases almost to its half in the one indicated by the broken line.

Then, FIG. 54 shows another example of the change in frequency characteristics of the photoacoustic signal detector sensitivity. In FIG. 54, the detector sensitivity frequency characteristics indicated by the solid line shows the state immediately after the living body test region is brought into contact with the photoacoustic signal detector. That is, the photoacoustic signal detector has an ambient air temperature of, for example, about 20° C., the living body has the body temperature of, for example, about 36° C., and there is a temperature difference of about 16° C. between these.

Then, the photoacoustic signal detector sensitivity frequency characteristics indicated by the broken line of FIG. 54 shows a state when about ten minutes have elapsed. The peak frequency is changed by about 10 KHz across the photoacoustic signal detector sensitivity frequency characteristics indicated by the solid line and broken line in FIG. 54.

A technique of utilizing the detector resonance characteristics to achieve the improvement of the detection sensitivity is well known (for example, see Edited by T. Sawada, "Photoacoustic spectroscopy and its application-PAS", Japan Scientific Society Press, 1982). However, in the second prior art, since the measurements are performed for the multiple modulation frequencies, it is impossible to utilize the resonance characteristics to improve the sensitivity.

As described above, in the noninvasive blood constituent concentration measuring method shown in the first and second prior arts, there are the following problems to be solved: (1) Because many parameters which are hardly kept constant exist in the measurement, the photoacoustic signal cannot be converted into the blood constituent concentration with a sufficient accuracy. (2) Due to the non-linearity in respect to the absorption coefficient and the modulation frequency dependence, even if the photoacoustic signal is measured for multiple wavelengths, the photoacoustic signal values for these multiple wavelengths cannot be converted into the blood constituent concentration by the simultaneous equations. (3) Due to the difficulty of the detector frequency characteristics correction, it is difficult to enhance the sensitivity for the photoacoustic signal detection by applying resonance type detectors. (4) The accuracy of the detected photoacoustic signal is deteriorated due to a boundary reflection between the test subject and the surrounding thereof, a pressure and vibration imposed to the ultrasonic detection unit, and a condition on sound collection and a temperature change in the ultrasonic detection unit.

On the other hand, in the third prior art, as shown in FIG. 51, the light source 500 and the acoustic wave detector 541 are placed in the surface in which the apparatus body 540 is brought into contact with the living body 499. However, the mounting state shown in FIG. 51 has the following problem to be solved.

That is, as described later, in the wearable type constituent concentration measuring apparatus of the invention, the light having a wavelength longer than 1 μm is suitable for the irradiation of living body. However the moisture occupying the large part of living body exhibits the strong absorption for the light having the wavelength longer than 1 μm. Therefore, in the case where the living body 499 of FIG. 51 is irradiated with the light source 500, the ultrasonic wave which is generated by the absorption of the glucose molecule, is localized in the surface of the irradiated portion immediately below the light source 500, and the ultrasonic wave is regarded as a spherical wave. As shown in FIG. 51, it is difficult to detect the ultrasonic wave using the acoustic wave detector 541 placed on the same surface next to the light source 500.

In the fourth prior art shown in FIG. 52, there is the following problem to be solved. That is, in the configuration shown in FIG. 52, assuming that r is a distance between the light source 500 and the ultrasonic detector 541, α is a light absorption coefficient of a glucose aqueous solution, and λ is an ultrasonic wave wavelength, it is necessary that the following formula (2) hold in order to measure the glucose concentration.

$$r \gg \alpha^{-1} \lambda / (2\pi)$$ [Formula 2]

For instance, provided that the light wavelength with which the living body 499 is irradiated is set at the glucose absorption band of about 1.6 μm, considering the water absorption coefficient is approximately $\alpha = 0.6$ mm$^{-1}$, it is desirable that r is 10 mm or more which is sufficiently larger as compared with 2 mm, and it is also desirable that the wavelength λ of the ultrasonic wave is 10 mm or less.

In the case where the light wavelength with which the living body 499 is irradiated is set at the glucose absorption band of about 2.1 μm, considering the water absorption coefficient becomes about four times the above case, it is desirable that r is 2.5 mm or more, and it is also desirable that the wavelength λ of the ultrasonic wave is 2.5 mm or less.

As shown above, it is necessary that the generated ultrasonic wave wavelength λ is made shorter as compared with the distance between the light source 500 and the ultrasonic detector 541, i.e., a thickness of the living body 499 which is the measurement objective.

In FIG. 52, since the living body 499 is soft, the distance between the light source 500 and the ultrasonic detector 541 is changed according to the force pressing the ultrasonic detector 541 against the living body 499. The spherical wave of the ultrasonic wave generated immediately below the light source 500 includes a portion which directly reaches the ultrasonic detector 541 and a portion which reaches the ultrasonic detector 541 after being repeatedly reflected by the boundary surface between the living body 499 and air.

Because the wavelength λ of the ultrasonic wave is small compared with the size of the living body 499, even if the distance is fixed between the light source 500 and the ultrasonic detector 541, the interference condition between the direct wave and the multiple indirect waves which reach the ultrasonic detector 541 changes depending on shape of the boundary between the living body and air, which affects the amount of ultrasonic wave detected by the ultrasonic detector 541.

Thus, in the fourth prior art, there is a problem that the error is caused on the ultrasonic wave detected by the ultrasonic detector 541 even if the shape of the living body 499 is slightly changed during the measurement.

On the other hand, in the photoacoustic method, there is a following problem. In the photoacoustic method, the desirable frequency of acoustic wave to detect depends on an object of the measurement. When the blood in the living body is set as the measurement object, it is desirable that the frequency of the acoustic wave to detect is the ultrasonic wave near several hundreds kilohertz. However, when the ultrasonic wave reaches the boundary from a medium 1 to a medium 2, there happen two phenomena. One of the phenomena is transmission across the boundary. The other is the reflection on the boundary surface. When the media considerably differ from each other in terms of the acoustic impedance, the large part of ultrasonic waves is reflected at the boundary surface and the transmission hardly occurs. Here, assuming that $Z_1$ is the acoustic impedance of the medium 1 and $Z_2$ is the acoustic impedance of the medium 2, a reflectance R is expressed by the following formula (3).

$$R = \frac{Z_2 - Z_1}{Z_2 + Z_1} \qquad \text{[Formula 3]}$$

Let us consider the reflectance when a finger of a human body is set as the test subject. FIG. 55 is a sectional view of a human finger. As shown in FIG. 55, in the human finger, a muscle 214 exists in the center of a bone 213, the bone 213 is surrounded by a fat 215, and the surroundings of the fat 215 are covered with cuticle 216. Table 1 shows acoustic impedance of each of these.

TABLE 1

| Region | Sound velocity (m/s) | Acoustic impedance |
|---|---|---|
| Cuticle | 1470 | 1.58 |
| Fat | 1490 | 1.6 |
| Muscle | 1600 | 2.1 |
| Bone | 4000 | 7.8 |

The reflectance amounts 65% at the boundary between the bone 213 and the fat 215, when the reflectance is computed from the acoustic impedance using the formula (3). Therefore, the large part of acoustic waves impinging on the bone 213 are reflected and scattered.

FIG. 56 shows an example in which the photoacoustic signal is reflected and scattered by the bone. FIG. 56 is a sectional view showing human finger, FIG. 56(*a*) shows how the photoacoustic signal is scattered by the bone, and FIG. 56(*b*) shows how the photoacoustic signal is attenuated by the bone. As shown in FIG. 56(*a*), when a line extending the path of an excitation light 219 incident to the finger completely hits the bone 213, the photoacoustic signal is scattered and the photoacoustic signal can hardly be detected by a detector 220. As shown in FIG. 56(*b*), when the bone 213 exists near the extended path of the excitation light 219, since a part of the photoacoustic signal is scattered, the intensity detected by the detector 220 is decreased. Thus, in the conventional photoacoustic method, there is the problem that the photoacoustic signal intensity varies across measurements by the influence of the reflection and scattering.

In the photoacoustic method where the acoustic wave propagating through the test subject is detected, it is necessary that the test subject and the detector 220 are brought into close contact with each other. The acoustic wave loss at the boundary surface between the test subject and the detector 220 changes depending on the contact pressure. Thus, there is also the problem that the photoacoustic signal intensity varies across each measurement by the change in pressing force.

In view of the foregoing problems, an object of the invention is to provide a noninvasive constituent concentration measuring apparatus and a constituent concentration measuring apparatus controlling method, in which the blood constituent concentration can accurately be measured, the high-sensitive measurement can also be performed using resonance type detector, the measurement can be performed in a short time so as not to place a burden on a subject, and the apparatus is compact so as to be attachable to a living body test region.

Another object of the invention is to provide a noninvasive constituent concentration measuring apparatus and a constituent concentration measuring apparatus controlling method.

Means for Solving Problem

A constituent concentration measuring apparatus according to one aspect of the present invention is characterized by comprising light generating means for generating light; frequency sweep means for sweeping a modulation frequency, the light generated by the light generating means being modulated in the modulation frequency; light modulation means for electrically intensity-modulating the light using a signal from the frequency sweep means, the light being generated by the light generating means; light outgoing means for outputting the intensity-modulated light toward an object to be measured; acoustic wave detection means for detecting an acoustic wave which is generated in the object to be measured by the outputted light; and integration means for integrating the acoustic wave in a swept modulation frequency range, the acoustic wave being detected by the acoustic wave detection means.

In one aspect of the invention, the light is electrically intensity-modulated using the modulation signal whose frequency is swept in a predetermined range, the object to be measured is irradiated with the intensity-modulated light to detect the photoacoustic signal which is an acoustic wave generated in the object to be measured by the irradiation light, and the detected photoacoustic signal is integrated to compute the constituent concentration which is the measurement objective in the object to be measured. Thus the change in sensitivity characteristics of the acoustic wave detection means can be tracked to measure the constituent concentration which is the measurement objective at the frequency where the optimal sensitivity is attainable.

A constituent concentration measuring apparatus according to one aspect of the invention comprising light generating means for generating light; light modulation means for electrically intensity-modulating the light at a constant frequency, the light being generated by the light generating means; light outgoing means for outputting the intensity modulated light toward an object to be measured, the intensity modulated light being intensity-modulated by the light modulation means; and acoustic wave detection means for detecting an acoustic wave which is emitted from the object to be measured irradiated with the intensity modulated light, the constituent concentration measuring apparatus characterized in that an acoustic matching substance and the object to be measured can be arranged between the light outgoing means and the acoustic wave detection means, the acoustic matching substance having acoustic impedance substantially equal to that of the object to be measured.

One aspect of the invention is characterized in that the photoacoustic signal is detected under the environment whose acoustic impedance is substantially equal to that of the object to be measured. The object to be measured is irradiated with a light intensity modulated at a constant frequency, the photoacoustic signal which is the acoustic wave emitted from the object to be measured is detected to measure the concentration of a particular constituent contained in the liquid by the acoustic wave detection means though the acoustic matching substance. The acoustic wave detection means detects the photoacoustic signal through the acoustic matching substance, which alleviates the signal loss caused by reflection of the acoustic wave. The reflection of the photoacoustic signal is caused by a boundary reflection between the object to be measured and surroundings, and the reflection of the photoacoustic signal also occurs at the contact between the object to be measured and the acoustic wave detection means. Here the object to be measured and the acoustic matching substance having the acoustic impedance substantially equal to that of the object to be measured can be arranged between the light outgoing means and the acoustic wave detection means. Thus reflection at the boundary between the object to be measured and the surroundings can be decreased.

A constituent concentration measuring apparatus according to one aspect of the invention is characterized by comprising light generating means for generating light; light modulation means for electrically intensity-modulating the light at a constant frequency, the light being generated by the light generating means; light outgoing means for outputting the intensity modulated light toward an object to be measured, the intensity modulated light being intensity-modulated by the light modulation means; acoustic wave detection means for detecting an acoustic wave which is emitted from the object to be measured irradiated with the intensity modulated light; and a container in which a space between the light outgoing means and the acoustic wave detection means is filled with an acoustic matching substance having acoustic impedance substantially equal to that of the object to be measured.

By instituting the container filled with the acoustic matching substance having the acoustic impedance substantially equal to that of the object to be measured, the object to be measured is arranged in the container filled with the acoustic matching substance having the acoustic impedance substantially equal to that of the object to be measured, and the photoacoustic signal from the object to be measured can be detected under the environment in which the object to be measured is surrounded by the acoustic matching substance. This configuration leads to an alleviation of the attenuation which is caused by the reflection of the photoacoustic signal at the boundary between the object to be measured and the surroundings as well as at the contact between the object to be measured and the acoustic wave detection means.

In the constituent concentration measuring apparatus, it is desirable that the light generating means generates two light beams having different wavelengths, and the light modulation means intensity-modulate each of the light beams into the intensity modulated light beams, the intensity modulated light beams having the same frequency and reverse phases.

The influence of the water on the photoacoustic signal can be removed by using the two intensity modulated light beams having the different wavelengths for the intensity modulated light. As for the modulation, the frequencies are equal and the phases are reversed to one another.

A constituent concentration measuring apparatus according to one aspect of the invention is characterized by comprising light generating means for generating light; light modulation means for electrically intensity-modulating the light at a constant frequency, the light being generated by the light generating means; light outgoing means for outputting the intensity modulated light toward an object to be measured, the intensity modulated light being intensity-modulated by the light modulation means; an acoustic wave generator which outputs an acoustic wave; and acoustic wave detection means for detecting the acoustic wave emitted from the object to be measured, which is irradiated with the intensity modulated light, and the acoustic wave transmitted from the acoustic wave generator through the object to be measured.

One aspect of the invention is characterized in that, when the constituent concentration which is the measurement objective of the object to be measured is measured by the photoacoustic method, the ultrasonic wave (in this case, referred to as acoustic wave) emitted from the acoustic wave generator which is placed near irradiation position of the excitation light, i.e., near the source of photoacoustic signal is detected as a reference signal to search for the arrangement which optimizes a positional relationship between the photoacoustic signal source and the acoustic wave detection means. The photoacoustic signal is detected under the optimum arrangement, which allows the constituent concentration to be measured using a propagation path which minimizes the adverse influence of scatterers existing in the object to be measured.

When the photoacoustic signal is detected in the arrangement in which the detected acoustic wave signal intensity becomes a predetermined value such that the attenuation amount of acoustic wave is kept constant, the photoacoustic signal can be detected while influences of uncertain factors are eliminated. The uncertain factors include the change in influence of the scatterers on the photoacoustic signal by the change in positional relationship between the photoacoustic signal generation source and the acoustic wave detection means as well as by the change at the contact between the acoustic wave detection means and the object to be measured. Therefore, the constituent concentration can be measured with no influence of the many parameters associated with the positional change of the constituent concentration measuring apparatus.

According to one aspect of the invention, the influence of the reflecting/scattering scatterers on the photoacoustic signal can be probed using the acoustic wave. Therefore, the photoacoustic signal can be detected with the optimum arrangement.

In searching the optimal arrangement of the devices in terms of the object to be measured in a measuring system by the photoacoustic method, means for adjusting the arrangement is mechanized to operate concurrently with the acoustic wave detection means, which allows the constituent concentration measurement to be automated to operate always under the optimum arrangement. In the invention, the intensity modulated light which is modulated by the constant frequency is used as the excitation light.

According to one aspect of the invention, the influence of the reflecting/scattering scatterers on the photoacoustic signal can be probed using the acoustic wave. Therefore, the photoacoustic signal can be detected with the optimum arrangement.

A constituent concentration measuring apparatus according to one aspect of the invention is characterized by comprising light generating means for generating two light beams having different wavelengths; light modulation means for electrically intensity-modulating each of the two light beams having the mutually different wavelengths using signals having the same frequency and reverse phases; light outgoing means for outputting the two intensity-modulated light beams having the mutually different wavelengths toward an object to be measured; and acoustic wave detection means for detecting an acoustic wave emitted from the object to be measured by the outputted light.

In one aspect of the invention, each of the two light beams having the mutually different wavelengths is electrically intensity-modulated using the signals having the same frequency and reverse phases, so that the acoustic wave corresponding to each of the two light beams having the mutually different wavelengths can be detected with no influence from a frequency dependence of the acoustic wave detection means.

One of the two light beams generates acoustic wave having the pressure corresponding to the total absorption in the state where the constituent of the measuring object and water are mixed together in the object to be measured, and the other light beam generates the acoustic wave having the pressure originating only from the water occupying the large part of the object to be measured, so that the pressure of the acoustic wave generated only by the constituent of the measuring object is detectable as the difference between two acoustic waves. As a result, quantity of the constitute in the measuring object can be measured.

With the two acoustic wave pressures, one generated by one of the two light beams corresponding to the total absorption in the state where the constituent of the measuring object and water are mixed together in the object to be measured, while another generated by the other light beam corresponding only to the water occupying the large part of the object to be measured, their frequencies are equal to each other and the phase are reversed to each other, therefore, the pressures are superposed to each other in the form of acoustic wave in the object to be measured, and the difference in pressure of the acoustic waves is directly detected. Accordingly, the difference in pressure of the acoustic waves can be obtained more accurately rather than by computing the difference from separate measurements of the pressure of the acoustic wave generated by one of the two light beams corresponding to the total absorption in the state where the constituent of the measuring object and water are mixed together in the object to be measured, as well as of the pressure of the acoustic wave generated by the other light beam corresponding only to the water occupying the large part of the object to be measured. The above point constitutes a novel advantage which does not exist in the conventional techniques.

In one aspect of the invention, the modulation frequency by which the two light beams having the mutually different wavelengths are electrically intensity-modulated can be set to the resonant frequency concerning the detection of the acoustic wave generated in the object to be measured. The photoacoustic signal is measured for the two light beams having mutually different wavelengths are selected by a consideration on the non-linearity regarding to the absorption coefficient in the measured value of the photoacoustic signal. Then, the acoustic wave generated in the object to be measured can be measured with a high accuracy from the measured values while the influences of the many parameters which are hardly kept constant, are eliminated.

In the constituent concentration measuring apparatus, the constituent concentration measuring apparatus further comprises frequency sweep means for sweeping a modulation frequency, the light generated by the light generating means being modulated in the modulation frequency; and integration means for integrating the acoustic wave in a swept modulation frequency range, the acoustic wave being detected by the acoustic wave detection means, the constituent concentration measuring apparatus characterized in that the light modulation means electrically intensity-modulate each of the two light beams having the mutually different wavelengths using the frequency sweep means and with mutually reverse modulation phases.

In one aspect of the invention, the photoacoustic signal generated in the object to be measured is integrated in the swept modulation signal range. The photoacoustic signal exploiting the high sensitivity in the frequency corresponding to the resonance frequency of the acoustic wave detection means is integrated even if the resonance frequency of the acoustic wave detection means suffers a drift. Thus the measurement can be performed always with the high-sensitivity resonance frequency.

In the constituent concentration measuring apparatus, it is desirable that the acoustic wave detection means track the modulation frequency to detect the acoustic wave emitted in the object to be measured, the modulation frequency being swept by the frequency sweep means, and the integration means integrate the acoustic wave in the modulation frequency range where the acoustic wave detection means has high detection sensitivity, the acoustic wave being detected by the acoustic wave detection means.

In one aspect of the invention, in the case where the resonance frequency of the acoustic wave detection means happens to change, the change in resonance frequency of the acoustic wave detection means in which the detection sensitivity becomes the maximum is determined from the result on the measurement of the photoacoustic signal emitted in the object to be measured by the irradiation light which is modulated by the frequency-swept modulation frequency, and the change in resonance frequency is tracked to integrate the detected value of the photoacoustic signal near the resonance frequency.

In the constituent concentration measuring apparatus, it is desirable to further comprise liquid constituent concentration computation means for computing a constituent concentration of a liquid constituent from the acoustic wave integrated by the integration means, the liquid constituent being set as a measuring object in the object to be measured.

In one aspect of the invention, theoretical or experimental values showing the relationship between the photoacoustic signal generated in the object to be measured and the constituent concentration set as the measuring object are prepared beforehand, and the constituent concentration of the measuring object is computed based on the detected value of the photoacoustic signal generated in the object to be measured.

In the constituent concentration measuring apparatus, the constituent concentration measuring apparatus further comprises an acoustic wave generator which outputs an acoustic wave, and it is desirable that the acoustic wave detection means detects the acoustic wave emitted from the object to be measured as well as said acoustic wave transmitted from the acoustic wave generator through the object to be measured.

According to one aspect of the invention, the influence of the reflecting/scattering scatterers on the photoacoustic signal can be probed using the acoustic wave. Therefore, the photoacoustic signal can be detected with the optimum arrangement.

In the constituent concentration measuring apparatus, it is desirable to further comprise drive means for varying at least one of positions of the acoustic wave generator and the acoustic wave detection means.

According to one aspect of the invention, the influence of the reflecting/scattering scatterers on the photoacoustic signal can be probed for each propagation path by changing the acoustic wave propagation path. Thus, the photoacoustic signal can be detected in the probed optimum arrangement.

In the constituent concentration measuring apparatus, it is desirable to further comprise control means for controlling the drive means such that intensity of the acoustic wave detected by the acoustic wave detection means becomes a particular value.

According to one aspect of the invention, the photoacoustic signal is automatically made to be detected in the probed optimum arrangement.

In the constituent concentration measuring apparatus, it is desirable that the light generating means set the light wavelengths of the two light beams to two light wavelengths where an absorption difference exhibited by the liquid constituent set as the measuring object is larger than the absorption difference exhibited by a solvent.

In the constituent concentration measuring apparatus, it is desirable that the light generating means sets one of the light wavelengths of the two light beams to a light wavelength where the liquid constituent set as the measuring object exhibits characteristic absorption, and the light generating means sets the other light wavelength to a wavelength where the solvent exhibits an equal absorption to that for the one of the light wavelengths.

One aspect of the invention is the case where the difference in absorption exhibited by the solvent is set to zero, in the light generating means in the constituent concentration measuring apparatus in which the light wavelengths of the two light beams are set to two light wavelengths so that the absorption difference exhibited by the liquid constituent set as the measuring object is larger than the absorption difference exhibited by the solvent. Therefore, the influence by the absorption of the solvent can be eliminated.

In the constituent concentration measuring apparatus, it is desirable that the light wavelengths of the two light beams are set to two wavelengths where an absorption difference exhibited by the liquid constituent set as the measuring object is larger than the absorption difference exhibited by other liquid constituents.

In the constituent concentration measuring apparatus, it is desirable to further comprise a coupler between the light outgoing means and the object to be measured, the coupler combining the outgoing light beams.

The light can be focused on the measurement region, so that the photoacoustic signal can efficiently be generated.

In the constituent concentration measuring apparatus, it is desirable to further comprise rectifying amplification means for detecting amplitude of the acoustic wave from the acoustic wave detection means.

The amplitude of the acoustic wave can be detected from the detected photoacoustic signal.

In the constituent concentration measuring apparatus, it is desirable to further comprise liquid constituent concentration computation means for computing a constituent concentration of a liquid constituent from pressure of the detected acoustic wave, the liquid constituent being set as a measuring object in the object to be measured.

In the constituent concentration measuring apparatus, it is desirable to further comprise recording means for recording the acoustic wave as a function of the modulation frequency, the acoustic wave being detected by the acoustic wave detection means.

By including the means for recording the photoacoustic signal detected by the acoustic wave detection means for each swept modulation frequency, if the resonance frequency of the acoustic wave detection means happens to change, still the modulation frequency sweep range of the irradiating light covers the range in which the resonance frequency possibly changes, the values measured with high accuracy can be selected from the detected photoacoustic signals, which are integrated and averaged to confirm that the constituent concentration is correctly measured.

A constituent concentration measuring apparatus according to one aspect of the invention is characterized by comprising light generating means for generating light; frequency sweep means for sweeping a modulation frequency, the light generated by the light generating means being modulated in the modulation frequency; light modulation means for electrically intensity-modulating the light using a signal from the frequency sweep means, the light being generated by the light generating means; light outgoing means for outputting the intensity-modulated light toward a test subject; acoustic wave detection means for detecting an acoustic wave which is emitted in the test subject by the outputted light; and integration means for integrating the acoustic wave in a swept modulation frequency range, the acoustic wave being detected by the acoustic wave detection means.

In one aspect of the invention, the light is electrically intensity-modulated using the modulation signal whose frequency is swept in a predetermined range, the test subject is irradiated with the intensity-modulated light to detect the photoacoustic signal which is an acoustic wave generated in the test subject by the irradiation light, and the detected photoacoustic signal is integrated to compute the constituent concentration which is the measurement objective in the test subject. At this point, the wavelength of the light with which the test subject is irradiated is set at the wavelength in which the constituent set as the measuring object exhibits the absorption. Thus, the change in sensitivity characteristics of the acoustic wave detection means can be tracked to measure the constituent concentration which is the measurement objective at the frequency where the optimal sensitivity is attainable.

A constituent concentration measuring apparatus according to one aspect of the invention comprising light generating means for generating light; light modulation means for electrically intensity-modulating the light at a constant frequency, the light being generated by the light generating means; light outgoing means for outputting the intensity modulated light toward a test subject, the intensity modulated light being intensity-modulated by the light modulation means; and acoustic wave detection means for detecting an acoustic wave which is emitted from the test subject irradiated with the intensity modulated light, the constituent concentration measuring apparatus is characterized in that an acoustic matching substance and the test subject can be arranged between the light outgoing means and the acoustic wave detection means, the acoustic matching substance having acoustic impedance substantially equal to that of the test subject.

One aspect of the invention is characterized in that the photoacoustic signal is detected under the environment whose acoustic impedance is substantially equal to that of the test subject. The test subject is irradiated with a light intensity modulated at a constant frequency, the photoacoustic signal which is the acoustic wave emitted from the test subject to be measured is detected to measure the concentration of a particular constituent contained in the liquid by the acoustic wave detection means though the acoustic matching substance. The acoustic wave detection means detects the photoacoustic signal through the acoustic matching substance, which alleviates the signal loss caused by reflection of the acoustic wave. The reflection of the photoacoustic signal is caused by a boundary reflection between the test subject and surroundings, and the reflection of the photoacoustic signal is also occurs at the contact between the test subject and the acoustic wave detection means. Here the test subject and the acoustic matching substance having the acoustic impedance substantially equal to that of the test subject can be arranged between the light outgoing means and the acoustic wave detection means. Thus reflection at the boundary between the test subject and surroundings can be decreased.

A constituent concentration measuring apparatus according to one aspect of the invention is characterized by comprising light generating means for generating light; light modulation means for electrically intensity-modulating the light at a constant frequency, the light being generated by the light generating means; light outgoing means for outputting the intensity modulated light toward a test subject, the intensity modulated light being intensity-modulated by the light modulation means; acoustic wave detection means for detecting an acoustic wave which is emitted from the test subject irradiated with the intensity modulated light; and a container in which a space between the light outgoing means and the acoustic wave detection means is filled with an acoustic matching substance having acoustic impedance substantially equal to that of the test subject.

By instituting the container filled with the acoustic matching substance having the acoustic impedance substantially equal to that of the test object to be measured, the test subject to be measured is arranged in the container filled with the acoustic matching substance having the acoustic impedance substantially equal to that of the test subject to be measured, and the photoacoustic signal from the test subject to be measured can be detected under the environment in which the test subject to be measured is surrounded by the acoustic matching substance. This configuration leads to an alleviation of the attenuation which is caused by the reflection of the photoacoustic signal at the boundary between the test subject to be measured and the surroundings as well as at the contact between the test subject to be measured and the acoustic wave detection means.

In the constituent concentration measuring apparatus, it is desirable that the container is filled with water as for the acoustic matching substance.

Because the acoustic impedance of the test subject is very close to that of the water, a detection of the photoacoustic signal under the environment where the test subject is surrounded by the water can decrease the attenuation of the photoacoustic signal due to the reflection which is caused by the boundary reflection between the test subject and the surroundings and by the contact between the test subject and the acoustic wave detection means.

In the constituent concentration measuring apparatus, it is desirable that the light generating means generates two light beams having different wavelengths, and the light modulation means intensity-modulate each of the light beams into the intensity modulated light beams, the intensity modulated light beams having the same frequency and reverse phases.

The influence of the water on the photoacoustic signal can be removed by using the two intensity modulated light beams having the different wavelengths for the intensity modulated light. As for the modulation, the frequencies are equal and the phases are reversed to one another.

In the constituent concentration measuring apparatus, it is desirable that a cross-sectional shape of the container is a semicircle, and the light outgoing means is positioned substantially at the center of the semicircle.

The cross-sectional shape of the inner wall surface of the container forms a semicircle, and the light outgoing means is arranged at the center of the circle. Therefore, the distance between the light outgoing means and the container side corresponding to an arc portion of the semicircle can be kept constant. Moreover, the distance between the light outgoing means and the container side corresponding to an arc portion of the semicircle is set to an extent in which the photoacoustic signal can be regarded as a plane wave, and the acoustic wave detection means is arranged on the side, which allows the radially spreading photoacoustic signal to be efficiently detected. Thus, the accuracy of photoacoustic signal can further be increased by improving the efficiency of sound collection by the acoustic wave detection means.

In the constituent concentration measuring apparatus, it is desirable that the two or more acoustic wave detection means are arranged on an arc portion of the semicircle of the container.

Two or more pieces of acoustic wave detection means are arranged in the container side corresponding to the arc portion of the semicircle, which allows the radially spreading photoacoustic signal to be detected more efficiently with the acoustic wave detection means.

In the constituent concentration measuring apparatus, it is desirable that a cross-sectional shape of the container is an ellipse, and the light outgoing means and the acoustic wave detection means are positioned substantially at the focal points of said ellipse respectively.

The cross-sectional shape of the inner wall surface formed an ellipse, and the light outgoing means and the acoustic wave detection means are arranged substantially at each of the two focal points of the ellipse respectively. Therefore, the photoacoustic signal can be scattered in the container side and efficiently collected by the acoustic wave detection means. Thus, the accuracy of photoacoustic signal can further be increased by improving the efficiency of sound collection by the acoustic wave detection means.

In the constituent concentration measuring apparatus, it is desirable that the bottom portion of the container forms a semi-ellipsoid containing the two focal points in sectional plane, and the light outgoing means and the acoustic wave detection means are positioned substantially at each of the two focal points of the semi-ellipsoid respectively.

The bottom portion of the inner wall surface of the container forms a semi-ellipsoid containing the two focal points in sectional plane, and the light outgoing means and the acoustic wave detection means are arranged at each of the two focal points of the semi-ellipsoid respectively. Therefore, the photoacoustic signal can be scattered in the bottom portion of the container and efficiently collected by the acoustic wave detection means. Thus, the accuracy of photoacoustic signal can further be increased by improving the efficiency of sound collection by the acoustic wave detection means.

In the constituent concentration measuring apparatus, it is desirable to comprise a reflection material on at least a part of the inner wall of the container.

The efficiency of collecting the photoacoustic signal onto the acoustic wave detection means can be improved by overlaying the reflection material onto at least a part of the inner wall of the container. Thus, the accuracy of photoacoustic signal detected by the acoustic wave detection means can further be increased.

In the constituent concentration measuring apparatus, it is desirable to comprise a sound absorbing material on at least a part of the inner wall of the container.

The multiple-reflected acoustic wave caused by the inhomogeneity of internal structure of the test subject is absorbed and removed by overlaying the sound absorbing material onto at least a part of the inner wall of the container, so that the photoacoustic signal emitted from the test subject can be detected efficiently. Therefore, the accuracy of photoacoustic signal detected by the acoustic wave detection means can further be increased.

In the constituent concentration measuring apparatus, it is desirable to further comprise an outgoing window on the inner wall of the container, the outgoing window being transparent for the intensity modulated light.

The container is furnished with an outgoing window transparent for the intensity modulated light, which allows the light outgoing means to be placed outside the container. Therefore, the light outgoing means can easily be arranged. The intensity modulated light can be outputted from the inner wall surface of the container, which allows the influence of surface irregularity on the inner wall of the container to be suppressed to decrease the reflection of the photoacoustic signal.

In the constituent concentration measuring apparatus, it is desirable that the light outgoing means includes an optical fiber which guides the intensity modulated light to the container.

The light outgoing means includes the optical fiber. Therefore, the light generating means and the light modulation means can be arranged at a place distant from the light outgoing means to guide the intensity modulated light to the position where the test subject is irradiated.

In the constituent concentration measuring apparatus, it is desirable to further comprise temperature measuring means for measuring a temperature of the acoustic matching substance; and temperature adjustment means for adjusting a temperature of the acoustic matching substance according to the temperature being measured by the temperature measuring means.

The temperature adjustment means is included to adjust the temperature of the acoustic matching substance according to the temperature measured by the temperature measuring means, which allows to stabilize temperature of the acoustic matching substance and the surface of the test subject. Thus, the disturbance of the photoacoustic signal intensity by the temperature change can be decreased, which leads to an improvement of the S/N ratio of photoacoustic signal.

A constituent concentration measuring apparatus according to one aspect of the invention is characterized by comprising light generating means for generating light; light modulation means for electrically intensity-modulating the light at a constant frequency, the light being generated by the light generating means; light outgoing means for outputting the intensity modulated light toward a test subject, the intensity modulated light being intensity-modulated by the light modulation means; an acoustic wave generator which outputs an acoustic wave; and acoustic wave detection means for detecting the acoustic wave emitted from the test subject which is irradiated with the intensity modulated light, as well as said acoustic wave transmitted from the acoustic wave generator through the test subject.

One aspect of the invention is characterized in that, when the constituent concentration which is the measurement objective is measured by the photoacoustic method, the ultrasonic wave (in this case, referred to as acoustic wave) emitted from the acoustic wave generator which is placed near irradiation position of the excitation light, i.e., near the source of photoacoustic signal is detected as a reference signal to search for the arrangement which optimizes a positional relationship between the photoacoustic signal source and the acoustic wave detection means. The photoacoustic signal is detected under the optimum arrangement, which allows the constituent concentration to be measured using a propagation path which minimizes the adverse influence of scatterers existing in the test subject to be measured.

When the photoacoustic signal is detected in the arrangement in which the detected acoustic wave signal intensity becomes a predetermined value such that the attenuation amount of acoustic wave is kept constant, the photoacoustic signal can be detected while the influences of uncertain factors are eliminated. The uncertain factors include the change in influence of the scatterers on the photoacoustic signal by the change in positional relationship between the photoacoustic signal generation source and the acoustic wave detection means as well as by the change at the contact between the acoustic wave detection means and the test subject. Therefore, the constituent concentration can be measured with no influence of the many parameters associated with the positional change of the constituent concentration measuring apparatus.

In searching the optimal arrangement of the test subject particularly the living body and the devices in terms of the object to be measured in a measuring system by the photoacoustic method, means for adjusting the arrangement is mechanized to operate concurrently with the acoustic wave detection means, which allows the constituent concentration measurement to be automated to operate always under the optimum arrangement. In the invention, the intensity modulated light which is modulated by the constant frequency is used as the excitation light.

According to one aspect of the invention, the influence of the reflecting/scattering scatterers on the photoacoustic signal can be probed using the acoustic wave. Therefore, the photoacoustic signal can be detected with the optimum arrangement.

A constituent concentration measuring apparatus according to one aspect of the invention is characterized by comprising light generating means for generating two light beams having different wavelengths; light modulation means for electrically intensity-modulating each of the two light beams having the mutually different wavelengths using signals having the same frequency and reverse phases; light outgoing means for outputting the two intensity-modulated light beams having the mutually different wavelengths toward a test subject; and acoustic wave detection means for detecting an acoustic wave emitted in the test subject by the outputted light.

In one aspect of the invention, each of the two light beams having the mutually different wavelengths is electrically intensity-modulated using the signals having the same frequency and reverse phases, so that the acoustic wave corresponding to each of the two light beams having the mutually different wavelengths can be detected with no influence from a frequency dependence of the acoustic wave detection means.

One of the two light beams generates acoustic wave having the pressure corresponding to the total absorption in the state where the constituent of the measuring object and water are mixed together in the test subject, and the other light beam generates the acoustic wave having the pressure originating only from the water occupying the large part of the test subject so that the pressure of the acoustic wave generated only by the constituent of the measuring object is detectable as the difference between two acoustic waves. As a result, quantity of the constitute in the measuring object can be measured.

With the two acoustic wave pressures, one generated by one of the two light beams corresponding to the total absorption in the state where the constituent of the measuring object and water are mixed together in the test subject to be measured, while another generated by the other light beam corresponding only to the water occupying the large part of the test subject to be measured, their frequencies are equal to each other and the phase are reversed to each other, therefore, the pressures are superposed to each other in the form of acoustic wave in the test subject, and the difference in pressure of the acoustic waves is directly detected. Accordingly, the difference in pressure of the acoustic waves can be obtained more accurately rather than by computing the difference from separate measurement of the pressure of the acoustic wave generated by one of the two light beams corresponding to the total absorption in the state where the constituent of the measuring object and water are mixed together in the test subject to be measured, as well as of the pressure of the acoustic wave generated by the other light beam corresponding only to the water occupying the large part of the test subject. The above point constitutes a novel advantage which does not exist in the conventional techniques.

In one aspect of the invention, the modulation frequency by which the two light beams having the mutually different wavelengths are electrically intensity-modulated can be set to the resonant frequency concerning the detection of the acoustic wave generated in the test subject to be measured. The photoacoustic signal is measured for the two light beams having mutually different wavelengths are selected by a consideration on the non-linearity regarding to the absorption coefficient in the measured value of the photoacoustic signal. Then, the acoustic wave generated in the test subject can be measured with a high accuracy from the measured values while the influences of the many parameters which are hardly kept constant, are eliminated.

In the constituent concentration measuring apparatus, it is desirable to further comprise second light outgoing means for outputting the light toward the test subject, the light being intermittently emitted at intervals which are longer than the repetition period for the same frequency.

According to one aspect of the invention, the photoacoustic signal emission amount by the absorption at the constituent, set as the measuring object is increased in the test subject, particularly in the living body tissue, so that the accurate constituent concentration can be measured in the noninvasive manner.

In the constituent concentration measuring apparatus, it is desirable that light from the second light outgoing means has a wavelength which exhibits a characteristic absorption of a constituent different from the constituent set as the measuring object.

Only the photoacoustic signal from the blood constituent can be increased by raising the temperature of the blood tissue as compared with the non-blood tissue.

In the constituent concentration measuring apparatus, it is desirable that light from the second light outgoing means has a wavelength which exhibits a characteristic absorption of hemoglobin in blood.

Only the photoacoustic signal from the blood containing the hemoglobin can be increased by raising the temperature of the hemoglobin.

In the constituent concentration measuring apparatus, it is desirable that an interval during which the second light outgoing means emits the light is an interval during which temperature rise of 2° C. or less is resulted is generated in the test subject.

The influence on the test subject can be suppressed to the minimum.

In the constituent concentration measuring apparatus, it is desirable that light intensity of the second light outgoing means is an intensity by which temperature rise of 2° C. or less is resulted in said test subject.

The influence on the test subject can be suppressed to the minimum.

In the constituent concentration measuring apparatus, the constituent concentration measuring apparatus further comprises frequency sweep means for sweeping a modulation frequency, the light generated by the light generating means being modulated in the modulation frequency; and integration means for integrating the acoustic wave in a swept modulation frequency range, the acoustic wave being detected by the acoustic wave detection means, and it is desirable that the light modulation means electrically intensity-modulate each of the two light beams having the mutually different wavelengths using the signal from the frequency sweep means and with mutually reverse modulation phases.

In one aspect of the invention, the photoacoustic signal generated in the test subject is integrated in the swept modulation signal range. The photoacoustic signal exploiting the high sensitivity in the frequency corresponding to the resonance frequency of the acoustic wave detection means is integrated even if the resonance frequency of the acoustic wave detection means suffers a drift. Thus measurement can be performed always with the high-sensitivity resonance frequency.

In the constituent concentration measuring apparatus, it is desirable that the acoustic wave detection means track the modulation frequency to detect the acoustic wave emitted in the test subject by the outputted light, the modulation frequency being swept by the frequency sweep means, and the integration means integrates the acoustic wave in the modulation frequency range where the acoustic wave detection means has high detection sensitivity, the acoustic wave being detected by the acoustic wave detection means.

In one aspect of the invention, in the case where the resonance frequency of the acoustic wave detection means happens to change, the change in resonance frequency of the acoustic wave detection means in which the detection sensitivity becomes the maximum is determined from the result on the measurement of the photoacoustic signal emitted in the test subject to be measured by the irradiation light which is modulated by the frequency-swept modulation frequency, and the change in resonance frequency is tracked to integrate the detected value of the photoacoustic signal near the resonance frequency.

In the constituent concentration measuring apparatus, it is desirable to further comprise constituent concentration computation means for computing a constituent concentration of a constituent from the acoustic wave integrated by said integration means, the constituent being set as a measuring object in the said test subject.

In one aspect of the invention, theoretical or experimental values showing the relationship between the photoacoustic signal generated in the test subject and the constituent concentration set as the measuring object are prepared beforehand, and the constituent concentration of the measuring object is computed based on the detected value of the photoacoustic signal generated in the test subject.

In the constituent concentration measuring apparatus, the constituent concentration measuring apparatus further comprises an acoustic wave generator which outputs an acoustic wave, and it is desirable that the acoustic wave detection means detect the acoustic wave emitted from the test subject as well as said acoustic wave transmitted from the acoustic wave generator through the test subject.

According to one aspect of the invention, the influence of the reflecting/scattering scatterers on the photoacoustic signal can be probed using the acoustic wave. Therefore, the photoacoustic signal can be detected with the optimum arrangement.

In the constituent concentration measuring apparatus, it is desirable to further comprise drive means for varying at least one of positions of the acoustic wave generator and the acoustic wave detection means.

According to one aspect of the invention, the influence of the reflecting/scattering scatterers on the photoacoustic signal can be probed for each propagation path by changing the acoustic wave propagation path. Thus, the photoacoustic signal can be detected in the probed optimum arrangement.

In the constituent concentration measuring apparatus, it is desirable to further comprise control means for controlling the drive means such that intensity of the acoustic wave detected by the acoustic wave detection means becomes a particular value.

According to one aspect of the invention, the photoacoustic signal is automatically made to be detected in the probed optimum arrangement.

In the constituent concentration measuring apparatus, it is desirable that the light outgoing means is fixed to the acoustic wave generator so as to keep the relative position to the acoustic wave generator.

According to one aspect of the invention, since the relative position between the light outgoing means and the acoustic wave generator is fixed, the former can automatically be moved to the optimum position following the latter acoustic wave generator.

In the constituent concentration measuring apparatus, it is desirable to further comprise pressing means for pressing the acoustic wave generator and the acoustic wave detection means against the test subject with pressing force whose pressure can be controlled.

According to one aspect of the invention, since the pressure for pressing the acoustic wave generator and the acoustic wave detection means against the test subject is controllable, the pressure at which the acoustic wave generator and the acoustic wave detection means come into contact with the test subject can be kept at a predetermined value. Therefore, the influence of the pressure on the test subject can be reduced.

In the constituent concentration measuring apparatus, it is desirable that the acoustic wave generator is placed in proximity of the intensity modulated light beam outputted from the light outgoing means.

According to one aspect of the invention, since the acoustic wave is outputted to a position close to the path of the intensity modulated light beam, the reflection/scattering can be examined more precisely for the propagation path of the photoacoustic signal.

In the constituent concentration measuring apparatus, it is desirable to further comprise a transmission window in a part of the acoustic wave generator, the transmission window transmitting said intensity modulated light beam.

According to one aspect of the invention, the test subject can be irradiated with the intensity modulated light through the acoustic wave generator. Therefore, the test subject can be irradiated with the intensity modulated light from the optimum position of the acoustic wave generator.

In the constituent concentration measuring apparatus, it is desirable that the frequency and/or the intensity of said outputted acoustic wave from said acoustic wave generator is variable.

According to one aspect of the invention, scatterers can be probed with the acoustic wave having the frequency equal to that of the photoacoustic signal detected by the acoustic wave detection means, so that the influence of the scatterers on the photoacoustic signal can be examined more correctly. The intensity of the acoustic wave outputted from the acoustic wave generator can be increased or decreased according to the intensity of the acoustic wave detected by the acoustic wave detection means, so that the detected intensity can be compared even if the intensity detected by the acoustic wave detection means is small.

In the constituent concentration measuring apparatus, it is desirable to further comprise an acoustic coupling element on the surface of the acoustic wave generator and/or the light outgoing means, the surface being in contact with the test subject, the acoustic coupling element having an acoustic impedance substantially equal to that of the test subject.

According to one aspect of the invention, the reflection/scattering can be reduced at the surface in which at least one of the acoustic wave generator and the acoustic wave detection means comes into contact with the test subject.

In the constituent concentration measuring apparatus, it is desirable that the light generating means sets the light wavelengths of the two light beams to two wavelengths where an absorption difference exhibited by the constituent set as the measuring object is larger than the absorption difference exhibited by a solvent.

In the constituent concentration measuring apparatus, it is desirable that the light generating means sets one of the light wavelengths of the two light beams to a light wavelength where the constituent set as the measuring object exhibits characteristic absorption, and the light generating means set the other light wavelength to a wavelength where the solvent exhibits an equal absorption to that for the one of the light wavelengths.

One aspect of the invention is the case where the difference in absorption exhibited by the solvent is set to zero, in the light generating means in the constituent concentration measuring apparatus in which the light wavelengths of the two light beams are set to two light wavelengths so that the absorption difference exhibited by the constituent set as the measuring object is larger than the absorption difference exhibited by the solvent. Therefore, the influence by the absorption of the solvent can be eliminated.

In the constituent concentration measuring apparatus, it is desirable that the light wavelengths of said two light beams are set to two wavelengths where an absorption difference exhibited by the constituent set as the measuring object is larger than the absorption difference exhibited by other constituents.

In the constituent concentration measuring apparatus, it is desirable that the light generating means sets the light wavelengths of the two light beams to two wavelengths where an absorption difference exhibited by the blood constituent set as the measuring object is larger than the absorption difference exhibited by a water.

In the constituent concentration measuring apparatus, it is desirable that the light generating means sets one of the light wavelengths of the two light beams to a light wavelength where the blood constituent set as the measuring object exhibits characteristic absorption, and the light generating means sets the other light wavelength to a wavelength where a water exhibits an equal absorption to that for the one of the light wavelengths.

One aspect of the invention is the case where the difference in absorption exhibited by the water is set to zero, in the light generating means in the constituent concentration measuring apparatus in which the light wavelengths of the two light beams are set to two light wavelengths so that the absorption difference exhibited by the blood constituent set as the measuring object is larger than the absorption difference exhibited by the water. Therefore, the influence by the absorption of the water can be eliminated.

In the constituent concentration measuring apparatus, it is desirable that the light wavelengths of the two light beams are set to two wavelengths where an absorption difference exhibited by the blood constituent set as the measuring object is larger than the absorption difference exhibited by other blood constituents.

In the constituent concentration measuring apparatus, it is desirable to further comprise a coupler between the light outgoing means and the test subject, the coupler combining the outgoing light beams.

The light can be focused on the measurement region, so that the photoacoustic signal can efficiently be generated.

In the constituent concentration measuring apparatus, it is desirable to further comprise rectifying amplification means for detecting amplitude of the acoustic wave from the acoustic wave detection means.

The amplitude of the acoustic wave can be detected from the detected photoacoustic signal.

In the constituent concentration measuring apparatus, it is desirable that the rectifying amplification means is a phase sensitive amplifier.

The amplitude of the acoustic wave can be detected from the photoacoustic signal with a high sensitivity.

In the constituent concentration measuring apparatus, it is desirable that diameters of the two outgoing light beams from the light outgoing means are substantially equal to each other.

The measurement accuracy can be improved by matching the measurement regions.

In the constituent concentration measuring apparatus, it is desirable to further comprise constituent concentration computation means for computing a constituent concentration of a constituent from pressure of the detected acoustic wave, the constituent being set as a measuring object in the test subject.

In the constituent concentration measuring apparatus, it is desirable that the constituent concentration computation means divide pressure of the acoustic wave, which is emitted by irradiating the two light beams having the mutually different wavelengths to the test subject, by pressure of the acoustic wave which is emitted when one of the two light beams is set to zero power.

As described above, the pressure of the acoustic wave generated by irradiating the test subject with the two light beams having the mutually different wavelengths is detected as the difference between the pressure of the acoustic wave generated by one of the two light beams corresponding to the total absorption in the state where the constituent of the measuring object and water are mixed together in the test subject and the pressure of the acoustic wave generated by the other light beam corresponding to the water alone occupying the large part of the test subject. The constituent concentration can be measured by dividing the difference by the acoustic wave pressure generated when one of the two light beams is set to zero power, i.e., the acoustic wave pressure generated solely by the water occupying the large part of the test subject according to the later-mentioned formula (5).

In the constituent concentration measuring apparatus, it is desirable that the light modulation means operates at the same frequency as a resonant frequency concerning detection of the acoustic wave generated in the test subject.

In one aspect of the invention, the modulation frequency by which the two light beams having the mutually different wavelengths are electrically intensity-modulated is set to the same frequency as the resonant frequency concerning the detection of the acoustic wave generated in the test subject. Therefore, the acoustic wave generated in the test subject can be measured with high accuracy.

In the constituent concentration measuring apparatus, it is desirable that the light generating means adjusts relative intensity of the two light beams having the mutually different wavelengths such that pressure of the acoustic wave becomes zero, the acoustic wave being generated by combining said two intensity-modulated light beams having the different wavelengths into a single light beam to irradiate water.

According to the above calibration, the relative intensity between the two light beams having the mutually different wavelengths can be set such that the intensity of the photoacoustic signal emitted from the water occupying the large part of test subject is equalized for the wavelengths of two light beams. Consequently for the whole system for measuring photoacoustic signal, the relative intensity between the two light beams having the mutually different wavelengths can be calibrated to improve the measurement accuracy.

In the constituent concentration measuring apparatus, it is desirable that the acoustic wave detection means is synchronized with the modulation frequency to detect the acoustic wave by phase sensitive detection.

The photoacoustic signal is detected by the phase-sensitive detection synchronized with the modulation frequency, so that the detection can be performed with a high accuracy.

In the constituent concentration measuring apparatus, it is desirable that the light generating means and the light modulation consists of two directly-modulated semiconductor laser light sources driven by rectangular-waveform signals having the same frequency and reverse phases.

In one aspect of the invention, the two light beams having the mutually different wavelengths can be generated and at the same time be modulated by using two directly-modulated semiconductor laser light sources driven by rectangular-waveform signals having the same frequency and reverse phases, so that the apparatus configuration can be simplified.

In the constituent concentration measuring apparatus, it is desirable that a blood constituent which is set as the measuring object is glucose or cholesterol.

In the case where the concentration of glucose or cholesterol is measured, the measurement can accurately be performed by irradiating the test subject with the light having the wavelength exhibiting the characteristic absorption.

In the constituent concentration measuring apparatus, it is desirable to further comprise recording means for recording the acoustic wave as a function of the modulation frequency, the acoustic wave being detected by the acoustic wave detection means.

By including the means for recording the photoacoustic signal detected by the acoustic wave detection means for each swept modulation frequency, if the resonance frequency of the acoustic wave detection means happens to change, still the modulation frequency sweep range of the irradiating light covers the range in which the resonance frequency possibly changes, the values measured with high accuracy can be selected from the detected photoacoustic signals, which are integrated and averaged to confirm that the constituent concentration is correctly measured.

In the constituent concentration measuring apparatus, it is desirable that the light outgoing means and the acoustic wave detection means are arranged at positions substantially opposing to each other.

In the photoacoustic signal emitted from the test subject, the largest signal intensity is detected in the direction in which the light outgoing means outputs the intensity modulated light. The accuracy of the photoacoustic signal detected with the acoustic wave detection means can further be improved by arranging the light outgoing means and the acoustic wave detection means at positions such that the light outgoing means and the acoustic wave detection means oppose to each other.

In the constituent concentration measuring apparatus, it is desirable to further comprise a light shielding hood surrounding at least a part of the optical path of the intensity modulated light, the light shielding hood preventing the intensity modulated light from leaking to the outside of the constituent concentration measuring apparatus.

According to one aspect of the invention, the intensity modulated light can be prevented from leaking to the outside of the constituent concentration measuring apparatus such as to a portion of the test subject other than potion for the testing.

In the constituent concentration measuring apparatus, it is desirable to further comprise enduing means in which at least the light outgoing means and the acoustic wave detection means are arranged in a portion which comes into contact with the test subject, the portion being located inside of an annular portion which is endued surrounding the test subject.

As described above, at least the light irradiation unit and the acoustic wave detection means, are inlaid onto an accessory having the annular portion which is endued surrounding the test subject. Thus, the change in distance between the light outgoing means and the acoustic wave detection means caused by the movement of the test subject, i.e., the change in thickness of a part of the test subject which is the measuring object located between the light outgoing means and the acoustic wave detection means is suppressed to stabilize the measured value of the acoustic wave emitted from the test subject during the measurement. In addition, deformation of the peripheries of the measurement portion in the test subject is prevented, which stabilizes the multiple reflections from peripheries of the measurement portion in the test subject. As a result, the constituent concentration set as the measuring object can correctly be measured.

In the constituent concentration measuring apparatus, it is desirable that the light outgoing means and the acoustic wave detection means are arranged at positions substantially opposing to each other in the annular portion of the enduing means.

As described above, the light outgoing means and the acoustic wave detection means are arranged at the positions where the light outgoing means and the acoustic wave detection means oppose to each other on annular potion of the enduing means. Thus, when the light outgoing means irradiates the test subject with the light, the acoustic wave detection means efficiently detects the resulting acoustic wave emitted from the test subject, and the constituent concentration set as the measuring object can be accurately measured in the test subject.

In the constituent concentration measuring apparatus, it is desirable that a layer of cushioning material covers at least a semicircular portion being in contact with the test subject inside the annular portion of said enduing means, the semicircular portion comprising position where said acoustic wave detection means is inlaid, the cushioning material having acoustic impedance approximately equal to that of the test subject.

As described above, the layer of cushioning material covers at least the semicircular portion being in contact with the test subject inside the annular portion of the enduing means, the semicircular portion includes the position where the acoustic wave detection means is arranged, and the cushioning material has the acoustic impedance approximately equal to that of test subject. Thus, of the acoustic wave emitted from the test subject, a part which directly reaches the acoustic wave detection means is efficiently detected, while the amount of acoustic wave emitted from the test subject which becomes a noise, is decreased which allows the constituent concentration to be measured more correctly. The acoustic wave which becomes the noise, is received by the acoustic wave detection means after multiple reflections generated at the interface between the test subject and the enduing means inside the annular portion.

In the constituent concentration measuring apparatus, it is desirable that a space between said layer of cushioning material and a inner surface of the annular portion of said enduing means is filled with a sound absorbing material.

As described above, the space between the layer of cushioning material and the inner surface on the annular portion of the enduing means is filled with the sound absorbing material. Thus, the constituent concentration can be measured more correctly by decreasing the amount of acoustic wave which becomes the noise in the acoustic wave emitted from the test subject. The acoustic wave which becomes the noise, is detected by the acoustic wave detection means after multiple reflections generated at the interface between the test subject and the enduing means inside the annular portion.

In the constituent concentration measuring apparatus, it is desirable that said light generating means generates two light beams having different wavelengths by multiple semiconductor laser devices.

As described above, the light generating means generates the two light beams having different wavelengths by the multiple semiconductor laser devices, which enables significant miniaturization and weight reduction of the constituent concentration measuring apparatus of the invention.

In the constituent concentration measuring apparatus, it is desirable that the light outgoing means includes a beam expander which enlarges the light beam diameter generated by said light generating means.

As described above, the light outgoing means includes the beam expander which enlarges the light beam diameter generated by the light generating means. Thus, the light beam with which the test subject is irradiated is enlarged, and the test subject can be irradiated with the relatively strong light without adverse influence on the test subject, so that the constituent concentration set as the measuring object can be measured more correctly in the test subject.

In the constituent concentration measuring apparatus, it is desirable that the enduing means is a ring fitted in a human finger, said light outgoing means is arranged on a dorsal side of said finger, while said acoustic wave detection means is arranged on a palm side of said finger.

As described above, the enduing means is the ring fitted to the human finger, the light outgoing means is arranged on the dorsal side of the finger, while the acoustic wave detection means is arranged on the palm side of the finger. Thus, the acoustic wave detection means easily comes into contact with the relatively soft skin of the finger, and the acoustic wave detection means can efficiently measure the acoustic wave generated in the finger, so that the constituent concentration can be measured more correctly. Further, the light outgoing means and the acoustic wave detection means are mounted in the inner surface of the ring, which allows the constituent concentration of the human body to be easily and continuously measured without imposing inconvenience for a daily life.

In the constituent concentration measuring apparatus, it is desirable that the enduing means is a bracelet fitted in a human arm, said light outgoing means is arranged on a palm side of a hand, and said acoustic wave detection means is arranged on a dorsal side of a hand.

As described above, the enduing means is the bracelet fitted on a human arm, the light outgoing means is arranged on the palm side on the hand, and the acoustic wave detection means is arranged on the dorsal side on the hand. Therefore, the acoustic wave detection means easily comes into contact with the relatively soft skin of the arm, and the acoustic wave detection means can efficiently measure the acoustic wave generated in the arm, so that the constituent concentration can be measured more correctly. Further, the light outgoing means and the acoustic wave detection means are mounted in the inner surface of the bracelet, which allows the constituent concentration of the human body to be easily and continuously measured without imposing inconvenience for a daily life.

A constituent concentration measuring apparatus controlling method according to one aspect of the invention is characterized by sequentially comprising a light generating procedure in which light generating means generates light; a frequency sweep procedure in which frequency sweep means sweeps a modulation frequency, the light generated in the light generating procedure being modulated in the modulation frequency; a light modulation procedure in which light modulation means electrically intensity-modulates the light using a signal swept in the frequency sweep procedure, the light being generated in the light generating procedure; a light outgoing procedure in which light outgoing means outputs the light toward an object to be measured, the light being intensity-modulated in the light modulation procedure; an acoustic wave detection procedure in which acoustic wave detection means detects an acoustic wave which is generated in the object to be measured by the light outputted in the light outgoing procedure; and an integration procedure in which integration means integrates the acoustic wave in a swept modulation frequency range, the acoustic wave being detected in the acoustic wave detection procedure.

In one aspect of the invention, the light is electrically intensity-modulated using the modulation signal whose frequency is swept in a predetermined range, the intensity-modulated light is outputted, the photoacoustic signal generated by the outputted light is detected, and the detected photoacoustic signal is integrated to compute the constituent concentration which is the measurement objective in the object to be measured. At this point, the wavelength of the outputted light is set at the wavelength in which the constituent set as the measuring object exhibits the absorption. Thus, the change in sensitivity characteristics of the acoustic wave detection means can be tracked to measure the constituent concentration which is the measurement objective at the frequency where the optimal sensitivity is attainable.

A constituent concentration measuring apparatus controlling method according to one aspect of the invention comprising a light generating procedure in which light generating means generates light; a light modulation procedure in which light modulation means electrically intensity-modulates the light at a constant frequency, the light being generated by said light generating procedure; a light outgoing procedure in which light outgoing means outputs the intensity modulated light toward an object to be measured, the intensity modulated light being intensity-modulated by said light modulation procedure; and an acoustic wave detection procedure in which acoustic wave detection means detects an acoustic wave which is emitted from said object to be measured by said intensity modulated light in said light outgoing procedure, the constituent concentration measuring apparatus controlling method characterized in that said light outgoing procedure and said acoustic wave detection procedure are performed in a container which is filled with an acoustic matching substance having acoustic impedance substantially equal to that of the object to be measured.

One aspect of the invention is characterized in that the photoacoustic signal is detected under the environment whose acoustic impedance is substantially equal to that of the object to be measured. A light intensity-modulated at a constant frequency is outputted, and the photoacoustic signal which is the acoustic wave generated by the outputted light is detected to measure the concentration of a particular constituent contained in the object to be measured by the acoustic wave detection means though the acoustic matching substance. The light outgoing procedure and the acoustic wave detection procedure are performed in the container which is filled with the acoustic matching substance having acoustic impedance substantially equal to that of the object to be measured. Thus, the photoacoustic signal can be detected under the environment in which the object to be measured is surrounded by the acoustic matching substance, and the attenuation can be decreased. The attenuation is caused by the photoacoustic signal reflection at the boundary between the object to be measured and surroundings, and also by dumping at the contact between the object to be measured and the acoustic wave detection means.

A constituent concentration measuring apparatus controlling method according to one aspect of the invention is characterized by sequentially comprising an optimum position detection procedure in which acoustic wave generators output acoustic waves from two or more different positions to object to be measured and acoustic wave detection means detects a position where intensity of said acoustic wave transmitted through said object to be measured becomes a particular value; and an acoustic wave detection procedure in which light outgoing means outputs intensity modulated light to said object to be measured from the position where intensity of said acoustic wave becomes the particular value, the intensity modulated light being intensity-modulated at a constant frequency, and said acoustic wave detection means detects the acoustic wave emitted from said object to be measured.

One aspect of the invention is characterized in that, when the constituent concentration which is the measurement object is measured by the photoacoustic method, the ultrasonic wave (in this case, referred to as acoustic wave) emitted from the acoustic wave generator which is placed near irradiation position of the excitation light, i.e., near source of photoacoustic signal is detected as a reference signal to search for an arrangement which optimizes a positional relationship between the photoacoustic signal source and the acoustic wave detection means. The photoacoustic signal is detected under the optimum arrangement, which allows the constituent concentration to be measured using a propagation path which minimizes the adverse influence of scatters on excitation light.

When the photoacoustic signal is detected in the arrangement in which the detected acoustic wave signal intensity becomes a predetermined value such that the attenuation amount of acoustic wave is kept constant, the photoacoustic signal can be detected while influences of uncertain factors are eliminated. The uncertain factors include the change in influence of the scatterers on the photoacoustic signal by the change in positional relationship between the photoacoustic signal generation source and the acoustic wave detection means as well as by the change at the contact between the acoustic wave detection means and the object to be measured. Therefore, the constituent concentration can be measured with no influence of the many parameters associated with the positional change of the constituent concentration measuring apparatus.

In searching the optimal arrangement of the devices in terms of the object to be measured in a measuring system by the photoacoustic method, means for adjusting the arrangement is mechanized to operate concurrently with the acoustic wave detection means, which allows the constituent concentration measurement to be automated to operate always under the optimum arrangement. In the invention, the intensity modulated light which is modulated by the constant frequency is used as the excitation light.

According to one aspect of the invention, the influence of the reflecting/scattering scatterers on the photoacoustic signal is probed in each propagation path by changing the acoustic wave propagation path, and then the photoacoustic signal is detected by outputting the intensity modulated light such that the photoacoustic signal propagates through the propagation path in which the acoustic wave intensity detected by the acoustic wave detection means becomes the particular value. Therefore, the photoacoustic signal can be detected in the optimum arrangement.

A constituent concentration measuring apparatus controlling method according to one aspect of the invention is characterized by sequentially comprising a light generating procedure in which light generating means generates two light beams having mutually different wavelengths; a light modulation procedure in which light modulation means electrically intensity-modulates each of the two light beams having the mutually different wavelengths using signals having the same frequency and reverse phases, the two light beams being generated in the a light generating procedure; a light outgoing procedure in which light outgoing means outputs the two light beams having the mutually different wavelengths to an object to be measured, the two light beams being intensity-modulated in the light modulation procedure; and an acoustic wave detection procedure in which acoustic wave detection means detects an acoustic wave emitted from said object to be measured by the light outputted in said light outgoing procedure.

In one aspect of the invention, each of the two light beams having the mutually different wavelengths is electrically intensity-modulated using the signals having the same frequency and reverse phases, so that the acoustic wave corresponding to each of the two light beams having the mutually different wavelengths can be detected with no influence from a frequency dependence of the acoustic wave detection means.

One of the two light beams generates acoustic wave having the pressure corresponding to the total absorption in the state where the constituent of the measuring object and water are mixed together in the object to be measured, and the other light beam generates the acoustic wave having the pressure originating only from the water occupying the large part of the object to be measured, so that the pressure of the acoustic wave generated only by the constituent of the measuring object is detectable as the difference between two acoustic waves. As a result, quantity of the constitute in the measuring object can be measured.

With the two acoustic wave pressures, one generated by one of the two light beams corresponding to the total absorption in the state where the constituent of the measuring object and water are mixed together in the object to be measured, while another generated by the other light beam corresponding only to the water occupying the large part of the object to be measured, their frequencies are equal to each other and the phase are reversed to each other, therefore, the pressures are superposed to each other in the form of acoustic wave in the object to be measured, and the difference in pressure of the acoustic waves is directly detected. Accordingly, the difference in pressure of the acoustic waves can be obtained more accurately rather than by computing the difference from separate measurements of the pressure of the acoustic wave generated by one of the two light beams corresponding to the total absorption in the state where the constituent of the measuring object and water are mixed together in the object to be measured, as well as of the pressure of the acoustic wave generated by the other light beam corresponding only to the water occupying the large part of the object to be measured. The above point constitutes a novel advantage which does not exist in the conventional techniques.

In one aspect of the invention, the modulation frequency by which the two light beams having the mutually different wavelengths are electrically intensity-modulated can be set to the resonant frequency concerning the detection of the acoustic wave generated in the object to be measured. The photoacoustic signal is measured for the two light beams having mutually different wavelengths are selected by a consideration on the non-linearity regarding to the absorption coefficient in the measured value of the photoacoustic signal. Then, the acoustic wave generated in the object to be measured can be measured with a high accuracy from the measured values while the influences of the many parameters which are hardly kept constant, are eliminated.

In the constituent concentration measuring apparatus controlling method, it is desirable to further comprise a frequency sweep procedure in which frequency sweep means sweeps a modulation frequency, the light generated in the light generating procedure being modulated in the modulation frequency; and an integration procedure in which integration means integrates the acoustic wave in a swept modulation frequency range, the acoustic wave being detected in the acoustic wave detection procedure.

In one aspect of the invention, the photoacoustic signal generated in the object to be measured is integrated in the swept modulation signal range. The photoacoustic signal exploiting the high sensitivity at the frequency corresponding to the resonance frequency of the acoustic wave detection means is integrated even if the resonance frequency of the acoustic wave detection means suffers a drift. Thus the measurement can be performed always with the high-sensitivity resonance frequency.

In the constituent concentration measuring apparatus controlling method, it is desirable that the acoustic wave detection procedure is a procedure in which the modulation frequency is tracked to detect the acoustic wave emitted in the said object to be measured by the irradiation light, the modulation frequency being swept in said frequency sweep procedure, and said integration procedure is a procedure in which the acoustic wave is integrated in the modulation frequency range where detection sensitivity of the acoustic wave is high in said acoustic wave detection procedure, the acoustic wave being detected in said acoustic wave detection procedure.

In one aspect of the invention, in the case where the resonance frequency of the acoustic wave detection means happens to change, the change in resonance frequency of the acoustic wave detection means in which the detection sensitivity becomes the maximum is determined from the result on the measurement of the photoacoustic signal generated by the outputted light which is modulated by the frequency-swept modulation frequency, and the change in resonance frequency is tracked to integrate the detected value of the photoacoustic signal near the resonance frequency.

In the constituent concentration measuring apparatus controlling method, it is desirable to further comprise a liquid constituent concentration computation procedure for computing a constituent concentration of a liquid constituent from the acoustic wave integrated in the integration procedure, the liquid constituent being set as a measuring object.

In one aspect of the invention, theoretical or experimental values showing the relationship between the photoacoustic signal generated in the object to be measured and the constituent concentration set as the measuring object are prepared beforehand, and the constituent concentration of the measuring object is computed based on the detected value of the photoacoustic signal generated in the object to be measured.

In the constituent concentration measuring apparatus controlling method it is desirable that the light outgoing procedure and said acoustic wave detection procedure are performed in a container which is filled with an acoustic matching substance having an acoustic impedance substantially equal to that of the object to be measured.

By instituting the container filled with the acoustic matching substance having the acoustic impedance substantially equal to that of the object to be measured, the object to be measured is arranged in the container filled with the acoustic matching substance having the acoustic impedance substantially equal to that of the object to be measured, and the photoacoustic signal from the object to be measured can be detected under the environment in which the object to be measured is surrounded by the acoustic matching substance. This configuration leads to an alleviation of the attenuation which is caused by the reflection of the photoacoustic signal at the boundary between the object to be measured and the surroundings as well as at the contact between the object to be measured and the acoustic wave detection means.

In the constituent concentration measuring apparatus controlling method, it is desirable that, in the acoustic wave detection procedure, said acoustic wave is detected through an acoustic matching substance having an acoustic impedance substantially equal to that of said object to be measured.

The photoacoustic signal is detected through the acoustic matching substance having acoustic impedance substantially equal to that of the object to be measured, so that the boundary reflection between the object to be measured and the surroundings thereof and the pressure and vibration impairing the acoustic wave detection means can be prevented.

In the constituent concentration measuring apparatus controlling method, it is desirable that, in the light outgoing procedure, said intensity modulated light is arranged on the inner wall of said container, and said intensity modulated light is outputted to said object to be measured through an outgoing window which is transparent for said intensity modulated light.

The light outgoing means can be arranged outside the container furnished with the outgoing window transparent for the intensity modulated light, so that the light outgoing means is easily placed. The intensity modulated light can be outputted from the inner wall surface of the container, so that the influence of surface irregularity on the inner wall of the container to be suppressed to decrease the reflection of the photoacoustic signal.

In the constituent concentration measuring apparatus controlling method, it is desirable that, in the object to be measured, a region irradiated with said intensity modulated light is covered with said acoustic matching substance in either sol or gel form.

In the object to be measured, the region irradiated with the intensity modulated light is covered with the liquid, sol or gel acoustic matching substance. Therefore, the photoacoustic signal can be detected from the object to be measured under the environment in which the object to be measured is surrounded by the acoustic matching substance.

In the constituent concentration measuring apparatus controlling method, the constituent concentration measuring apparatus controlling method further comprises an optimum position detection procedure in which acoustic wave generators output acoustic waves from two or more different positions to said object to be measured and acoustic wave detection means detects a position where intensity of said acoustic wave transmitted through said object to be measured becomes a particular value, the constituent concentration measuring apparatus controlling method characterized in that said light outgoing means outputs intensity modulated light to said object to be measured from the position where intensity of said acoustic wave becomes the particular value.

According to one aspect of the invention, the influence of the reflecting/scattering scatterers on the photoacoustic signal is probed in each propagation path by changing the acoustic wave propagation path, and then the photoacoustic signal is detected by outputting the intensity modulated light such that the photoacoustic signal propagates through the propagation path in which the acoustic wave intensity detected by the acoustic wave detection means becomes the particular value. Therefore, the photoacoustic signal can be detected in the optimum arrangement.

In the constituent concentration measuring apparatus controlling method, it is desirable that the light generating procedure is a procedure for setting the light wavelengths of said two light beams to two light wavelengths where an absorption difference exhibited by the liquid constituent set as the measuring object is larger than the absorption difference exhibited by a solvent.

In the constituent concentration measuring apparatus controlling method, it is desirable that the light generating procedure is a procedure for setting one of the light wavelengths of said two light beams to a light wavelength where the liquid constituent set as the measuring object exhibits characteristic absorption, and while the other light wavelength is set to a wavelength where the solvent exhibits an equal absorption to that for said one of the light wavelengths.

One aspect of the invention is the case where the difference in absorption exhibited by the solvent is set to zero, in the light generating procedure in the constituent concentration measuring apparatus controlling method in which the light wavelengths of the two light beams are set to two light wavelengths so that the absorption difference exhibited by the liquid constituent set as the measuring object is larger than the absorption difference exhibited by the solvent. Therefore, the influence by the absorption of the solvent can be eliminated.

In the constituent concentration measuring apparatus controlling method, it is desirable that the light generating procedure is a procedure in which the light wavelengths of said two light beams are set to two wavelengths where an absorption difference exhibited by the liquid constituent set as the measuring object is larger than the absorption difference exhibited by other liquid constituents.

In the constituent concentration measuring apparatus controlling method, it is desirable that the two light beams from said light outgoing means are combined and outputted to said object to be measured.

The light can be focused on the measurement region, so that the photoacoustic signal can efficiently be generated.

In the constituent concentration measuring apparatus controlling method, it is desirable that the detected acoustic wave is further rectified and amplified to detect amplitude of the acoustic wave.

The amplitude of the ultrasonic wave can be detected from the detected photoacoustic signal.

In the constituent concentration measuring apparatus controlling method, it is desirable to further comprise a liquid constituent concentration computation procedure for computing a constituent concentration of a liquid constituent from pressure of the acoustic wave detected in said acoustic wave detection procedure, the liquid constituent being set as a measuring object.

In the constituent concentration measuring apparatus controlling method, it is desirable to further comprise a recording procedure for recording the acoustic wave as a function of the modulation frequency after said acoustic wave detection procedure, the acoustic wave being detected in said acoustic wave detection procedure.

By including the means for recording the photoacoustic signal detected by the acoustic wave detection means for each swept modulation frequency, if resonance frequency of the acoustic wave detection means happens to change, still the modulation frequency sweep range of the irradiating light covers the range in which the resonance frequency possibly changes, the values measured with high accuracy can be selected from the detected photoacoustic signals, which are integrated and averaged to confirm that the constituent concentration is correctly measured.

In the constituent concentration measuring apparatus controlling method, it is desirable that, in the light outgoing procedure, an object to be measured is placed in contact with an outgoing surface of said intensity modulated light, and said object to be measured is directly irradiated with said intensity modulated light.

The object to be measured is arranged so as to come into contact with the outgoing surface of the intensity modulated light, and the object to be measured is directly irradiated with the intensity modulated light. Thus, the attenuation of intensity modulated light caused by the absorption in the acoustic matching substance and the like can be prevented. Accordingly, since the object to be measured can efficiently be irradiated with the intensity modulated light, the photoacoustic signal emitted from the object to be measured is increased, and the accuracy can further be improved in the photoacoustic signal detected by the acoustic wave detection means.

A constituent concentration measuring apparatus controlling method according to one aspect of the invention is characterized by sequentially comprising a light generating procedure in which light generating means generates light; a frequency sweep procedure in which frequency sweep means sweeps a modulation frequency, the light generated in said light generating procedure being modulated in the modulation frequency; a light modulation procedure in which light modulation means electrically intensity-modulates the light using a signal swept in said frequency sweep procedure, the light being generated in said light generating procedure; a light outgoing procedure in which light outgoing means outputs the light intensity-modulated in said light modulation procedure; an acoustic wave detection procedure in which acoustic wave detection means detects an acoustic wave which is generated by the light emitted in said light outgoing procedure; and an integration procedure in which integration means integrates the acoustic wave in a swept modulation frequency range, the acoustic wave being detected in said acoustic wave detection procedure.

In one aspect of the invention, the light is electrically intensity-modulated using the modulation signal whose frequency is swept in a predetermined range, the intensity-modulated light is outputted, the photoacoustic signal generated by the outputted light is detected, and the detected photoacoustic signal is integrated to compute the constituent concentration which is the measurement objective in the test subject. At this point, the wavelength of the outputted light is set at the wavelength in which the constituent set as the measuring object exhibits the absorption. Thus, the change in sensitivity characteristics of the acoustic wave detection means can be tracked to measure the constituent concentration which is the measurement objective at the frequency where the optimal sensitivity is attainable.

A constituent concentration measuring apparatus controlling method according to one aspect of the invention comprising a light generating procedure in which light generating means generates light; a light modulation procedure in which light modulation means electrically intensity-modulates the light at a constant frequency, the light being generated in said light generating procedure; a light outgoing procedure in which light outgoing means outputs the intensity modulated light intensity-modulated in said light modulation procedure; and an acoustic wave detection procedure in which acoustic wave detection means detects an acoustic wave generated by said intensity modulated light in said light outgoing procedure, the constituent concentration measuring apparatus controlling method characterized in that said light outgoing procedure and said acoustic wave detection procedure are performed in a container filled with an acoustic matching substance having an acoustic impedance substantially equal to that of a test subject.

One aspect of the invention is characterized in that the photoacoustic signal is detected under the environment whose photoacoustic signal is substantially equal to the acoustic impedance of the test subject. The intensity modulated light which is intensity-modulated in the constant frequency is outputted, the photoacoustic signal which is of the acoustic wave generated by the outputted light is detected to measure the concentration of the particular constituent contained in the liquid by the acoustic wave detection means though the acoustic matching substance. The light outgoing procedure and the acoustic wave detection procedure are performed in the container which is filled with the acoustic matching substance having an acoustic impedance substantially equal to that of the test subject. Therefore, the photoacoustic signal can be detected under the environment in which the test subject is surrounded by the acoustic matching substance, and the attenuation can be decreased. The attenuation is caused by the reflection of photoacoustic signal on the boundary between the test subject and surroundings, and the attenuation also occurs at the contact between the test subject and the acoustic wave detection means.

A constituent concentration measuring apparatus controlling method according to one aspect of the invention is characterized by sequentially comprising an optimum position detection procedure in which acoustic wave generators output acoustic waves from two or more different positions to a test subject and acoustic wave detection means detects a position where intensity of said acoustic wave transmitted through said test subject becomes a particular value; and an acoustic wave detection procedure in which light outgoing means outputs intensity modulated light from the position where intensity of said acoustic wave transmitted through said test subject becomes the particular value, the intensity modulated light being intensity-modulated at a constant frequency, and said acoustic wave detection means detects the acoustic wave emitted by said intensity modulated light.

One aspect of the invention is characterized in that, when the constituent concentration which is the measurement objective is measured by the photoacoustic method, the ultrasonic wave (in this case, referred to as acoustic wave) emitted from the acoustic wave generator which is placed near irradiation position of the excitation light, i.e., near source of photoacoustic signal is detected as a reference signal to search for a arrangement which optimizes a positional relationship between the photoacoustic signal source and the acoustic wave detection means. The photoacoustic signal is detected under the optimum arrangement, which allows the constituent concentration to be measured using a propagation path which minimizes the adverse influence of scatterers such as a bone.

When the photoacoustic signal is detected in the arrangement in which the detected acoustic wave signal intensity becomes a predetermined value such that the attenuation amount of acoustic wave is kept constant, the photoacoustic signal can be detected while influences of uncertain factors are eliminated. The uncertain factors include the change in influence of the scatterers on the photoacoustic signal by the change in positional relationship between the photoacoustic signal generation source and the acoustic wave detection means as well as by the change at the contact between the acoustic wave detection means and the test subject. Therefore, the constituent concentration can be measured with no influence of the many parameters associated with the positional change of the constituent concentration measuring apparatus.

When the test subject, particularly the living body and the devices are optimally arranged in a measuring system of the photoacoustic method, means for adjusting the arrangement is mechanized to operate concurrently with the acoustic wave detection means, which becomes the constituent concentration measurement to be automated in the optimum arrangement. In the invention, the intensity modulated light which is modulated by the constant frequency is used as the excitation light.

According to one aspect of the invention, the influence of the reflecting/scattering scatterers on the photoacoustic signal is probed in each propagation path by changing the acoustic wave propagation path, and then the photoacoustic signal is detected by outputting the intensity modulated light such that the photoacoustic signal propagates through the path in which the acoustic wave intensity detected by the acoustic wave detection means becomes the particular value. Therefore, the photoacoustic signal can be detected in the optimum arrangement.

A constituent concentration measuring apparatus controlling method according to one aspect of the invention is characterized by sequentially comprising a light generating procedure in which light generating means generates two light beams having different wavelengths; a light modulation procedure in which light modulation means electrically intensity-modulates each of the two light beams having the mutually different wavelengths using signals having the same frequency and reverse phases, the two light beams having the mutually different wavelengths being generated in said light generating procedure;

a light outgoing procedure in which light outgoing means outputs the two intensity-modulated light beams having the mutually different wavelengths, which are intensity-modulated in said light modulation procedure; and an acoustic wave detection procedure in which acoustic wave detection means detects an acoustic wave generated by the light emitted in said light outgoing procedure.

In one aspect of the invention, each of the two light beams having the mutually different wavelengths is electrically intensity-modulated using the signals having the same frequency and reverse phases, so that the acoustic wave corresponding to each of the two light beams having the mutually different wavelengths can be detected with no influence from a frequency dependence of the acoustic wave detection means.

One of the two light beams generates acoustic wave having the pressure corresponding to the total absorption in the state where the constituent of the measuring object and water are mixed together in the test subject, and the other light beam generates the acoustic wave having the pressure originating only from the water occupying the large part of the test subject so that the pressure of the acoustic wave generated only by the constituent of the measuring object is detectable as the difference between two acoustic waves. As a result, quantity of the constitute in the measuring object can be measured.

With the two acoustic wave pressures, one generated by one of the two light beams corresponding to the total absorption in the state where the constituent of the measuring object and water are mixed together in the test subject to be measured, while another generated by the other light beam corresponding only to the water occupying the large part of the test subject to be measured, their frequencies are equal to each other and the phase are reversed to each other, therefore, the pressures are superposed to each other in the form of acoustic wave in the test subject, and the difference in pressure of the acoustic waves is directly detected. Accordingly, the difference in pressure of the acoustic waves can be obtained more accurately rather than by computing the difference from separate measurement of the pressure of the acoustic wave generated by one of the two light beams corresponding to the total absorption in the state where the constituent of the measuring object and water are mixed together in the test subject to be measured, as well as of the pressure of the acoustic wave generated by the other light beam corresponding only to the water occupying the large part of the test subject. The above point constitutes a novel advantage which does not exist in the conventional techniques.

In one aspect of the invention, the modulation frequency by which the two light beams having the mutually different wavelengths are electrically intensity-modulated can be set to the resonant frequency concerning the detection of the acoustic wave generated in the test subject to be measured. The photoacoustic signal is measured for the two light beams having mutually different wavelengths which are selected by a consideration on the non-linearity regarding to the absorption coefficient in the measured value of the photoacoustic signal. Then, the acoustic wave generated in the test subject can be measured with a high accuracy from the measured values while the influences of the many parameters which are hardly kept constant, are eliminated.

In the constituent concentration measuring apparatus controlling method, the constituent concentration measuring apparatus controlling method further comprises a second light outgoing procedure in which second light outgoing means outputs the light intermittently emitted at intervals which are longer than the repetition period for said same frequency, the constituent concentration measuring apparatus controlling method characterized in that, in said acoustic wave detection procedure, said acoustic wave detection means detects the acoustic wave generated by the light beams outputted in said light outgoing procedure and said second light outgoing procedure.

According to one aspect of the invention, the photoacoustic signal emission amount by the absorption at the constituent set as the measuring object is increased in the test subject, particularly in the living body tissue, so that the accurate constituent concentration can be measured in the noninvasive manner.

In the constituent concentration measuring apparatus controlling method, it is desirable that the second light outgoing means outputs the light having a wavelength which exhibits a characteristic absorption of a constituent different from the constituent set as the measuring object.

Only the photoacoustic signal from the blood constituent can be increased by raising the temperature of the blood tissue as compared with the non-blood tissue.

In the constituent concentration measuring apparatus controlling method, it is desirable that the second light outgoing means emits the light having a wavelength which exhibits a characteristic absorption of hemoglobin in blood.

Only the photoacoustic signal from the blood containing the hemoglobin can be increased by raising the temperature of the hemoglobin.

In the constituent concentration measuring apparatus controlling method, it is desirable that the second light outgoing means emits the light at intervals during which temperature rise of 2° C. or less is resulted in the test subject.

The influence on the test subject can be suppressed to the minimum.

In the constituent concentration measuring apparatus controlling method, it is desirable that the second light outgoing means emits the light of an intensity by which temperature rise of 2° C. or less is resulted in the test subject.

The influence on the test subject can be suppressed to the minimum.

In the constituent concentration measuring apparatus controlling method, it is desirable to further comprise a frequency sweep procedure in which frequency sweep means sweeps a modulation frequency, the light generated in said light generating procedure being modulated in the modulation frequency; and an integration procedure in which integration means integrates the acoustic wave in a swept modulation frequency range, the acoustic wave being detected in said acoustic wave detection procedure.

In one aspect of the invention, the photoacoustic signal generated in the test subject is integrated in the swept modulation signal range. The photoacoustic signal exploiting the high sensitivity in the frequency corresponding to the resonance frequency of the acoustic wave detection means is integrated even if the resonance frequency of the acoustic wave detection means suffers a drift. Thus measurement can be performed always with the high-sensitivity resonance frequency.

In the constituent concentration measuring apparatus controlling method, it is desirable that, in the acoustic wave detection procedure, the modulation frequency swept in said frequency sweep procedure is tracked to detect the acoustic wave emitted by the irradiated light, and in said integration procedure, the acoustic wave is integrated in the modulation frequency range having high detection sensitivity in said acoustic wave detection procedure, the acoustic wave being detected by said acoustic wave detection procedure.

In one aspect of the invention, in the case where the resonance frequency of the acoustic wave detection means happens to change, the change in resonance frequency of the acoustic wave detection means in which the detection sensitivity becomes the maximum is determined from the result on the measurement of the photoacoustic signal emitted in the test subject to be measured by the irradiation light which is modulated by the frequency-swept modulation frequency, and the change in resonance frequency is tracked to integrate the detected value of the photoacoustic signal near the resonance frequency.

In the constituent concentration measuring apparatus controlling method, it is desirable to further comprise a constituent concentration computation procedure for computing a constituent concentration of a constituent from the acoustic wave integrated by said integration procedure, the constituent being set as a measuring object.

In one aspect of the invention, theoretical or experimental values showing the relationship between the photoacoustic signal generated in the test subject and the constituent concentration set as the measuring object are prepared beforehand, and the constituent concentration of the measuring object is computed based on the detected value of the photoacoustic signal generated in the test subject.

In the constituent concentration measuring apparatus controlling method, it is desirable that the light outgoing procedure and said acoustic wave detection procedure are performed in a container which is filled with an acoustic matching substance having an acoustic impedance substantially equal to that of a test subject.

The light outgoing procedure and the acoustic wave detection procedure are performed in the container filled with the acoustic matching substance having an acoustic impedance substantially equal to that of the test subject, which allows the photoacoustic signal to be detected under the environment in which the test subject is surrounded by the acoustic matching substance. Therefore, the degradation of the photoacoustic signal can be reduced. The degradation of the photoacoustic signal is caused by the boundary reflection between the test subject and the surrounding thereof as well as at the contact between the test subject and the acoustic wave detection means.

In the constituent concentration measuring apparatus controlling method, it is desirable that, in the acoustic wave detection procedure, said acoustic wave is detected through an acoustic matching substance having an acoustic impedance substantially equal to that of said test subject.

The photoacoustic signal is detected through the acoustic matching substance having acoustic impedance substantially equal to that of the test subject; so that the boundary reflection between the test subject and the surroundings thereof and the pressure and vibration impairing the acoustic wave detection means can be prevented.

In the constituent concentration measuring apparatus controlling method, it is desirable that, in the light outgoing procedure, said intensity modulated light is arranged on the inner wall surface of said container, and said intensity modulated light is outputted through an outgoing window which is transparent for said intensity modulated light.

The light outgoing means can be arranged outside the container by being furnished with an outgoing window transparent for the intensity modulated light in the container, so that the light outgoing means is easily placed. The intensity modulated light can be outputted from the inner wall surface of the container, so that the influence of surface irregularity on the inner wall of the container can be suppressed to decrease the reflection of the photoacoustic signal.

In the constituent concentration measuring apparatus controlling method, it is desirable that, in the test subject, a region irradiated with said intensity modulated light is covered with said acoustic matching substance in either sol or gel form.

In the test subject, the region irradiated with the intensity modulated light is covered with the liquid, sol or gel acoustic matching substance. Therefore, the photoacoustic signal can be detected from the test subject under the environment in which the test subject is surrounded by the acoustic matching substance.

In the constituent concentration measuring apparatus controlling method, it is desirable that the container is filled with water as for said acoustic matching substance.

Because the acoustic impedance of the test subject is very close to that of the water, a detection of the photoacoustic signal under the environment where the test subject is surrounded by the water can decrease the attenuation of the photoacoustic signal due to the reflection which is caused by the boundary reflection between the test subject and the surroundings and by the contact between the test subject and the acoustic wave detection means.

In the constituent concentration measuring apparatus controlling method, it is desirable to further comprise an optimum position detection procedure in which acoustic wave generators output acoustic waves from two or more different positions and acoustic wave detection means detects a position where intensity of said acoustic wave transmitted through said test subject becomes a particular value.

According to one aspect of the invention, the influence of the reflecting/scattering scatterers on the photoacoustic signal can be probed for each propagation path by changing the acoustic wave propagation path.

In the constituent concentration measuring apparatus controlling method, it is desirable that, the light outgoing means output the light from the position where intensity of the acoustic wave becomes the particular value.

The photoacoustic signal can be detected under the optimum arrangement by outputting the intensity modulated light such that the photoacoustic signal propagates through the propagation path in which the acoustic wave intensity detected by the acoustic wave detection means becomes the particular value. Additionally the photoacoustic signal can always be detected in the optimum arrangement by keeping the optimum position detection means to operate automatically on the light outgoing means.

In the constituent concentration measuring apparatus controlling method, it is desirable that, in the acoustic wave detection procedure, said light outgoing means emits the light through a transmission window furnished in a part of said acoustic wave generator, the transmission window being transparent for said intensity modulated light.

According to one aspect of the invention, the test subject can be irradiated with the intensity modulated light through the acoustic wave generator. Therefore, the test subject can be irradiated with the intensity modulated light from the optimum position of the acoustic wave generator.

In the constituent concentration measuring apparatus controlling method, it is desirable that, in the optimum position detection procedure, said acoustic wave generator outputs said acoustic wave having the substantially the same frequency as said intensity modulated light, or said acoustic wave generator increases or decreases the intensity of the acoustic wave outputted according to the intensity of said acoustic wave detected in said acoustic wave detection means.

According to one aspect of the invention, the influence of the scatterers on the photoacoustic signal can be probed with the acoustic wave having the frequency equal to that of the photoacoustic signal detected by the acoustic wave detection means. The intensity of the acoustic wave outputted from the acoustic wave generator can be increased or decreased according to the intensity of the acoustic wave detected by the acoustic wave detection means, so that the detected intensity can be compared even if the intensity detected by the acoustic wave detection means is small.

In the constituent concentration measuring apparatus controlling method, it is desirable that, in the optimum position detection procedure, the acoustic wave generator and the acoustic wave detection means detect the acoustic wave by pressing the acoustic wave generator and the acoustic wave detection means against the test subject with pressing force whose pressure can be controlled.

According to one aspect of the invention, since the pressure for pressing the acoustic wave generator and the acoustic wave detection means against the test subject is controllable, the pressure at which the acoustic wave generator and the acoustic wave detection means come into contact with the test subject can be kept at a predetermined value. Therefore, the influence of the pressure on the test subject can be reduced.

In the constituent concentration measuring apparatus controlling method, it is desirable that the light generating procedure is a procedure in which the light wavelengths of said two light beams to two wavelengths where an absorption difference exhibited by the constituent set as a measuring object is larger than the absorption difference exhibited by a solvent.

In the constituent concentration measuring apparatus controlling method, it is desirable that the light generating procedure is a procedure for setting one of the light wavelengths of said two light beams is set to a wavelength where the constituent set as the measuring object exhibits characteristic absorption while the other light wavelength is set to a wavelength in which the solvent exhibits an equal absorption to that for said one of the light wavelengths.

One aspect of the invention is the case where the difference in absorption exhibited by the solvent is set to zero, in the light generating procedure in the constituent concentration measuring apparatus controlling method in which the light wavelengths of the two light beams are set to two light wavelengths so that the absorption difference exhibited by the constituent set as the measuring object is larger than the absorption difference exhibited by the solvent. Thereby, the influence by the absorption of the solvent can be eliminated.

In the constituent concentration measuring apparatus controlling method, it is desirable that the light generating procedure is a procedure in which the light wavelengths of said two light beams are set to two wavelengths where an absorption difference exhibited by the liquid constituent set as the measuring object is larger than the absorption difference exhibited by other liquid constituents.

In the constituent concentration measuring apparatus controlling method, it is desirable that the light generating procedure is a procedure for setting the light wavelengths of said two light beams to two wavelengths where an absorption difference exhibited by the blood constituent set as the measuring object is larger than the absorption difference exhibited by a water.

In the constituent concentration measuring apparatus controlling method, it is desirable that the light generating procedure is a procedure for setting one of the light wavelengths of said two light beams to a light wavelength where the blood constituent set as the measuring object exhibits characteristic absorption while the other light wavelength is set to a wavelength where a water exhibits an equal absorption to that for said one of the light wavelengths.

One aspect of the invention is the case where the difference in absorption exhibited by the water is set to zero, in the light generating procedure in the constituent concentration measuring apparatus in which the light wavelengths of the two light beams are set to two light wavelengths so that the absorption difference exhibited by the blood constituent set as the measuring object is larger than the absorption difference exhibited by the water. Therefore, the influence by the absorption of the water can be eliminated.

In the constituent concentration measuring apparatus controlling method, it is desirable that the light generating procedure is a procedure for setting the light wavelengths of said two light beams to two wavelengths where an absorption difference exhibited by the blood constituent set as the measuring object is larger than the absorption difference exhibited by other blood constituents.

In the constituent concentration measuring apparatus controlling method, it is desirable that the two light beams are combined and irradiated from said light outgoing means.

The light can be focused on the measurement region, so that the photoacoustic signal can efficiently be generated.

In the constituent concentration measuring apparatus controlling method, it is desirable that the detected acoustic wave is further rectified and amplified to detect amplitude of the acoustic wave.

The amplitude of the acoustic wave can be detected from the detected photoacoustic signal.

In the constituent concentration measuring apparatus controlling method, it is desirable that the rectifying amplification is phase sensitive amplification.

The amplitude of the ultrasonic wave can be detected from the photoacoustic signal with a high sensitivity.

In the constituent concentration measuring apparatus controlling method, it is desirable that diameters of the two light beams from said light outgoing means are substantially equal to each other.

The measurement accuracy can be improved by matching the measurement regions.

In the constituent concentration measuring apparatus controlling method, it is desirable to further comprise a constituent concentration computation procedure for computing the concentration of a constituent from pressure of the acoustic wave detected by said acoustic wave detection, the constituent being set as a measuring object.

In the constituent concentration measuring apparatus controlling method, it is desirable that the constituent concentration computation procedure is a procedure for measuring pressure of the acoustic wave generated by said two light beams having the mutually different wavelengths, and the pressure of the generated acoustic wave is generated when one of said two light beams is set to zero power, and then diving the pressure of the acoustic wave generated by said two light beams by the pressure of the acoustic wave generated when one of said two light beams is set to zero power.

As described above, the pressure of the acoustic wave generated by irradiating the test subject with the two light beams having the mutually different wavelengths is detected as the difference between the pressure of the acoustic wave generated by one of the two light beams corresponding to the total absorption in the state where the constituent of the measuring object and water are mixed together in the test subject and the pressure of the acoustic wave generated by the other light beam corresponding to the water alone occupying the large part of the test subject. The constituent concentration can be measured by dividing the difference by the acoustic wave pressure generated when one of the two light beams is set to zero, i.e., the acoustic wave pressure generated solely by the water occupying the large part of the test subject according to the later-mentioned formula (5).

In the constituent concentration measuring apparatus controlling method, it is desirable that the light modulation procedure is a procedure for performing modulation with the same frequency as a resonant frequency concerning detection of the generated acoustic wave.

In one aspect of the invention, the modulation frequency by which the two light beams having the mutually different wavelengths are electrically intensity-modulated is set to the same frequency as the resonant frequency concerning the detection of the acoustic wave generated in the test subject. Therefore, the acoustic wave generated in the test subject can be measured with high accuracy.

In the constituent concentration measuring apparatus controlling method, it is desirable to further comprise an intensity adjustment procedure between said light modulation procedure and said light outgoing procedure, the intensity adjustment procedure adjusting relative intensity of said two light beams having the mutually different wavelengths such that pressure of the acoustic wave becomes zero, the acoustic wave being generated by combining said two intensity-modulated light beams having the different wavelengths into a single light beam to irradiate water.

According to the above calibration, the relative intensity between the two light beams having the mutually different wavelengths can be set such that the intensity of the photoacoustic signal emitted from the water occupying the large part of test subject is equalized for the wavelengths of two light beams. Consequently for the whole system for measuring photoacoustic signal, the relative intensity between the two light beams having the mutually different wavelengths can be calibrated to improve the measurement accuracy.

In the constituent concentration measuring apparatus controlling method, it is desirable that the acoustic wave detection procedure is a procedure for synchronizing with said modulation frequency to detect the acoustic wave by phase sensitive detection.

The photoacoustic signal is detected by the phase-sensitive detection synchronized with the modulation frequency, so that the detection can be performed with a high accuracy.

In the constituent concentration measuring apparatus controlling method, it is desirable that the light generating procedure and the light modulation procedure are a procedure for directly modulating each of the two semiconductor laser light sources using the rectangular-waveform signals having the same frequency and reverse phases.

In one aspect of the invention, the two light beams having the mutually different wavelengths can be generated and at the same time be modulated by using two directly-modulated semiconductor laser light sources driven by rectangular-waveform signals having the same frequency and reverse phases, so that the apparatus configuration can be simplified.

In the constituent concentration measuring apparatus controlling method, it is desirable that a blood constituent which is set as the measuring object is glucose or cholesterol.

In the case where the concentration of glucose or cholesterol is measured, the measurement can accurately be performed by irradiating the test subject with the light having the wavelength exhibiting the characteristic absorption.

In the constituent concentration measuring apparatus controlling method, it is desirable to further comprise a recording procedure after said acoustic wave detection procedure, recording procedure recording the acoustic wave as a function of the modulation frequency, the acoustic wave being detected by said acoustic wave detection procedure.

By including the means for recording the photoacoustic signal detected by the acoustic wave detection means for each swept modulation frequency, if the resonance frequency of the acoustic wave detection means happens to change, still the modulation frequency sweep range of the irradiating light covers the range in which the resonance frequency possibly changes, the values measured with high accuracy can be selected from the detected photoacoustic signals, which are integrated and averaged to confirm that the constituent concentration is correctly measured.

In the constituent concentration measuring apparatus controlling method, it is desirable that, in the light outgoing procedure, a test subject is placed in contact with an outgoing surface of said intensity modulated light.

The test subject is arranged so as to come into contact with the outgoing surface of the intensity modulated light, and the test subject is directly irradiated with the intensity modulated light. Thus, the attenuation of intensity modulated light caused by the absorption in the acoustic matching substance and the like can be prevented. Accordingly, since the test subject can efficiently be irradiated with the intensity modulated light, the photoacoustic signal emitted from the test subject is increased, and the accuracy can further be improved in the photoacoustic signal detected by the acoustic wave detection means.

Effect of the Invention

In the noninvasive constituent concentration measuring apparatus and constituent concentration measuring apparatus controlling method according to the invention, when the photoacoustic signal emitted following irradiation of the liquid or the test subject with the intensity-modulated light is detected to measure the constituent concentration, the modulation frequency at which the light is intensity-modulated is swept in a range where the acoustic wave detection means possibly shows the resonant high sensitivity, and the photoacoustic signal is measured at the frequency where the modulation frequency matches the resonance frequency of the acoustic wave detection means. Therefore, the constituent concentration set as the measuring object can correctly be measured.

In the noninvasive constituent concentration measuring apparatus and constituent concentration measuring apparatus controlling method according to the invention, the two light beams having the mutually different wavelengths are intensity-modulated at the same frequency, the liquid or the test subject is irradiated with the intensity-modulated light beams to measure the photoacoustic signal generated in the liquid or the test subject. Therefore, the unevenness on the frequency characteristics of the acoustic wave detection means does not have adverse influence. In addition, the modulation frequency at which the light is intensity-modulated is swept in the range spanning the resonance frequency of the acoustic wave detection means which is possibly changed, and the photoacoustic signal is measured at the frequency which matches the resonance frequency of the acoustic wave detection means. Therefore, the detection is hardly affected by the external influence, and the measurement can correctly be performed.

In the constituent concentration measuring apparatus and constituent concentration measuring apparatus controlling method according to the invention, the photoacoustic signal is detected under the environment of the acoustic impedance which is substantially equal to the acoustic impedance of the object to be measured or the test subject, so that signal attenuation can be minimized. The attenuation is caused by the boundary reflection between the test subject and the surroundings thereof, as well as by the contact between the test subject and the acoustic wave detection means. Furthermore, the decrease in sound collection efficiency of acoustic wave detection means and the decrease in accuracy of the photoacoustic signal can also be prevented.

According to the invention, the arrangement in which the positional relationship between the photoacoustic signal generation source and the acoustic wave detection means becomes optimum is searched for. Thus, the constituent concentration can be measured by detecting the photoacoustic signal in the optimum arrangement in which the scatterers such as a bone has little influence.

Furthermore, the photoacoustic signal is detected in the arrangement in which the signal intensity of the detected acoustic wave becomes the predetermined value, so that the constituent concentration can be measured without influence of the many parameters associated with a change in placement of the constituent concentration measuring apparatus.

Furthermore, the influence of the pressure pressing the test subject is reduced by pressing the acoustic wave detection means against the test subject with a constant pressure.

Accordingly, in the photoacoustic method, the influence of the reflection/scattering or the influence of the pressure pressing the test subject can be reduced to improve the measurement accuracy of the photoacoustic signal.

In the noninvasive constituent concentration measuring apparatus and constituent concentration measuring apparatus controlling method according to the invention, the two light beams having the mutually different wavelengths are selected in consideration of the non-linearity of the photoacoustic signal in respect to the absorption coefficient, the photoacoustic signals for the light beams are measured, and the constituent concentration set as the measuring object can correctly be computed while the influence of the many parameters which are hardly kept constant are eliminated.

In the constituent concentration measuring apparatus and constituent concentration measuring apparatus controlling method according to the invention, the two light beams having the mutually different wavelengths are selected in consideration of the non-linearity of the photoacoustic signal in respect to the absorption coefficient, the photoacoustic signals, for the light beams are measured, and the constituent concentration set as the measuring object can correctly be computed while the influence of the many parameters which are hardly kept constant are eliminated. In the noninvasive constituent concentration measuring apparatus and constituent concentration measuring apparatus controlling method according to the invention, the two light beams having the mutually different wavelengths are intensity-modulated by the signals having the same frequency, the test subject is irradiated with the intensity-modulated light beams to measure the photoacoustic signal generated in the test subject. Therefore, the unevenness on the frequency characteristics of the acoustic wave detection means does not affect the measurement. Furthermore, the invention enables an application of the resonance type detector which is effective for the improvement of the acoustic wave detection sensitivity, and the measurement can be performed in a short time even for physically debilitated persons or ambulatory animals. Furthermore, in the constituent concentration measuring apparatus and constituent concentration measuring apparatus controlling method according to the invention, either the forward propagation type that detects the acoustic wave propagating in the direction of irradiation or the backward propagation type that detects the acoustic wave propagating back to the irradiation can be configured. Particularly, the latter is convenient for miniaturization.

In the constituent concentration measuring apparatus and constituent concentration measuring apparatus controlling method according to the invention, the constituent contained in the liquid can correctly be measured in the noninvasive manner. In the constituent concentration measuring apparatus and constituent concentration measuring apparatus controlling method according to the invention, the test subject is irradiated with three light beams to measure the photoacoustic signal from the test subject. Thus, the constituent concentration contained in the test subject can correctly be measured in the noninvasive manner. Particularly, the background signal from non-blood tissues can be removed, when the third light wavelength is set at the wavelength in which the blood alone exhibits absorption.

In the noninvasive constituent concentration measuring apparatus according to the invention, the constituent concentration of the test subject can be measured in the noninvasive manner. The size of the test subject including its sides is kept constant, and moreover reflected wave from those sides is suppressed. Therefore, the constituent concentration can be measured stably and correctly. In the noninvasive constituent concentration measuring apparatus according to the invention, the compact and contact apparatus can be realized by forming the apparatus in the ring shape or the bracelet shape, and the apparatus can be fitted while carried.

BRIEF DESCRIPTION OF THE DRAWINGS

FIG. 24 shows a first mode of the blood constituent concentration measuring apparatus;

FIG. 25 shows a second mode of the blood constituent concentration measuring apparatus;

FIG. 30 shows an example in which the blood constituent concentration measuring apparatus is applied to a fingertip of a human body;

FIG. 32 shows an example in which the blood constituent concentration measuring apparatus is applied to the finger of the human body;

FIG. 35(a) is an external view, FIG. 35(b) is a top view of the acoustic wave generator, FIG. 35(c) is a perspective view of the acoustic wave generator, and FIG. 35(d) is a bottom view of the acoustic wave generator;

DESCRIPTION OF THE REFERENCE NUMERALS

Figure 1:
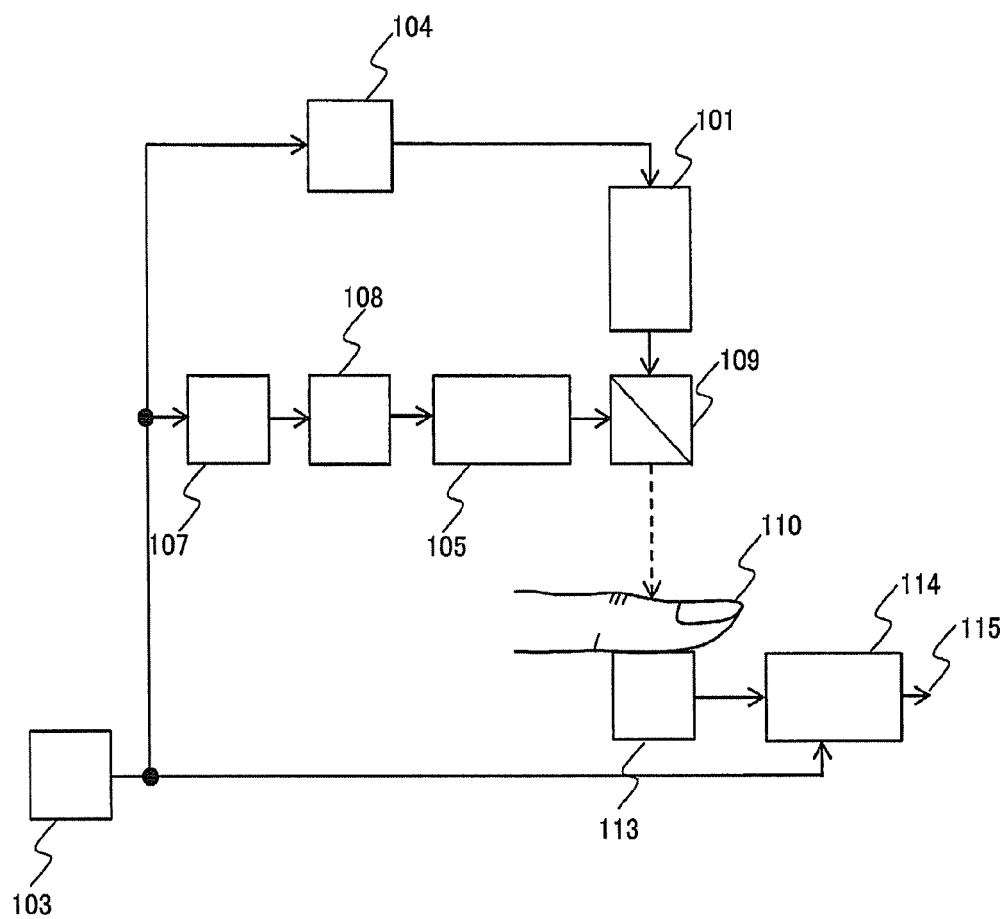
FIG. 1 is an explanatory view showing a configuration of a blood constituent concentration measuring apparatus according to an embodiment.

1 intensity modulated light
2 acoustic wave
3 photoacoustic signal
4 output signal
5 control signal
11 light generation unit
12 light modulation unit
13 light outgoing unit
14 ultrasonic detection unit
15 sound absorbing material
16 temperature measurement unit
17 outgoing window
18 reflection material
21 container
22 inside
23 excitation light source
24 acoustic wave generator
25 acoustic wave detector
26 control unit
27 drive unit
28 acoustic coupling element
29 transmission window
31 power supply
32 phase sensitive amplifier
33 signal processor
34 display processor
35 connection cable
36 temperature regulating unit
37 heater
38 preamplifier
39 light source chip
40 lens
41 beam splitter
42 optical fiber
51 oscillator
52 180°-phase shifter
53 drive circuit
55 coupler
56 acoustic matching substance
57 filter
58 phase sensitive amplifier
59 photoacoustic signal output, terminal
97 living body test region
99 lens
100 oscillator
101 first light source
102 drive circuit
103 oscillator
104 drive circuit
105 second light source
106 third light source
107 180°-phase-shift circuit
108 drive circuit
109 coupler
110 living body test region
111 living body test region
112 light source
113 ultrasonic detector
114 phase sensitive amplifier
115 output terminal
116 drive circuit
117 drive circuit
118 frequency divider
119 180°-phase shifter
120 coupler
121 ultrasonic detector
122 filter
123 synchronous detection amplifier
124 photoacoustic signal output terminal
125 control circuit
126 acoustic coupler
127 ultrasonic detector
128 phase sensitive amplifier
129 computing device
130 enduing unit
131 living body
132 annular support frame
133 light irradiation unit
135 ultrasonic detection unit
136 cushioning material
137 sound absorbing material
138 contact thermometer
139 lens
140 lens
141 calibration test sample
142 acoustic coupler
143 thermometer
193 living body
194 output waveform of first light source
195 output waveform of second light source
196 output waveform of third light source
197 photoacoustic signal by first light source
198 photoacoustic signal by second light source
199 temperature change by third light source
200 summation of photoacoustic signals
201 light irradiation
202 sound source
203 observation point
204 model A
205 model B
206 model C
207 enduing unit 208 Δs₁
209 Δs₂
210 connection cable
211 light from first light source (λ₁)
212 light from second light source (λ₂)
213 bone
214 muscle
215 fat
216 cuticle
217 reflecting location
218 blood vessel
219 excitation light
220 detector
221 display unit
222 frame
297 drive circuit
298 oscillator
299 180°-phase shifter
300 control circuit
301 first light source
302 second light source
303 drive circuit
304 irradiation light
305 ultrasonic detector
306 cushioning material
307 sound absorbing material
308 coupler
309 living body test region
310 connection cable
311 frame
312 preamplifier
313 irradiation window
314 light source chip
315 output beam
316 reflecting mirror
317 concave mirror
318 first semiconductor laser
319 second semiconductor laser
320 electrode pad
321 substrate
322 optical waveguide
323 coupler
324 vibration membrane
325 fixed electrode
326 wiring cavity
327 acoustic coupler
328 ultrasonic detector
329 phase sensitive amplifier
330 computing device
400 living body
401 semiconductor laser device
402 drive power supply
404 acoustic wave generator
405 test subject
403 oscillator
406 acoustic coupling element
407 acoustic wave detector
408 phase sensitive amplifier
409 output terminal
410 hole
413 irradiation window
414 light source, chip
415 output beam
416 reflecting mirror
417 irradiation light
418 cushioning material
419 display unit
421 light irradiation unit
428 wrist band
429 insertion key
430 opening
431 release button
432 lens
433 light sources chassis
499 living body
500 light source
501 first semiconductor light source
502 lens
503 oscillator
504 drive current source
505 second semiconductor light source
506 lens
507 180°-phase-shift circuit
508 drive current source
509 coupler
510 living body test region
511 calibration test sample
512 acoustic coupler
513 ultrasonic detector
514 phase sensitive amplifier
515 output terminal
516 acoustic lens
517 acoustic matching device
518 ultrasonic detector
519 high pass filter
520 synchronous detection amplifier
521 photoacoustic signal output terminal
522 temperature measurement device
523 first semiconductor light source
524 drive current source
525 oscillator
526 lens
527 second semiconductor light source
528 drive current source
529 180°-phase shifter
530 lens
531 coupler
532 third semiconductor light source
533 drive current source
534 frequency divider
535 lens
536 coupler
537 living body test region
540 apparatus body
541 acoustic wave detector
601 first light source
604 drive power supply
605 second light source
608 drive power supply
609 coupler
610 living body test region
613 ultrasonic detector
616 pulse light source
617 chopper plate
618 motor
619 acoustic sensor
620 waveform observing apparatus
621 frequency analyzer
701 first semiconductor light source
702 drive current source
703 oscillator
704 lens
705 second semiconductor light source
706 drive current source 707 180°-phase shifter
708 lens
709 coupler
710 third semiconductor light source
711 drive current source
712 frequency divider
713 lens
714 coupler
715 liquid sample
716 sample cell
717 acoustic matching device
718 ultrasonic detector
719 high pass filter
720 synchronous detection amplifier
721 photoacoustic signal output terminal
722 temperature measurement device
801 first semiconductor light source
802 lens
803 oscillator
804 drive current source
805 second semiconductor light source
806 lens
807 180°-phase-shift circuit
808 drive current source
809 coupler
810 living body test region
811 calibration specimen
812 acoustic coupler
813 ultrasonic detector
814 phase sensitive amplifier
815 output terminal

BEST MODE FOR CARRYING OUT THE INVENTION

Embodiments of the invention will be described below. The invention is not limited to the following embodiments. In the following embodiments, the constituent concentration measuring apparatus and the constituent concentration measuring apparatus controlling method are described in the form of a blood constituent concentration measuring apparatus and a control method of blood constituent concentration measuring apparatus. However, when the living body which is of the test subject is replaced by the liquid which is of the object to be measured, when the blood which is of the test subject is replaced by the liquid which is of the object to be measured, and when the water is replaced by the liquid solvent, the invention can be realizes as the liquid constituent concentration measuring apparatus or the liquid constituent concentration measuring apparatus controlling method. The test subject is not limited to the living body and the blood. For example, "lymph" and "tear" are also included in the test subject. In the case where the living body is used as the test subject, the constituent set as the measuring object is not limited to the blood constituent, but the constituent includes the constituents such as "lymph constituent" and "tear constituent". Thus, in the invention, various constituents can be measured according to the measuring object.

First Embodiment

A constituent concentration measuring apparatus according to a first embodiment is a blood constituent concentration measuring apparatus including light generating means for generating two light beams having different wavelengths; light modulation means for electrically intensity-modulating each of the two light beams having the mutually different wavelengths using signals having the same frequency and reverse phases; light outgoing means for multiplexing the two intensity-modulated light beams having the mutually different wavelengths into one light flux to output the light toward a living body; acoustic wave detection means for detecting an acoustic wave generated in the living body by the outputted light; and blood constituent concentration computation means for computing a blood constituent concentration in the living body from pressure of the detected acoustic wave. The blood constituent concentration computation means according to the first embodiment is applied in the first embodiment, and the blood constituent concentration computation means according to the first embodiment can also be applied in the later-mentioned second embodiment, third embodiment, fourth embodiment, fifth embodiment, and sixth embodiment.

In the blood constituent concentration measuring apparatus according to the first embodiment, the light generating means can set one of the light wavelengths of the two light beams at the wavelength in which the blood constituent exhibits the characteristic absorption, and the light generating means can set the other light wavelength at the wavelength in which the water exhibits the absorption parallelly equal to that in one of the light wavelengths.

A configuration according to the first embodiment will be described with reference to FIG. 1. FIG. 1 shows a basic configuration of a blood constituent concentration measuring apparatus according to the first embodiment. In FIG. 1, a first light source 101 which is of a part of the light generating means is intensity-modulated in synchronization with an oscillator 103 which is of a part of the light modulation means by a drive circuit 104 which is of a part of the light modulation means.

On the other hand, a second light source 105 which is of a part of the light generating means is intensity-modulated in synchronization with the oscillator 103 by a drive circuit 108 which is of a part of the light modulation means. However, output of the oscillator 103 is supplied to the drive circuit 108 through a 180°-phase-shift circuit 107 which is of a part of the light modulation means, and thereby the second light source 105 is configured so as to be intensity-modulated with the signal whose phase is changed by 180° with respect to the first light source 101.

In the wavelengths of the first light source 101 and second light source 105 shown in FIG. 1, the wavelength of one of the two light beams is set at the wavelength in which the blood constituent exhibits the characteristic absorption, and the wavelength of the other light beam is set at the wavelength in which the water exhibits the absorption parallelly equal to that in the wavelength of one of the two light beams.

The first light source 101 and the second light source 105 output the light beams having the different wavelengths respectively, the light beams are multiplexed as one light flux by a coupler 109 which is of the light outgoing means, and a living body test region 110 which is of the test subject is irradiated with the light. The acoustic waves, i.e., photoacoustic signals generated in the living body test region 110 by the light beams outputted from the first light source 101 and the second light source 105 are detected by an ultrasonic detector 113 which is of the acoustic wave detection means, and the photoacoustic signals are converted into the electric signals proportional to the acoustic pressure of the photoacoustic signals. The synchronous detection is performed to the electric signal by a phase sensitive amplifier 114 which is of a part of the acoustic wave detection means synchronized with the oscillator 103, and the electric signal proportional to the acoustic pressure is outputted to an output terminal 115.

The intensity of the signal outputted to the output terminal 115 is proportional to a light quantity in which the light beam outputted from each of the first light source 101 and second light source 105 is absorbed by the constituent in the living body test region 110, so that the signal intensity is proportional to the mount of constituent in the living body test region 110. Accordingly, the blood constituent concentration computation means (not shown) computes the mount of constituent of the measuring object in the blood of the living body test region 110 from the measured value of the intensity of the signal outputted to the output terminal 115.

In the blood constituent concentration measuring apparatus according to the first embodiment, the two light beams having different wavelengths outputted from the first light source 101 and second light source 105 are intensity-modulated using the signals having the same period, i.e., the same frequency. Therefore, the blood constituent concentration measuring apparatus according to the first embodiment has a feature that the blood constituent concentration measuring apparatus according to the first embodiment is not affected by the unevenness of the frequency characteristics of the ultrasonic detector 113. This is the excellent point as compared with the currently existing techniques.

As described above, the blood constituent concentration measuring apparatus according to the first embodiment can measure the blood constituent with high accuracy.

The control method of blood constituent concentration measuring apparatus according to the first embodiment is a control method of blood constituent concentration measuring apparatus sequentially including a light generating procedure in which the light generating means generates the two light beams having mutually different wavelengths; a light modulation procedure in which the light modulation means electrically intensity-modulates each of the two light beams having the mutually different wavelengths generated in the light generating procedure using signals having the same frequency and reverse phases; a light outgoing procedure in which the light outgoing means multiplexes the two intensity-modulated light beams having the different wavelengths intensity-modulated in the light modulation procedure into one light flux to output the light toward the living body; an acoustic wave detection procedure in which the acoustic wave detection means detects the acoustic wave generated in the living body by the light outputted in the light outgoing procedure; and a constituent concentration computation procedure in which the blood constituent concentration in the living body is computed from pressure of the detected acoustic wave. The blood constituent concentration computation procedure according to the first embodiment is applied in the first embodiment, and the blood constituent concentration computation procedure according to the first embodiment can also be applied in the later-mentioned second embodiment, third embodiment, fourth embodiment, fifth embodiment, and sixth embodiment.

The control method of blood constituent concentration measuring apparatus according to the first embodiment can also be formed in a control method of blood constituent concentration measuring apparatus in which, in the light generating procedure, the wavelength of one of the two light beams is set at the wavelength in which the blood constituent exhibits the characteristic absorption, and the wavelength of the other light beam is set at the wavelength in which the water exhibits the absorption parallelly equal to that in the wavelength of one of the two light beams.

A method in which the two light beams having different wavelengths is generated and each of the two light beams having different wavelengths is electrically intensity-modulates by a modulator using the signals having the same frequency and 180°-different phases may be adopted as the method of electrically intensity-modulating each of the two light beams having different wavelengths. Alternately, as shown in FIG. 1, a direct modulation method in which the drive circuit 104 and the drive circuit 108 cause the first light source 101 and the second light source 105 to emit the light and simultaneously perform the intensity modulation may be adopted as the method of electrically intensity-modulating each of the two light beams having different wavelengths.

Figure 9:
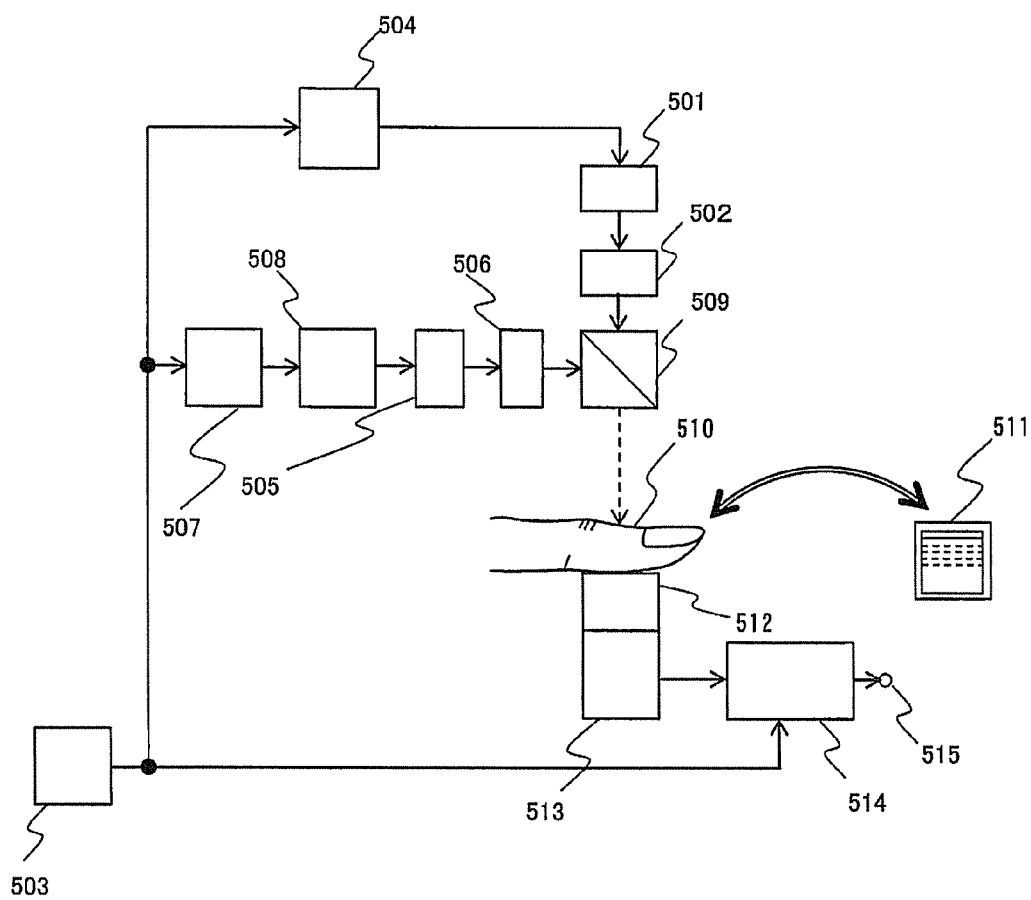
FIG. 9 is an explanatory view showing a configuration example of the blood constituent concentration measuring apparatus according to the embodiment.

The two light beams having different wavelengths intensity-modulated through the above procedure are multiplexed into one light flux by the coupler 109 shown in FIG. 9, the living body is irradiated with the light, the acoustic waves, i.e., the photoacoustic signals generated in the living body by the two light beams having different wavelengths with which the living body is irradiated are detected by the ultrasonic detector 113 shown in FIG. 1, the detected photoacoustic signals are converted into the electric signals, the electric signals are synchronous-detected by the phase sensitive amplifier 114 shown in FIG. 1, and the electric signals being proportional to the photoacoustic signals are outputted to the output terminal 115. Then, in the blood constituent concentration computation procedure, the blood constituent concentration in the living body is computed from the pressure of the acoustic wave detected in the acoustic wave detection procedure.

In the control method of blood constituent concentration measuring apparatus according to the first embodiment, the two light beams having different wavelengths outputted from the first light source 101 and second light source 105 are intensity-modulated using the signals having the same period, i.e., the same frequency. Therefore, the control method of blood constituent concentration measuring apparatus according to the first embodiment has a feature that the control method of blood constituent concentration measuring apparatus according to the first embodiment is not affected by the unevenness of the frequency characteristics of the ultrasonic detector. This is the excellent point as compared with the currently existing techniques.

As described above, the control method of blood constituent concentration measuring apparatus according to the first embodiment can measure the blood constituent with high accuracy.

In the blood constituent concentration measuring apparatus according to the first embodiment, the light modulation means can also be formed in means for performing the modulation with the same frequency as the resonant frequency concerning the detection of the acoustic wave generated in the living body. The light modulation means described in the first embodiment is similar to those of the later-mentioned second embodiment, third embodiment, fourth embodiment, fifth embodiment, and sixth embodiment.

The two light beams having different wavelengths is modulated with the same frequency as the resonant frequency concerning the detection of the acoustic wave generated in the living body, which allows the acoustic wave generated in the living body to be detected with high sensitivity.

In the control method of blood constituent concentration measuring apparatus according to the first embodiment, the light modulation procedure can also be formed in a procedure of performing the modulation with the same frequency as the resonant frequency concerning the detection of the acoustic wave generated in the living body.

The two light beams having different wavelengths is modulated with the same frequency as the resonant frequency concerning the detection of the acoustic wave generated in the living body, which allows the acoustic wave generated in the living body to be detected with high sensitivity.

In the blood constituent concentration measuring apparatus according to the first embodiment, the blood constituent concentration computation means can also be formed in means for dividing the pressure of the acoustic wave generated by irradiating the living body with the two light beams having different wavelengths by the pressure of the acoustic wave which is generated when one of the two light beams is set to zero.

The blood constituent concentration can be measured with high accuracy by the division.

In the control method of blood constituent concentration measuring apparatus according to the first embodiment, the blood constituent concentration computation procedure can also formed in a procedure for dividing the pressure of the acoustic wave generated by irradiating the living body with the two light beams by the pressure of the acoustic wave which is generated when one of the two light beams is set to zero.

The blood constituent concentration can be measure with high accuracy by the above division.

In the blood constituent concentration measuring apparatus according to the first embodiment, the light generating means can be formed in means for adjusting the relative intensity of two light beams having the different wavelengths such that the pressure of the acoustic wave becomes zero. The pressure of the acoustic wave is generated by irradiating water with the two intensity-modulated light beams having the different wavelengths multiplexed into one light flux. The light generating means described in the first embodiment is similar to those of the later-mentioned second embodiment, third embodiment, fourth embodiment, fifth embodiment, and sixth embodiment.

In the blood constituent concentration measuring apparatus according to the first embodiment, for example, as shown in FIG. 1, as with the measurement of the blood constituent concentration, the water for calibration instead of the living body test region 110 is irradiated with one light flux into which are multiplexed, and the relative intensity of the light beams outputted from the first light source 101 and second light source 105 is adjusted such that the photoacoustic signal detected by the ultrasonic detector 113 becomes zero.

In adjusting the intensity of the light outputted from each of the first light source 101 and second light source 105 in the above-described manner, the relative intensity of each of two light beams outputted from the first light source 101 and second light source 105 can easily equally be adjusted, so that the blood constituent concentration can be measured with high accuracy.

In the control method of blood constituent concentration measuring apparatus according to the first embodiment, control method of blood constituent concentration measuring apparatus can also further include an intensity adjustment procedure between the light modulation procedure and the light outgoing procedure. In the intensity adjustment procedure, the intensity-modulated two light beams having the different wavelengths are multiplexed into one light flux, the water is irradiated with the light, and the relative intensity of each of the two light beams is adjusted such that the pressure of the acoustic wave generated by the irradiation becomes zero.

In the control method of blood constituent concentration measuring apparatus according to the first embodiment, for example, after the procedure of multiplexing the intensity-modulated two light beams having the different wavelengths into one light flux, the two light beams having the different wavelengths are multiplexed into one light flux, the light is outputted to the water, and the relative intensity of each of the two light beams is adjusted such that the pressure of the acoustic wave generated by the irradiation becomes zero. Therefore, the relative intensity of each of the two light beams outputted from the first light source 101 and second light source 105 can easily equally be adjusted, so that the blood constituent can easily be measured.

In the blood constituent concentration measuring apparatus according to the first embodiment, the acoustic wave detection means can also be formed in means for synchronizing the modulation frequency to perform the detection by the synchronous detection. The acoustic wave detection described in the first embodiment is similar to those of the later-mentioned second embodiment, third embodiment, fourth embodiment, fifth embodiment, and sixth embodiment.

In the blood constituent concentration measuring apparatus according to the first embodiment, for example, the photoacoustic signals corresponding to each of the light beams outputted from the first light source 101 and the second light source 105 are detected and converted into the electric signals by the ultrasonic detector 113, and the electric signals are detected by the synchronous detection in which each of the light beams outputted from the first light source 101 and the second light source 105 are synchronized with the intensity-modulated signals.

In the phase sensitive amplifier 114, the detection accuracy is increased in the photoacoustic signals corresponding to the light beams outputted from the first light source 101 and the second light source 105, which allows the photoacoustic signal to be measured with higher accuracy.

In the control method of blood constituent concentration measuring apparatus according to the first embodiment, the acoustic wave detection procedure can also be formed in a procedure for synchronizing the modulation frequency to perform the detection by the synchronous detection.

In the control method of blood constituent concentration measuring apparatus according to the first embodiment, for example, the photoacoustic signals corresponding to each of the two light beams having the different wavelengths is synchronized with the intensity-modulated signals of each of the two light beams having the different wavelengths to perform the detection by the synchronous detection.

The detection accuracy is increased in the photoacoustic signals corresponding each of to the light beams outputted from the first light source 101 and the second light source 105, which allows the photoacoustic signal to be measured with higher accuracy.

In the blood constituent concentration measuring apparatus according to the first embodiment, the light generating means and the light modulation means can also be formed in means for directly modulating each of the two semiconductor laser light sources using the rectangular-waveform signals having the same frequency and reverse phases. The light generating means described in the first embodiment is similar to those of the later-mentioned second embodiment, third embodiment, fourth embodiment, fifth embodiment, and sixth embodiment.

The two semiconductor laser light sources have apparatus configurations in which the modulations are directly performed using the rectangular-waveform signals having the same frequency and reverse phases, which allows the apparatus configuration to be simplified.

In the control method of blood constituent concentration measuring apparatus according to the first embodiment, the light generating procedure and the light modulation procedure can be formed in a procedure in which each of the two semiconductor laser light sources are directly modulated using the rectangular-waveform signals having the same frequency and reverse phases.

The two semiconductor laser light sources are directly modulated using the rectangular-waveform signals having the same frequency and reverse phases, which allows the apparatus configuration to be simplified.

The detailed technology which is fundamental to the blood constituent concentration measuring apparatus and control method of blood constituent concentration measuring apparatus according to the first embodiment will be described below.

A configuration of the blood constituent concentration measuring apparatus according to the first embodiment will be described with reference to FIG. 1. As shown in FIG. 1, the blood constituent concentration measuring apparatus according to the first embodiment includes the first light source 101, the second light source 105, the drive circuit 104, the drive circuit 108, the 180°-phase-shift circuit 107, the coupler 109, the ultrasonic detector 113, the phase sensitive amplifier 114, the output terminal 115, and the oscillator 103.

The oscillator 103 is connected to each of the drive circuit 104, the 180°-phase-shift circuit 107, and the phase sensitive amplifier 114 through signal lines, and the oscillator 103 transmits the signal to each of the drive circuit 104, the 180°-phase-shift circuit 107, and the phase sensitive amplifier 114.

The drive circuit 104 receives the signal transmitted from the oscillator 103. The drive circuit 104 supplies drive electric power to the first light source 101, connected to the drive circuit 104 through the signal line, to cause the first light source 101 to emit the light.

The 180°-phase-shift circuit 107 receives the signal transmitted from the oscillator 103, and the 180°-phase-shift circuit 107 transmits the signal whose phase is changed by 180° with respect to the received signal to the drive circuit 108 connected to the 180°-phase-shift circuit 107 through the signal line.

The drive circuit 108 receives the signal transmitted from the 180°-phase-shift circuit 107. The drive circuit 108 supplies drive electric power to the second light source 105, connected to the drive circuit 108 through the signal line, to cause the second light source 105 to emit the light.

Each of the first light source 101 and the second light source 105 outputs the light beams having the different wavelengths, and each of the outputted light beams is guided to the coupler 109 by light wave transmission means.

The light beam outputted from the first, light source 101 and the light beam outputted from the second light source 105 are inputted to the coupler 109, the light beams are multiplexed into one light flux, and a predetermined position of the living body test region 110 is irradiated with the light to generate the acoustic wave, i.e., the photoacoustic signal in the living body test region 110.

The ultrasonic detector 113 detects the photoacoustic signal of the living body test region 110 to convert the photoacoustic signal into the electric signal, and the ultrasonic detector 113 transmits the electric signal to the phase sensitive amplifier 114 connected to the ultrasonic detector 113 through the signal line.

The phase sensitive amplifier 114 receives the synchronous signal transmitted from the oscillator 103. The synchronous signal is necessary for the synchronous detection. The phase sensitive amplifier 114 also receives the electric signal transmitted from the ultrasonic detector 113. The electric signal is proportional to the photoacoustic signal. Then, the phase sensitive amplifier 114 performs the synchronous detection, amplification, and filtering to output the electric signal which is proportional to the photoacoustic signal to the output terminal 115.

The first light source 101 is synchronized with the oscillation frequency of the oscillator 103 to output the intensity-modulated light. On the other hand, the second light source 105 is synchronized with the oscillation frequency of the oscillator 103, which is of the signal whose phase is changed by 180° by the 180°-phase-shift circuit 107, to output the intensity-modulated light.

Thus, in the blood constituent concentration measuring apparatus according to the first embodiment, the light outputted from the first light source 101 and the light outputted from the second light source 105 are intensity-modulated using the signals having the same frequency. Therefore, in the blood constituent concentration measuring apparatus according to the first embodiment, there is no problem of the unevenness of the frequency characteristics of the measuring system which becomes troublesome when the intensity modulation is performed with the plural frequencies in the conventional technique.

On the other hand, the non-linear absorption coefficient dependence existing in the measured value of the photoacoustic signal, which becomes troublesome in the conventional technique, can be solved by performing the measurement using the light beams having the plural wavelengths for giving the equal absorption coefficient in the blood constituent concentration measuring apparatus according to the first embodiment.

That is, in the case where background absorption coefficients $\alpha_1^{(b)}$, $\alpha_2^{(b)}$ and molar absorptions $\alpha_1^{(O)}$, $\alpha_2^{(O)}$ of the blood constituent set as the measuring object are already known for light beams having a wavelength $\lambda_1$ and wavelength $\lambda_2$ respectively, the simultaneous equations including measured values $s_1$ and $s_2$ of the photoacoustic signal in the wavelengths are expressed by the formula (1). The unknown blood constituent concentration M is determined by solving the formula (1). At this point C is a variable coefficient which is hardly controlled or calculated, i.e., C is an unknown multiplier depending on an acoustic coupling state, ultrasonic detector sensitivity, a distance between the irradiation portion and the detection portion (hereinafter defined as r), specific heat, a thermal expansion coefficient, sound velocity, the modulation frequency, and the absorption coefficient.

When the difference is generated in Cs of the first line and second line of the formula (i), the difference is uniquely an amount concerning the irradiation light, i.e., the difference by the absorption coefficient. At this point, when a combination of the wavelength $\lambda_1$ and the wavelength $\lambda_2$ is selected such that the parentheses of the lines of the formula (1), i.e., the absorption coefficients are equal to each other, the absorption coefficients are equal to each other, and C in the first line is equal to C in the second line. However, when the above operation is exactly performed, it is inconvenient because the combination of the wavelength $\lambda_1$ and the wavelength $\lambda_2$ depends on the unknown blood constituent concentration M.

At this point, the background ($\alpha_i^{(b)}$, i=1 and 2) is remarkably larger than a term ($M\alpha_i^{(O)}$ including the blood constituent concentration M in an occupying ratio in the absorption coefficient (parenthesis in each line) of the formula (1). In the case, the problem is sufficiently solved by equalizing the absorption coefficient of the background $\alpha_i^{(b)}$ instead of precisely equalizing the absorption coefficient in each line. That is, the two light beams having the mutually different wavelength $\lambda_1$ and wavelength $\lambda_2$ may be selected such that absorption coefficients $\alpha_1^{(b)}$ and $\alpha_2^{(b)}$ of the background are equal to each other. Thus, when C in the first line is equalized to C in the second line, Cs are deleted as an unknown constant, and the blood constituent concentration M of the measuring object is expressed by the following formula (4).

$$M = \frac{(s_1 - s_2)\alpha_1^{(b)}}{s_2\alpha_1^{(0)} - s_1\alpha_2^{(0)}} \cong \frac{\alpha_1^{(b)}}{\alpha_1^{(0)} - \alpha_2^{(0)}} \frac{s_1 - s_2}{s_2}$$  [Formula 4]

In the deformation of the rear stage of the formula (4), quality of $s_1 \cong s_2$ is used.

Referring to the formula (4), in the denominator, the difference in absorption coefficient of the blood constituent of the measuring object emerges in wavelength $\lambda_1$ and wavelength $\lambda_2$. As the difference is increased, the difference signal $s_1-s_2$ of the photoacoustic signal is increased, and the measurement becomes easy. In order to maximize the difference, it is good that the wavelength in which the constituent absorption coefficient $\alpha_1^{(0)}$ of the measuring object becomes the maximum is selected as the wavelength and the wavelength in which $\alpha_2^{(0)}=0$, i.e., the constituent of the measuring object does not exhibit the absorption characteristics is selected as the wavelength $\lambda_2$. At this point, from the condition in the second wavelength $\lambda_2$, it is necessary that $\alpha_1^{(b)}=\alpha_2^{(b)}$, i.e., the background absorption coefficient is equal to the absorption coefficient of the first wavelength $\lambda_1$.

In addition in the formula (4), the photoacoustic signal $s_1$ emerges only in the form of the difference of $s_1-s_2$ between the photoacoustic signal $s_1$ and the photoacoustic signal $s_2$. For example, when glucose is set at the constituent of the measuring object, as described above, there is only the difference 0.1% or less between the intensity of the photoacoustic signal $s_1$ and the intensity of the photoacoustic signal $s_2$.

However, in the denominator of the formula (4), it is sufficient that the photoacoustic signal $s_2$ has the accuracy of about 5%. Accordingly, the accuracy is easily kept in measuring the difference $s_1-s_2$ between the photoacoustic signal $s_1$ and the photoacoustic signal $s_2$ to divide the measured value by the separately measured photoacoustic signal $s_2$ rather than sequentially separately measuring the photoacoustic signal $s_1$ and the photoacoustic signal $s_2$. Accordingly, in the blood constituent concentration measuring apparatus according to the first embodiment, when the light beams having the wavelength $\lambda_1$ and wavelength $\lambda_2$ are intensity-modulated into the light beams having the reverse phases to irradiate the living body, the difference signal $s_1-s_2$ of the photoacoustic signals is measured. The difference signal $s_1-s_2$ of the photoacoustic signals is generated in the living body while the photoacoustic signal $s_1$ and the photoacoustic signal $s_2$ are mutually superposed.

As described above, in measuring the blood constituent concentration, using the two light beams having the mutually different particular wavelengths, the measurement is performed not by separately measuring the photoacoustic signals generated in the living body, but by measuring the difference between the photoacoustic signals, and furthermore measuring one of the photoacoustic signals while the other photoacoustic signal is set to zero, and computing the measured values by the formula (4). Therefore, the blood constituent concentration can easily be measured.

Figure 2:
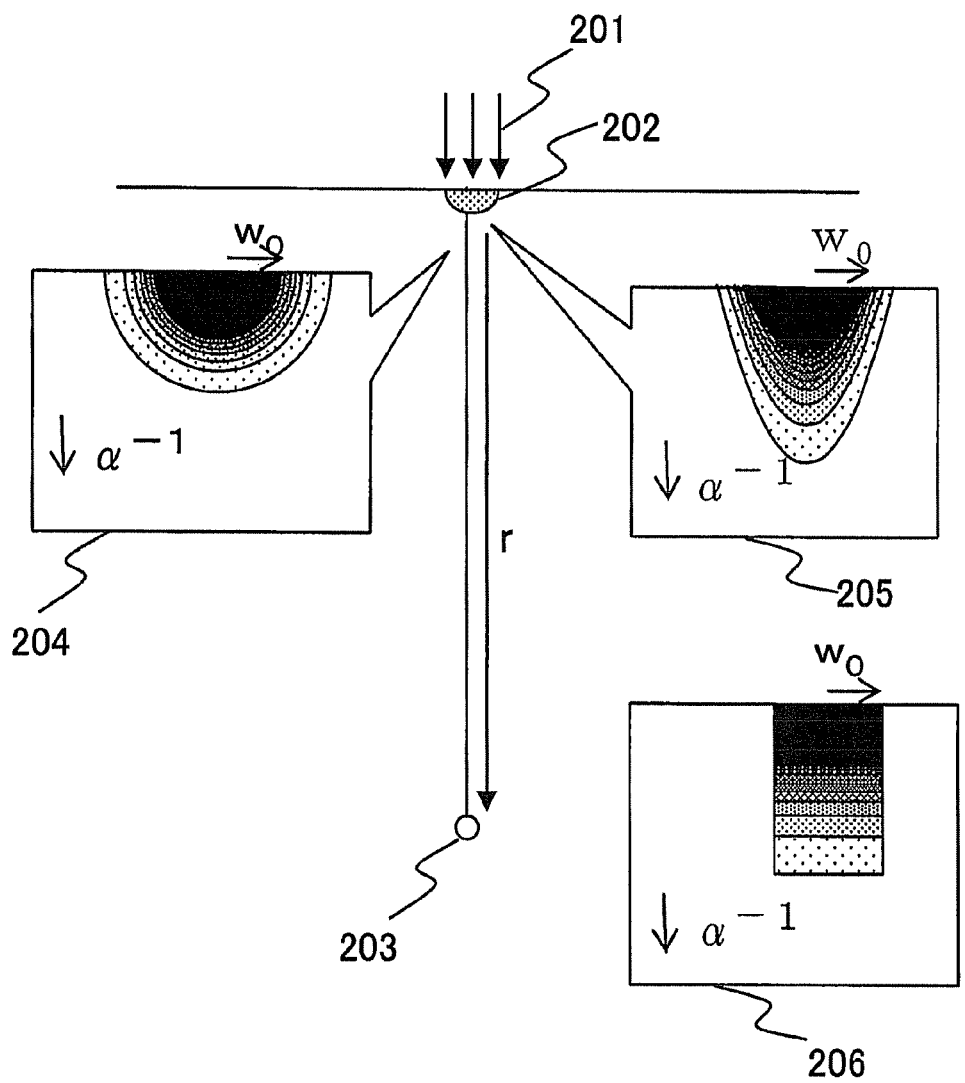
FIG. 2 is an explanatory view of a sound source distribution in a living body.

Then, the acoustic pressure generated by the light irradiation will be described with reference to FIG. 2. FIG. 2 is an explanatory view of a base direct photoacoustic method according to the first embodiment, and FIG. 2 shows an arrangement of an observation point in the direct photoacoustic method along with sound source distribution models. In FIG. 2, light irradiation 201 is perpendicularly incident to the living body, which generates a sound source 202 near the surface of the region irradiated with the light as described above.

For the acoustic wave which is generated from the sound source 202 to propagate through the living body (for the sake of simplicity, it is assumed that acoustic wave is even), acoustic pressure p(r) of the acoustic wave is observed at an observation point 203. The observation point 203 is located on the extension line of the irradiation light and the observation point 203 is separated away from the sound source by a distance r.

In the living body, the background (water) exhibits the strong absorption for the light having the wavelength 1 μm or longer, which is used in the blood constituent concentration measuring apparatus according to the first embodiment, so that the sound source 202 is localized in the surface of the region irradiated with the light. As a result, the generated acoustic wave is regarded as a spherical wave.

A wave equation, which describes the acoustic wave propagation shown in FIG. 2, is determined from an equation of fluid dynamics. That is, assuming that a density change, a pressure change, and a flow velocity change are small, an equation of continuity and a Navier Stokes equation are set as linear equations, and the equation of continuity, the Navier Stokes equation, and a state equation which described a relationship between the pressure and the density in the fluid (water) are simultaneously solved to determine the wave equation. At this point, the state equation includes a temperature as a parameter, and temperature change is captured through the state equation when a heat source Q exists.

When heat transfer is neglected, the micro pressure change p is described by an inhomogeneous Helmholtz equation.

$$\left(\frac{1}{c^2}\frac{\partial^2}{\partial t^2} - \nabla^2\right)p = \frac{\beta}{C_p}\frac{\partial Q}{\partial t}$$  [Formula 5]

Where c is sound velocity, β is a thermal expansion coefficient, and $C_p$ is a specific heat capacity at constant pressure.

In the case of the blood constituent concentration measuring apparatus according to the first embodiment, the living body is irradiated with the light, which is intensity-modulated at a constant period T, and an acoustic pressure change, is detected in synchronization with the constant period T. Therefore, assuming that modulation frequency is set as f=1/T and modulation angular frequency is set as ω=2πf, it is necessary to pay notice only to the amount having time dependence exp (−iωt) in all the mounts. As a result, time differentiation becomes a product with −iω.

Because the heat source Q is caused by non-radiative relaxation subsequent to the irradiation light absorption, the heat source Q is proportional to the absorption coefficient α and a distribution of the heat source Q is equal to a spatial distribution of irradiation light (including scattered light if exist) in a medium. That is, when the light intensity is set at I at each point, Q=αI is obtained. Thus, the basic equation for the steady-state direct photoacoustic method is expressed by the following formula (6).

$$(\nabla^2 + k^2)p = i\frac{\beta}{C_p}\alpha\omega I. \quad \text{[Formula 6]}$$

At this point, a wave number $k=\omega/c=2\pi\lambda_1$ ($\lambda$ is a wavelength of an acoustic wave) of the acoustic wave is introduced.

In a sufficiently distant site (r) $\alpha^{-1}$), the solution is expressed by the following formula (7) under a boundary condition of p (r→∞)→0 of the formula (6).

$$p(r) = \frac{1}{4\pi i}\frac{\beta}{C_p}\alpha\omega \int_{V'} \frac{I(\vec{r'})\exp[ik|\vec{r}-\vec{r'}|]}{|\vec{r}-\vec{r'}|} d\vec{r'} \quad \text{[Formula 7]}$$

For some light distributions, the observed acoustic pressure is computed by the formula (7). A model A 204 of the light distribution is assumed to be a hemispherical distribution in which the intensity is attenuated at a rate of $e^{-\alpha r'}$ with respect to a moving radius r'. The model A 204 corresponds to the case where the scattering is significantly large and the light beams are scattered all the directions once the irradiation light beams are incident.

On the other hand, model B 205 and a model C 206 shown in FIG. 2 correspond to the case where the scattering is not generated, and the model B 205 and the model C 206 correspond to the case where a Gaussian type beam having a radius $w_0$ and uniformly circular beam having the radius $w_0$ are incident. The light intensity distribution of each model is shown in FIG. 2.

In addition to the already used condition of $r \gg \alpha^{-1}$, when $r \gg w_0$ and $N=w_0^2/(r\lambda) \ll 1$ (N is defined with $\alpha^{-1}$ instead of $w_0$ for the model A) hold, the computation result by the formula (7) is summarized as follows:

$$p(r) = \frac{\beta c}{4\pi C_p}\alpha F(k\alpha^{-1})P_0\frac{e^{ikr}}{ir} \quad \text{[Formula 8]}$$

Where P0 is all power of the irradiation light, and F(ξ) is computed as follows:

$$F(\xi) = \begin{cases} \arctan(\xi) - (i/2)\log(1+\xi^2) & \text{for } A \\ \xi/(1+i\xi) & \text{for } B, C \end{cases} \quad \text{[Formula 9]}$$

Figure 3:
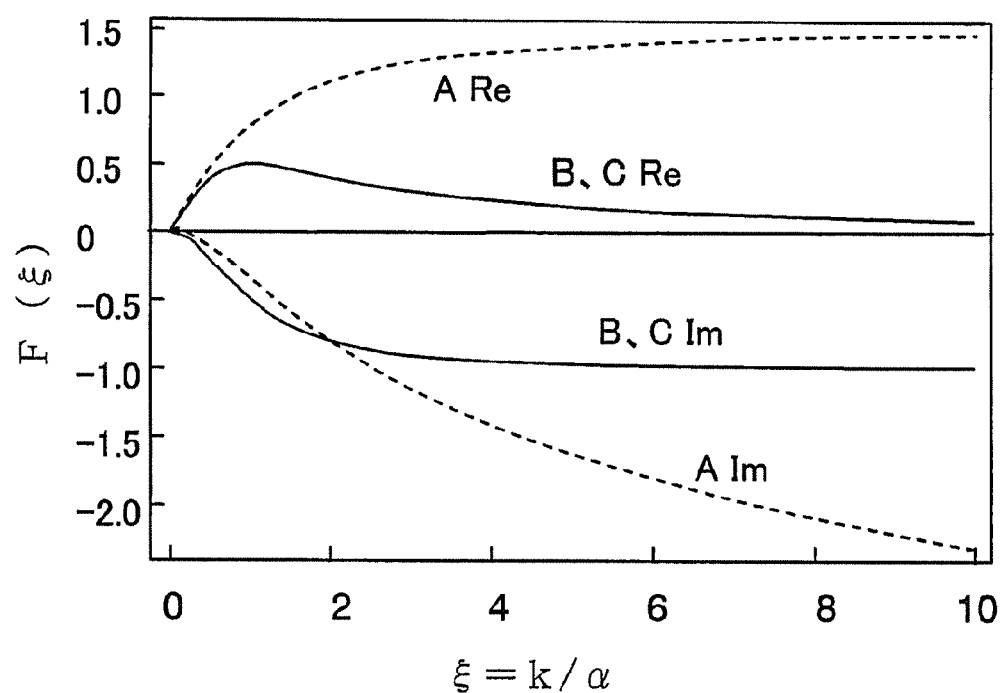
FIG. 3 is an explanatory view of a shape function for the sound source distribution in the living body.

The information on the sound source distribution is consolidated into the shape function $F(k\alpha^{-1})$. FIG. 3 shows a graph of the shape function.

According to the above result, when $\xi=k\alpha^{-1}$ is small, i.e., when the acoustic wave wavelength is much longer than the absorption length ($\lambda$) a–1), the photoacoustic signal does not include any pieces of the information on the absorption coefficient. This is because $F(\xi)\cong\xi$ in $\xi\ll 1$ leads to $\alpha F(\xi)\cong k$. Accordingly, when the acoustic wave wavelength is much longer than the absorption length, i.e., when the modulation frequency is excessively low, it is found that the blood constituent concentration cannot be measured by the photoacoustic method.

Accordingly, in the direct photoacoustic method in which the measurement is performed to the living body, it is necessary that the modulation frequency is set to i.e., $f \cong \alpha c/(2\pi)$ or more. In the case where the irradiation light wavelength is close to 1.6 µm, it is necessary that the modulation frequency f is set to 150 kHz or more. In the case where the irradiation light wavelength is close to 2.1 µm, it is necessary that the modulation frequency f is set to 0.6 MHz or more.

Because there is no difference in the results of the model B 205 and model C 206, it is found that the intensity distribution of the light perpendicular to an optical axis has no influence on the signal. However, the simplification can be permitted only in the case where $N=w_0^2/(r\lambda) \ll 1$ holds. N is an amount called Fresnel number, and the Fresnel number N indicates a phase change width generated by contribution of the acoustic wave from each point of the sound source according to the expansion of the sound source in the direction perpendicular to a visual axis when the sound source is viewed from the observation point. The Fresnel number sufficiently smaller than 1 is equivalent to the fact that the sound source is not enlarged in the direction perpendicular to the visual axis.

In this case, there is generated an extremely convenient feature that the beam diameter $w_0$ of the irradiation light has no influence on the photoacoustic signal. The following two reasons can be cited.

First, the influence of the scattering is suppressed in the living body. It is assumed that the model A 204 is the limit state where the scattering is large. However, in the living body, actually the degree of the scattering is not so large as compared with the model A 204. Generally, the scattering phenomenon is characterized by a scattering coefficient $\mu_s$ and anisotropy g. The anisotropy g is an average $<\cos\theta>$ of a cosine of a scattering angle θ, and it is reported that the anisotropy g is approximately 0.9 as a value of the living body, particularly the value of a skin (for example, see Journal of Applied Optics, vol. 32, 1993, pp 435-447). That is, the scattering in the actual living body mainly includes small angle scattering $<\theta>\cong 26°$.

A rate at which the light is decreased from the incident light flux by the scattering during the light propagation in a unit length is given by a reduction scattering coefficient $\mu'_s=\mu_s(1-g)$, and the reduction scattering coefficient $\mu'_s=\mu_s(1-g)$ of about 1 mm$^{-1}$ is actually measured for the light wavelength 1 µm or longer (see Non-Patent Document 3). The reduction scattering coefficient $\mu'_s=\mu_s(1-g)$ of about 1 mm$^{-1}$ has the degree similar to the value of the absorption coefficient α (0.6 mm$^{-1}$ for the light wavelength of about 1.6 µm and 2.4 mm$^{-1}$ for the light wavelength of about 2.1 µm) which is of the rate at which the light is decreased from the incident light flux by the absorption during the light propagation in a unit length.

That is, in the living body, the irradiation light receives the scattering only two times during the absorption length $\alpha^{-1}$, and the scattering angle is small. As a result, the light distribution (sum of the incident light flux and the scattering light) in the living body is gradually enlarged in the beam diameter direction as the depth is increased, and the light distribution is apparently formed in a pinhead. An actual observation example of the above light distribution is also reported (see Journal of Applied Optics, vol. 40, 2001, pp 5770-5777). At this point, in a plane of a depth z, it is expected that the total amount of light distribution is still attenuated according to the exp(-αZ). This is because same scattering is generated at small scattering angles.

Accordingly, in the case where the photoacoustic signal is independent of the beam diameter of the irradiation light, the beam diameter of the light distribution at each depth does not become problematic, and only the total amount of light distribution at each depth has an influence on the shape function F(λ) When the light distribution is exp(-αz), resultantly the light distribution is similar to the cases of the model B 205 and model C 206 in which the scattering is not generated. Therefore, it is expected that the scattering has no influence on the shape function.

In the irradiation with light beams having the wavelength $\lambda_1$ and the wavelength $\lambda_2$, it is essential to equalize the shape functions in the method of the first embodiment. Accordingly, it is not desirable that the difference in scattering exists in the wavelength $\lambda_1$ and the wavelength $\lambda_2$. There is no actual measurement report on which the scattering dependence on the wavelength in the skin for the light wavelength 1.3 µm or longer. However, the constant reduction scattering coefficient $\mu'$ is reported for the blood (see Journal of Biomedical Optics, vol. 4, 1999, p 36-46).

Accordingly, for example, even if the scattering slightly has the influence on the shape function, the wavelength dependence is small, and there is a possibility that the scattering actually has the influence on the shape function. As described above, when the Fresnel number is set small, the influence of the scattering itself on the shape function can be suppressed. Therefore, the equalization of the shape function is justified irrespective of the scattering dependence on the wavelength, and it is found that the method of the first embodiment has high reliability.

Second, the modulation frequency can be optimized. In the irradiation of the human body with the light, there is an acceptable limit of the light intensity depending on the irradiated region, the wavelength, the irradiation time, and the like. When the beam diameter $w_0$ is enlarged in the range where the Fresnel number N is small, the total power $P_0$ of the irradiation light can be increased to increase the photoacoustic signal without exceeding the limit of the light intensity.

Assuming that the limit of the light intensity is set at $I_{max}$, $P_0 = \pi w_0^2 I_{max}$ and the Fresnel number N is expressed in the form of $N = f/(\pi cr)(P_0/I_{max})$ by the total power $P_0$. In consideration of the distance r which is of an amount (for example, about 10 mm in a fingertip and about 40 mm in a wrist) determined by the thickness of the living body test region 110, it is necessary to decrease the total power $P_0$ when k, i.e., the modulation frequency $f(\propto k)$ is increased while N is kept constant. However, because magnitude of the shape function $|F(k\alpha^{-1})|$ is not increased in proportion with k, the detected acoustic wave is decreased. Accordingly, it is found that the excessively high modulation frequency is not desirable.

when an acoustic pressure amplitude $P_a$ given by the formula (8) is rewritten using N and $I_{max}$, the flowing formula (10) is obtained.

$$Pa = Psup \frac{|F(k\alpha^{-1})|}{k\alpha^{-1}} N \qquad [\text{Formula 10}]$$

At this point, an acoustic pressure upper limit $P_{sup}$ is expressed by the following formula (11).

$$Psup = \frac{\pi \beta c}{2Cp} \text{Imax} \qquad [\text{Formula 11}]$$

In the formula (10), $|F(\xi)|/\xi$ is a function which is monotonously decreased for $\xi$, and the low modulation frequency has an advantage only from the viewpoint of signal amplitude.

In this case, $\xi = k\alpha^{-1}$ which maximizes $\partial P_a/\partial \alpha = -(P_{sup}N/\alpha)$ $\xi d(|F(\xi)|/\xi)/d\xi$, which is of a rate of change for $\alpha$ of the formula (10), gives the optimum modulation frequency. $\xi$, which gives the optimum modulation frequency, is 2.49 in the model A 204, and $\xi$ is 2½ in the model B 205 and model C 206. The value of $|F(\xi)|/\xi$ is 0.620 in the model A 204 for $\xi$ which gives the optimum modulation frequency, and the value of $|F(\xi)|/\xi$ is $\frac{1}{3}^{1/2}$ in the model B 205 and model C 206. That is, the optimum modulation frequency exists as a meeting point for contradictory demands of the sensitivity between the signal intensity and the absorption coefficient $\alpha$.

As described above, it is thought that the light distribution in the actual living body is close to those of the model B 205 and model C 206. Therefore, the optimum modulation frequency is $2\pi f = 1.41 c\alpha$ and, at this point, it is expected that the signal amplitude is 57.7% for the maximum value $P_{sup}N$ at $f \to 0$.

Figure 4:
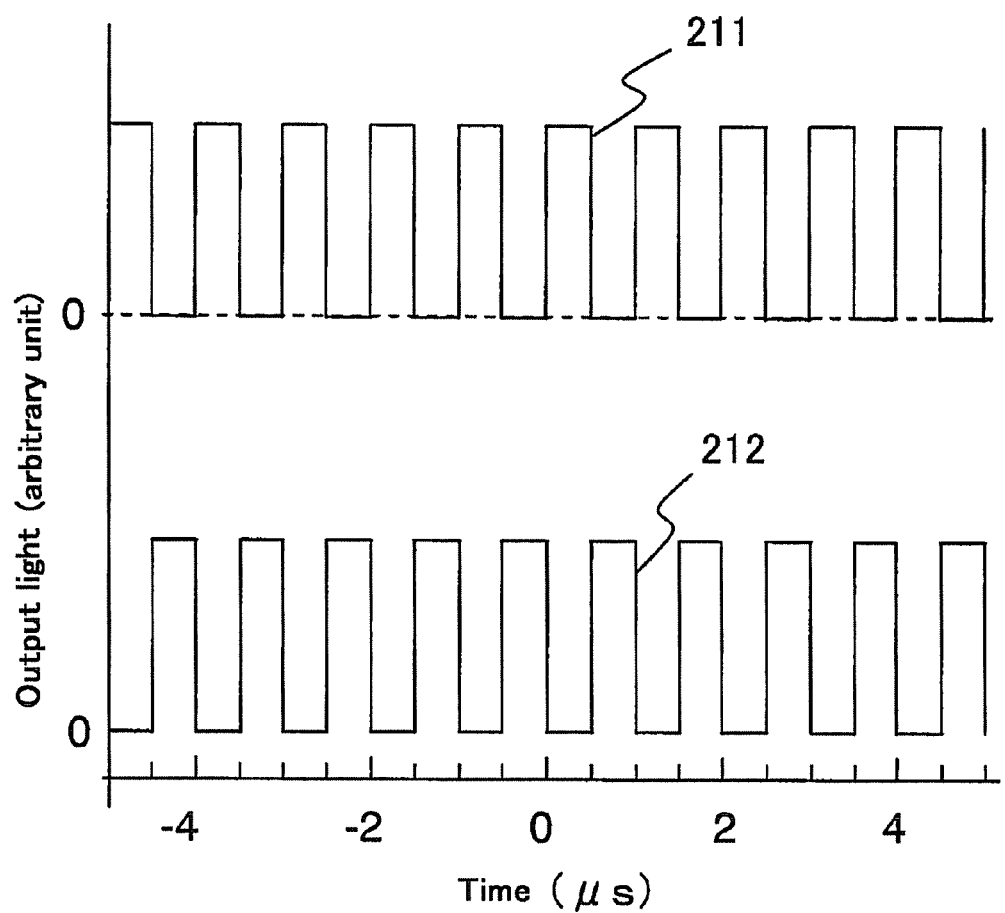
FIG. 4 is an explanatory view showing a photoacoustic signal of the blood constituent concentration measuring apparatus according to the embodiment.

A principle of the blood constituent concentration measuring apparatus according to the first will be described below with reference to FIG. 3. The first light source 101 shown in FIG. 1 is intensity-modulated in synchronization with the oscillator 103, and the light outputted by the first light source 101 has a waveform shown in an upper part of FIG. 4 as light 211 of a first light source ($\lambda_1$).

On the other hand, the second light source 105 shown in FIG. 1 is also intensity-modulated in synchronization with the oscillator 103. Because the 180° phase change is imparted to the signal transmitted from the oscillator 103 by the 180°-phase-shift circuit 107, the light outputted from the second light source 105 is intensity-modulated with the signal having the reverse phase with respect to the light outputted from the first light source 101, and thereby the light outputted from the second light source 105 has a waveform which is shown as the light of second light source ($\lambda_2$) 212 in the lower part of FIG. 5.

FIG. 3 shows the signal with which the first light source 101 and the second light source 105 are intensity-modulated having a period of 1 µs, namely, the modulation frequency f is 1 MHz and a pulse duty factor is 50%.

At this point, in the formula (6), it is assumed that a sinusoidal change is generated in the irradiation light, and FIG. 3 shows that the living body is irradiated with the rectangular-waveform light. This is not contradictory because of the following reason.

The formula (5) is linear, and the constituents having the different frequency components can independently be dealt with. The non-linearity possessed by the Navier Stokes equation itself has the influence on the formula (5), when amplitude of the acoustic wave is increased. However, in the photoacoustic signal in the blood constituent concentration measuring apparatus according to the first embodiment, the generated acoustic wave is weak and the linear formula (5) can be applied. Although the rectangular-waveform includes an odd-number order harmonic component, the amplitude of the sinusoidal component of the basic period in the odd-number order harmonic component can be replaced by I of the formula (6). In the light source, the intensity modulation is performed more easily in the rectangular waveform as compared with the sinusoidal waveform. Additionally, because the rectangular waveform has the sinusoidal component having the basic period of $4/\pi = 1.27$ times, the rectangular waveform has slightly better efficiency as compared with the sinusoidal waveform having the same amplitude.

The two light beams having different wavelengths respectively outputted from the first light source 101 and second light source 105 are multiplexed by the coupler 109, and the living body test region 110 is irradiated with the multiplexed light. At this point, it can be thought that each of the two light beams having the different wavelengths generates the acoustic pressure independently expressed by the formula (8).

From the linearity of the formula (5), it is already clear that the acoustic waves are linearly superposed. The two light beams having the different wavelengths are not so strong to an extent in which the absorption is saturated, so that the heat generations Q by the two light beams having the different wavelengths are also linearly superposed. Even if the absorption is saturated, the linear superposition of the heat generation still holds when the absorption has uneven spread and, at the same time, when the interval between the two light beams having the different wavelengths is broader than an even width. These conditions are well satisfied for the water in which the absorption is commonly generated for the two light beams having the different wavelengths.

As described above, the photoacoustic signals having the acoustic pressures independently expressed by the formula (8) are generated by the two light beams having the different wavelengths, and the superposed acoustic pressure is detected by the ultrasonic detector 113. Accordingly, the superposed acoustic pressure is expressed by the following formula.

$$p(r) = s_1 - s_2 \quad \text{[Formula 12]}$$
$$= \frac{\beta c}{4\pi Cp} \{\alpha_1 F(k\alpha_1^{-1}) - \alpha_2 F(k\alpha_2^{-1})\} P_0 \frac{e^{ikr}}{ir}$$

Figure 6:
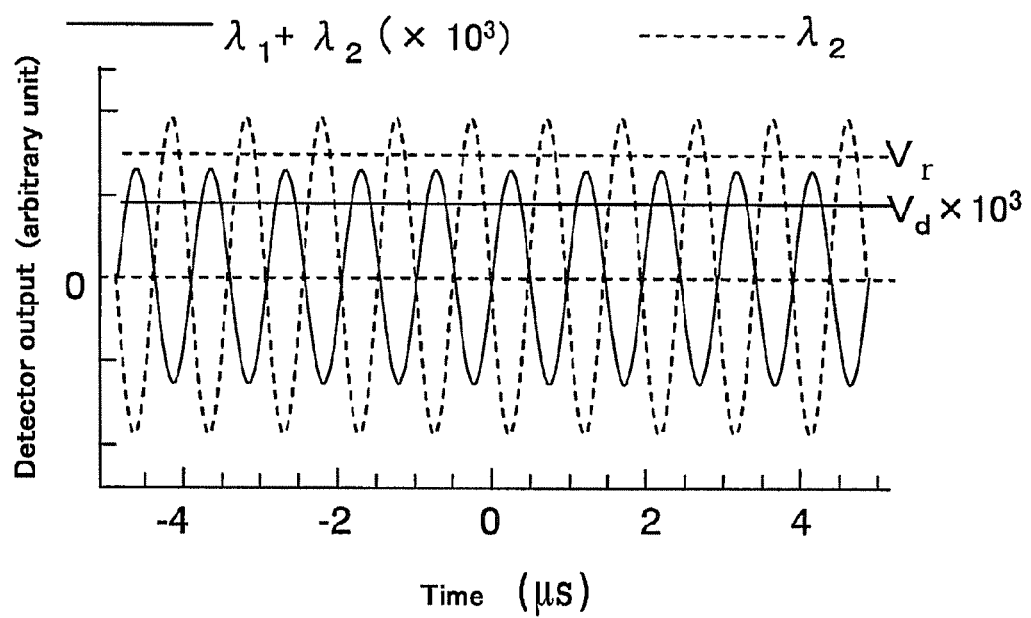
FIG. 6 is an explanatory view showing the photoacoustic signal of the blood constituent concentration measuring apparatus according to the embodiment.

At this point, the reason why $\alpha_i F(k\alpha_i^{-1})$ (i=1 and 2) is superposed in the shape of the difference is that the incident light beams of the two light beams having the different wavelengths are intensity-modulated in the reverse phases. The solid line of FIG. 6 shows the waveform of the basic-period sinusoidal component in the electric signal obtained by detecting and converting the acoustic pressure by the ultrasonic detector 113. The amplitude (rms value) of the signal shown by the solid line in FIG. 6 is measured by the phase sensitive amplifier 114 synchronized with the oscillator 103, and the amplitude is outputted in the form of the signal shown by Vd in FIG. 6 to the output terminal 115.

From the formula (12) and the formula (1), the unknown constant C is expressed by the following formula.

$$C = \frac{\beta c}{4\pi Cp} F(k\alpha^{-1}) P_0 \frac{1}{r} \quad \text{[Formula 13]}$$

Then, a principle of computing the blood constituent concentration set as the measuring object using the formula (4) will be described. Because the difference signal $s_1-s_2$ of the photoacoustic signals corresponding to the light beams outputted from the first light source 101 and the second light source 105 is already obtained, the blood constituent concentration M of the measuring object can be computed from the formula (4) when the photoacoustic signal $s_2$ is measured.

Figure 5:
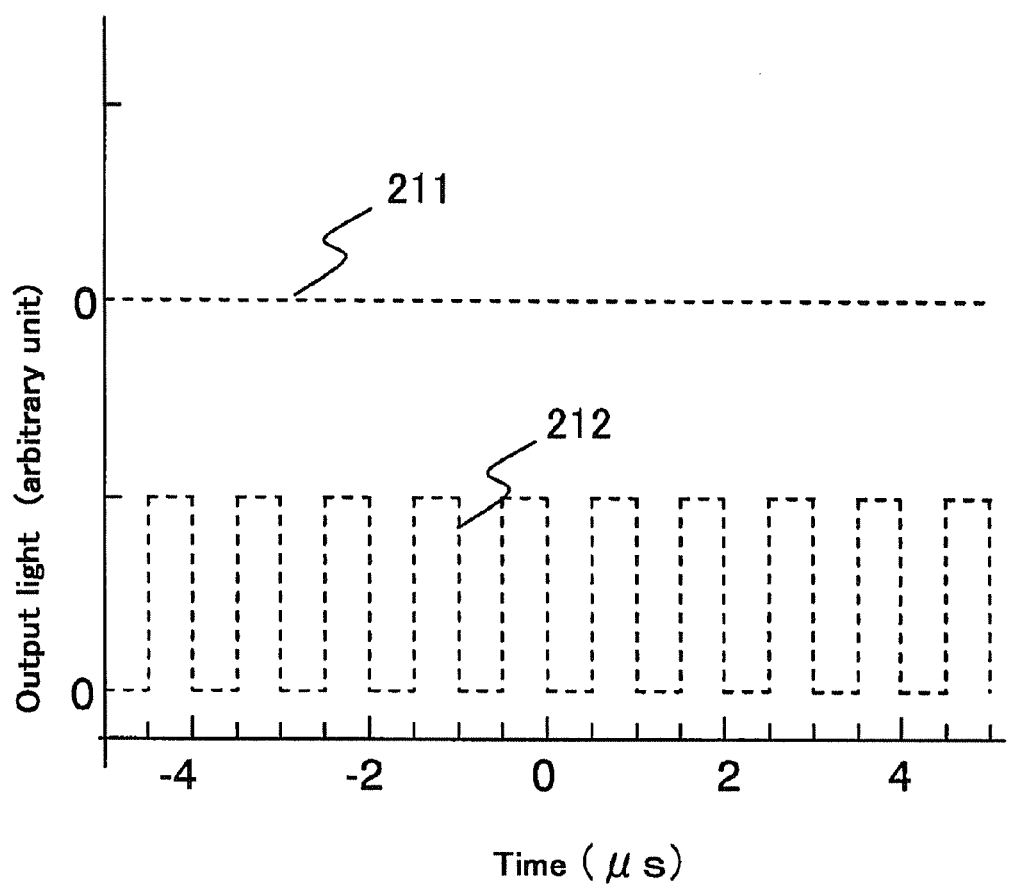
FIG. 5 is an explanatory view showing the photoacoustic signal of the blood constituent concentration measuring apparatus according to the embodiment.

Therefore, the photoacoustic signal is measured while the living body is irradiated only with the light of second light source ($\lambda_2$) 212 shown in FIG. 5. That is, as shown in FIG. 5, the output of the first light source 101 is caused to become zero while the waveform of the light outputted from the second light source 105 is maintained. This can be realized by blocking the light outputted from the first light source 101 shown in FIG. 1 with a mechanical shutter or by decreasing the output of the drive circuit 104 below an oscillation threshold of the first light source 101.

When the value of the photoacoustic signal measured in the above state is detected and converted into the electric signal by the ultrasonic detector 113, the waveform shown by the broken line in FIG. 6 is obtained as the basic-period sinusoidal component. Similarly, to the above method, an rms amplitude of the waveform shown by the broken line in FIG. 6 is measured by the phase sensitive amplifier 114, and the rms amplitude is outputted in the form of the signal shown by Vr in FIG. 6 to the output terminal 115.

The photoacoustic signal $S_2$ has the reverse phase with respect to the difference signal $s_1-s_2$ between the photoacoustic signals. The photoacoustic signal $S_2$ has several orders of magnitude more the difference signal $s_1-s_2$ between the photoacoustic signals. For example, in the case of the blood sugar level measurement of the normal subject, the photoacoustic signal $S_2$ is 1000 times or more the difference signal $s_1-s_2$ between the photoacoustic signals. Accordingly, the sensitivity and a time constant of the phase sensitive amplifier 114 are switched during the interval between the measurements of the photoacoustic signal $S_2$ and the difference signal $s_1-s_2$ of the photoacoustic signals.

When the two measured values $V_d$ and $V_r$ are obtained by the measurements, $s_1-s_2$ and $s_2$ in the formula (4) are replaced by the two measured values $V_d$ and $V_r$ to compute the blood constituent concentration M set as the measuring object.

The specific absorbance $\alpha_1^{(0)}/\alpha_1^{(b)}$ ($\alpha_2^{(0)}/\alpha_1^{(b)}$ is further required when $\alpha_2^{(0)}$ is not zero) is further required for the conversion of a ratio $V_d/V_r$ of the measured values to the blood constituent concentration M.

Figure 7:
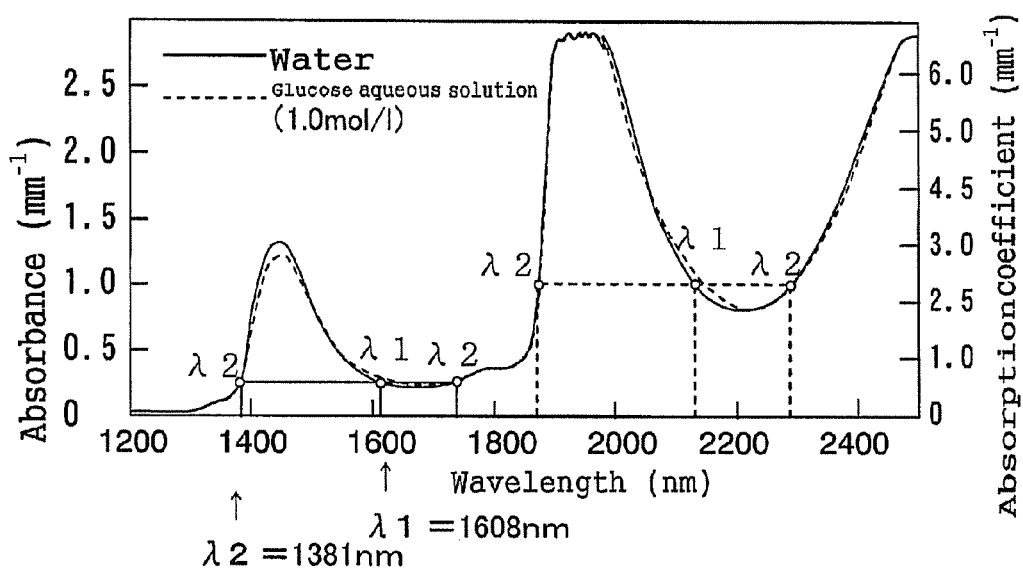
FIG. 7 is an explanatory view showing a pair of wavelengths used along with the light absorption properties of water and glucose.

FIG. 7 shows the specific absorbance value and a method of selecting the wavelength $\lambda_1$ and wavelength $\lambda_2$ to be measured. As described above, the wavelength $\lambda_1$ and wavelength $\lambda_2$ have the same background absorption coefficient.

FIG. 7 shows a method of selecting the wavelengths corresponded to the first light source 101 and the second light source 105 in the blood constituent concentration measuring apparatus according the first embodiment when the blood sugar level is measured.

FIG. 7 shows absorbances (OD) of water and glucose aqueous solution (concentration 1.0M) in the light wavelength range of 1.2 μm to 2.5 μm. The absorbance OD has a relationship of $\beta=OD\ln10$ with the absorption coefficient $\alpha$. A scale of the absorption coefficient $\alpha$ is shown in a vertical axis on the right side of FIG. 7.

In FIG. 7, although it is observed that the absorption by the glucose molecule exists slightly near 1.6 μm and 2.1 μm, the absorption by the glucose molecule is much smaller than that by the water.

Figure 8:
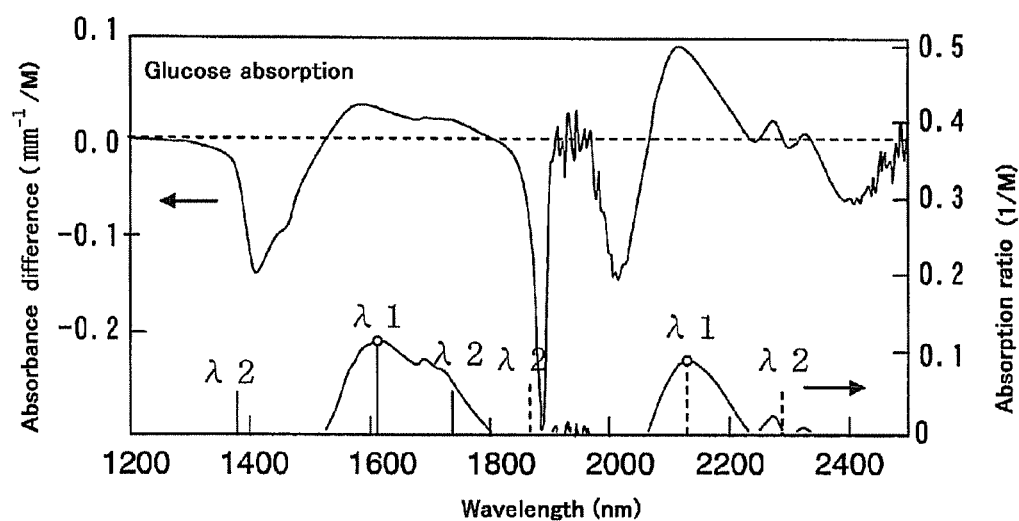
FIG. 8 is an explanatory view showing the light absorption properties of water and glucose.

The upper part of FIG. 8 shows the difference in absorbance between water and glucose, and the lower part of FIG. 8 shows the specific absorbance in which the absorbance is divided by the water absorbance.

From the specific absorbance shown in FIG. 8, it is observed that the clear maximum of the absorbance by the glucose molecule is located at 1608 nm and 2126 nm. For example, for the absorption wavelength by the glucose molecule, the wavelength of the first light source 101 is set at 1608 nm (specific absorbance is 0.114 M$^{-1}$). The wavelength $\lambda_1$ is shown by the vertical solid line with (o) in FIG. 8.

The absorption coefficient $\lambda_1^{(b)}$ of the background (water) at the wavelength 1608 nm is 0.608 mm$^{-1}$ from FIG. 7. The wavelength $\lambda_2$ in which $\alpha_2^{(b)}=\alpha_1^{(b)}$ is the wavelength of 1381 nm or the wavelength of 1743 nm from the water absorption spectrum of FIG. 7. The value of $\alpha_2^{(0)}$ is checked with the specific absorbance spectrum of FIG. 8 for each of the candidates of the wavelength $\lambda_2$ of the second light source 105. As a result, while the specific absorbance becomes zero at the wavelength of 1381 nm, the wavelength of 1743 nm is located in the absorption band of the glucose molecule, and the specific absorbance is 0.0601 M$^{-1}$ at the wavelength of 1743 nm. Because the measurement is easily performed when the absorbance difference $\alpha_1^{(0)} - \alpha_2^{(0)}$ is larger as much as possible, in the case of above, the wavelength of 1381 nm is selected as the wavelength $\lambda_2$ of the second light source 105.

In the case where the wavelength of 2126 nm is set at the wavelength $\lambda_1$ of the first light source 101 (specific absorbance is 0.0890 $M^{-1}$) in the long wavelength side, becomes of the same way as described above the wavelengths of 1837 nm and 2294 nm exist as the wavelength in which the water molecule exhibits the absorption coefficient equal to the absorption coefficient $\alpha_1^{(b)} = 2.361$ $mm^{-1}$ at the wavelength of 2126 nm. Both the wavelengths of 1837 nm and 2294 nm are located outside the glucose absorption (shown by the vertical dotted line in FIG. 8), so that either 1837 nm or 2294 nm may be selected as the wavelength $\lambda_2$ of the second light source 105.

EXAMPLES

Then, specific examples in the first embodiment will be described below.

First Example-1

In the blood constituent concentration measuring apparatus according to the first embodiment shown in FIG. 1, it is effective that a laser light source is used as the first light source 101 and the second light source 105. In selecting the laser light source, it is necessary to estimate the necessary output laser power level.

In irradiating the human body with the light, there is the acceptable limit of the light intensity. Generally one-tenths of the intensity in which affection is generated in 50% individual is defined as the maximum tolerance in JIS C6802. According to JIS C6802, the maximum tolerance is 1 mW per 1 $mm^2$ in the continuous irradiation of non-visible infrared light (wavelength 0.8 μm or longer) for the skin.

In a first example, the blood constituent of the measuring object is set at blood sugar, the irradiation light wavelength is set at 1.6 μm, and the modulation frequency f is set at 150 kHz or more because of the above-described principle. The wavelength $\lambda = c/f$ becomes 10 mm or less in the photoacoustic signal generated in the living body test region 110. When the fingertip is set as the living body test region 110, the distance r between the irradiation region irradiated with the light and the detection portion in which the ultrasonic detector 113 comes into contact with the living body test region 110 becomes 10 mm, the beam diameter $w_o$ having the Fresnel number of $N = W_o^2/(r\lambda)$ is computed in $W_o^2 \le 10$ $mm^2$. An irradiation light beam area is computed by multiplying $\pi$. When the maximum tolerance is integrated to compute the maximum irradiation light power, the maximum tolerance becomes 31 mW.

When the irradiation light is set at the 2.1 μm band, the maximum power becomes 8 mW from the similar computation, and this optical output can sufficiently be supplied by the semiconductor laser.

The compact semiconductor laser has a long life, and the semiconductor laser has an advantage that the intensity modulation is easily performed by modulating injection current. Therefore, in the first example, the semiconductor laser is used as the first light source 101 and the second light source 105.

FIG. 9 shows a configuration example of the blood constituent concentration measuring apparatus according to the first example. The configuration of the first example shown in FIG. 9 of the blood constituent concentration measuring apparatus according to the first embodiment is the forward propagation type which detects the acoustic wave propagating in the irradiation light direction, and the first example has the configuration similar to the basic configuration of the blood constituent concentration measuring apparatus shown in FIG. 1. The first light source 101, the second light source 105, the drive circuit 104, the drive circuit 108, the 180°-phase-shift circuit 107, the coupler 109, an ultrasonic detector 113, the phase sensitive amplifier 114, the output terminal 115, and the oscillator 103 which are shown in FIG. 1 correspond to a first semiconductor light source 501 and a lens 502, a second semiconductor light source 505 and a lens 506, a drive current source 504, a drive current source 508, a 180°-phase-shift circuit 507, a coupler 509, an ultrasonic detector 513 and an acoustic coupler 512, a phase sensitive amplifier 514, an output terminal 515, and an oscillator 503 which are shown in FIG. 9 respectively. All the components shown in FIG. 9 have the similar functions as those shown in FIG. 1.

However, the light beams outputted from the first semiconductor light source 501 and the second semiconductor light source 505 shown in FIG. 9 are caused to converge into parallel light fluxes by the lens 502 and lens 506 respectively, the parallel light fluxes are multiplexed by the coupler 509 into one light flux, and the living body test region 510 is irradiated with the light. The acoustic coupler 512 shown in FIG. 9 is placed between the ultrasonic detector 513 and the living body test region 510 to have a function of enhancing photoacoustic signal transmission efficiency between the ultrasonic detector 513 and the living body test region 510.

FIG. 9 also shows a calibration test sample 511. The function of the calibration test sample 511 will be described later.

The first semiconductor light source 501 is intensity-modulated by the drive current source 504 in synchronization with the oscillator 503, the output light is collected into the parallel light flux by lens 502, and the parallel light flux is inputted to the coupler 509. The second semiconductor light source 505 is intensity-modulated by the drive current source 508 in synchronization with the oscillator 503, the output light is collected into the parallel light flux by lens 506, and the parallel light flux is inputted to the coupler 509. At this point, because the output of the oscillator 503 is transmitted to the drive current source 508 through the 180°-phase-shift circuit 507, the light outputted from the second semiconductor light source 505 is intensity-modulated by the signal having the reverse phase with respect to the light outputted from the first semiconductor light source 501.

The light beams outputted from each of the first semiconductor light source 501 and the second semiconductor light source 505 are inputted to the coupler 509, and the light beams are multiplexed into one light flux, and the living body test region 510 is irradiated with the one light flux.

The light with which the living body test region 510 is irradiated generates the photoacoustic signal in the living body test region 510, the generated photoacoustic signal is detected by the ultrasonic detector 513 through the acoustic coupler 512, and the photoacoustic signal is converted into the electric signal proportional to the acoustic pressure of the photoacoustic signal.

The synchronous detection, the amplification, and the filtering are performed to the signal which is detected by the ultrasonic detector 513 and converted into the electric signal proportional to the acoustic pressure of the photoacoustic signal, and the signal is outputted to the output terminal 515 by the phase sensitive amplifier 514 synchronized with the oscillator 503.

As described above, the wavelength of the first semiconductor light source 501 is set at 1608 nm, and the wavelength of the second semiconductor light source 505 is set at 1381 nm. The oscillation frequency of the oscillator 503, i.e., the modulation frequency f is set at 207 kHz such that $\xi=k\alpha_1^{(b)}=2^{1/2}$ is obtained.

The optical output of the first semiconductor light source 501 is set at 5.0 mW, and the optical output of the second semiconductor light source 505 is also set at 5.0 mW.

The light beam diameter with which the living body test region 510 is irradiated is set as $w_0=2.7$ mm such that the Fresnel number N becomes 0.1 while the distance r between the irradiation portion and the detection portion is set at 10 mm.

In this state of things, the irradiation intensity to the skin of the living body test region 510 is 0.44 mW/mm² in the light in which the light beams outputted from the first semiconductor light source 501 and second semiconductor light source 505 are multiplexed, and the irradiation intensity is in a safe level which is lower than a half of the maximum tolerance. However, the irradiation intensity is in a dangerous level for eyes. Therefore, it is necessary that light shielding hoods (not shown in FIG. 9) is placed in the coupler 509 and the living body test region 510 such that the light reflected or scattered from the acoustic coupler 512 is not directly incident to the eyes during the measurement, or during in which the living body test region 510 is not placed.

The ultrasonic detector 513 is a frequency flat type electrostrictive device (PZT) into which an FET (field effect transistor) amplifier is incorporated, and the acoustic coupler 512 is an acoustic matching gel.

In the above configuration, first the optical output of the first semiconductor light source 501 is set to zero, and the living body test region 510 is irradiated only with the light outputted from the second semiconductor light source 505 as shown in FIG. 9. Then, in the output terminal 515 of the phase sensitive amplifier 514 whose time constant is set at 0.1 second, the voltage of Vr=20 μV is obtained as the electric signal corresponding to the photoacoustic signal $s_2$.

At this point, it is necessary to search the optimum phase difference in each measurement, because the phase difference θ between the synchronous signal transmitted from the oscillator 503 in the phase sensitive amplifier 514 and the signal in which the photoacoustic signal is detected and converted into the electric signal by the ultrasonic detector 513 is changed by the modulation frequency f and the distance r between the irradiation portion where the living body test region 510 is irradiated with the light and the contact portion which comes into contact with the acoustic coupler 512. It is effective that the search of the phase difference is performed by measuring the photoacoustic signal $s_2$ having the large signal amplitude.

In the case of the two-phase type phase sensitive amplifier, because the type phase sensitive amplifier has ability to always automatically determine the phase difference θ, it is not necessary to manually perform the search of the phase difference. That is, the phase and amplitude are determined by measuring the photoacoustic signal $s_2$ in an R–θ mode in which unknown phase and amplitude can be measured, and using the measured value of the phase the difference signal $s_1-s_2$ of the photoacoustic signals is measured in an X measuring mode in which the amplitude can be measured while noise suppression ratio is improved by 3 dB when the phase is already known.

When the first semiconductor light source 501 emits the light, $V_d=7.7$ nV (the direct measured value becomes −7.7 nV because the phase is reversed) is obtained at the output terminal 515 in the form of the electric signal corresponding to the difference signal $s_1-s_2$ of the photoacoustic signals. Then, the optical output of the first semiconductor light source 501 is set to zero again, and the photoacoustic signal $s_2$ is measured while the sensitivity and time constant of the phase sensitive amplifier 514 are returned to the original state, and the voltage of Vr=22 μV is obtained. The value of Vr becomes 21 μV from the average of the two times of yr.

As described above, it is desirable that the signal corresponding to the photoacoustic signal $s_2$, i.e., Vr is measured twice before and after measuring the difference signal $s_1-s_2$ of the photoacoustic signals.

The drift of the unknown multiplier C can be corrected during measuring the difference signal $s_1-s_2$ by the above procedure. The drift of the unknown multiplier C is derived from the change in the distance r caused by the change in pressing force of the fingertip of the subject and from the local temperature change caused by the light irradiation.

The glucose concentration M of 3.2 mM (58 mg/dl) is determined from the measured values, the specific absorbance value 0.114 $M^{-1}$ at the wavelength of 1608 nm, and the formula (4).

The acoustic pressure upper limit $P_{sup}$ of 0.17 Pa is obtained for $I_{max}=1$ mW/mm² using the values for the water, i.e., $C_p=1$ (cal/g·deg)=4.18×10³ (J/kg·K), β=300 ppm/deg, and c=1.51×10³ (m/s). When the acoustic pressure upper limit $P_{sup}$ is multiplied by the Fresnel number N=0.1, the attenuation of $1/3^{1/2}$ associated with $\xi=2^{1/2}$, and an actual irradiation power ratio of 0.22, the expected amplitude of the acoustic pressure is 2.1 mPa.

On the contrary, because nominal sensitivity of the ultrasonic detector 513 is 66 mV/Pa, it is calculated the output voltage of the output terminal 515 is 140 μV. However, the actually measured value of the photoacoustic signal $s_2$ is one-sevenths of 140 μV. This is attributed to the incompleteness of the acoustic coupler 512.

First Example-2

In a first example-2, for the purpose of the improvement of the acoustic coupling state, an acryl plate having the thickness of 6.6 mm is formed in the same diameter of 10 mmφ as that of the ultrasonic detector 513 in order to cause the acoustic coupler 512 to be a resonance type. One of the surfaces of the acoustic coupler 512 is attached to the ultrasonic detector 513 through vacuum grease, and the other surface is in contact with the living body test region 510 through the acoustic matching gel.

In the above configuration, as a result of the two-time measurement in the same procedure, the measured values of the photoacoustic signal $s_2$ are 150 nV and 153 μV, and the measured value of the difference signal $s_1-s_2$ between the photoacoustic signals is 59 nV. In the above measurement, the time constant of the phase sensitive amplifier 514 is three seconds. The glucose concentration M of 3.4 mM (61 mg/dl) is determined from the measured values.

First Example-3

In the first Example-2, the resonant frequency does not completely coincide with the modulation frequency f in the acoustic coupler 512. Therefore, in a first Example-3, during measuring the forestage photoacoustic signal $s_2$, the frequency of the oscillator 503 is swept in a range of several percent to operate the two-phase type phase sensitive amplifier 514 in the R–θ mode, and the modulation frequency f is set such that the output of the signal output terminal 515 becomes the maximum. Therefore, in the acoustic coupler 512, the resonant frequency is caused to completely coincide with the modulation frequency f.

Through the same procedures as the first Example-2 except for the above procedure, 600 μV and 604 μV are obtained by the two-time measurements. The measured value of the difference signal $s_1-s_2$ between the photoacoustic signals is 0.25 nV. In this case, the time constant of the phase sensitive amplifier 514 is one second. The glucose concentration M of 3.6 mM (65 mg/dl) is determined from the measured values.

The frequency flat type electrostrictive device (PZT) is used as the ultrasonic detector 513 in the first Example-1, first Example-2, and first Example-3. However, even in the normal type electrostrictive device (PET), by searching the modulation frequency f in which the amplitude of the signal obtained at the output terminal 515 is maximum, the measurement can be performed with the increased sensitivity by utilizing resonance characteristics. Therefore, the normal type electrostrictive device (PET) is suitable for the miniaturization and cost reduction.

First Example-4

A first Example-4 is a case where the calibration test sample 511 is introduced as the means for adjusting the light powers outputted from the first semiconductor light source 501 and the second semiconductor light source 505 such that the light power are equalized.

In the configuration of the calibration test sample 511, water is sealed in a glass container, or the water in which the scatterers, such as latex powders, are dispersed is sealed in the glass container. The scatterers such as latex powders simulate the scattering in the living body.

In order to secure the evenness of the transmittances for the wavelength $\lambda_1$ and wavelength $\lambda_2$ in the glass of the surface of the calibration test sample 511, which is irradiated with the light (upper surface in FIG. 9), it is effective that a pipe shaped margin having a diameter through which the irradiation beam passes is provided in the upper surface of the calibration test sample 511 to prevent the direct contact with the surface, or it is effective that the calibration test sample 511 is cleaned with a predetermined product through a predetermined procedure before the use of the calibration test sample 511.

The calibration procedure in which the calibration test sample 511 is attached instead of the living body test region 510 is performed as follows.

First the optical output of the first semiconductor light source 501 is set to zero, and the calibration test sample 511 is irradiated only with the light outputted from the second semiconductor light source 505 as shown in FIG. 9. The two-phase type phase sensitive amplifier 514 is operated in the R–θ mode, and the phase θ at that time is determined and fixed. In the resonance type ultrasonic wave detection, at this stage, similarly the optimum modulation frequency f is searched in order to cause the resonant frequency and modulation frequency of the acoustic coupler 512 to coincide with each other.

First the decrease in signal outputted to the output terminal 515 of the phase sensitive amplifier 514 is observed while the light outputted to the first semiconductor light source 501 is increased, and the sensitivity and time constant of the phase sensitive amplifier 514 are changed in accordance with the decrease in signal outputted to the output terminal 515. Then, the optical output of the first semiconductor light source 501 is fixed at the time when the output obtained at the output terminal 515 becomes zero.

Through the above procedure, the calibration can be performed with the calibration test sample 511 into the state, in which the relative intensity of the light outputted from the first semiconductor light source 501 and the relative intensity of the light outputted from the second semiconductor light source 505 are equal to each other and the light beams outputted from the first semiconductor light source 501 and second semiconductor light source 505 are intensity-modulated by the signals having the reverse phases.

A method of turning on a power supply of the blood constituent measuring apparatus according to the first example-4 while the calibration test sample 511 is attached instead of the living body test region 510 can be defined to perform the above sequences as POST (Power On Self Test) in a power-on operation.

Second Example-1

Figure 10:
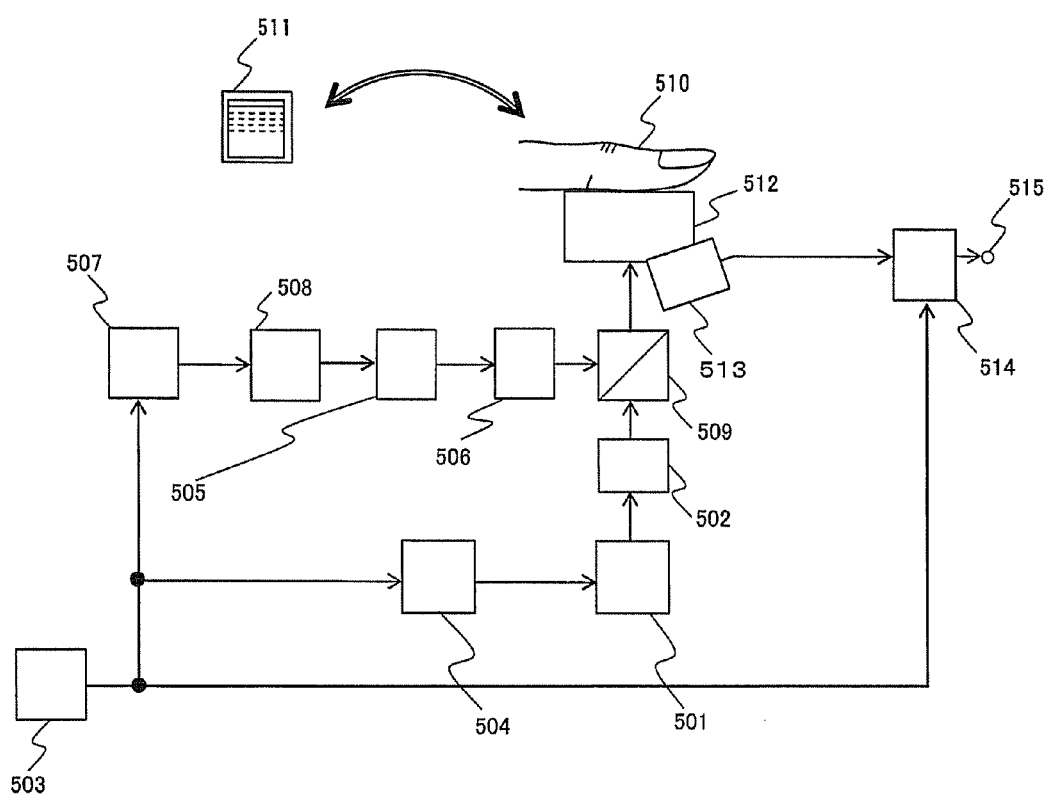
FIG. 10 is an explanatory view showing a configuration example of the blood constituent concentration measuring apparatus according to the embodiment.

A second example-1 is a rearward propagation type which detects the acoustic wave propagating in the opposite direction to the irradiation light. As shown in FIG. 10, the configuration of the second example has the configuration in which, in the configuration of the first example of the blood constituent concentration measuring apparatus shown in FIG. 9, the acoustic coupler 512 is placed between the coupler 509 and the living body test region 510, one of the surfaces of the acoustic coupler 512 is in contact with the living body test region 510, the light multiplexed by the coupler 509 is incident to the other surface of the acoustic coupler 512, the incident light passes through the acoustic coupler 512, and the living body test region 510 is irradiated with the light. The ultrasonic detector 513 is placed on the side where the multiplexed light is incident to the acoustic coupler 512.

The operation of the blood constituent concentration measuring apparatus according to the second example-1 differs from that of the first example in that, as shown in FIG. 10, the light outputted from the coupler 509 passes through the acoustic coupler 512, the living body test region 510 is irradiated with the light, the photoacoustic signal generated in the living body test region 510 propagates through the acoustic coupler 512 again, and the photoacoustic signal is detected by the ultrasonic detector 513.

In the above configuration, because the irradiation light passes through the acoustic coupler 512, it is desirable that the acoustic coupler 512 has the small light absorption and the acoustic impedance close to the living body (water).

In the second example-1, the acoustic coupler 512 is made of quartz glass having the small light absorption. The quartz glass has the acoustic impedance eight times the water, only about one-fifths of the generated acoustic pressure becomes the propagation wave in the quartz glass, and the acoustic pressure is observed by the ultrasonic detector 513. Accordingly, because the quartz glass brings a disadvantage from the viewpoint of sensitivity, it is necessary that the acoustic coupler 512 itself has the resonance characteristics to increase the sensitivity. That is, the thickness (corresponding to the propagation length of the light flux in the glass in the drawing) of the quartz glass is set at 14 mm which becomes a substantially half of the wavelength ($\lambda$=27.85 mm) of the acoustic wave for the modulation frequency f of 200 kHz.

The acoustic wave in the quartz glass is regarded as the spherical wave in the far site from the living body test region 510, so that the ultrasonic detector 513 is placed at an angle of 150° with respect to the incident light flux (when the ultrasonic detector having a hole through which the incident light flux passes is used, the ultrasonic detector can be placed in the completely rearward direction of 180°).

In the configuration of the second example-1, the distance r between the irradiation portion where the living body test region 510 is irradiated with the light and the detection unit where the ultrasonic detector 513 detects the photoacoustic signal in the acoustic coupler 512 is fixed to a constant value (in this case, r=14 mm) which is determined by a size of the acoustic coupler 512.

The first semiconductor light source 501, the second semiconductor light source 505, and the ultrasonic detector 513 are similar to those of the first example. For the purpose of safety, a test body sensing switch (neglected in FIG. 10) is arranged such that light irradiation is not performed when no object is placed on the acoustic coupler 512.

Similarly to the first example, during measuring the fore-stage photoacoustic signal $s_2$, the frequency of the oscillator 503 is swept to search the modulation frequency f which coincides with the resonant frequency of the acoustic coupler 512. Through the same procedure as the first example, 200 μV and 206 μV are obtained as the photoacoustic signal $s_2$ by the two-time measurements. The measured value of the difference signal $s_1-s_2$ between the photoacoustic signals is 79 nV when the time constant of the phase sensitive amplifier 514 is set at one second. The glucose concentration M of 3.4 mM (61 mg/dl) is determined from the measured values.

Second Example-2

In the second example-2, the acoustic coupler 512 is made of low-density polyethylene. The low-density polyethylene is excellent for the acoustic wave coupling (pressure loss is lower than 9%) because the acoustic impedance of the low-density polyethylene differs from that of the water only by 18%. However, the low-density polyethylene slightly absorbs the light and the low-density polyethylene is excessively soft. However, the low-density polyethylene has the advantage in that, due to the softness, the low-density polyethylene comes into close contact with the living body not to require a supply material such as the acoustic matching gel. High-density polyethylene having the rigidity is not suitable because the high-density polyethylene is not transparent for the light.

In the second example-2, the thickness of the acoustic coupler 512 is set at 10 mm which is substantially equal to the acoustic wave wavelength for the modulation frequency f of 200 kHz, and the distance r between the irradiation portion and the detection portion is also set at the fixed value of 10 mm.

Similarly to the second example-1, 300 μV and 289 μV are obtained as the photoacoustic signal $s_2$ by the two-time measurements. The measured value of the difference signal $s_1-s_2$ between the photoacoustic signals is 117 nV when the time constant of the phase sensitive amplifier 514 is set at one second. The glucose concentration M of 3.5 mM (63 mg/dl) is determined from the measured values.

The reason why the measured signal is not increased while the low-density polyethylene has the low-pressure loss is that the acoustic coupler 512 is deformed by the pressing force of the living body test region 510 and thereby the size becomes unstable to insufficiently increase the sensitivity improvement by the resonance.

Second Example-3

The second example-3 is the case where the calibration means with the calibration test sample 511 is introduced to the second example-2. In this case, in the calibration test sample 511, the container in which the water or the water containing the scatterers is sealed is made of the same material as the acoustic coupler 512.

The surface irradiated with the light is the surface of which the calibration test sample 511 is in contact with the acoustic coupler 512 shown in FIG. 10. In order to secure cleanness for a long term, the calibration test sample 511 is cleaned with the predetermined product through the predetermined procedure before the use of the calibration test sample 511.

The calibration procedure, which is performed by attaching the calibration test sample 511, instead of the living body test region 510 and the like are similar to the first example-4.

Third Example

Examples for the glucose concentration in the blood, i.e., the blood sugar level are shown in the first example and the second example. However, in addition to the glucose, the blood contains many components such as cholesterol, lipid, protein, and an inorganic component. The blood constituent concentration measuring apparatus and control method of blood constituent concentration measuring apparatus according to the first embodiment are applied to cholesterol in a third example. The blood constituent concentration measuring apparatus and control method of blood constituent concentration measuring apparatus in the third example can also be applied in examples in the later-mentioned second embodiment, third embodiment, fourth embodiment, fifth embodiment, and sixth embodiment.

Figure 11:
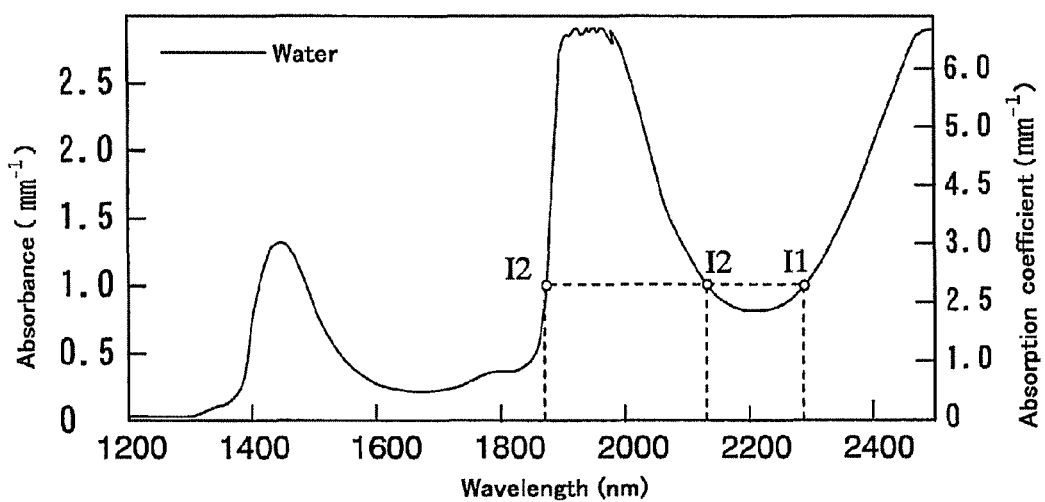
FIG. 11 is an explanatory view showing the light absorption properties of water.
Figure 12:
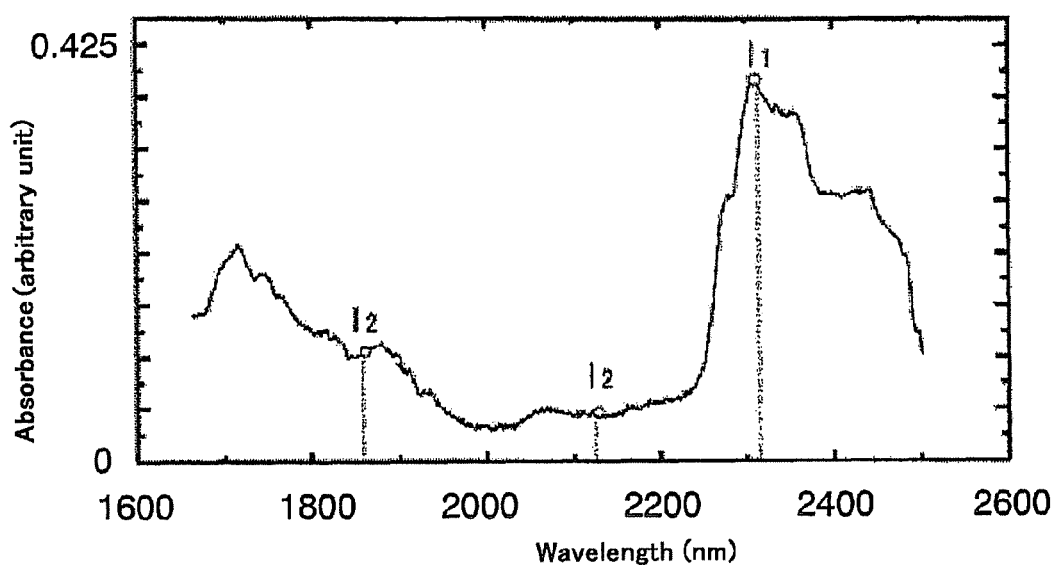
FIG. 12 is an explanatory view showing the light absorption properties of cholesterol.

FIG. 11 shows the absorbance of water in a frequency range of 1200 nm to 2500 nm. FIG. 12 shows the absorbance of cholesterol in a frequency range of 1600 nm to 2600 nm. Referring to the spectrum shown in FIG. 12, it is observed that the clear maximum of the absorption by the cholesterol molecule exists in 2310 nm.

The absorption coefficient $\alpha_1^{(b)}$ of the background (water) at the wavelength of 2310 nm is 1.19 mm$^{-1}$ from FIG. 11. The wavelength $\lambda_2$ in which $\alpha_2^{(b)}=\alpha_2^{(b)}$ is obtained is the wavelength of 2120 nm or the wavelength of 1880 nm from the water absorption spectrum of FIG. 11. The value of $\alpha_2^{(b)}$ is confirmed for each of the candidates of the wavelength $\lambda_2$ of the second light source 105 by the absorption spectrum of FIG. 12. As a result, in the cholesterol molecule, it is found that the absorption is large at the wavelength of 1880 nm as compared with the absorption in the wavelength of 2120 nm. Because the measurement is easily performed when the absorbance difference $\alpha_1^{(0)}-\alpha_2^{(0)}$ is large as much as possible, in this case, 2120 nm is selected as the wavelength of the second light source. Accordingly, the measurement is performed while the wavelength of the first light source is set at 2310 nm and the wavelength of the second light source is set at 2120 nm.

Figure 13:
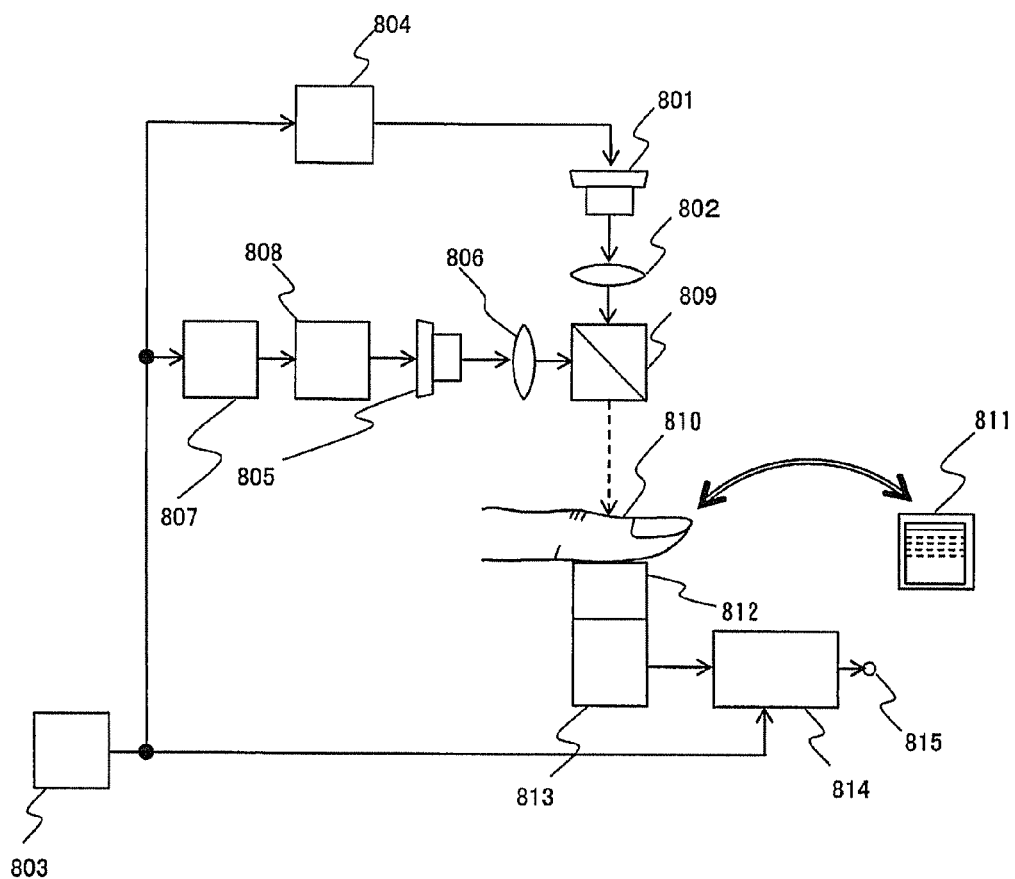
FIG. 13 is an explanatory view showing a configuration example of the blood constituent concentration measuring apparatus according to the embodiment.

FIG. 13 shows a configuration of the blood constituent concentration measuring apparatus according the third example. The configuration of the third example of the blood constituent concentration measuring apparatus shown in FIG. 13 is the forward propagation type which detects the photoacoustic signal propagating in the irradiation light direction. The third example has the basic configuration similar to that of the blood constituent concentration measuring apparatus shown in FIG. 1.

That is, a first semiconductor light source 801 and a lens 802, a second semiconductor light source 805 and a lens 806, a drive current source 804, a drive current source 808, a 180°-phase-shift circuit 807, a coupler 809, an ultrasonic detector 813 and an acoustic coupler 812, a phase sensitive amplifier 814, an output terminal 815, and an oscillator 803 which are shown in FIG. 13 have the same functions as those of the first light source 101, the second light source 105, the drive circuit 104, the drive circuit 108, the 180°-phase-shift circuit 107, the coupler 109, the ultrasonic detector 113, the phase sensitive amplifier 114, the output terminal 115, and the oscillator 103 which are shown in FIG. 1 respectively.

The first semiconductor light source 801 is intensity-modulated by the drive current source 804 in synchronization with the oscillator 803, the output light is collected into the parallel light flux by lens 802, and the parallel light flux is inputted to the coupler 809. The second semiconductor light source 805 is also intensity-modulated by the drive current source 808 in synchronization with the oscillator 803, the output light is collected into the parallel light flux by lens 806, and the parallel light flux is inputted to the coupler 809.

At this point, because the output of the oscillator 803 is transmitted to the drive current source 808 through the 180°-phase-shift circuit 807, the light outputted from the second semiconductor light source 805 is intensity-modulated by the signal having the reverse phase with respect to the light outputted from the first semiconductor light source 801.

The light beams outputted from the first semiconductor light source 801 and the second semiconductor light source 805 are inputted to the coupler 809, and the light beams are multiplexed into one light flux, and the living body test region 810 which is of the test subject is irradiated with the one light flux.

The light with which the living body test region 810 is irradiated generates the photoacoustic signal in the living body test region 810, the generated photoacoustic signal is detected by the ultrasonic detector 813 through the acoustic coupler 812, and the ultrasonic detector 813 converts the photoacoustic signal into the electric signal proportional to the acoustic pressure of the photoacoustic signal.

The phase sensitive amplifier 814 performs synchronized the oscillator the synchronous detection, the amplification, and the filtering to the signal converted into the electric signal, and the phase sensitive amplifier 814 outputs the signal to the output terminal 815.

The wavelength of the first semiconductor light source 801 is set at 2310 nm, and the wavelength of the second semiconductor light source 805 is set at 2120 nm. The oscillation frequency of the oscillator 803, i.e., the modulation frequency f is set at 207 kHz such that $\xi = k\alpha_1^{(b)} = 2^{1/2}$ is obtained.

The optical output of the first semiconductor light source 801 is set at 5 mW, and the optical output of the second semiconductor light source 805 is also set at 5 mW.

The light beam diameter with which the living body test region 810 is irradiated is set as $w_0 = 2.7$ mm such that the Fresnel number N becomes 0.1 while the distance r between the irradiation portion and the detection portion in the living body test region 810 is set at 10 mm.

In this state of things, the irradiation intensity to the skin of the living body test region 810 is 0.44 mW/mm$^2$ in the light in which the light beams outputted from the first semiconductor light source 801 and the second semiconductor light source 805 are multiplexed, and the irradiation intensity is in the safe level which is lower than a half of the maximum tolerance. However, in consideration of the leakage to the outside, it is preferable that light shielding hoods (not shown) is placed in the coupler 809 and the living body test region 810.

The ultrasonic detector 813 is the frequency flat type electrostrictive device (PZT) into which the field effect transistor (FET) amplifier is incorporated. An acoustic matching gel is used as the acoustic coupler 812.

In the above configuration of FIG. 13, the optical output of the first semiconductor light source 801 is set to zero, and the living body test region 810 is irradiated only with the light outputted from the second semiconductor light source 805. Then, in the output terminal 815 of the phase sensitive amplifier 814 whose time constant is set at 0.1 second, the voltage of Vr=40 μV is obtained as the electric signal corresponding to the photoacoustic signal $s_2$.

It is necessary to search the optimum phase difference in each measurement, because the phase difference θ between the synchronous signal transmitted from the oscillator 803 in the phase sensitive amplifier 814 and the signal in which the photoacoustic signal is detected and converted into the electric signal by the ultrasonic detector 813 is changed by the modulation frequency f and the distance r between the irradiation portion where the living body test region 810 is irradiated with the light and the contact portion which comes into contact with the acoustic coupler 812. It is effective that the search of the phase difference is performed by measuring the photoacoustic signal $s_2$ having the large signal amplitude as the phase basis.

In the case of the two-phase type phase sensitive amplifier, because the type phase sensitive amplifier can has ability to always automatically determine the phase difference θ, the phase difference can automatically be adjusted by utilizing the function. That is, the phase and amplitude are determined by measuring the photoacoustic signal $s_2$ in the R–θ mode in which unknown phase and amplitude can be measured, and the difference signal $s_1 - s_2$ of the photoacoustic signals is measured in the X measuring mode in which the amplitude can be measured while noise suppression ratio is improved by 3 dB when the phase is already known.

When the first semiconductor light source 801 emits the light, the output of about 10 nV is obtained at the output terminal 815 in the form of the electric signal Vd corresponding to the difference signal $s_1 - s_2$ of the photoacoustic signals. Then, the optical output of the first semiconductor light source 801 is set to zero again, and the photoacoustic signal $s_2$ is measured while the sensitivity and time constant of the phase sensitive amplifier 814 are returned to the original state, and the voltage of Vr=42 μV is obtained. The value of Vr becomes 41 μV from the average of the two times of Vr.

As described above, it is desirable that the signal Vr corresponding to the photoacoustic signal $s_2$ is measured twice before and after measuring the difference signal $s_1 - s_2$ of the photoacoustic signals. The drift of the unknown multiplier C can be corrected during measuring the difference signal $s_1 - s_2$ through the above procedure. The drift of the unknown multiplier C is derived from the change in distance r caused by the change in pressing force of the fingertip of the subject and from the local temperature change caused by the light irradiation.

When the photoacoustic signal derived from the cholesterol in the living body test region is measured with the ultrasonic detector in the above measuring system, the output value of several hundreds nV can be obtained as the difference signal $s_1 - s_2$ of the photoacoustic signals.

Although the living body blood constituent concentration measuring apparatus and the living body control method of blood constituent concentration measuring apparatus are described in the third example, the third example can also be applied to the liquid instead of the living body. That is, as can be seen from the description of the direct photoacoustic method based on the first embodiment and the constituent concentration computation method shown in the formula (4), the liquid constituent concentration measuring apparatus and liquid constituent concentration measuring apparatus controlling method according to the third embodiment can also be realized to measuring objects except for the living body. In this case, when the two wavelengths having the same absorption coefficient for the liquid and the different absorption coefficients for the object material are used, the constituent in the liquid can be detected without interruption of the absorption of the liquid. In the above embodiment and examples, fruit is placed instead of the living body test region, the liquid constituent concentration measuring apparatus functions as a fruit sugar content meter. This is because sucrose and fruit sugar, which are of a sugar constituent of the fruit, has the absorption in the wavelength similar to the glucose which is of the blood sugar constituent. Thus, the measuring apparatus and measuring apparatus controlling method according to the first embodiment could clearly be applied to various objects without departing from the spirit of the first embodiment.

Fourth Example

Figure 58:
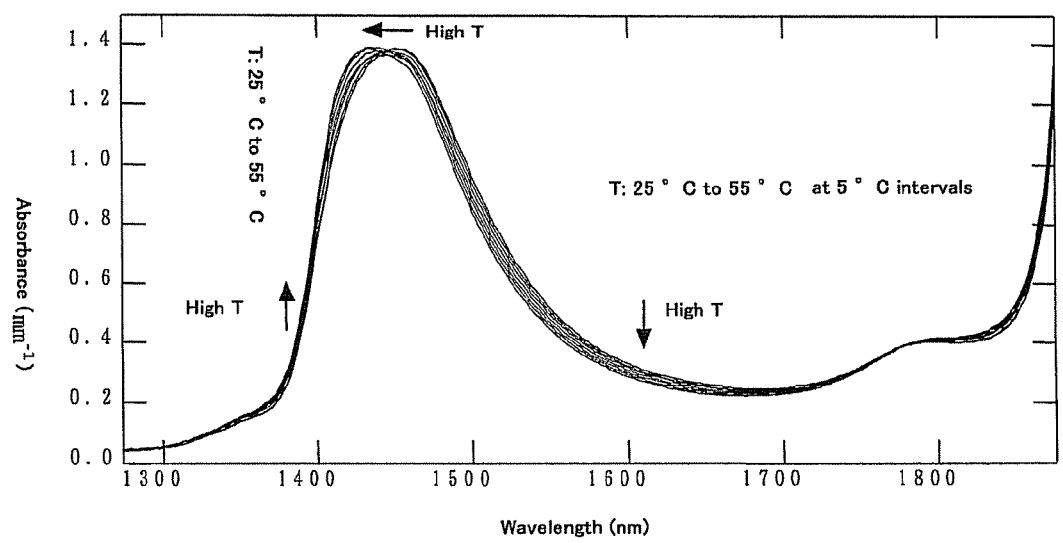
FIG. 58 is an explanatory view showing a computation principle of the blood constituent concentration measuring apparatus according to the embodiment (addendum)

FIG. 58 shows a configuration of a blood constituent concentration measuring apparatus according to a fourth example. The fourth example is the case where a contact thermometer 138 is further introduced to the blood constituent concentration measuring apparatus described in the first example-1 to the first example-4.

In the configuration shown in FIG. 58, the wavelength value of the first light source 101 is set at 1608 nm, and the wavelength of the second light source 105 is set at 1381 nm. These wavelengths are based on the water absorbance at a water temperature of 39° C. as shown in FIG. 7. The reference temperature 39° C. is higher than an ordinary temperature of the body temperature, and exactly it is necessary that the setting of the wavelength of the laser light source is changed according to the body temperature of the subject, i.e., temperature of the living body test region 110. This is because the light absorption properties of the water are changed depending on the water temperature.

FIG. 58 shows the water absorbance which depends on the water temperature. FIG. 58 shows the absorbance of a water absorption band having the maximum near the wavelength of 1450 nm for the water temperature in the range of 25° C. to 55° C. at intervals of 5° C. when the water temperature is set at the parameter. As can be seen from FIG. 58, the water absorption band is shifted toward the short wavelength direction as the water temperature rises, and thereby the absorption is increased on the short wavelength side while the absorption is decreased on the long wavelength side.

Figure 59:
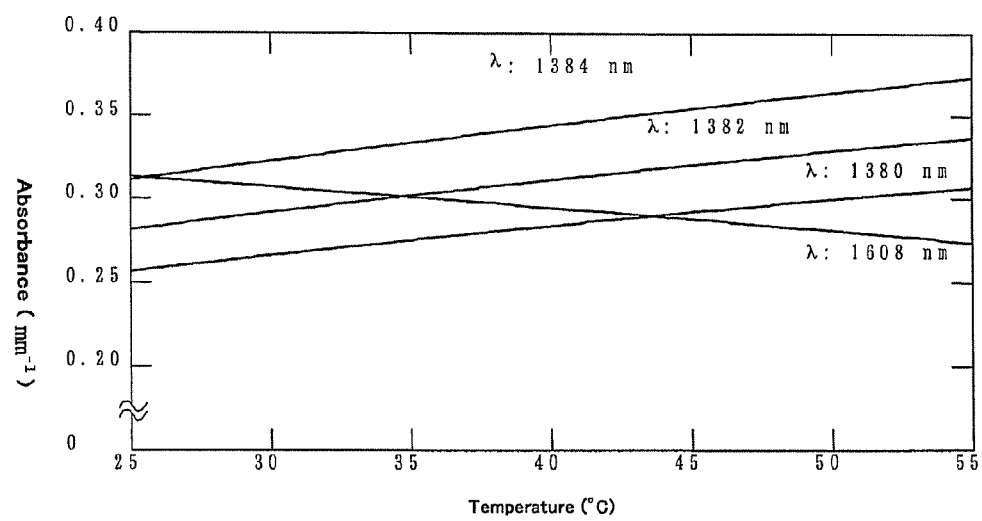
FIG. 59 is an explanatory view showing the computation principle of the blood constituent concentration measuring apparatus according to the embodiment (addendum)

In order to check the detailed characteristics, FIG. 59 shows the temperature change of the water absorbance at a constant wavelength. On the long wavelength side, the water absorbance is decreased at a rate of $1.366 \times 10^{-3}$ mm$^{-1}$/° C. for the temperature in the wavelength of 1608 nm of the first light source 101. On the other hand, on the short wavelength side, the water absorbance is increased at a rate of $1.596 \times 10^{-3}$ mm$^{-1}$/° C. in the wavelength of 1381 nm of the second light source 105.

As a result, the difference in absorbance between the two wavelengths is decreased at a rate of $2.962 \times 10^{-3}$ mm$^{-1}$/° C. for the temperature, and the specific absorbance is decreased at a rate of $1.001 \times 10^{-2}$/° C. for the temperature. When the specific absorbance value of 0.114 M$^{-1}$ of the glucose at 1608 nm is used for the change rate, it is found that underestimate of 87.78 mM (1581 mg/dl) per deviation of 1/° C. is generated for the glucose concentration M from the reference temperature of the body temperature.

In order correct to the error, the contact thermometer 138 is placed on the light irradiation side of the living body test region 110 to measure the local body temperature near the light irradiation portion, and the value in which the correction coefficient of 1581 mg/dl/° C. is multiplied by the temperature difference between the measured body temperature value and the reference temperature is added to the computation value of the glucose concentration M by the formula (4). The reason why the contact thermometer 138 is placed on the light irradiation side is that the surface temperature on the irradiation side of the living body test region where the light absorption is generated is involved in the correction. For example, when the surface temperature on the irradiation side is replaced by the living body surface temperature on the side which is contact with the side of the ultrasonic detector 113, because the body surface temperature which is in unavoidable thermal contact with the ultrasonic detector 113 is used, there is a fear that the large error is generated.

Figure 57:
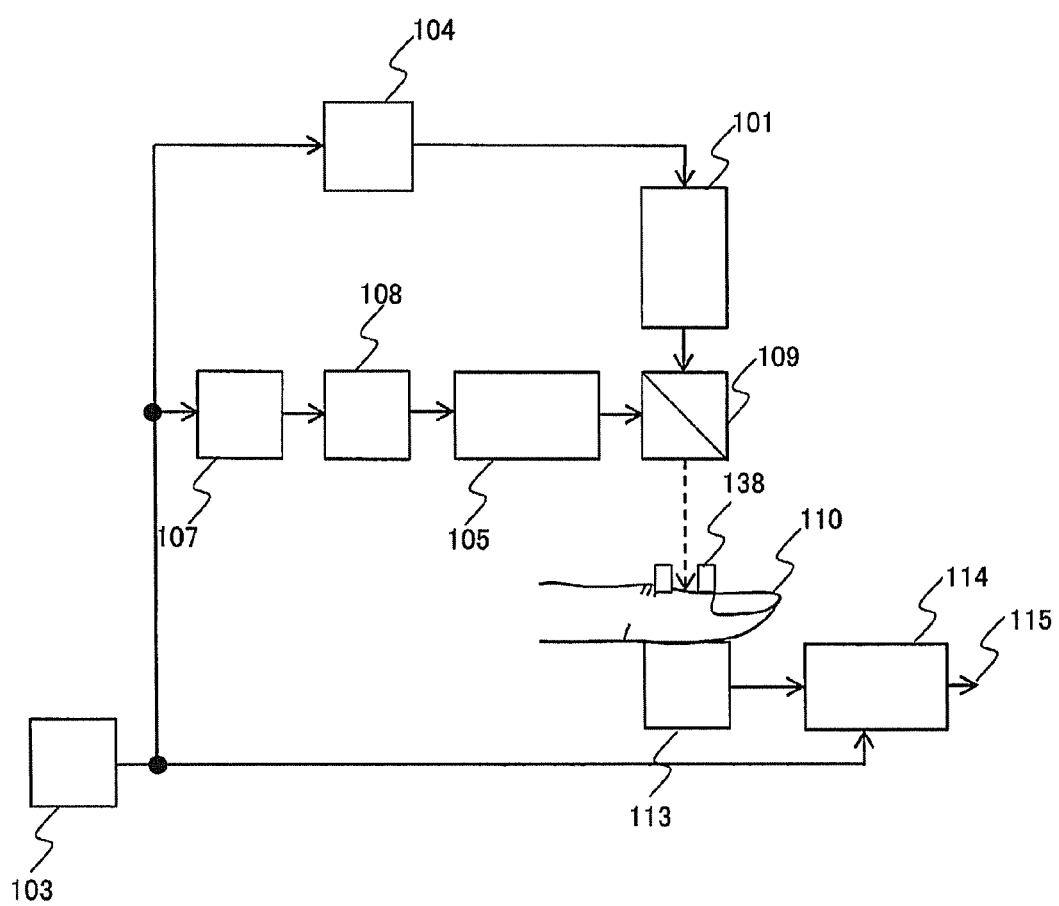
FIG. 57 is an explanatory view showing a configuration of the blood constituent concentration measuring apparatus according to the embodiment (addendum)
Figure 60:
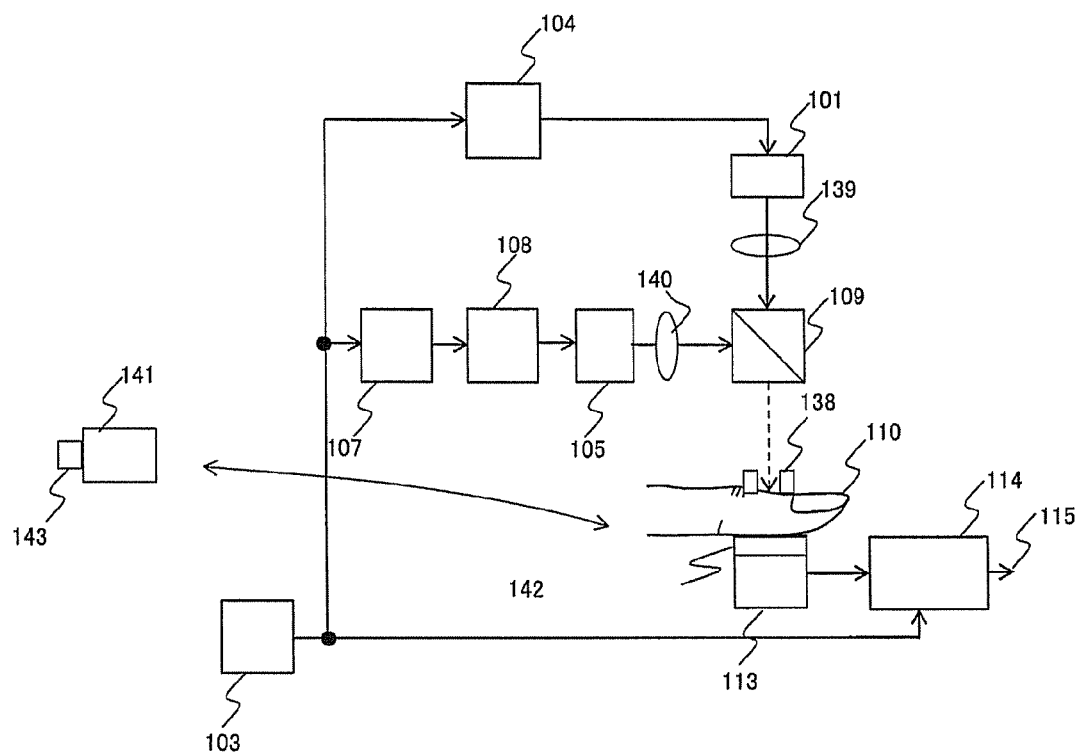
FIG. 60 is a view showing an example of the blood constituent concentration measuring apparatus according to the embodiment (addendum)

In the case where the calibration test sample is used in the blood constituent concentration measuring apparatus shown in FIG. 57, the correction based on the surface body temperature measurement may be performed as follows. FIG. 60 shows an example in which the calibration test sample is further applied to the blood constituent concentration measuring apparatus shown in FIG. 57.

A thermometer 143, which measures the liquid temperature in the calibration test sample 141, is attached to the calibration test sample 141. In the above procedure, the scale reading of the thermometer is recorded as a calibration temperature at the time when the photoacoustic signal outputted from the output terminal 115 becomes zero to fix the output the drive circuit 104. In the following measurement of the living body test region 110, the correction is performed using the calibration temperature instead of the reference temperature of the correction computation method shown in the example. That is, the local body temperature near the light irradiation portion is measured by the contact thermometer 138, and the value in which the correction coefficient of 1581 mg/dl/° C. is multiplied by the temperature difference between the measured body temperature value and the calibration temperature may be added to the computation value of the glucose concentration M by the formula (4).

In the case where constant-temperature means (neglected in FIG. 60) for keeping the liquid temperature constant is placed in the calibration test sample 141, in measuring the living body test region 110, the thermometer 143 placed in the calibration test sample 141 and the contact thermometer 138 of the living body test region 110 are simultaneously operated, and the temperature difference can also be determined from the difference in scale reading. Particularly, in this case, when the thermometer 143 and the contact thermometer 138 are formed by the same kind of thermometer, for example, a balance configuration which accurately reads the difference in output between the thermometer 143 and the contact thermometer 138 can be formed with a bridge circuit. In the balance configuration, because the accuracy of the absolute temperature is not required for the thermometer 143 and the contact thermometer 138, the example can be realized using a simple temperature measuring device such as a thermistor.

Fifth Example

Figure 61:
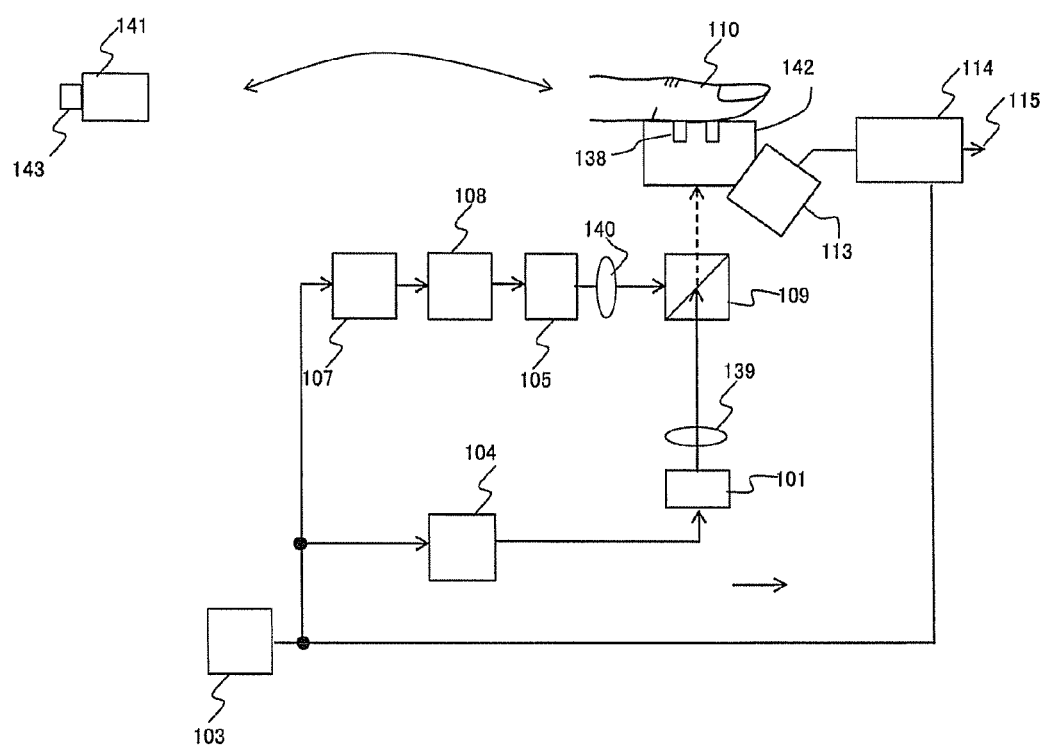
FIG. 61 is a view showing an example of the blood constituent concentration measuring apparatus according to the embodiment (addendum).

FIG. 61 shows a configuration of a blood constituent concentration measuring apparatus according to a fifth example. The fifth example is the case where the contact thermometer 138 is further introduced to the blood constituent concentration measuring apparatus described in the second example-1 to second example-3.

In the fifth example, because of the correction based on the surface body temperature measurement, it is preferable that the contact thermometer 138 is embedded in the surface of the acoustic coupler 142, which is in contact with the living body test region 110. In this case, it is desirable to use the contact thermometer 138 having the acoustic impedance close to the acoustic impedance of the acoustic coupler 142. This is because the disturbance of the ultrasonic wave propagation in the acoustic coupler 142 by the contact thermometer 138 is suppressed. The following correction based on the surface body temperature value measured by the contact thermometer 138 is performed by the same computation method as the fourth example. The calibration procedure which is performed by attaching the calibration test sample 141 instead of the living body test region 110, the correction based on the surface body temperature value measured by the contact thermometer 138, and the like can be performed according to the fourth example.

Second Embodiment

Figure 14:
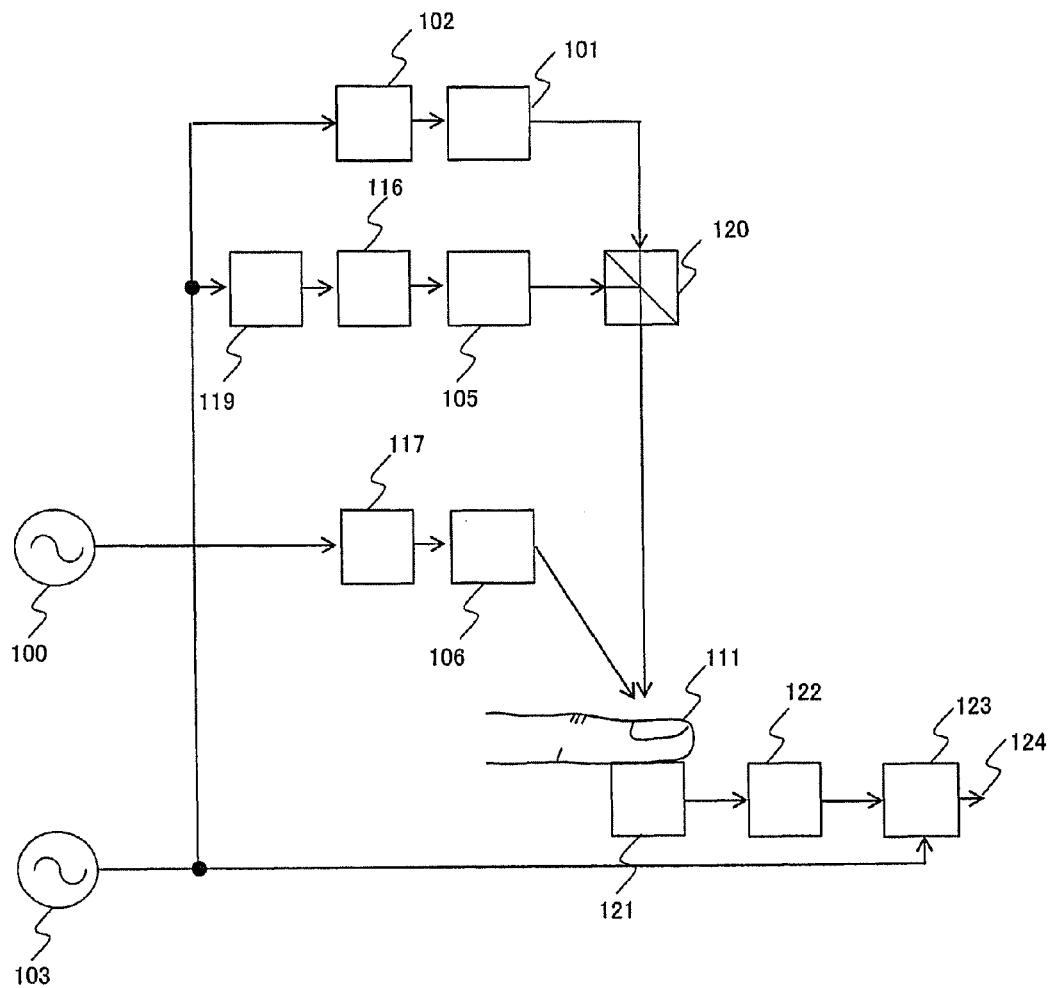
FIG. 14 is an explanatory view showing the embodiment of the blood constituent concentration measuring apparatus according to the embodiment.
Figure 15:
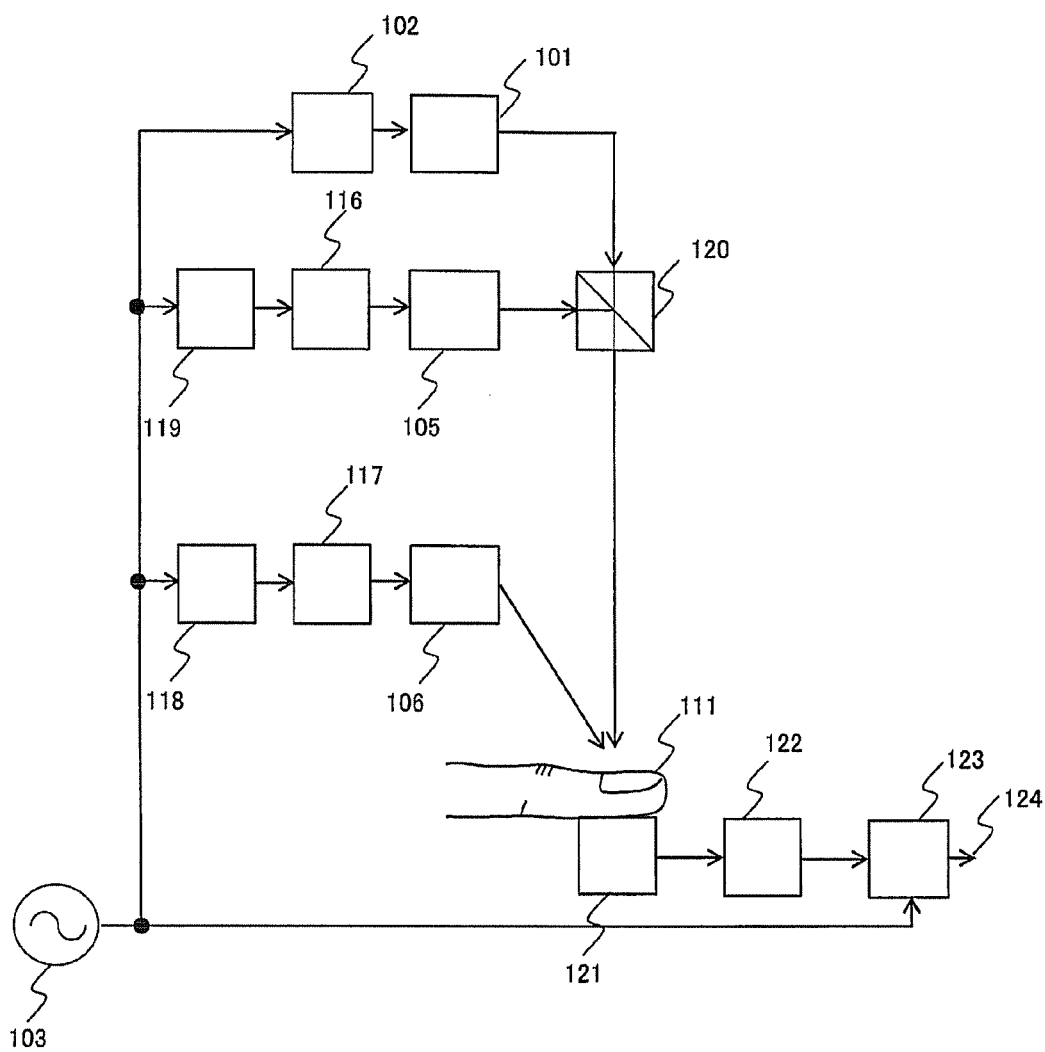
FIG. 15 is an explanatory view showing the embodiment of the blood constituent concentration measuring apparatus according to the embodiment.

FIGS. 14 and 15 show a blood constituent concentration measuring apparatus according a second embodiment. In FIGS. 14 and 15, the numeral 100 designates the oscillator, the numeral 101 designates the first light source, the numeral 102 designates the drive circuit, the numeral 103 designates the oscillator, the numeral 105 designates the second light source, the numeral 116 designates the drive circuit, the numeral 106 designates a third light source, the numeral 117 designates a drive circuit, the numeral 118 designates a frequency divider, the numeral 119 designates a 180°-phase shifter, the numeral 120 designates a coupler, the numeral 111 designates a living body test region, the numeral 121 designates an ultrasonic detector, the numeral 122 designates a filter, the numeral 123 designates a synchronous detection amplifier, and the numeral 124 designates a photoacoustic signal output terminal. The oscillator 103, the drive circuit 102, and the first light source 101 constitute a first irradiation unit which is of the light outgoing means. The oscillator 103, the 180°-phase shifter 119, the drive circuit 116, and the second light source 105 constitute a second irradiation unit which is of the light outgoing means. The oscillator 100, the drive circuit 117, and the third light source 106 constitute a third irradiation unit which is of the second light outgoing means. The ultrasonic detector 121 and the filter 122 constitute the acoustic wave detection means.

In FIG. 14, the oscillator 103 oscillates at a constant frequency to determine the frequency in which the first light source 101 and the second light source 105 are intensity modulated. The oscillator 100 is an oscillator which oscillates intermittently, and the oscillator 100 determines a period during which the third light source 106 is intensity-modulated. The oscillator 100 may oscillate at a constant frequency, or the oscillator 100 may oscillate at random times. The oscillator 100 may intermittently oscillate at intervals longer than the repetition intervals of the constant frequency of the oscillator 103. As a result, the third light source 106 is configured to be intensity modulated at light emission repetition intervals longer than those of the first light source 101 and the second light source 105, and the third light source 106 is also configured to be intensity modulated to an extent in which the photoacoustic signal is not generated.

The first light source 101, the second light source 105, and the third light source 106 may be configured to be intensity modulated by the same oscillator. For example, in FIG. 15, the oscillator 103 oscillates at a constant frequency to determine the frequency in which the first light source 101, the second light source 105, and the third light source 106 are intensity modulated. The frequency of the signal from the oscillator 103 is divided by the frequency divider 118, which allows the third light source 106 to oscillate periodically at intervals longer than the repetition intervals of the constant frequency in which the first light source 101 and the second light source 105 are intensity modulated.

The function and action of FIG. 14 are similar to those of FIG. 15 except for the determination of the oscillation frequency of the third light source, so that the description will be performed with reference to FIG. 14. In FIG. 14, the signal from the oscillator 103 is inputted to the drive circuit 102, and the drive circuit 102 drives the first light source 101. The signal from the oscillator 103 is inputted to the 180°-phase shifter 119, and the signal is reversed. The reversed signal is inputted to the drive circuit 116, and the drive circuit 116 drives the second light source 105. The first light source 101 and the second light source 105 are intensity-modulated using the signals having the same modulation frequency and reverse phases.

The first light source 101, the second light source 105, and the third light source 106 are driven to emit the modulated light beams having predetermined wavelengths by the drive circuit 102, the drive circuit 116, and the drive circuit 117 respectively. The coupler 120 multiplexes the light beam from the first light source 101 and the light beam from the second light source 105, and the living body test region 111 which is of the test subject is irradiated with the multiplexed light beam. When the configuration in which the light beam from the third light source 106 is also multiplexed is formed, the light can be focused on the living body test region 111, so that the photoacoustic signal can efficiently be generated. Multiplexing the light beam from the first light source 101, the light beam from the second light source 105, and the light beam from the third light source 106 can also be applied in the first embodiment and the later-mentioned third embodiment, fourth embodiment, fifth embodiment, and sixth embodiment in addition to the second embodiment.

The ultrasonic detector 121 is placed in the surface opposite to the surface irradiated with the multiplexed light beam from the coupler 120 and the output light of the third light source 106 with respect to the living body test region 111. The ultrasonic detector 121 receives the acoustic wave, i.e., the photoacoustic signal generated in the living body test region 111, the ultrasonic detector 121 converts the photoacoustic signal into the electric signal proportional to the acoustic pressure, and the ultrasonic detector 121 outputs the electric signal. The filter 122 passes the signal having the same frequency as the oscillation frequency of the oscillator 103. The synchronous detection amplifier 123 performs the synchronous detection of the signal inputted from the filter 122 using the synchronous signal inputted from the synchronous signal input terminal, and the synchronous detection amplifier 123 outputs the amplitude of the synchronous-detected ultrasonic wave to the photoacoustic signal output terminal 124. The synchronous detection amplification enables the amplitude of the ultrasonic wave to be detected from the photoacoustic signal with high sensitivity. The synchronous detection amplification performed by the synchronous detection amplifier 123 can also be applied in the first embodiment and the later-mentioned third embodiment, fourth embodiment, fifth embodiment, and sixth embodiment in addition to the second embodiment.

At this point, it is defined that $\lambda_1$ is the light wavelength outputted from the first light source 101, $\lambda_2$ is the light wavelength outputted from the second light source 105, and $\lambda_3$ is the light wavelength outputted from the third light source 106. The absorption is generated only in the region having the large blood density by irradiating the living body with the light having the wavelength $\lambda_3$, and the temperature rises by the photothermal conversion. For example, the light having the wavelength of about 800 nm is used in a photo CT method, it is reported that the temperature is changed by about 0.1° C. inside the living body, and it is known that the temperature rise of about 0.1° C. is not harmful. The acoustic pressure P generated by the intermittent light irradiation is expressed as follows.

$$P = \frac{\pi \beta c}{2Cp} I \qquad \text{[Formula 14]}$$

Where I is irradiation light intensity, $\beta$ is a thermal expansion coefficient, c is sound velocity, and $C_p$ is specific heat. In the above parameters, only $\beta$ and c depends on the temperature. Because the thermal expansion coefficient $\beta$ is changed 3% per 1° C., the photoacoustic signal is changed by about 0.3% by the temperature change of 0.1° C. according to the formula (14). Because the photoacoustic signal is changed by 0.017% by the change amount of 5 mg/dL of glucose, the 20-fold signal change is generated by the temperature change of 0.1° C. The temperature rise by the simultaneous irradiation of the light having the wavelength $\lambda_3$ increases the photoacoustic signal generated in the region where the blood density is high.

The blood constituent computation method according to the second embodiment will be described below with reference to the following formula. When the absorption coefficients $\alpha_1^{(b)}$, $\alpha_2^{(b)}$ to which the background water mainly contributes and the molar absorption coefficients $\alpha_1^{(0)}$, $\alpha_2^{(0)}$ of the blood constituent are known each other for the wavelengths $\lambda_1$ and $\lambda_2$, the concentration M is determined by solving the formula (1) which is of the simultaneous equations including the photoacoustic signal measured value $s_1$ and $s_2$ in the wavelengths.

Where C is a variable coefficient which is hardly controlled or calculated, i.e., C is an unknown multiplier depending on the acoustic coupling, the ultrasonic detector sensitivity, the distance r between the irradiation portion and the detection portion, the specific heat, the thermal expansion coefficient, the sound velocity, the modulation frequency, and the absorption coefficient. When C is deleted in the formula (1), the formula (4) is obtained, and the concentration M can be determined from the photoacoustic signal s and the already known absorption coefficient $\alpha$. However, in the formula (1), it is assumed that the absorption coefficient $\alpha_1^{(b)}$, $\alpha_2^{(b)}$ to which the background water mainly contributes are substantially equal to each other for the wavelengths $\lambda_1$ and $\lambda_2$. The formula (1) also has the feature of $s_1 \cong s_2$.

In the method according to the second embodiment, the blood portion differs from the tissue portion such as the cuticle, the cell, and the fat in the acoustic generation amount of the water, so that the formula (1) is rewritten as follows.

$$C_b(\alpha_1^{(b)}+M\alpha_1^{(0)})+C_t\alpha_1^{(b)}=s_1$$

$$C_b(\alpha_2^{(b)}+M\alpha_2^{(0)})+C_t\alpha_2^{(b)}=s_2 \qquad \text{[Formula 15]}$$

Where $C_b$ is an unknown coefficient in the blood and $C_t$ is an unknown coefficient in the tissue such as the cuticle, the cell, and the fat. The photoacoustic signal generated in the region having the high blood density is amplified by the temperature change caused by the simultaneous irradiation of the light beam having the wavelength $\lambda_3$. When A is an amplification rate, the formula (15) is rewritten as follows.

$$AC_b(\alpha_1^{(b)}+M\alpha_1^{(0)})+C_t\alpha_1^{(b)}=s_{1+}$$

$$AC_b(\alpha_2^{(b)}+M\alpha_2^{(0)})+C_t\alpha_2^{(b)}=s_{2+} \qquad \text{[Formula 16]}$$

When a difference between the formula (16) and the formula (15) is determined, the following formula (17) is obtained.

$$(A-1)(\alpha_1^{(b)}+M\alpha_1^{(0)})=s_{1+}-s_1=\Delta s_1$$

$$(A-1)(\alpha_2^{(b)}+M\alpha_2^{(0)})=s_{2+}-s_2=\Delta s_2 \qquad \text{[Formula 17]}$$

Therefore, the water photoacoustic signal is removed from the tissue which is on the non-blood region.

At this point, when (A−1) is deleted in the formula (17), the following formula is obtained.

$$M = \frac{(\Delta s_1 - \Delta s_2)\alpha_1^{(b)}}{\Delta s_2 \alpha_1^{(0)} - \Delta s_1 \alpha_2^{(0)}} \qquad \text{[Formula 18]}$$

$$= \frac{\alpha_1^{(b)}}{\alpha_1^{(0)} - \alpha_2^{(0)}} \frac{\Delta s_1 - \Delta s_2}{\Delta s_2}$$

Similarly to the formula (4), the concentration M can be determined from the difference acoustic signal $\Delta s$ and the already known absorption region coefficient $\alpha$. However, in the formula (18), it is assumed that the absorption coefficient $\alpha_2^{(b)}$ to which the background water mainly contributes are substantially equal to each other for the wavelengths $\lambda_1$ and $\lambda_2$. The formula (18) also has the feature of $\Delta s_1 \cong \Delta s_2$.

In the second embodiment, not only the accuracy of the constituent concentration computation is improved by the separation of the blood constituent, but also the background signal from the non-blood tissue can be removed. In the non-blood tissue, the existence of glucose is so small that the glucose can be omitted, and the percentage of the photoacoustic signal generation amount of total is large. Accordingly, when as compared with the conventional technique, the method of the second embodiment has the advantage that the background in which the temperature change is expected in the tissue has no influence on the measurement result.

Figure 16:
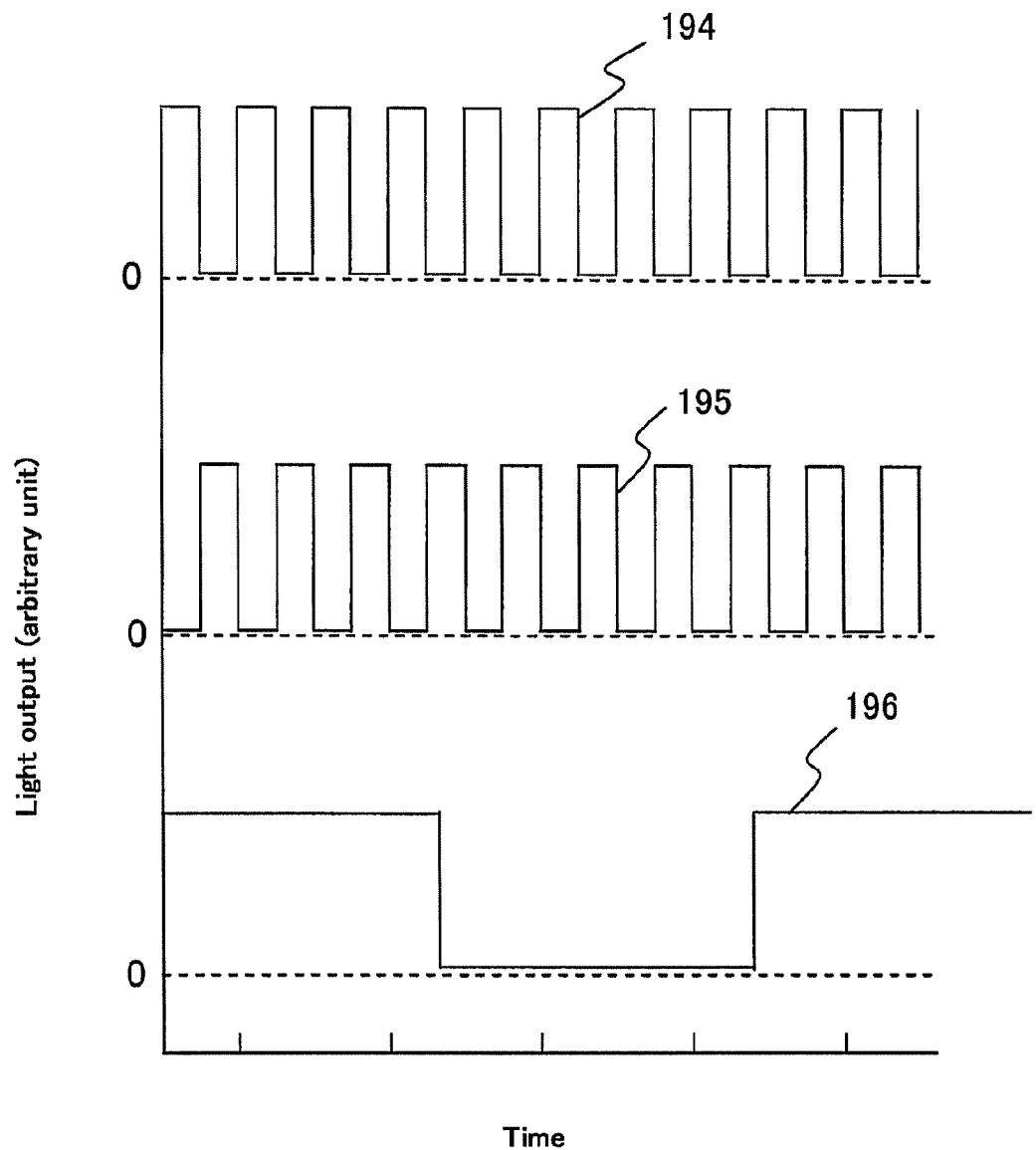
FIG. 16 is an explanatory view showing the photoacoustic signal in the embodiment.

FIG. 16 is a view showing a blood constituent computation method according to the second embodiment. The measuring procedure in the second embodiment will be described in detail with reference to FIG. 15. The first light source 101 is intensity-modulated by the oscillator 103 through the drive circuit 102, and the first light source 101 emits the light having an output waveform 194 with the wavelength $\lambda_1$ as shown in the upper part of FIG. 16. On the other hand, the second light source 105 is intensity-modulated in synchronization with the first light source 101. The second light source 105 is modulated into the reverse phase with respect to the first light source 101 by the 180°-phase shifter 119, and thereby the second light source 105 emits the light having an output waveform 195 with the wavelength λ2 as shown in the intermediate portion of FIG. 16. The third light source 106 is intensity-modulated in the frequency in which the oscillation frequency of the oscillator 103 is divided by the frequency divider 118, and the third light source 106 is intensity-modulated in synchronization with the oscillator 103. The third light source 106 emits the light having an output waveform 196 with the wavelength $\lambda_3$ as shown in the lower part of FIG. 16.

Figure 17:
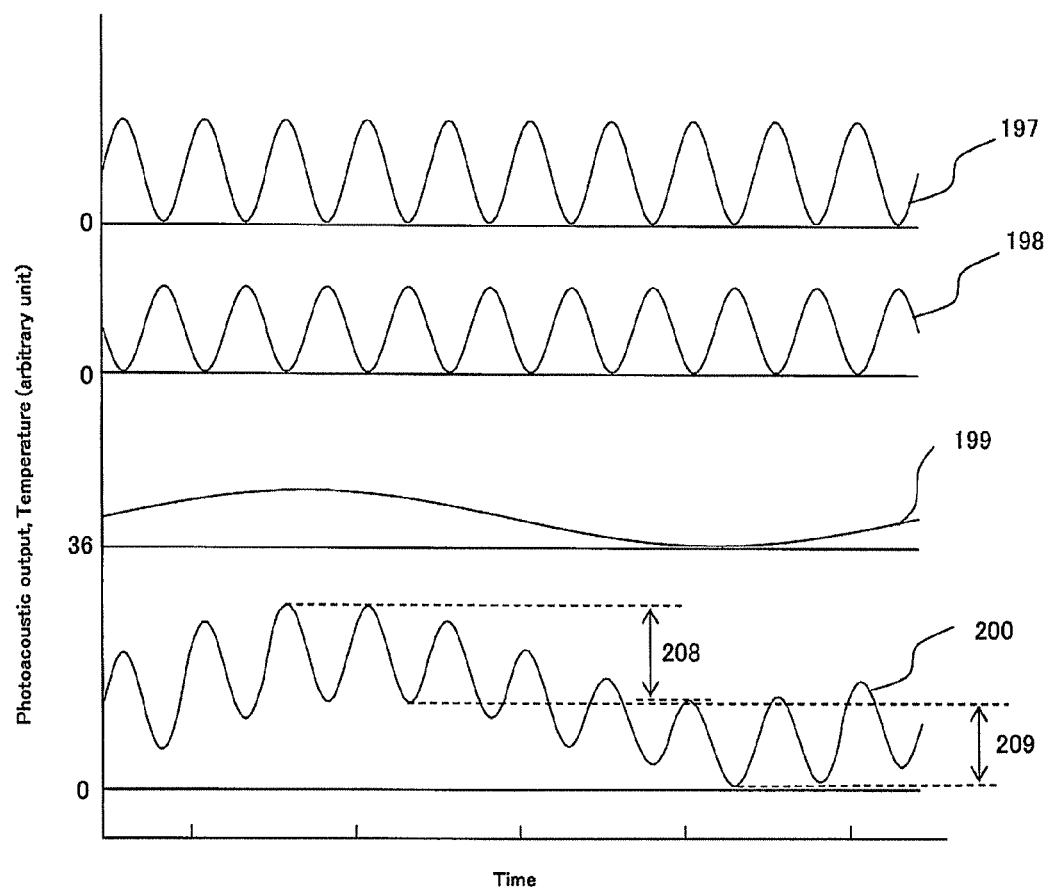
FIG. 17 is an explanatory view showing the photoacoustic signal in the embodiment.

FIG. 17 is a view showing the photoacoustic signal measured by the second embodiment. The photoacoustic signal measured in the second embodiment will be described with reference to FIG. 15. The two light beams having the mutually different wavelengths are multiplexed by the coupler 120, and the living body test region 111 is irradiated with the multiplexed light. At this point, it is assumed that each of the light beams independently generates the acoustic wave. This is because the linear superposition of the acoustic waves is already secured by the linearity of the Helmholtz equation. Accordingly, an photoacoustic signal 197 is generated by the first light source (wavelength $\lambda_1$) as shown in the first stage of FIG. 17 and an photoacoustic signal 198 is generated by the second light source (wavelength $\lambda_2$) as shown in the second stage of FIG. 17. Further, a temperature change 199 is generated by the third light source (wavelength $\lambda_3$) as shown in the third stage of FIG. 17. Therefore, the photoacoustic signal is detected as acoustic pressure by the ultrasonic detector 121, and the photoacoustic signal passes through the filter 122. A summation 200 of the photoacoustic signal receives the modulation shown in the fourth stage of FIG. 17.

$\Delta s_1$:208 is obtained from the difference between a first peak value and a second peak value in the summation 200 of the detected photoacoustic signal. $\Delta s_2$:209 is obtained from the difference between a first valley value and a second valley value in the summation 200 of the detected photoacoustic signal, and the constituent concentration M can be computed from the formula (17). Alternately, because the signal amplitude in the temperature rise corresponds to $As_1 - As_2$ and the signal amplitude in the temperature fall corresponds to $s_1 - s_2$, $\Delta s_1 - \Delta s_2$ can be obtained by taking the difference between the signal amplitude in the temperature rise and the signal amplitude in the temperature fall. Alternately, there is also a method of measuring the photoacoustic signal under the irradiation having the wavelength $\lambda_1$ or $\lambda_2$ in order to obtain the signals $\Delta s_1$ and $\Delta s_2$. In this case, the output of the second light source 105 is set to zero while the waveform of the first light source 101 is maintained.

This can be realized by blocking the light outputted from the first light source 101 or second light source 105 with a mechanical shutter before the input to the coupler 120 or by decreasing the output of the drive circuit 102 or drive circuit 116 below the oscillation threshold of the first light source 101 or second light source 105.

As described above, the third light source having the wavelength in which the hemoglobin of the blood constituent existing only in the blood exhibits the characteristic absorption with respect to the first light source and the second light source is added to perform the measurement using the modulation frequency in which the photoacoustic signal is not generated. Therefore, the temperature rise is generated in the region where the blood density is high by the blood absorption, and the photoacoustic signal generated from the change in sound velocity is increased. As a result, the change in photoacoustic signal corresponds to the temperature change of the blood, and the photoacoustic signal generated in the blood region can be increased. Accordingly, the temperature change can separately be generated only in the blood region without directly imparting the pressure to the living body, so that the blood region can efficiently be determined. The second embodiment is a technique of being able to reproducing the separation of the blood region and the non-blood region in the noninvasive manner.

Although the living body blood constituent concentration measuring apparatus and living body control method of blood constituent concentration measuring apparatus are described in the second embodiment, the second embodiment can also applied to the liquid instead of the living body. That is, the blood constituent concentration measuring apparatus and control method of blood constituent concentration measuring apparatus according to the second embodiment can also be realized for the measuring objects other than the living body. In this case, when the two wavelengths having the same absorption coefficient for the liquid and the different absorption coefficients for the object material are used, the constituent in the liquid can be detected without interruption of the absorption of the liquid. In the above embodiment and examples, fruit is placed instead of the living body test region, the liquid constituent concentration measuring apparatus and the control method of liquid constituent concentration measuring apparatus function as the fruit sugar content meter. This is because the sucrose and fruit sugar, which are of the sugar constituent of the fruit, has the absorption in the wavelength similar to the glucose which is of the blood sugar constituent. Thus, the measuring apparatus and measuring apparatus controlling method according to the first embodiment could clearly be applied to various objects without departing from the spirit of the first embodiment.

EXAMPLES

Specific examples in the second embodiment will be described below.

First Example

Figure 18:
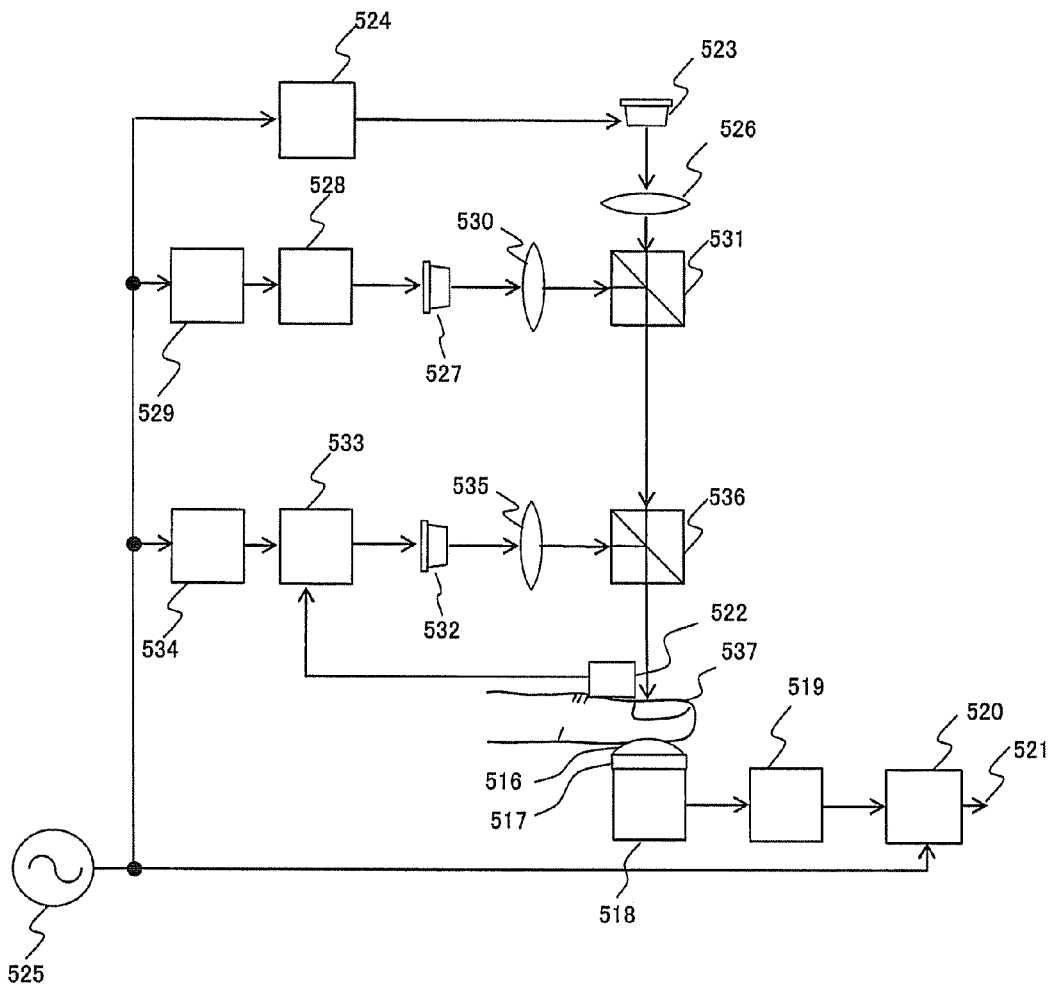
FIG. 18 is an explanatory view showing an example of the blood constituent concentration measuring apparatus according to the embodiment.

FIG. 18 shows configurations of the blood constituent concentration measuring apparatus and control method of blood constituent concentration measuring apparatus according to the first example. In FIG. 18, the numeral 523 designates a first semiconductor light source, the numeral 524 designates a drive current source, the numeral 525 designates an oscillator, the numeral 526 designates a lens, the numeral 527 designates a second semiconductor light source, the numeral 528 designates a drive current source, the numeral 529 designates a 180°-phase shifter, the numeral 530 designates a lens, the numeral 531 designates a coupler, the numeral 532 designates a third semiconductor light source, the numeral 533 designates a drive current source, the numeral 534 designates a frequency divider, the numeral 535 designates a lens, the numeral 536 designates a coupler, the numeral 537 designates a living body test region, the numeral 516 designates an acoustic lens, the numeral 517 designates an acoustic matching device, the numeral 518 designates an ultrasonic detector, the numeral 519 designates a high pass filter, the numeral 520 designates a synchronous detection amplifier, the numeral 521 designates a photoacoustic signal output terminal, and the numeral 522 designates a temperature measurement device.

In FIG. 18, the oscillator 525 oscillates at a constant frequency to determine the frequency in which the first semiconductor light source 523 and the second semiconductor light source 527 are intensity modulated. The frequency of the signal from the oscillator 525 is divided by the frequency divider 534, and thereby the third semiconductor light source 532 periodically oscillates at intervals longer than the repetition interval of the constant frequencies in which the first semiconductor light source 523 and the second semiconductor light source 527 are intensity modulated.

The signal from the oscillator 525 is inputted to the drive current source 524, and the drive current source 524 drives the first semiconductor light source 523. The signal from the oscillator 525 is inputted to the 180°-phase shifter 529, and the signal is reversed.

The reversed signal is inputted to the drive current source 528, and the drive current source 528 drives the second semiconductor light source 527. The first semiconductor light source 523 and the second semiconductor light source 527 are intensity-modulated using the signals having the same modulation frequency and reverse phases.

The first semiconductor light source 523, the second semiconductor light source 527, the third semiconductor light source 532 are driven by the drive current source 524, the drive current source 528, and the drive current source 533 respectively. The first semiconductor light source 523, the second semiconductor light source 527, the third semiconductor light source 532 output the modulated light beams having the predetermined wavelengths respectively. The light from the first semiconductor light source 523 is converted into the beam by the lens 526, the light from the second semiconductor light source 527 is converted into the beam by the lens 530, and the beams are multiplexed into one beam by the coupler 531. The light from the third semiconductor light source 532 is converted into the beam by the lens 535, and the coupler 536 further multiplexes the beam and the beam from the coupler 531. The living body test region 537, which is of the test subject, is irradiated with multiplexed beam. As described above, multiplexing the light beam from the first light source 523, the light beam from the second light source 527, and the light beam from the third semiconductor light source 532 can also be applied in the first embodiment and the later-mentioned third embodiment, fourth embodiment, fifth embodiment, and sixth embodiment in addition to the first example.

The temperature measurement device 522 is placed near the living body test region 537 irradiated with the output light of the coupler 536, the temperature change of the living body test region 537 generated by the light of the third semiconductor light source 532 is detected, the output of the temperature measurement device 522 is inputted to a control terminal of the drive current source 533, and drive current of the drive current source 533 is adjusted such that the temperature change of the living body test region 537 becomes the desired value.

The acoustic lens 516, the acoustic matching device 517, and the ultrasonic detector 518 are placed while coming into contact with the surface opposite to the surface of the living body test region 537 irradiated with the light beam from the coupler 536. The acoustic lens 516 focuses the acoustic wave, i.e., the photoacoustic signal generated in the living body test region 537, and the acoustic lens 516 efficiently transmits the photoacoustic signal to the ultrasonic detector 518 through the acoustic matching device 517. The acoustic matching device 517 enhances the transmission efficiency between the acoustic lens 516 and the ultrasonic detector 518. The ultrasonic detector 518 receives the photoacoustic signal generated in the living body test region 537, and the ultrasonic detector 518 converts the photoacoustic signal into the electric signal proportional to the acoustic pressure to output the electric signal. The high pass filter 519 passes the signal having the same frequency as the oscillation frequency of the oscillator 525. The synchronous detection amplifier 520 performs the synchronous detection of the signal inputted from the high pass filter 519 using the synchronous signal inputted from the synchronous signal input terminal, and the synchronous detection amplifier 520 outputs the amplitude of the synchronous-detected photoacoustic signal to the photoacoustic signal output terminal 521.

In the above configuration, the wavelength of the first semiconductor light source 523 is set at 1380 nm, the wavelength of the second semiconductor light source 527 is set at 1608 nm, and the wavelength of the third semiconductor light source 532 is set at 800 nm. The first semiconductor light source 523 and the second semiconductor light source 527 are intensity-modulated in the modulation frequency of 200 kHz. The temperature rise is 2° C. or less which is not harmful to the human body. Accordingly, the maximum allowable temperature is 39° C. when the initial temperature is set at 37° C. For example, in consideration of a thermal diffusion coefficient of the living body, in order to generate the temperature modulation in the range of 0.1 to 0.2° C. in the living body, a frequency dividing rate of the frequency divider is set such that the modulation frequency of the third semiconductor light source 532 is set to 100 Hz or less. Because the modulation frequency which generates the desired temperature change depends on the wavelength and the beam diameter of the light source, it is necessary that the adjustments including the light source output are performed while a temperature measurement device and the photoacoustic signal intensity are observed. However, in order to shorten the measurement time to the minimum, it is effective that the output light of the third semiconductor light source 532 is coaxial with the output light beams of the first semiconductor light source 523 and second semiconductor light source 527 to select and adjust the lens 535 such that the beam diameters are equal to one another. In consideration of the above conditions, the light source output is set at 5 mW. The lens 526, the lens 530, and the lens 535 are adjusted to set the beam diameters at 3 mm respectively. Equalizing the beam diameters of the first semiconductor light source 523 and second semiconductor light source 527 can also be applied in the first embodiment and the later-mentioned third embodiment, fourth embodiment, fifth embodiment, and sixth embodiment in addition to the second embodiment.

The photoacoustic signal from the living body, which is generated by irradiating the living body test region 537 with the light reaches the ultrasonic detector 518 through the acoustic lens 516 and the acoustic matching device 517. The acoustic lens 516, which focuses the ultrasonic wave into a central portion of the ultrasonic detector 518, is made of a material having the acoustic impedance close to the living body. For example, the acoustic lens 516 is made of silicone. The acoustic matching device 517 is made of the material having the acoustic impedance which is substantially located at the midpoint between the acoustic impedances of the acoustic lens 516 and ultrasonic detector 518. For example, the acoustic matching device 517 is made of acryl. The ultrasonic detector 518 is a piezoelectric device or a capacitor microphone which is designed to have a natural frequency similar to the modulation frequencies of the first semiconductor light source 523 and the second semiconductor light source 527. The photoacoustic signal is converted into the electric signal by the ultrasonic detector 518, and the amplitude of the ultrasonic wave is detected by the synchronous detection amplifier 520.

When the first semiconductor light source 523 is blocked, namely, in the case of only the second semiconductor light source 527, the output level of the synchronous detection amplifier 520 is about 20 μV. When the first semiconductor light source 523 and the second semiconductor light source 527 simultaneously emit the light beams while the third semiconductor light source 532 is blocked, the output level of the synchronous detection amplifier 520 is about 5 nV. Further, the third semiconductor light source 532 is added, and the signal is detected while the temperature modulation is performed. The output level of the synchronous detection amplifier 520 is 5.37 nV in the temperature rise. The output level of the synchronous detection amplifier 520 is 5.33 nV in the temperature fall.

$\Delta s_1 - \Delta s_2$ in the formula (18) becomes 42.1 pV from the difference between the output levels. $\Delta s_2$ of 60.3 nV is determined by reading the difference between the valley value in the temperature rise and the valley value in the temperature fall using, e.g., an oscilloscope. Thus, the glucose concentration M of 3 mM (50 mg/dL) is determined from the formula (18) using the already known specific absorbance value 0.114 $M^{-1}$ in 1608 nm.

The blood constituent concentration measurement described in the first example is the forward propagation type in which the photoacoustic signal is measured in the surface opposite to the surface irradiated with the light with respect to the living body test region 537. On the other hand, the rearward propagation type in which the photoacoustic signal is measured in the same surface as the surface irradiated with the light with respect to the living body test region 537 can also be configured, and the operation of the rearward propagation type is similar to the frontward propagation type.

Although the living body blood constituent concentration measuring apparatus and living body control method of blood constituent concentration measuring apparatus are described in the first example, the first example can also applied to the liquid instead of the living body. That is, the blood constituent concentration measuring apparatus and control method of blood constituent concentration measuring apparatus according to the first example can also be realized for the measuring objects other than the living body. In this case, when the two wavelengths having the same absorption coefficient for the solvent and the different absorption coefficients for the constituent in the liquid are used, the constituent in the liquid can be detected without interruption of the absorption of the solvent.

Second Example

Figure 19:
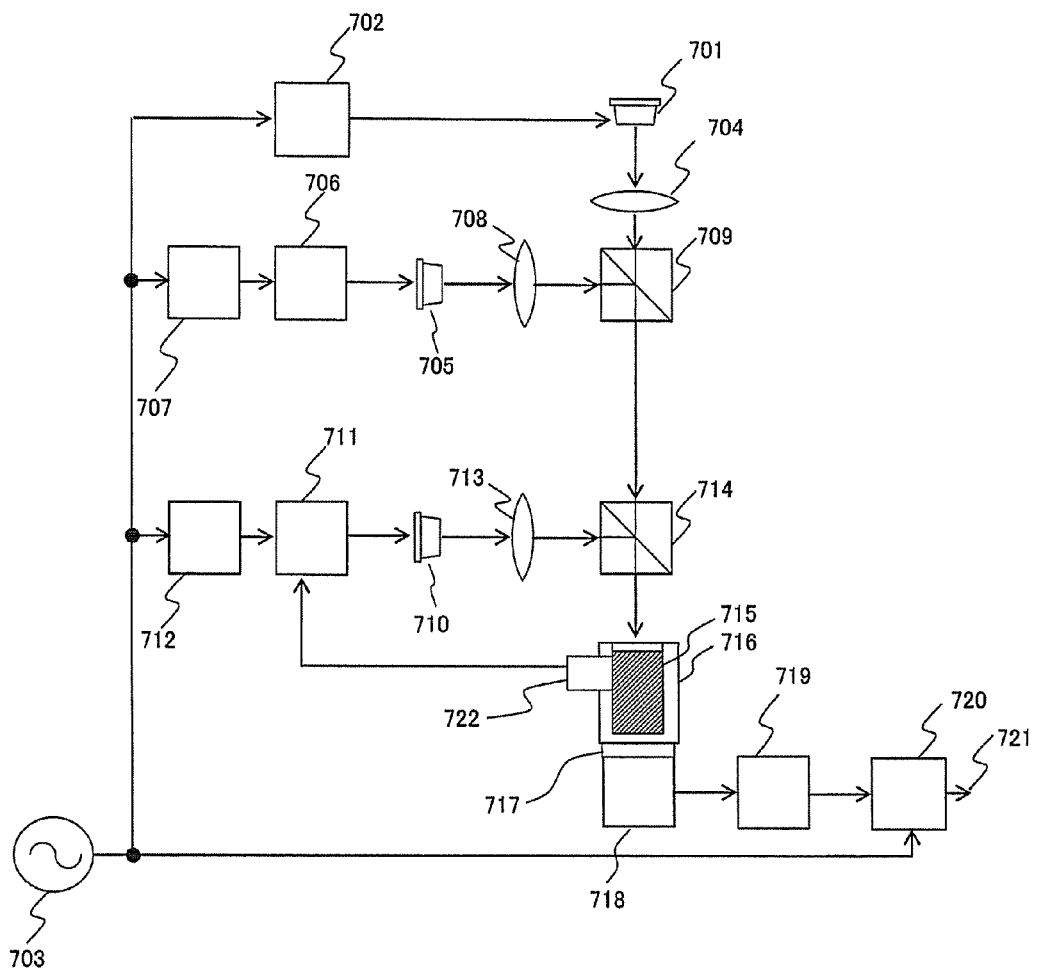
FIG. 19 is an explanatory view showing an example of the blood constituent concentration measuring apparatus according to the embodiment.

FIG. 19 shows a second example in which the inventions of blood constituent concentration measuring apparatus and the control method of blood constituent concentration measuring apparatus according to the second embodiment is used for liquid constituent analysis. Liquid foods and beverages to which sugars are added can be cited as an example of the liquid sample. In FIG. 19, the numeral 701 designates a first semiconductor light source, the numeral 702 designates a drive current source, the numeral 703 designates an oscillator, the numeral 704 designates a lens, the numeral 705 designates a second semiconductor light source, the numeral 706 designates a drive current source, the numeral 707 designates a 180°-phase shifter, the numeral 708 designates a lens, the numeral 709 designates a coupler, the numeral 710 designates a third semiconductor light source, the numeral 711 designates a drive current source, the numeral 712 designates a frequency divider, the numeral 713 designates a lens, the numeral 714 designates a coupler, the numeral 715 designates a liquid sample, the numeral 716 designates a sample cell, the numeral 717 designates an acoustic matching device, the numeral 718 designates an ultrasonic detector, the numeral 719 designates a high pass filter, the numeral 720 designates a synchronous detection amplifier, the numeral 721 designates a photoacoustic signal output terminal, and the numeral 722 designates a temperature measurement device.

For the purpose of avoidance of overlap, the components in the second example different from the first example of the blood constituent concentration measuring apparatus and control method of blood constituent concentration measuring apparatus shown in FIG. 18 will be mainly described.

The liquid sample 715 is irradiated with the light multiplexed by the coupler 714. The temperature measurement device 722 is placed in the sample cell 716 near the region irradiated with the output light of the coupler 714, and the output terminal of the temperature measurement device 722 is connected to the control terminal of the drive current source 711 through the signal line. The temperature measurement device 722 has the function of measuring the temperature of the liquid sample 715 to output the measurement result to the output terminal in the form of the electric signal.

The acoustic matching device 717 is placed while coming into contact with the surface opposite to the surface of the sample cell 716 irradiated with the output light of the coupler 714. The ultrasonic detector 718 is placed through the acoustic matching device 717. The acoustic matching device 717 has the function of enhancing the photoacoustic signal transmission efficiency between the sample cell 716 and the ultrasonic detector 718.

In the second example, the measuring object is a sugar concentration contained in a food solution in which a fat content and water are mixed together. Because the sugar concentration contained only in the fat content of the mixed solution in which the fat content and water are mixed, in FIG. 19, the wavelength of the first semiconductor light source 701 is set at 1380 nm, the wavelength of the second semiconductor light source 705 is set at 1608 nm, and the wavelength of the third semiconductor light source 710 is set at 1710 nm in which the fat content exhibits the remarkable absorption.

The modulation frequencies of the first semiconductor light source 701 and the second semiconductor light source 705 are set at 200 kHz. In consideration of a thermal diffusion coefficient of liquid, the frequency dividing rate of the frequency divider 712 is set such that the temperature modulation is generated in the range of 0.1 to 0.2° C. in the liquid, and the modulation frequency of the third semiconductor light source 710 is set to 100 Hz or less. Actually, because the modulation frequency which generates the desired temperature change depends on the wavelength and the beam diameter of the light source, the adjustments including the light source output is performed while the temperature measured by the temperature measurement device 722 and the photoacoustic signal intensity are observed.

In order to shorten the measurement time, it is effective that the output light of the third semiconductor light source 710 is coaxial with the output light beams of the first semiconductor light source 701 and the second semiconductor light source 705 to select and adjust the lens 713 such that the beam diameters are equal to one another.

In consideration of the above conditions, the light source outputs of the first semiconductor light source 701, the second semiconductor light source 705, and the third semiconductor light source 710 are set at 12 mW. The lens 704, the lens 708, and the lens 713 are adjusted to set the beam diameters of the first semiconductor light source 701, the second semiconductor light source 705, and the third semiconductor light source 710 at 4 mm respectively.

When the liquid sample 715 is irradiated with the irradiation light beams from the first semiconductor light source 701, the second semiconductor light source 705, and the third semiconductor light source 710, the acoustic wave, i.e., the photoacoustic signal generated in the liquid sample 715 reaches the ultrasonic detector 718 through the sample cell 716 and the acoustic matching device 717. The acoustic matching device 717 is made of the material such as aluminum having the acoustic impedance which is substantially located at the midpoint between the acoustic impedances of the sample cell 716 such as glass and the ultrasonic detector 718 such as ceramic.

An acoustic matching agent is applied between the sample cell 716 and the acoustic matching device 717 and between the acoustic matching device 717 and the ultrasonic detector 718 to reduce the influence of the reflection due to the existence of an air layer. The ultrasonic detector 718 is the piezoelectric device or capacitor microphone which is designed to have the natural frequency similar to the modulation frequencies of the first semiconductor light source 701 and the second semiconductor light source 705. The photoacoustic signal is converted into the electric signal by the ultrasonic detector 718, and the electric signal passes through the high pass filter 719. At this point, the blocking frequency and the time constant are set such that the electric signal is not attenuated near 200 kHz, but attenuated in 1 kHz by 20 dB or more.

The electric signal outputted from the high pass filter 719 is detected by the synchronous detection amplifier 720. When the output of the first semiconductor light source 701 is blocked, namely, in the case of only the second semiconductor light source 705, the output of the synchronous detection amplifier 720 is about 120 RV. When the first semiconductor light source 701 and the second semiconductor light source 705 simultaneously emit the light beams while the output of the third semiconductor light source 710 is blocked, the obtained output of the synchronous detection amplifier 720 is about 12 nVp-p. Further, the third semiconductor light source 710 is added, and the temperature modulation is performed. The output of the synchronous detection amplifier 720 is 4.33 μVp-p in the temperature rise. The output of the synchronous detection amplifier 720 is 4.36 μVp-p in the temperature fall. In the formula (18), $\Delta s_1 - \Delta s_2$ becomes 30 nV from the difference between the outputs.

In the second example, $\Delta s_2$ of 5.4 μV is determined by reading the difference between the valley value in the temperature rise and the valley value in the temperature fall using, e.g., the oscilloscope.

As a result, the glucose concentration M of 45 mM (750 mg/dL) is determined from the formula (18) using the already known specific absorbance value 0.114 $M^{-1}$ in the wavelength of 1608 nm.

The blood constituent concentration measurement described in the second example is the forward propagation type in which the photoacoustic signal is measured in the surface opposite to the light irradiation surface with respect to the liquid sample 715. On the other hand, the rearward propagation type in which the photoacoustic signal is measured in the same surface as the surface irradiated with the light with respect to the liquid sample 715 can also be configured, and the operation of the rearward propagation type is similar to the frontward propagation type.

In the above configuration of the invention in the embodiment and examples, the fruit is placed instead of the liquid sample, the liquid constituent concentration measuring apparatus functions as the fruit sugar content meter. This is because the sucrose and the fruit sugar, which are of the sugar constituent of the fruit, has the absorption in the wavelength similar to the glucose which is of the blood sugar constituent.

Third Embodiment

A blood constituent concentration measuring apparatus of a third embodiment is a blood constituent concentration measuring apparatus including light generating means for generating light; frequency sweep means for sweeping a modulation frequency, the light generated by the light generating means being modulated in the modulation frequency; light modulation means for electrically intensity-modulating the light using a signal from the frequency sweep means, the light being generated by the light generating means; light outgoing means for outputting the intensity-modulated light toward the living body; acoustic wave detection means for detecting an acoustic wave which is generated in the living body by the outputted light; and integration means for integrating the acoustic wave in a swept modulation frequency range, the acoustic wave being detected by the acoustic wave detection means.

The blood constituent concentration measuring apparatus according to the third embodiment will be described with reference to FIG. 20. A configuration example of the blood constituent concentration measuring apparatus of the third embodiment shown in FIG. 20 includes a light source 112 which is of the light generating means, a lens 99 which is of the light outgoing means, a drive circuit 104 and an oscillator 103 which are of the modulation means, a control circuit 125 which is of the frequency sweep means, an acoustic coupler 126, an ultrasonic detector 127, and a phase sensitive amplifier 128 which are of the acoustic wave detection means, and a computing device 129 which is of the integration means.

The oscillator 103 is connected to the drive circuit 104, the phase sensitive amplifier 128, and the control circuit 125 through the signal lines. The oscillator 103 transmits the oscillation signal to the drive circuit 104 and the phase sensitive amplifier 128 respectively, and the oscillator 103 receives the signal which controls the sweep of the oscillation frequency from the control circuit 125.

The drive circuit 104 receives the signal transmitted from the oscillator 103. The drive circuit 104 supplies the drive electric power to the light source 112, connected to the drive circuit 104 through the signal line, to cause the light source 112 to emit the light. The drive circuit 104 intensity-modulates the light outputted from the light source 112 in synchronization with the oscillation frequency of the oscillator 103. The light wavelength outputted from the light source 112 is set at the wavelength in which the blood constituent of the measuring object in the living body exhibits the absorption.

The light emitted from the light source 112 passes through the lens 99, a predetermined position of the living body test region 110 is irradiated with the light, and the photoacoustic signal is generated in the living body test region 110.

The ultrasonic detector 127 detects the acoustic wave generated in the living body test region 110 through the acoustic coupler 126, the ultrasonic detector 127 converts the acoustic wave into the electric signal proportional to the magnitude of the detected acoustic wave, and the ultrasonic detector 127 transmits the electric signal to the phase sensitive amplifier 128 connected to the ultrasonic detector 127 through the signal line. At this point, one of surfaces of the acoustic coupler 126 is in contact with the living body test region 110, and the other surface is in contact with the ultrasonic detector 127, and thereby the acoustic coupler 126 has the function of efficiently transmitting the photoacoustic signal generated in the living body test region 110 to the ultrasonic detector 127.

The phase sensitive amplifier 128 receives the signal transmitted from the oscillator 103 to form the synchronous signal for the synchronous detection, and the phase sensitive amplifier 128 receives the electric signal proportional to the magnitude of the photoacoustic signal transmitted from the ultrasonic detector 127. The phase sensitive amplifier 128 performs the synchronous detection, the amplification, and the filtering to the electric signal, and the phase sensitive amplifier 128 transmits the electric signal to the computing device 129 connected to the phase sensitive amplifier 128 through the signal line.

The computing device 129 receives the signal transmitted from the phase sensitive amplifier 128, and the computing device 129 integrates the received signal in the oscillation frequency range which is received from the control circuit 125 and swept by the oscillator 103. Then, from the detection result of the integrated photoacoustic signal, the computing device 129 selects the detection value in the resonance frequency in which the detection sensitivity of the ultrasonic detector 127 is increased, and the computing device 129 integrates the selected value. At this point, the blood constituent concentration of the measuring object can be computed from the integrated detection value using the computing device 129 or an external device (not shown).

The computing device 129 receives the signal transmitted from the phase sensitive amplifier 128, the computing device 129 transmits the received signal and the control signal to the control circuit 125 connected to the computing device 129 through the signal line. The control signal controls the oscillator 103 from the oscillation frequency which is swept by the oscillator 103 and received from control circuit 125 such that the oscillation frequency of the oscillator 103, i.e., the sweep range of the modulation frequency includes the range of the change in resonance frequency of the ultrasonic detector 127.

Figure 21:
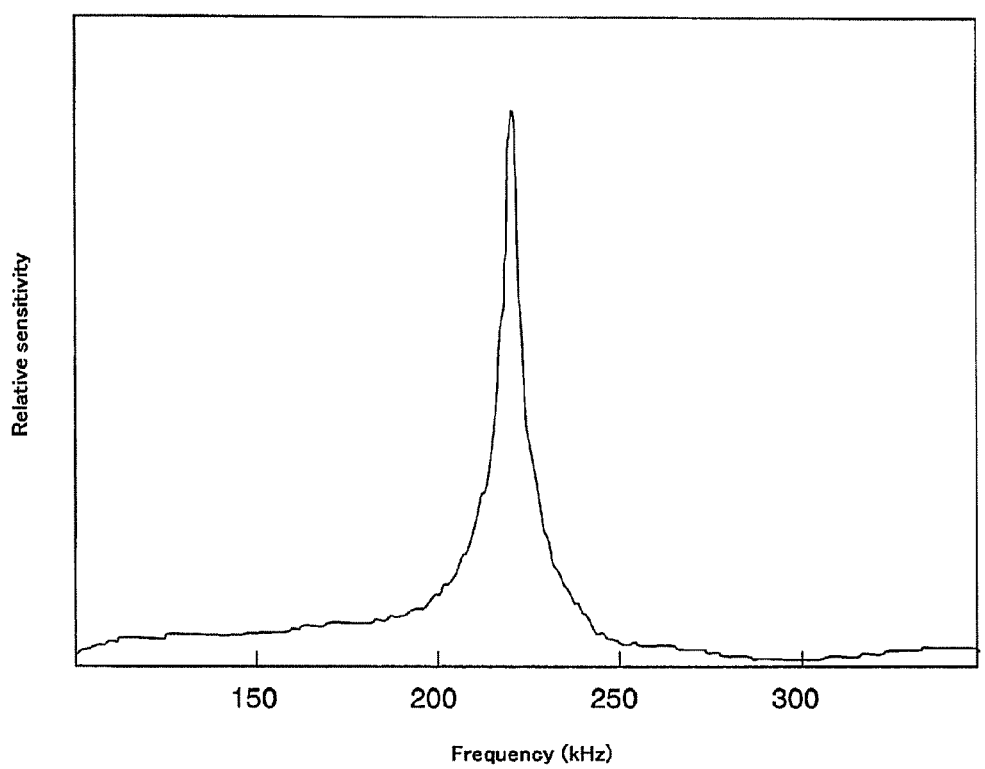
FIG. 21 is an explanatory view showing sensitivity characteristics of an ultrasonic detector according to the embodiment.

In an example of the sensitivity characteristics of the ultrasonic detector shown in FIG. 21, for example, the computing device 129 may transmit the signal for controlling the sweep of the oscillation frequency of the oscillator 103 to the control circuit 125 such that the modulation frequency of the light source 112 is swept in the range broader than the frequency of a half-value width of the resonance characteristics. The computing device 129 may also transmit the signal for controlling the sweep of the oscillation frequency of the oscillator 103 to the control circuit 125 such that the modulation frequency of the light source 112 is swept in the frequency range of a fraction of the peak value of the resonance characteristics, e.g., a half of the peak value. The control circuit 125 controls the oscillation frequency of the oscillator 103 according to the control signal transmitted from the computing device 129.

As described above, in the blood constituent concentration measuring apparatus of the third embodiment, even if the resonance characteristics of the ultrasonic detector 127 is changed, the modulation frequency of the light with which the living body is irradiated is swept to detect the photoacoustic signal in the living body. Therefore, the value, which is detected with high sensitivity in association with the resonance frequency of the ultrasonic detector 127, is selected from the detection values of the photoacoustic signal, and the value is integrated, which allows the blood constituent concentration to be correctly measured.

A control method of blood constituent concentration measuring apparatus of the third embodiment is a control method of blood constituent concentration measuring apparatus sequentially including a light generating procedure in which light generating means generates light; a frequency sweep procedure in which frequency sweep means sweeps a modulation frequency, the light generated in the light generating procedure being modulated in the modulation frequency; a light modulation procedure in which light modulation means electrically intensity-modulates the light using a signal swept in the frequency sweep procedure, the light being generated in the light generating procedure; a light outgoing procedure in which light outgoing means outputs the light toward living body; the light being intensity-modulated in the light modulation procedure; an acoustic wave detection procedure in which acoustic wave detection means detects an acoustic wave, i.e., an photoacoustic signal which is generated in the living body by the light outputted in the light outgoing procedure; and an integration procedure in which integration means integrates the acoustic wave in a swept modulation frequency range, the acoustic wave being detected in the acoustic wave detection procedure.

Figure 20:
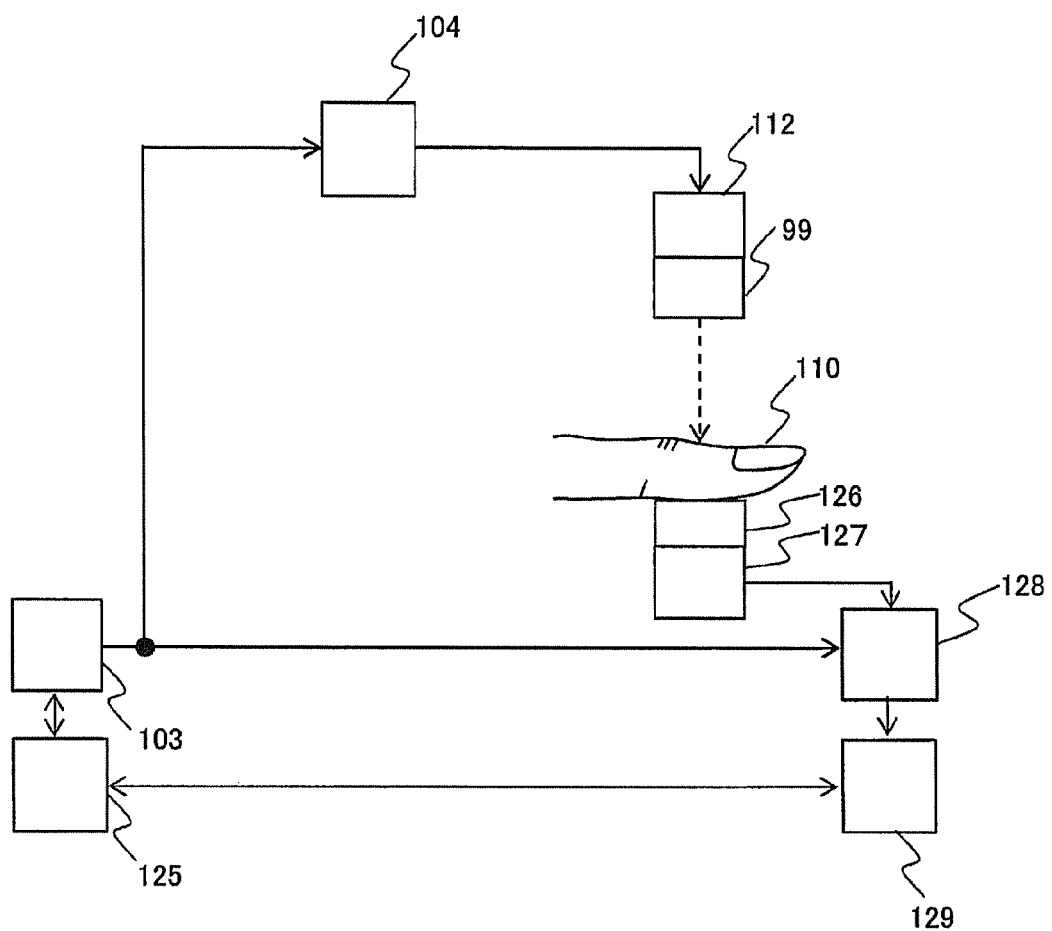
FIG. 20 is an explanatory view showing a configuration of the blood constituent concentration measuring apparatus according to the embodiment.

In the control method of blood constituent concentration measuring apparatus of the third embodiment, the control circuit 125 shown in FIG. 20 controls the frequency, the output of the oscillator 103 which is swept in the oscillation frequency is transmitted to the drive circuit 104, the drive circuit 104 which receives the swept frequency drives the light source 112 including, e.g., the semiconductor laser to cause to generate the light, and the light is intensity-modulated. In this case, the light source 112 generates the light, and the generated light can be intensity-modulated by the swept frequency. At this point, the light wavelength generated by the light source 112 is set at the wavelength in which the blood constituent of the measuring object exhibits the absorption.

As described above, the living body is irradiated with the intensity-modulated light, the photoacoustic signal generated in the living body by the intensity-modulated light is detected by the ultrasonic detector 127 through the acoustic coupler 126 shown in FIG. 20, the photoacoustic signal is converted into the electric signal proportional to the magnitude of the photoacoustic signal, the synchronous detection, the amplification, and the filtering are performed to the electric signal by the phase sensitive amplifier 128, the electric signals are integrated for a predetermined time and averaged, and the electric signal is transmitted to the computing device 129.

As described above, the detected photoacoustic signals are integrated as the electric signals proportional to the pressure in the modulation frequency range which is swept by the computing device 129 shown in FIG. 20, the detection value or frequency in the resonance frequency where the detection sensitivity is increased is selected from the integrated electric signals proportional to the magnitude of the photoacoustic signal, and the integration is performed in the selected frequency range to compute the blood constituent concentration.

According to the above method, even if the resonance frequency of the ultrasonic detector 127, which detects the photoacoustic signal in the living body, is changed, the detection values of the photoacoustic signals can be selected and integrated in the frequency corresponding to the resonance frequency of the ultrasonic detector 127 to compute the blood constituent concentration. Therefore, the blood constituent concentration can correctly be measured.

A blood constituent concentration measuring apparatus of the third embodiment is a blood constituent concentration measuring apparatus including light generating means for generating two light beams having different wavelengths; frequency sweep means for sweeping a modulation frequency, the light generated by the light generating means being modulated in the modulation frequency; light modulation means for electrically intensity-modulating each of the two light beams having the mutually different wavelengths using signals having reverse phases where the signals are swept in the frequency sweep means; light outgoing means for multiplexing into one light flux to output the two intensity-modulated light beams having the mutually different wavelengths toward a living body; acoustic wave detection means for detecting an acoustic wave i.e., a photoacoustic signal generated in the living body by the outputted light; and integration means for integrating the acoustic wave in a swept modulation frequency range, the acoustic wave being detected by the acoustic wave detection means.

In the blood constituent concentration measuring apparatus of the third embodiment, the light generating means can set one of the light wavelengths at the wavelength in which the blood constituent exhibits the characteristic absorption, and the light generating means can set the other light wavelength at the wavelength in which the water exhibits the absorption similar to that in one of the light wavelengths.

A configuration of the blood constituent concentration measuring apparatus of the third embodiment will be described with reference to FIG. 22. The blood constituent concentration measuring apparatus of the third embodiment includes a first light source 301 and a second light source 302 which are of the light generating means, a coupler 308 which is of the light outgoing means an oscillator 298, a drive circuit 303, a drive circuit 297, and a 180°-phase shifter 299 which are of the modulation means, a control circuit 300 which is of the frequency sweep means, an acoustic coupler 327, an ultrasonic detector 328, and a phase sensitive amplifier 329 which are of the acoustic wave detection means, and a computing device 330 which is of the integration means.

The oscillator 298 is connected to the drive circuit 303, the 180°-phase shifter 299, the phase sensitive amplifier 329, and the control circuit 300 through the signal lines respectively. The oscillator 298 transmits the oscillation signal to the drive circuit 303, the 180°-phase shifter 299, and the phase sensitive amplifier 329 respectively, and the oscillator 298 receives the signal which controls the sweep of the oscillation frequency from the control circuit 300.

The drive circuit 303 receives the signal transmitted from the oscillator 298. The drive circuit 303 supplies the drive electric power to the first light source 301, connected to the drive circuit 303 through the signal line, to cause the first light source 301 to emit the light. Then, the drive circuit 303 intensity-modulates the light outputted from the first light source 301 in synchronization with the oscillation frequency of the oscillator 298.

The 180°-phase shifter 299 receives the signal transmitted from the oscillator 298, and the 180°-phase shifter 299 transmits the signal in which the 180°-phase change is imparted to the received signal to the drive circuit 297 connected to the 180°-phase shifter 299 through the signal line.

The drive circuit 297 receives the signal transmitted from the 180°-phase shifter 299. The drive circuit 297 supplies the drive electric power to the second light source 302, connected to the drive circuit 297 through the signal line, to cause the second light source 302 to emit the light. The drive circuit 297 intensity-modulates the light outputted from the second light source 302 in synchronization with the signal in which the 180°-phase change is imparted to the oscillation frequency of the oscillator 298. Accordingly, the light beams outputted from the first light source 301 and the second light source 302 are modulated using the opposite-phase signals each other.

Figure 22:
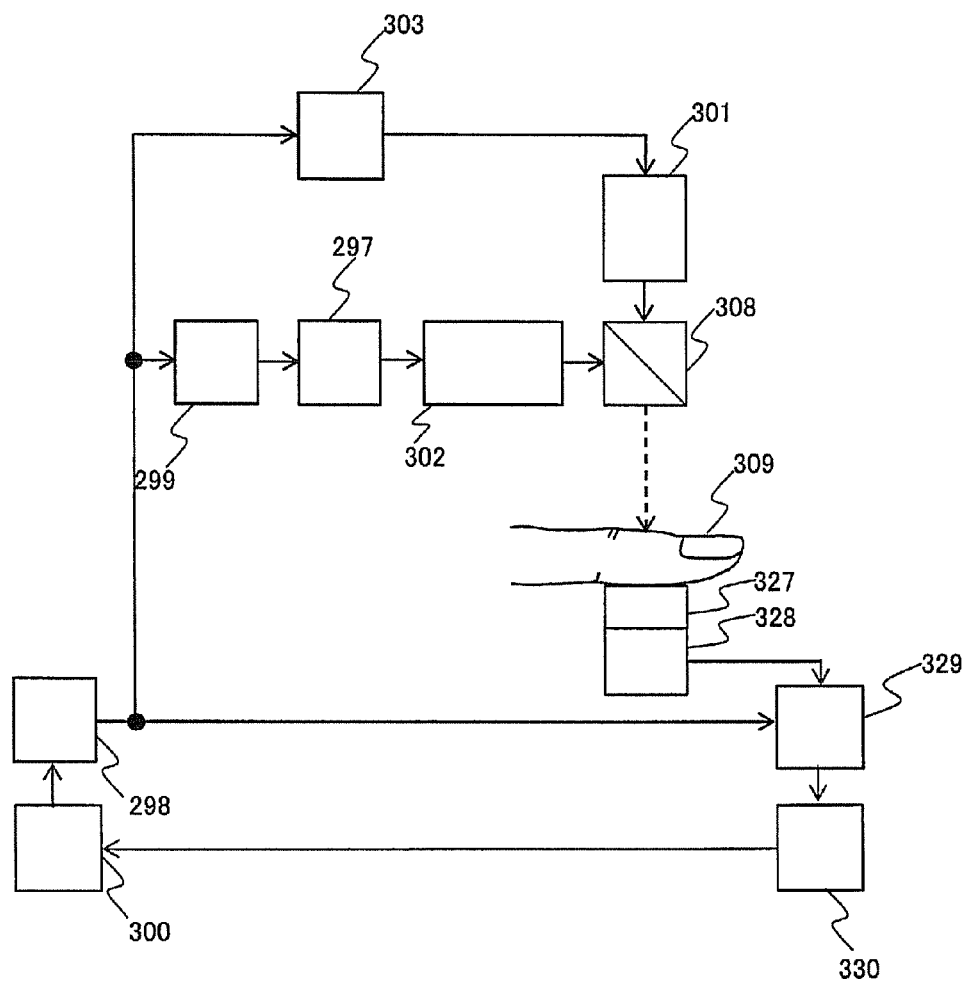
FIG. 22 is an explanatory view showing a configuration of the blood constituent concentration measuring apparatus according to the embodiment.

For the wavelengths of the first light source 301 and second light source 302 shown in FIG. 22, one of the light wavelengths is set at the wavelength in which the blood constituent set as the measuring object exhibits the characteristic absorption, and the other light wavelength is set at the wavelength in which the water exhibits the absorption similar to that in one of the light wavelengths.

The first light source 301 and the second light source 302 emit the light beams having the different wavelengths as described above, the light beams outputted from the first light source. 301 and second light source 302 are inputted to the coupler 308 connected to the first light source 301 and the second light source 302 by the light wave transmission means respectively.

The light beam outputted from the first light source 301 and the light beam outputted from the second light source 302 are inputted to the coupler 308, and the light beams are multiplexed into one light flux. Then, the predetermined position of the living body test region 309 as the test subject is irradiated with the light flux, and the acoustic wave, i.e., the photoacoustic signal is generated in the living body test region 309.

The ultrasonic detector 328 detects the photoacoustic signal generated in the living body test region 309 through the acoustic coupler 327, the ultrasonic detector 328 converts the photoacoustic signal into the electric signal proportional to the magnitude of the photoacoustic signal, and the ultrasonic detector 328 transmits the electric signal to the phase sensitive amplifier 329 connected to the ultrasonic detector 328 through the signal line.

The wavelengths of the first light source 301 and the second light source 302 are set at the light wavelengths in which the difference in absorption exhibited by the blood constituents set as the measuring object is larger than the difference in absorption exhibited by the water. Alternatively, the difference in absorption exhibited by the water may be set to zero, and one of the light wavelengths may be set at the wavelength in which the blood constituent set as the measuring object exhibits the characteristic absorption, and the other light wavelength may be set at the wavelength in which the water exhibits the absorption similar to that in one of the light wavelengths. It is desirable that the wavelengths of the first light source 301 and the second light source 302 are set at the wavelengths in which the difference in absorption exhibited by the blood constituents set as the measuring object is larger than the difference in absorption exhibited by other blood constituents except for the blood constituents set as the measuring object. Setting the wavelengths of the first light source 301 and the second light source 302 at the above values can also be applied in the first embodiment, the second embodiment, and the later-mentioned third embodiment, fourth embodiment, fifth embodiment, and sixth embodiment in addition to the third embodiment.

Because the light beams outputted from the first light source 301 and the second light source 302 are modulated in the reverse phases, the photoacoustic signal generated in the living body test region 309 by the light beam in which the light beams outputted from first light source 301 and the second light source 302 are multiplexed is detected by the ultrasonic detector 328 as the difference in magnitude of the photoacoustic signals. At the stage of the photoacoustic signal, the photoacoustic signal which is generated by the absorptions of the water and the blood constituent set as the measuring object for the multiplexed light with which the living body test region 309 is irradiated and the photoacoustic signal which is generated only by the absorption of the water are superposed to each other in the difference in magnitude of the photoacoustic signals One of the surfaces of the acoustic coupler 327 is in contact with the living body test region 309, the other surface is in contact with the ultrasonic detector 328, and the acoustic coupler 327 has the function of efficiently transmitting the photoacoustic signal generated in the living body test region 309 to the ultrasonic detector 328.

The phase sensitive amplifier 329 receives the signal transmitted from the oscillator 298 to form the synchronous signal for the synchronous detection, and the phase sensitive amplifier 329 receives the electric signal proportional to the magnitude of the photoacoustic signal transmitted from the ultrasonic detector 328. The phase sensitive amplifier 329 performs the synchronous detection, the amplification, and the filtering to the electric signal, and the phase sensitive amplifier 329 transmits the electric signal to the computing device 330 connected to the phase sensitive amplifier 329 through the signal line.

The computing device 330 receives the signal transmitted from the phase sensitive amplifier 329, and the computing device 330 integrates the received signal in the oscillation frequency range which is received from the control circuit 300 and swept by the oscillator 298. Then, from the detection result of the integrated photoacoustic signal, the computing device 330 selects the detection value in the resonance frequency in which the detection sensitivity of the ultrasonic detector 328 is increased, and the computing device 330 integrates the selected value and the blood constituent concentration is computed. At this point, the blood constituent concentration of the measuring object can be computed from the integrated detection value using the computing device 330 or an external device (not shown).

The computing device 330 receives the signal transmitted from the phase sensitive amplifier 329, the computing device 330 transmits the control signal to the control circuit 300 connected to the computing device 330 through the signal line. The control signal controls the oscillator 298 from the received signal and the oscillation frequency which is swept by the oscillator 298 and received from control circuit 300 such that the oscillation frequency of the oscillator 298, i.e., the sweep range of the modulation frequency includes the range of the change in resonance frequency of the ultrasonic detector 328.

In an example of the sensitivity characteristics of the ultrasonic detector shown in FIG. 21, for example, the computing device 330 may transmit the signal for controlling the sweep of the oscillation frequency of the oscillator 298 to the control circuit 300 such that the modulation frequencies of the first light source 301 and the second light source 302 are swept in the range broader than the frequency of a half-value width of the resonance characteristics. The computing device 330 may also transmit the signal for controlling the sweep of the oscillation frequency of the oscillator 298 to the control circuit 300 such that the modulation frequencies of the first light source 301 and the second light source 302 are swept in the frequency range of a fraction of the peak value of the resonance characteristics, e.g., a half of the peak value. The control circuit 300 controls the oscillation frequency of the oscillator 298 according to the control signal transmitted from the computing device 330.

As described above, in the blood constituent concentration measuring apparatus of the third embodiment, the light outputted from the first light source 301 and the light outputted from the second light source 302 are intensity-modulated using the signals having the same frequency. Therefore, in the third embodiment, there is no influence of the unevenness of the frequency characteristics in the measuring system, which becomes troublesome in the conventional technique when the intensity modulation is performed using the signals having the plural frequencies.

As described above, in the blood constituent concentration measuring apparatus of the third embodiment, even if the resonance characteristics of the ultrasonic detector 328 is changed, the modulation frequency of the light with which the living body is irradiated is swept to the photoacoustic signal in the living body. Therefore, the value, which is detected with high sensitivity in association with the resonance frequency of the ultrasonic detector 328, is selected from the detection values of the photoacoustic signal, and the value is integrated, which allows the blood constituent concentration to be correctly measured.

A control method of blood constituent concentration measuring apparatus of the third embodiment is a control method of blood constituent concentration measuring apparatus sequentially including a light generating procedure in which light generating means generates two light beams having different wavelengths; a frequency sweep procedure in which the frequency sweep means sweeps a frequency, the light generated in the light generating procedure being modulated in the frequency; a light modulation procedure in which light modulation means electrically intensity-modulates each of the two light beams having the mutually different wavelengths using signals having the reverse phases, where the signals are swept in the frequency sweep procedure; a light outgoing procedure in which light outgoing means multiplexes into one light flux to output the two intensity-modulated light beams having the mutually different wavelengths toward the living body, which are intensity-modulated in the light modulation procedure; an acoustic wave detection procedure in which acoustic wave detection means detects an acoustic wave i.e., a photoacoustic signal generated in the living body by the light outputted in the light outgoing procedure; and an integration procedure in which integration means integrates the acoustic wave in a swept modulation frequency range, the acoustic wave being detected in the acoustic wave detection procedure.

In the control method of blood constituent concentration measuring apparatus of the third embodiment, the control circuit 300 shown in FIG. 22 controls the frequency, the output of the oscillator 298 which is swept in the oscillation frequency is transmitted to the drive circuit 297 through the drive circuit 303 and 180°-phase shifter 299 respectively, the drive circuit 303 and drive circuit 297 which receive the swept frequency drive the first light source 301 and the second light source 302 to cause to emit the light beams respectively, and the light beams are intensity-modulated. In this case, the first light source 301 and the second light source 302 emit the light beams respectively, and the emitted light beams can be intensity-modulated by the swept frequency.

The wavelengths of the first light source 301 and the second light source 302 are set at the two light wavelengths in which the difference in absorption exhibited by the blood constituents set as the measuring object is larger than the difference in absorption exhibited by the water. Alternatively, the difference in absorption exhibited by the water may be set to zero, and one of the light wavelengths may be set at the wavelength in which the blood constituent set as the measuring object exhibits the characteristic absorption, and the other light wavelength may be set at the wavelength in which the water exhibits the absorption similar to that in one of the light wavelengths. It is desirable that the wavelengths of the first light source 301 and the second light source 302 are set at the wavelengths in which the difference in absorption exhibited by the blood constituents set as the measuring object is larger than the difference in absorption exhibited by other blood constituents except for the blood constituents set as the measuring object. Setting the wavelengths of the first light source 301 and the second light source 302 at the above values can also be applied in the first embodiment, the second embodiment, and the later-mentioned fourth embodiment, fifth embodiment, and sixth embodiment in addition to the third embodiment.

The light beam outputted from the first light source 301 and the light beam outputted from the second light source 302 are inputted to the coupler 308, and the light beams are multiplexed into one light flux. Then, the predetermined position of the living body test region 309 is irradiated with the light flux, and thereby the acoustic wave, i.e., the photoacoustic signal is generated in the living body test region 309.

As described above, the living body is irradiated with the intensity-modulated light beam, and the photoacoustic signal generated in the living body by the intensity-modulated light is detected by the ultrasonic detector 328 through the acoustic coupler 327 shown in FIG. 22, and the photoacoustic signal is converted into the electric signal proportional to the magnitude of the photoacoustic signal. Then, the phase sensitive amplifier 329 performs the synchronous detection, the amplification, and the filtering to the electric signal, the electric signals are integrated and averaged for the predetermined time, and the electric signal is transmitted to the computing device 330.

As described above, the detected photoacoustic signal is integrated as the electric signal proportional to the pressure in the frequency range which is swept by the computing device 330 shown in FIG. 22, the detection value or frequency in the resonance frequency in which the detection sensitivity is increased is selected in the electric signals proportional to the magnitude of the integrated photoacoustic signal, the integration is performed in the selected range, and the blood constituent concentration is computed.

According to the above method, even if the resonance frequency of the ultrasonic detector 328, which detects the photoacoustic signal in the living body, is changed, the detection values of the photoacoustic signals can be selected and integrated in the frequency corresponding to the resonance frequency of the ultrasonic detector 328 to compute the blood constituent concentration. Therefore, the blood constituent concentration can correctly be measured.

A blood constituent concentration measuring apparatus of the third embodiment is a blood constituent concentration measuring apparatus in which the acoustic wave detection means tracks the modulation frequency to detect the acoustic wave, i.e., the photoacoustic signal generated the living body to be measured, the modulation frequency being swept by the frequency sweep means, and the integration means integrates the acoustic wave in the modulation frequency range where the acoustic wave detection means has high detection sensitivity, the photoacoustic signal being detected by the acoustic wave detection means.

The configuration of the blood constituent concentration measuring apparatus of the third embodiment is similar to that of the blood constituent concentration measuring apparatus described with reference to FIGS. 20 and 22.

In the above blood constituent concentration measuring apparatus described with reference to FIGS. 20 and 22, a blood constituent concentration measuring apparatus of the third embodiment is the case, in which the magnitude of the photoacoustic signal detected by the ultrasonic detector 127 or the ultrasonic detector 328 according to the sweep of the modulation frequency is tracked and monitored as the output of the phase sensitive amplifier 128 or the phase sensitive amplifier 329 by the computing device 129 or the computing device 330, the modulation frequency in which the sensitivity of the ultrasonic detector 127 or the ultrasonic detector 328 is increased is searched, and the magnitude of the photoacoustic signal detected in the range of the modulation frequency in which the sensitivity of the ultrasonic detector 127 or the ultrasonic detector 328 is increased is obtained and integrated from the output of the phase sensitive amplifier 128 or the phase sensitive amplifier 329.

As described above, in the blood constituent concentration measuring apparatus of the third embodiment, the magnitude of the photoacoustic signal detected near the modulation frequency in which the sensitivity of the ultrasonic detector 127 and the ultrasonic detector 328 becomes the maximum is obtained and integrated from the output of the phase sensitive amplifier 128 and phase sensitive amplifier 329, and the blood constituent concentration can correctly be measured.

A control method of blood constituent concentration measuring apparatus of the third embodiment is a constituent concentration measuring apparatus controlling method in which the acoustic wave detection procedure is a procedure in which the modulation frequency is tracked to detect the acoustic wave generated in the living body, the modulation frequency being swept in the frequency sweep procedure, and the integration procedure is a procedure in which the acoustic wave is integrated in the modulation frequency range where detection sensitivity of the photoacoustic signal is high in the acoustic wave detection procedure, the acoustic wave being detected in the photoacoustic signal detection procedure.

In the above control method of blood constituent concentration measuring apparatus, the control method of blood constituent concentration measuring apparatus of the third embodiment is the case in which, in the acoustic wave detection procedure, for example, in the blood constituent concentration measuring apparatus described with reference to FIGS. 20 and 22, the ultrasonic detector 127 or the ultrasonic detector 328 detects the acoustic wave according to the sweep of the modulation frequency, in the integration procedure, the magnitude of the photoacoustic signal detected by the ultrasonic detector 127 or the ultrasonic detector 328 is tracked and monitored as the output of the phase sensitive amplifier 128 or the phase sensitive amplifier 329 to search the point of the modulation frequency in which the sensitivity of the ultrasonic detector 127 or the ultrasonic detector 328 is increased by the computing device 129 or the computing device 330, and the magnitude of the photoacoustic signal detected in the modulation frequency range where the ultrasonic detector 127 or the ultrasonic detector 328 has the high detection sensitivity is obtained and integrated from the output of the phase sensitive amplifier 128 or the phase sensitive amplifier 329.

As described above, in the control method of blood constituent concentration measuring apparatus of the third embodiment, the acoustic wave, i.e., the photoacoustic signal generated in the living body by irradiating the living body with the light signal in which the intensity modulation frequency is swept, the modulation frequency corresponding to the resonance frequency in which the sensitivity of the ultrasonic detector is increased is searched from the detected value, and the photoacoustic signal is detected near the modulation frequency corresponding to the resonance frequency in which the sensitivity of the ultrasonic detector becomes the maximum. Therefore, the control method of blood constituent concentration measuring apparatus of correctly measuring the blood constituent can be provided.

A blood constituent concentration measuring apparatus of the third embodiment is a blood constituent concentration measuring apparatus further including blood constituent concentration computation means for computing the blood constituent concentration in the living body from the magnitude of the detected photoacoustic signal.

The configuration of the blood constituent concentration measuring apparatus of the third embodiment is the case in which, for example, similarly to the blood constituent concentration measuring apparatus described with reference to FIGS. 20 and 22, the computing device 129 or the computing device 330 has the function as the blood constituent concentration computation means.

That is, the blood constituent concentration measuring apparatus of the third embodiment is the case in which, in the blood constituent concentration measuring apparatus shown in FIGS. 20 and 22, the computing device 129 or the computing device 330 has the function as the blood constituent concentration computation means for computing the blood constituent concentration according to the predetermined computation method after the signal received from the phase sensitive amplifier 128 or the phase sensitive amplifier 329 is integrated and averaged.

As to the predetermined computation method, for example, numerical data or a theoretical formula indicating the relationship between the blood constituent amount of the measuring object in the living body and the magnitude of the photoacoustic signal generated by irradiating the living body with the light having the wavelength in which the blood constituent of the measuring object exhibits the absorption may be used.

As described above, in the blood constituent concentration measuring apparatus of the third embodiment, the blood constituent concentration can easily be measured by including the blood constituent concentration computation means.

A control method of blood constituent concentration measuring apparatus of the third embodiment is a control method of blood constituent concentration measuring apparatus further including a blood constituent concentration computation procedure of computing the blood constituent concentration in the living body from the magnitude of the photoacoustic signal detected in the acoustic wave detection procedure.

The control method of blood constituent concentration measuring apparatus of the third embodiment is the case where the acoustic wave detection procedure of the control method of blood constituent concentration measuring apparatus further comprises the blood constituent concentration computation procedure, in which the computing device 129 or the computing device 330 of the constituent concentration measuring apparatus described with reference to FIGS. 20 and 22 computes the blood constituent concentration according to the predetermined computation method after the signal received from the phase sensitive amplifier 128 or the phase sensitive amplifier 329 is integrated and averaged.

As to the predetermined computation method, for example, numerical data or the theoretical formula indicating the relationship between the blood constituent amount of the measuring object in the living body and the magnitude of the photoacoustic signal generated by irradiating the living body with the light having the wavelength in which the blood constituent of the measuring object exhibits the absorption may be used.

As described above, in the control method of blood constituent concentration measuring apparatus of the third embodiment, the blood constituent concentration can easily be measured by including the blood constituent concentration computation procedure.

A blood constituent concentration measuring apparatus of the third embodiment further includes recording means for recording the photoacoustic signal detected by the acoustic wave detection means corresponding to the swept modulation frequency.

The configuration of the blood constituent concentration measuring apparatus of the third embodiment is the case in which, for example, in the blood constituent concentration measuring apparatus described with reference to FIGS. 20 and 22, a recorder (not shown) which is of the recording means is connected to the computing device 129 or the computing device 330.

The recorder records the signal corresponding to the modulation frequency. The computing device 129 or the computing device 330 receives the signal from the phase sensitive amplifier 128 or the phase sensitive amplifier 329, and the signal is proportional to the magnitude of the photoacoustic signal generated in the living body test region 110 or the living body test region 309.

In the case where the resonance frequency is changed in the ultrasonic detector 127 or the ultrasonic detector 328, the recording performed by the recorder can determine whether or not the modulation frequency sweep range of the light with which the living body test region 110 or the living body test region 309 is irradiated includes the range where the resonance frequency is changed. The recording performed by the recorder can also determine whether or not the value accurately measured in the modulation frequency corresponding to the resonance frequency is selected from the values of the photoacoustic signals detected by the ultrasonic detector 127 or the ultrasonic detector 328. In addition to the third embodiment, the recording means can also be applied to the first embodiment, the second embodiment, and the later-mentioned fourth embodiment, fifth embodiment, and sixth embodiment.

As described above, in the blood constituent concentration measuring apparatus of the third embodiment, the blood constituent concentration can appropriately be measured by including the recording means.

A control method of blood constituent concentration measuring apparatus according to the third embodiment is a control method of blood constituent concentration measuring apparatus further including a recording procedure in which the photoacoustic signal detected by the acoustic wave detection procedure is recorded corresponding to the swept modulation frequency after the acoustic wave detection procedure.

The control method of blood constituent concentration measuring apparatus of the third embodiment is the case in which, for example, in the control method of blood constituent concentration measuring apparatus described with reference to FIGS. 20 and 22 further includes the recording procedure of recording the signal received by the computing device 129 or the computing device 330 from the phase sensitive amplifier 128 or the phase sensitive amplifier 329 in the recorder (not shown) connected to the computing device 129 or the computing device 330 corresponding to the swept oscillation frequency after the acoustic wave detection procedure of the control method of blood constituent concentration measuring apparatus.

In the case where the resonance frequency is changed in the ultrasonic detector 127 or the ultrasonic detector 328, the recording performed by the recorder can determine whether or not the modulation frequency sweep range of the light with which the living body test region 110 or the living body test region 309 is irradiated includes the range where the resonance frequency is changed. The recording performed by the recorder can also determine whether or not the value accurately measured in the modulation frequency corresponding to the resonance frequency is selected from the values of the photoacoustic signals detected by the ultrasonic detector 127 or the ultrasonic detector 328.

As described above, in the control method of blood constituent concentration measuring apparatus of the third embodiment, the blood constituent concentration can appropriately be measured by including the recording procedure. In addition to the third, embodiment, the recording procedure can also be applied to the first embodiment, the second embodiment, and the later-mentioned fourth embodiment, fifth embodiment, and sixth embodiment.

Fourth Embodiment

Figure 23:
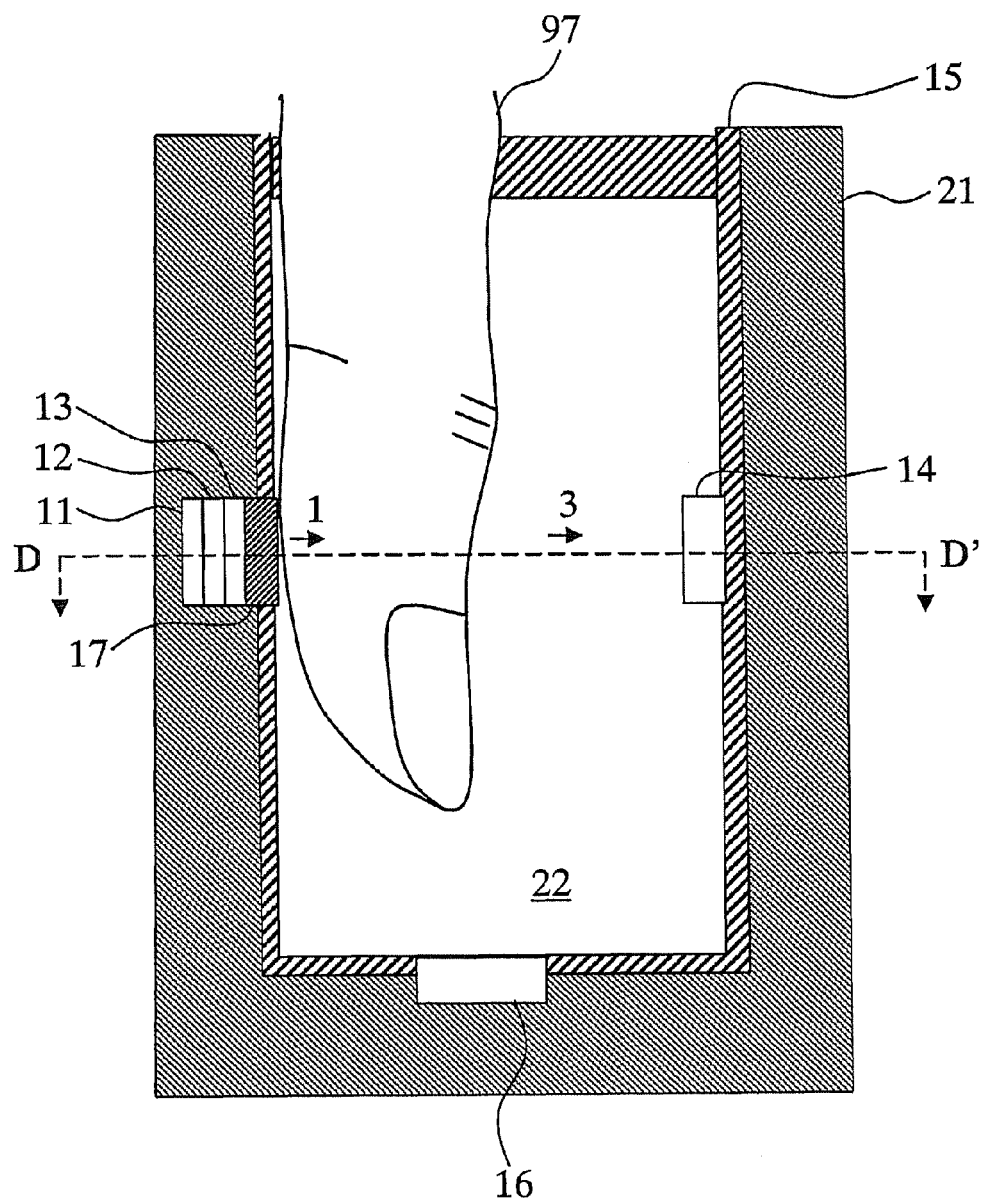
FIG. 23 is a schematic view showing an example of the blood constituent concentration measuring apparatus according to the embodiment.

FIG. 23 is a schematic view showing an example of a blood constituent concentration measuring apparatus according to a fourth embodiment. The blood constituent concentration measuring apparatus shown in FIG. 23 includes a light generation unit 11 which is of the light generating means for generating the light, a light modulation unit 12 which is of the light modulation means for electrically intensity-modulating the light generated by the light generation unit 11 at constant frequency, a light outgoing unit 13 which is of the light outgoing means for outputting intensity modulated light 1 intensity-modulated by the light modulation unit 12 toward the living body test region 97 which is of the test subject, and an ultrasonic detection unit 14 which is of the acoustic wave detection means for detecting an acoustic wave, i.e., a photoacoustic signal 3 generated from the living body test region 97 irradiated with the intensity modulated light 1. In the blood constituent concentration measuring apparatus, the living body test region 97 and the acoustic matching substance which have the substantially same acoustic impedance as the living body test region 97 can be arranged in an inside 22 located between the light outgoing unit 13 and the ultrasonic detection unit 14.

The blood constituent concentration measuring apparatus shown in FIG. 23 further includes a container 21, a sound absorbing material 15, a temperature measurement unit 16, and an outgoing window 17. In the container 21, the inside 22 located between the light outgoing unit 13 and the ultrasonic detection unit 14 is filled with the acoustic matching substance having the substantially equal acoustic impedance as the living body test region 97. The sound absorbing material 15 is arranged in an inner wall surface of the container 21. The temperature measurement unit 16 measures the temperature of the acoustic matching substance arranged in the container 21. The outgoing window 17 is transparent for the intensity modulated light 1 arranged in the inner wall surface of the container 21. FIG. 23 shows the state in which the acoustic matching substance and the living body test region 97 are arranged in the inside 22 of the container 21. The light outgoing unit 13 and the ultrasonic detection unit 14 are arranged across the living body test region 97 in the inside 22 filled with the acoustic matching substance having the substantially equal acoustic impedance as the living body test region 97, and the surfaces of the outgoing window 17 and ultrasonic detection unit 14 are in contact with the acoustic matching substance respectively.

FIG. 23 shows an example in which the light outgoing unit 13 and the ultrasonic detection unit 14 are arranged at positions substantially facing each other. The photoacoustic signal 3 emitted from the living body test region 97 is detected with the largest signal intensity in the direction in which the light outgoing unit 13 outputs the intensity modulated light 1. The accuracy of the photoacoustic signal detected by the ultrasonic detection unit 14 can further be improved by arranging the light outgoing unit 13 and the ultrasonic detection unit 14 while substantially facing each other. In addition to the fourth embodiment, the arrangement in which the light outgoing unit 13 and the ultrasonic detection unit 14 substantially face each other can also applied to the first embodiment, the second embodiment, the third embodiment, and the later-mentioned, fifth embodiment and sixth embodiment.

The light generation unit 11 generates the light. For example, a fluorescent lamp, a halogen lamp, laser including semiconductor laser light generating devices including a light generating diode, and light generating devices including a light generating diode can be cited as an example of the light generation unit 11. It is preferable that the light generation unit 11 emits the light having the wavelength absorbed by the constituent whose concentration is measured. For example, the laser and light generating device having the wavelength selectivity is preferable for the light generation unit 11.

The light modulation unit 12 electrically intensity-modulates the light generated by the light generation unit 11 at a constant frequency. The light modulation unit including the oscillator, the drive circuit, and the 180°-phase shifter can be cited.

Preferably, the light generation unit 11 generates the two light beams having the wavelengths $\lambda_1$ and $\lambda_2$, and preferably the light modulation unit 12 intensity-modulates the light beams having the wavelengths $\lambda_1$ and $\lambda_2$ into the intensity modulated light 1 having the same frequency and reverse phases. For example, assuming that the glucose blood concentration is set at an index of the blood sugar level and water is used as the acoustic matching substance, because glucose exhibits the absorption at 1600 nm, the wavelength near 1600 nm may be selected as the wavelength $\lambda_1$ and the wavelength near 1400 nm in which the absorption coefficients of water are equal to each other may be selected as the wavelength $\lambda_2$.

The concentration measured in the case where the wavelength absorbed by the blood constituent is selected as the wavelength $\lambda_1$ and the wavelength in which the absorption coefficients of water are equal to those in the wavelength $\lambda_1$ is selected as the wavelength $\lambda_2$ will be described below. When the absorption coefficients $\alpha_1^{(b)}$, $\alpha_2^{(b)}$ to which the background water mainly contributes and the molar absorption coefficients $\alpha_1^{(0)}$, $\alpha_2^{(0)}$ of the blood constituent are known for the wavelengths $\lambda_1$ and $\lambda_2$, the concentration M is determined by solving the formula (1) which is of the simultaneous equations including the photoacoustic signal measured value $s_1$ and $s_2$ in the wavelengths. Where C is a variable coefficient which is hardly controlled or calculated, i.e., C is an unknown multiplier depending on the acoustic coupling, the ultrasonic detector sensitivity, the distance r between the irradiation portion and the living body test region, the specific heat, the thermal expansion coefficient, the sound velocity, the modulation frequency, and the absorption coefficient. When C is deleted in the formula (1), the formula (4) is obtained, and the concentration M can be determined from the photoacoustic signal $s_1$, $s_2$ and the already known absorption coefficient. However, in the formula (4), it is assumed that the absorption coefficient $\alpha_1^{(b)}$, $\alpha_2^{(b)}$ to which the background water mainly contributes are substantially equal to each other for the wavelengths $\lambda_1$ and $\lambda_2$. The formula (4) also has the feature of $s_1 \cong s_2$. Thus, the influence of the water on the photoacoustic signal can be removed by utilizing the two intensity modulated light beams having the mutually different wavelengths in which the frequencies are equal to each other and the phases are reversed to each other for the intensity modulated light 1.

The light outgoing unit 13 outputs the intensity modulated light 1 which is intensity-modulated by the light modulation unit 12. The light outgoing unit 13 is a member arranged in the portion where the intensity modulated light 1 is outputted, and preferably the light outgoing unit 13 is made of the material transparent to the intensity modulated light 1. Glass and plastic can be cited as an example of the transparent material. In the case where the light outgoing unit 13 is in contact with the acoustic matching substance, preferable the light outgoing unit 13 is made of the material which does not react with the acoustic matching substance. A quartz plate, an optical glass plate, and a sapphire plate can be cited. The light outgoing unit 13 may include an optical fiber which can guide the intensity modulated light 1. The light generation unit 11 and the light modulation unit 12 are arranged at positions distant from the light outgoing unit 13 by including the optical fiber, which allows the intensity modulated light 1 to be guided to the position where the living body test region 97 is irradiated.

The ultrasonic detection unit 14 detects the photoacoustic signal 3 which is of the acoustic wave. Examples of the ultrasonic detection unit include the ultrasonic detection unit such as a crystal microphone, a ceramic microphone, and a ceramic ultrasonic wave sensor in which the magneto-striction effect or electro-striction effect is utilized, the ultrasonic detection unit such as a moving-coil microphone and a ribbon microphone in which electromagnetic induction is utilized, the acoustic wave detector such as a capacitor microphone in which electrostatic effect is utilized, and the ultrasonic detection unit such as a magneto-striction vibrator in which magneto-striction is utilized. The ultrasonic detection unit including crystal such as PZT and PVDF can be cited as an example of the ultrasonic detection unit in which piezoelectric effect is utilized. An underwater microphone such as a hydrophone is preferably used because the acoustic wave propagating through the acoustic matching substance is detected. Preferably, a layer (for example, silicone rubber) for performing the matching with the acoustic impedance of the acoustic matching substance is formed in the surface of the ultrasonic detection unit.

The temperature measurement unit 16 is a thermometer which measures the temperature of the acoustic matching substance. The acoustic matching substance is preferably in a liquid, sol, or gel, so that a contact type thermometer can be used as the temperature measurement unit 16. A non-contact type radiation thermometer may be used.

The blood constituent concentration measuring apparatus shown in FIG. 23 may further include a thermostat unit (not shown) which adjusts the temperature of the acoustic matching substance according to the temperature measured by the temperature measurement unit 16. A heater can be cited as an example of the thermostat unit. The temperatures of the acoustic matching substance and photoacoustic signal surface can be stabilized by adjusting the temperature of the acoustic matching substance according to the temperature measured by the temperature measurement unit 16. For example, the temperature of the acoustic matching substance can be adjusted according to the temperature rise. The stabilization of the temperatures of acoustic matching substance and photoacoustic signal surface stabilizes the change in photoacoustic signal 3 caused by the temperature change, so that the computation accuracy of the blood constituent concentration is increased.

In the container 21 shown in FIG. 23, the inside 22 can be filled with the acoustic matching substance.

FIG. 23 shows the example in which the sound absorbing material 15 is included in the inner wall surface of the container 21. The sound absorbing material 15 absorbs the photoacoustic signal 3. For example, the sound absorbing material 15 can be made of the material in which metal oxide powders (titanium oxide or tungsten oxide) are included in an epoxy resin. The multiple-reflection acoustic wave generated from the unevenness of the internal structure of the living body test region 97 can be absorbed and removed by including the sound absorbing material 15 in at least one part of the inner wall surface of the container 21. Therefore, the ultrasonic detection unit 14 can efficiently detect the photoacoustic signal 3 emitted from the living body test region 97.

FIG. 23 also shows the example in which the container 21 includes the outgoing window 17. The outgoing window 17 is transparent to the intensity modulated light 1. The transparent glass and plastic can be cited as an example of the outgoing window 17. Preferably, the outgoing window 17 is scratch resistant, and the quartz plate, the optical glass plate, and the sapphire plate can be cited as an example of the outgoing window 17. Preferably, the outgoing window 17 is made of the material which does not absorb the intensity modulated light 1. The light outgoing unit 13 can be arranged outside the inside 22 of the container 21 by including the outgoing window 17, so that the light outgoing unit 13 can easily be arranged. Because the intensity modulated light 1 can be outputted from the inner wall surface of the container 21, the irregularity is eliminated in the inner wall surface of the container 21, and the reflection of the photoacoustic signal 3 can be decreased.

The acoustic matching substance has the substantially same acoustic impedance as the living body test region 97. Examples of the acoustic matching substance include rubber, a soft solid such as resin, a liquid, and sol or gel. The water may be used as the acoustic matching substance. That is, the container 21 may be filled with the water which is of the acoustic matching substance. Because the acoustic impedance of the living body is close to the water, when the photoacoustic signal 3 is detected under the environment in which the inside 22 which is of the surroundings of the living body test region 97 is surrounded by the water, the degradation of the photoacoustic signal 3 can be decreased. The degradation of the photoacoustic signal 3 is caused by the boundary reflection between the living body test region 97 and the inside 22 which is of the surroundings thereof and by the contact between the living body test region 97 and the ultrasonic detection unit 14.

Figure 24:
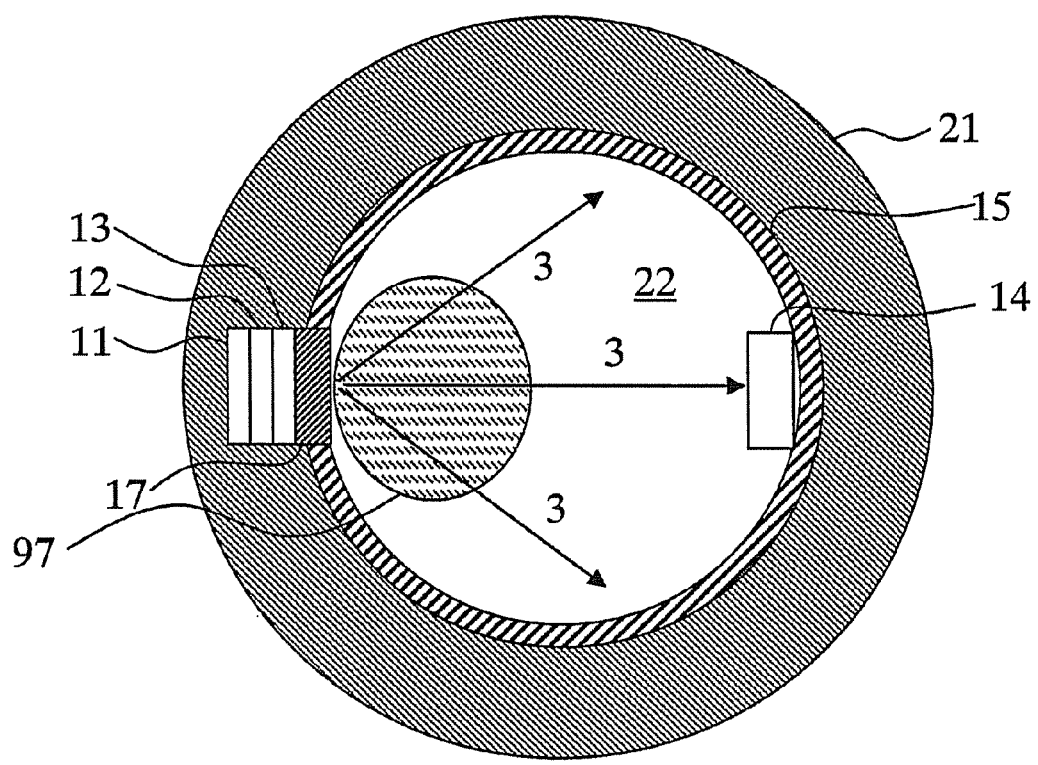
FIG. 24 is a transverse sectional view taken on line D-D' of FIG. 23.

FIG. 24 is a transverse sectional view taken on line D-D' of FIG. 23, and FIG. 24 shows a first mode of the blood constituent concentration measuring apparatus. In the container 21, the shape in transverse section is formed in the circle. The light outgoing unit 13 and the ultrasonic detection unit 14 are arranged in the side face of the container 21 while substantially facing each other.

Figure 25:
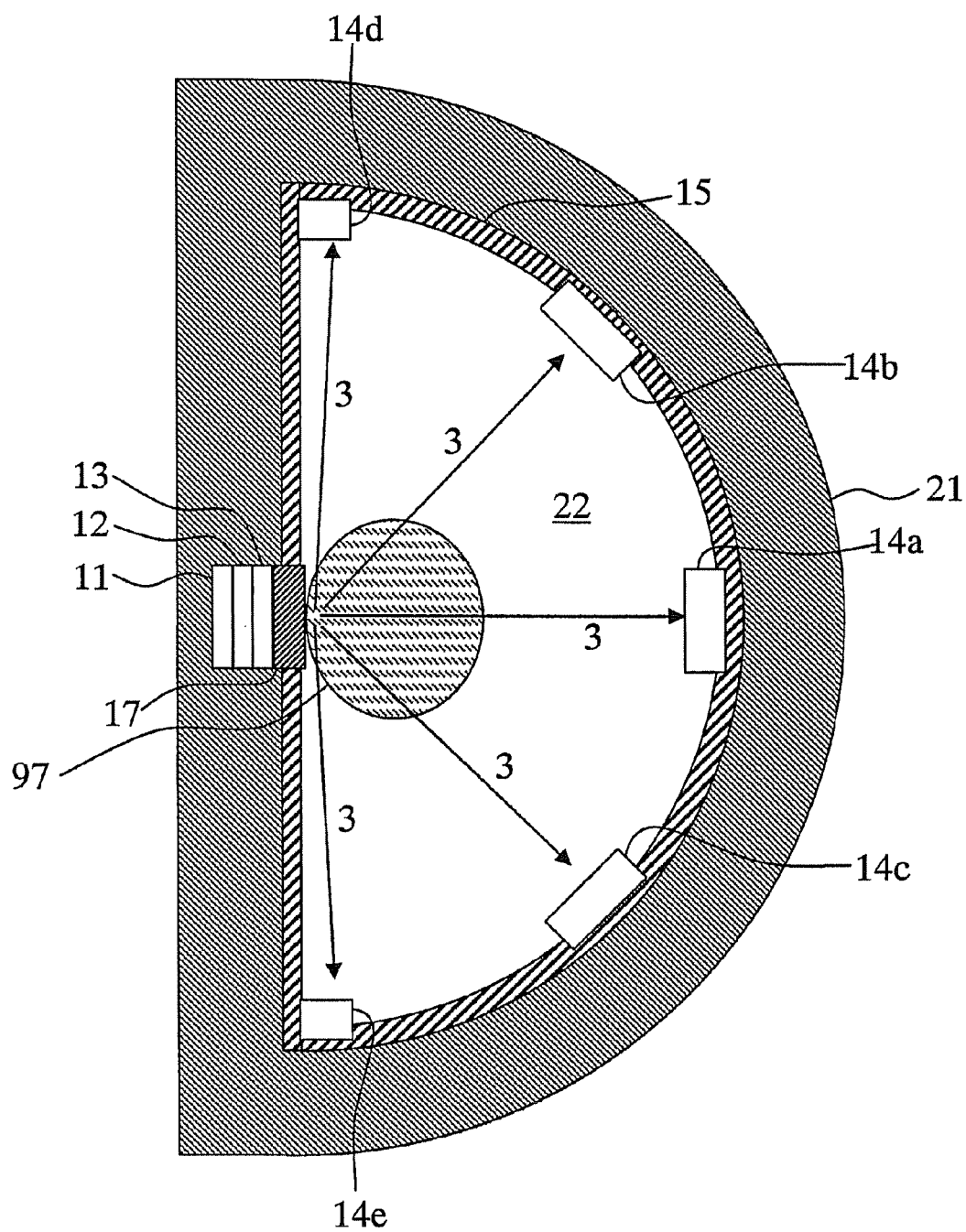
FIG. 25 is a transverse sectional view taken on line D-D' of FIG. 23.

FIG. 25 is a transverse sectional view taken on line D-D' of FIG. 23, and FIG. 25 shows a second mode of the blood constituent concentration measuring apparatus. In the container 21 shown in FIG. 25, the shape in transverse section is formed in the semi-circle, and the light outgoing unit 13 is arranged at the position of the substantial center point of the semi-circle. FIG. 25 also shows the example in which ultrasonic detection units 14a, 14b, 14c, 14d, and 14e are arranged in the arc portion of the semi-circle of the container 21. The ultrasonic detection unit 14a is arranged at the position where the ultrasonic detection unit 14a faces the light outgoing unit 13, and the ultrasonic detection units 14b to 14e are arranged in the arc portion in the dispersed manner.

As shown in FIG. 25, the shape in transverse section of the container 21 is formed in the semi-circle, and the light outgoing unit 13 is arranged in the substantial center point of the circle. Therefore, the distance between the side face of the case corresponding to the arc portion of the semi-circle and the light outgoing unit 13 can be uniformed. Accordingly, when the living body test region 97 is placed so as to be pressed against the flat surface including the center of the semi-circle, the photoacoustic signal 3 is generated in the substantial center of the semi-circle, and the photoacoustic signal 3 spreads radially. At this point, the distance between the ultrasonic detection units 14a to 14e and the generation source of the photoacoustic signal 3 is kept constant, so that the ultrasonic detection units 14a to 14e can detect the same-phase photoacoustic signals 3. When the photoacoustic signals 3 detected by the ultrasonic detection units 14a to 14e are multiplexed, the photoacoustic signal 3 can efficiently be detected. When the detection signals are compared to each other at the same time, the influence caused by the structure inside the living body test region 97 can also be corrected. Thus, the accuracy of the photoacoustic signal can further be increased by improving the sound collective state in the acoustic wave detection means. The acoustic wave detection means can more efficiently detect the radially spread photoacoustic signal by arranging two acoustic wave detection means in the side face of the case corresponding to the arc portion of the semi-circle.

Figure 26:
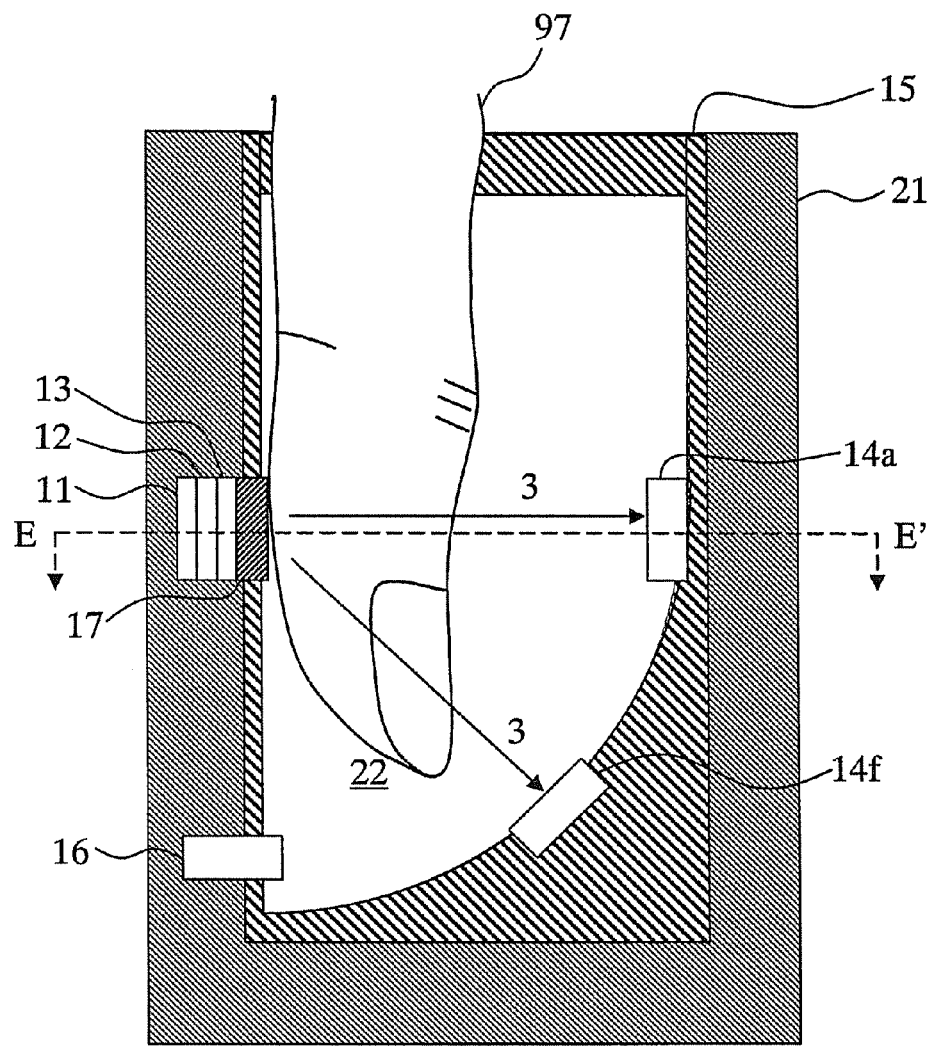
FIG. 26 is a longitudinal sectional showing a fourth mode of the blood constituent concentration measuring apparatus.

FIG. 26 is a longitudinal sectional showing a fourth mode of the blood constituent concentration measuring apparatus. In the blood constituent concentration measuring apparatus shown in FIG. 26, the bottom surface inside the container 21 is formed in a hemisphere. The blood constituent concentration measuring apparatus of the fourth mode can be used in the case where the section E-E' is the transverse section shown in FIG. 25. In FIG. 26, an ultrasonic detection unit 14*f* is shown in the bottom surface, and the ultrasonic detection unit 14*f* is arranged at the position where the distance from the light outgoing unit 13 is substantially equal to the distance between the light outgoing unit 13 and the ultrasonic detection unit 14*a*. Thus, the photoacoustic signal 3 spreading radially from the living body test region 97 can be detected more efficiently by utilizing the ultrasonic detection unit 14*f* in addition to the ultrasonic detection units 14*a* to 14*e* shown in FIG. 25. The section E-E' is not limited to FIG. 25. For example, the shape in transverse section may be formed in a sector having arbitrary angles such as 45 degrees, 90 degrees, and 135 degrees.

Figure 27:
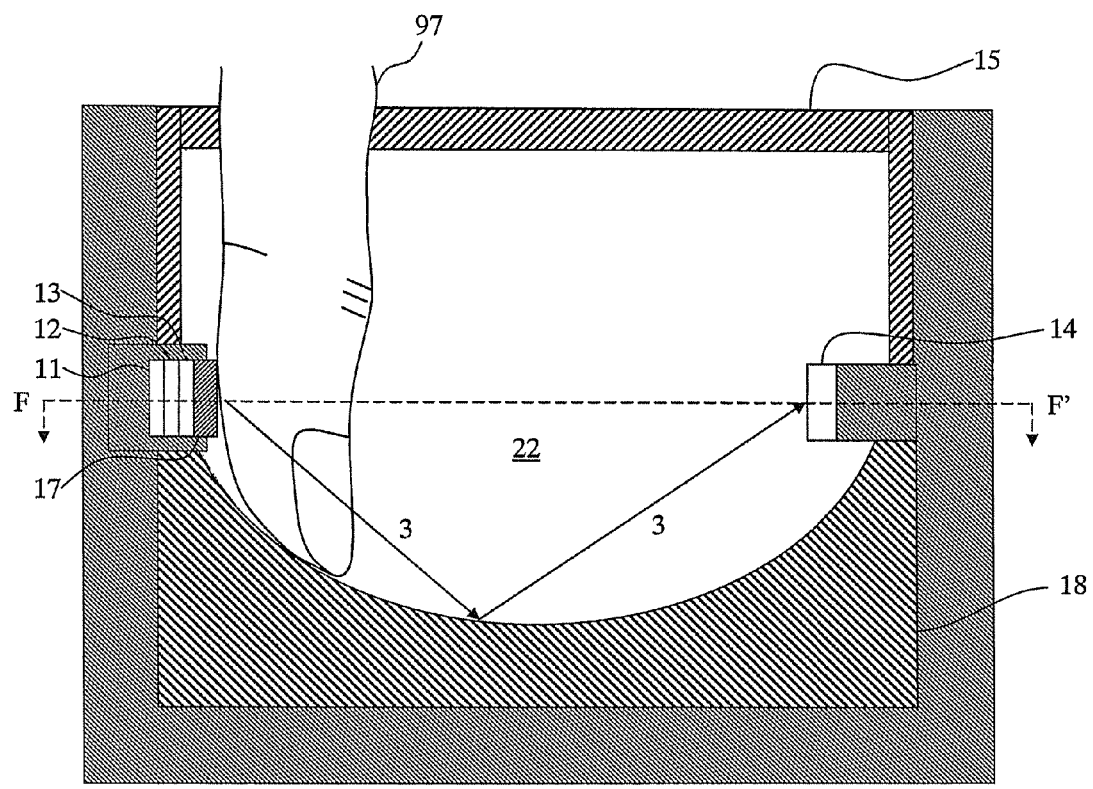
FIG. 27 is a longitudinal sectional showing a fifth mode of the blood constituent concentration measuring apparatus.
Figure 28:
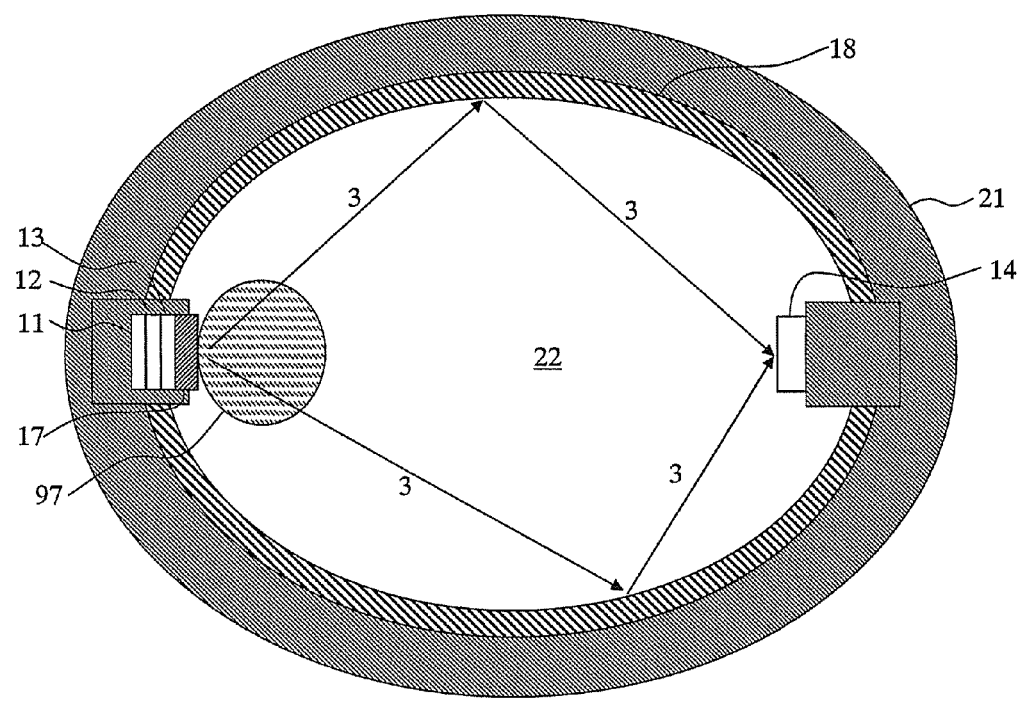
FIG. 28 is a transverse sectional view taken on line F-F' of FIG. 27.

A fifth mode of the blood constituent concentration measuring apparatus will be described with reference to FIGS. 27 and 28. FIG. 27 is a longitudinal sectional showing the fifth mode of the blood constituent concentration measuring apparatus. FIG. 28 is a transverse sectional view taken on line F-F' of FIG. 27. In the blood constituent concentration measuring apparatus shown in FIGS. 27 and 28, the container 21 is formed in the elliptic hemisphere including two focal points in section, and the light outgoing unit 13 and the ultrasonic detection unit 14 are arranged at the two focal points respectively. The container 21 is formed in the elliptic hemisphere including the two focal points in section, and the light outgoing unit 13 and the ultrasonic detection unit 14 are arranged near the two focal points respectively. Therefore, the photoacoustic signal 3 can be scattered at the bottom portion of the case and efficiently collected by the ultrasonic detection unit 14. Because the distance in which the photoacoustic signal 3 reaches the ultrasonic detection unit 14 is not changed, the photoacoustic signal 3 is hardly affected by the influence of the multiple-scattering acoustic wave. Thus, the accuracy of the photoacoustic signal 3 can further be increased by improving the sound collective state in the acoustic wave detection means. As shown in FIG. 27, the container 21 includes the reflection material 18 in the inner wall surface of the bottom portion. The reflection material 18 reflects the photoacoustic signal 3. Preferably, the reflection material 18 does not react with the water. For example, when the water is used as the acoustic matching substance, the stable metal such as stainless steel and aluminum can be cited. The efficiency of collecting the photoacoustic signal 3 with acoustic wave detection means can be improved by including the reflection material 18 in at least one part of the inner wall surface of the container 21. Therefore, the accuracy of the photoacoustic signal 3 detected by the ultrasonic detection unit 14 can be further increased.

Although the bottom surface is described in the fifth mode of the blood constituent concentration measuring apparatus, as shown in FIG. 28, the container 21 may be formed in the ellipse in transverse section, and the light outgoing unit 13 and the ultrasonic detection unit 14 may be arranged at the substantial focal points of the ellipse respectively. The shape of the inner wall surface is formed in the ellipse in transverse section, and the light outgoing unit 13 and the ultrasonic detection unit 14 are arranged at the substantial focal points of the ellipse respectively. Therefore, the photoacoustic signal 3 can be scattered by the side face of the inner wall surface of the container 21 and efficiently collected by the ultrasonic detection unit 14. Thus, the accuracy of the photoacoustic signal 3 can further be increased by improving the sound collective state in the ultrasonic detection unit 14.

As described above, by including the container 21, the living body test region 97 is arranged in the inside 22 of the container 21 filled with the acoustic matching substance having the substantially equal acoustic impedance as the living body test region 97, and the photoacoustic signal 3 can be detected from the living body test region 97 under the environment in which the inside 22 which is of the surroundings of the living body test region 97 is surrounded by the acoustic matching substance. The photoacoustic signal 3 is detected under the environment in which the inside 22 which is of the surroundings of the living body test region 97 is surrounded by the acoustic matching substance, which allows the degradation of the photoacoustic signal 3 to be decreased. The degradation of the photoacoustic signal 3 is caused by the boundary reflection between the living body test region 97 and the inside 22 which is of the surroundings thereof and by the contact between the living body test region 97 and the ultrasonic detection unit 14.

The living body test region 97 is a human living body. Although the finger is shown in FIGS. 23 to 28 by way of example, any part of the living body may be used as the living body test region 97. For example, a hand and an arm may be used as the living body test region 97.

An animal, a bird, and plants such as fruit and vegetable may be used as the living body test region 97 which is of the object to be measured. The object to be measured includes a pipe through which a liquid flows and the container such as a bottle and a tank in which the liquid sol or gel is reserved. For example, when the object to be measured is the fruit, the sugar of the fruit can be measured in the noninvasive manner.

As described above, the control method of blood constituent concentration measuring apparatus according to the fourth embodiment including the light generating procedure in which the light generating means generates the light; the light modulation procedure for electrically intensity-modulating the light generated from the light generating procedure at a constant frequency; the light outgoing procedure in which the light modulation means outputs the intensity modulated light 1 intensity-modulated in the light modulation procedure toward the living body test region 97; and the acoustic wave detection procedure in which the acoustic wave detection means detects the acoustic wave, i.e., the photoacoustic signal 3 emitted from the living body test region 97 irradiated with the intensity modulated light 1 in the light outgoing procedure. The control method of blood constituent concentration measuring apparatus is characterized in that the light outgoing procedure and the acoustic wave detection procedure are performed in the container 21 filled with the acoustic matching substance having the substantially equal acoustic impedance as the living body test region 97.

Thus, the living body test region 97 and the acoustic matching substance having the substantially equal acoustic impedance as the living body test region 97 can be arranged between the light outgoing unit 13 and the ultrasonic detection unit 14, so that the acoustic matching substance can be placed between the living body test region 97 and the ultrasonic detection unit 14 to reduce the boundary reflection at the interface between the living body test region 97 and the inside 22 which is of the surroundings thereof.

Preferably, in the light outgoing procedure, as described above, the light generation unit 11 generates the two light beams having the mutually different wavelengths $\lambda_1$ and $\lambda_2$ and, in the light modulation procedure, the light modulation unit 12 intensity-modulates these light beams having the different wavelengths $\lambda_1$ and $\lambda_2$ into the intensity modulated lights 1 having the same frequency and reverse phases.

As shown in FIGS. 23 to 28, preferably, in the light outgoing procedure, the living body test region 97 is arranged while being contact with the outgoing surface of the intensity modulated light 1 and the living body test region 97 is directly irradiated with the intensity modulated light 1. The outgoing window 17 acts as the outgoing surface in FIGS. 23 to 28. The light outgoing unit 13 acts as the outgoing surface, when the outgoing window 17 is not included. The living body test region 97 is arranged so as to come into contact with the outgoing surface of the intensity modulated light 1, and the living body test region 97 is directly irradiated with the intensity modulated light 1. Therefore, the degradation of the intensity modulated light 1 caused by the absorption in the acoustic matching substance can be prevented. Accordingly, because the living body test region 97 is efficiently irradiated with the intensity modulated light 1, the intensity is increased in the photoacoustic signal 3 emitted from the living body test region 97, and the accuracy of the photoacoustic signal 3 detected by the ultrasonic detection unit 14 can further be increased. The arrangement in which the living body test region 97 is in contact with the intensity modulated light 1 can also be applied in the first embodiment, the second embodiment, third embodiment, and the later-mentioned fifth embodiment and sixth embodiment in addition to the fourth embodiment.

As shown in FIGS. 23 to 28, preferably, in the acoustic wave detection procedure, the photoacoustic signal 3 is detected through the acoustic matching substance having the substantially equal acoustic impedance as the living body test region 97. FIGS. 23 to 28 show the example in which the detection is performed through the acoustic matching substance with which the inside 22 of the container 21 is filled. However, a solid-state substance such as silicone rubber arranged between the living body test region 97 and the ultrasonic detection unit 14 may be used. The photoacoustic signal 3 is detected through the acoustic matching substance having the substantially equal acoustic impedance as the living body test region 97, so that the boundary reflection between the living body test region 97 and the inside 22 which is of the surroundings thereof and the pressure and vibration applied to the ultrasonic detection unit 14 can be prevented.

As shown in FIGS. 23 to 28, preferably, in the light outgoing procedure, the intensity modulated light 1 is arranged in the inner wall surface of the container 21 and the living body test region 97 is irradiated with the intensity modulated light 1 through the outgoing window 17 which is transparent to the intensity modulated light 1. The container 21 includes the outgoing window 17 which is transparent to the intensity modulated light 1, which allows the light outgoing unit 13 to be arranged outside the container 21. Therefore, the light outgoing unit 13 is easily arranged. Because the intensity modulated light 1 can be outputted from the inner wall surface of the container 21, the irregularity is eliminated in the inner wall surface of the container 21, and the reflection of the photoacoustic signal 3 can be decreased.

As shown in FIGS. 23 to 28, in the living body test region 97, preferably the region irradiated with the intensity modulated light 1 is covered with the liquid, sol, or gel acoustic matching substance. In the living body test region 97, the region irradiated with the intensity modulated light 1 is covered with the liquid, sol, or gel acoustic matching substance, so that the photoacoustic signal 3 can be detected from the living body test region 97 under the environment in which the inside 22 which is of the surroundings of the living body test region 97 is surrounded by the acoustic matching substance.

EXAMPLES

Specific examples in the fourth embodiment will be described below.

First Example

Figure 29:
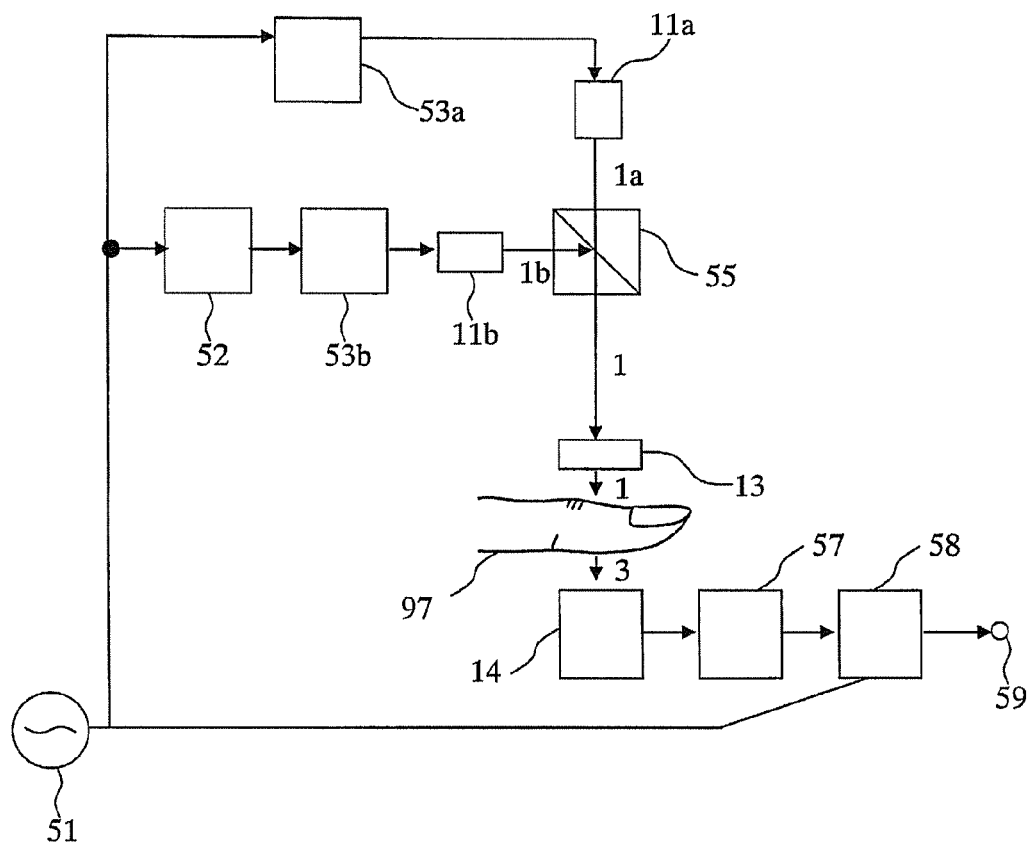
FIG. 29 is a circuit diagram showing an example of the blood constituent concentration measuring apparatus.

A first example in which the light generating means generates the two light beams having the different wavelengths and the light modulation means intensity-modulates the two light beams into the intensity modulated light beams having the same frequency and reverse phases will be described below with reference FIG. 29. FIG. 29 is a circuit diagram showing an example of the blood constituent concentration measuring apparatus. An oscillator 51 drives drive circuits 53a and 53b at a constant frequency. A 180°-phase shifter 52 is arranged between the oscillator 51 and the drive circuit 53b, and the drive circuit 53b is driven in the phase reversed to the phase of the drive circuit 53a. Light generation units 11a and 11b generate the light beams having the different wavelengths. The drive circuit 53a intensity-modulates the light generated by the light generation unit 11a, and the drive circuit 53a outputs the intensity modulated light 1a. The drive circuit 53b intensity-modulates the light generated by the light generation unit 11b, and the drive circuit 53b outputs the intensity modulated light 1b. Therefore, the intensity modulated light beams 1a and 1b having the different wavelengths in which the frequencies are equal to each other while the phases reversed to each other can be generated. In the first example, the oscillator 51, the drive circuits 53a and 53b, and the 180°-phase shifter 52 correspond to the light modulation unit 12 shown in FIG. 23.

A coupler 55 multiplexes the intensity modulated light beams 1a and 1b, and the light outgoing unit 13 outputs the multiplexed light as the intensity modulated light 1. The living body test region 97 is irradiated with the intensity modulated light 1 outputted from the light outgoing unit 13, and the photoacoustic signal 3 emitted from the living body test region 97 is detected by the ultrasonic detection unit 14. In the photoacoustic signal 3 detected by the ultrasonic detection unit 14, the photoacoustic signal 3 is extracted by the filter 57, and the photoacoustic signal 3 is outputted from the photoacoustic signal output terminal 59 after the photoacoustic signal output terminal 59 is amplified by the phase sensitive amplifier 58.

Second Example

Figure 30:
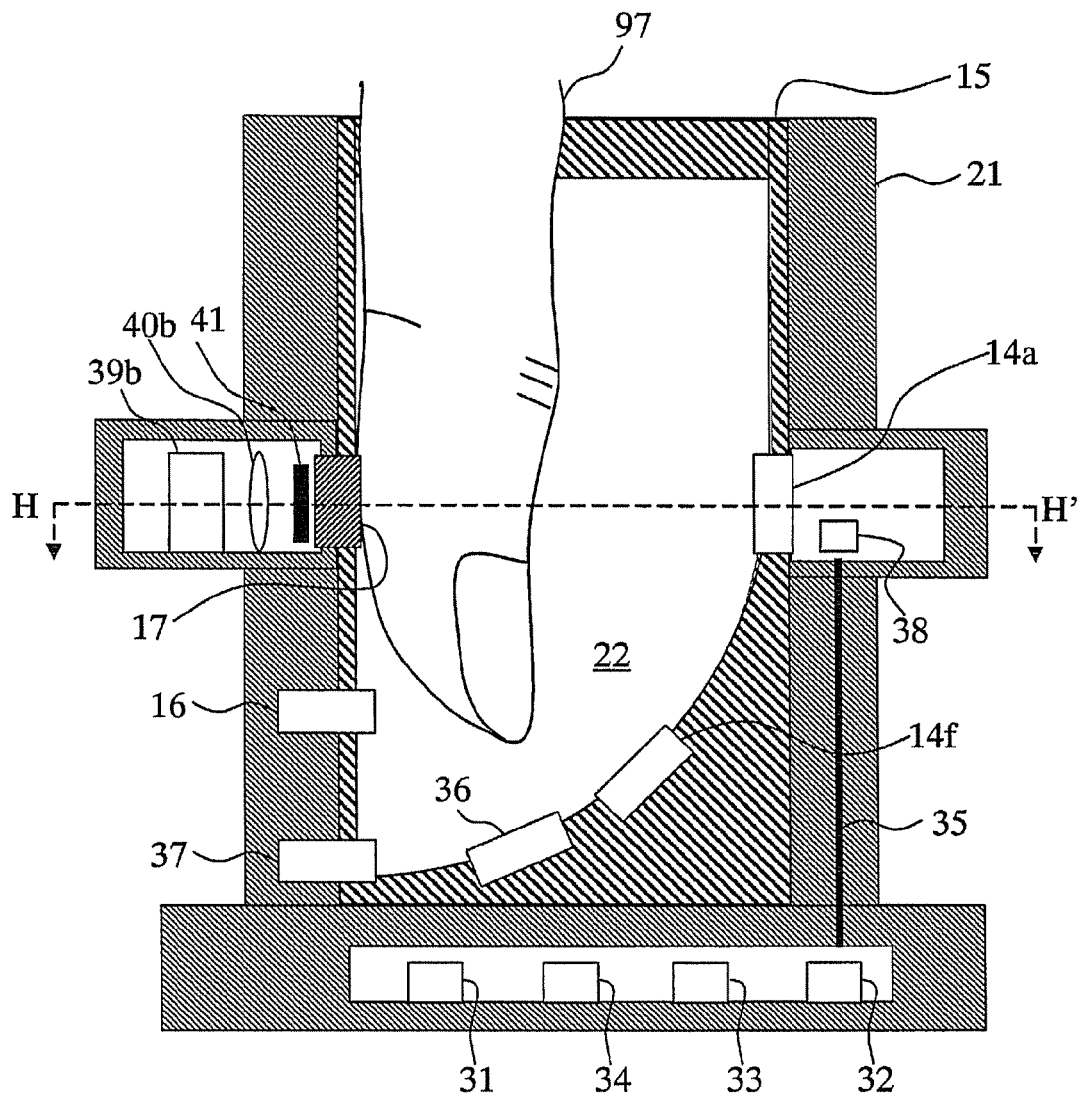
FIG. 30 is a longitudinal sectional view of the blood constituent concentration measuring apparatus.
Figure 31:
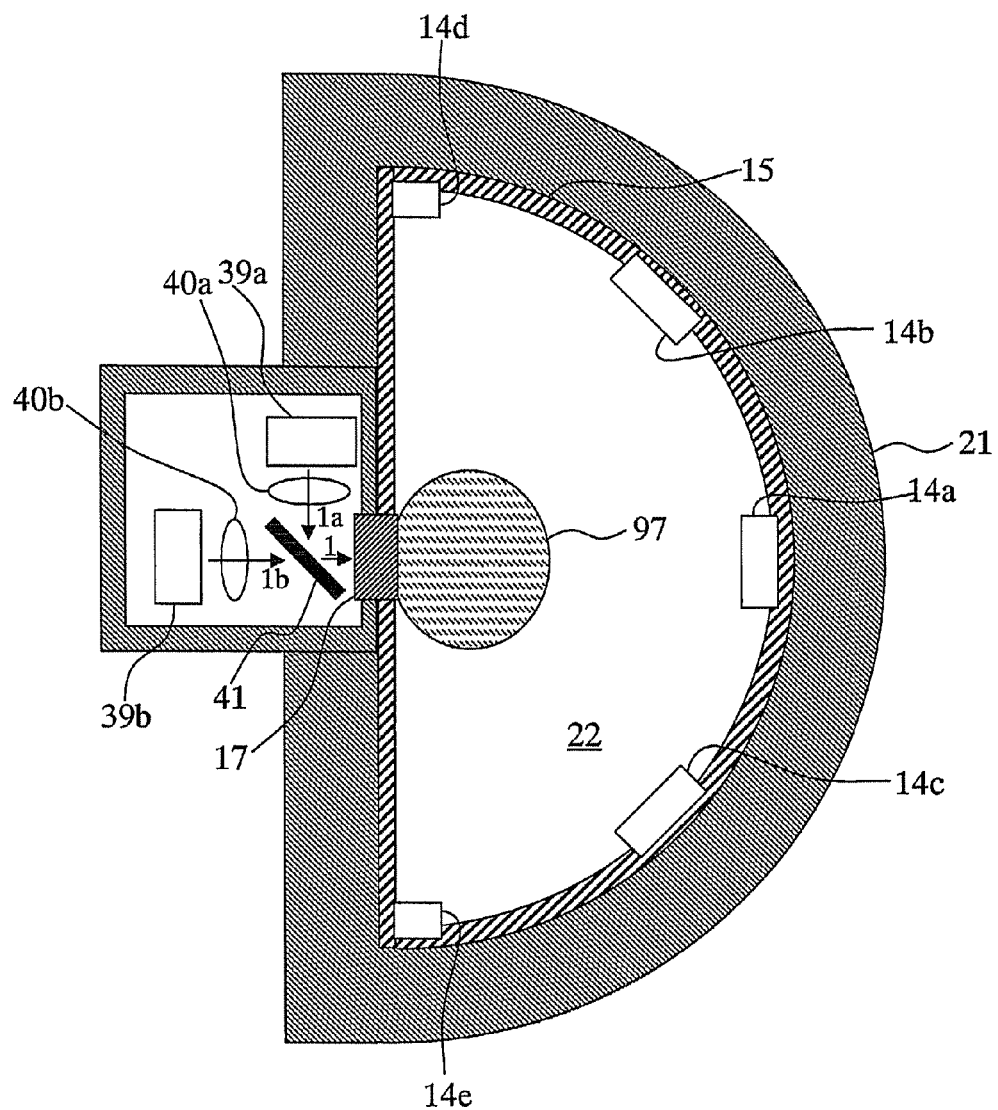
FIG. 31 is a transverse sectional view taken on line H-H' of FIG. 30.

A second example of the blood constituent concentration measuring apparatus of the fourth mode shown in FIGS. 25 and 26 will be described with reference to FIGS. 30 and 31. FIG. 30 is a longitudinal sectional view of the blood constituent concentration measuring apparatus, and FIG. 30 shows an example in which the blood constituent concentration measuring apparatus is applied to a fingertip of the human body. FIG. 31 is a transverse sectional view taken on line H-H'. Referring to FIGS. 30 and 31, the inside 22 of the cylindrical container 21 into which the living body test region 97 is inserted is filled with water, the outgoing window 17 and the ultrasonic detection unit 14 are embedded in the inner wall of the container 21. A power supply 31 which supplies the electric power to a light source chip 39b and the ultrasonic detection unit 14, a phase sensitive amplifier 32 which amplifies the output signal of the ultrasonic detection unit 14, a signal processor 33 which computes the blood constituent concentration, and a display processing unit 34 which display data on a display device (not shown) placed outside the base are provided in the base of the container. The ultrasonic detection unit 14 and the signal processor 33 are connected to each other with a connection cable 35. A temperature regulating unit 36 is placed in the inner wall of the container 21, a heater 37 and a temperature measurement unit 16 are incorporated into the container 21 so as to come into contact with the inside 22 of the container 21.

The bottom portion of the cylindrical container 21 is formed in a quarter sphere having a radius of 5 cm. In the ultrasonic detection unit 14 incorporated into the container 21, a preamplifier 38 which amplifies the photoacoustic signal 3 detected by the ultrasonic detection unit 14 are placed. The crystal such as PZT and PVDF having the piezoelectric effect is used as the ultrasonic detection unit 14. A matching layer is formed in the surface of the ultrasonic detector unit 14 to match the acoustic impedance with the water. When silicone rubber which is frequently used in a percutaneous treatment tool is used as the matching layer of the ultrasonic detection unit 14, the reflection can be decreased by 9% in the surface.

In the inner wall of the container 21 filled with the water, the inner wall of the container 21 except for the surface of the ultrasonic detection unit 14 is filled with a sound absorbing material 15 in order to decrease the reflection at the interface between the materials of the matching layer and container 21. The material in which metal oxide powders (titanium oxide or tungsten oxide) are included in the epoxy resin is effectively used as the sound absorbing material which prevents the reflection. In the light outgoing unit 13 shown in FIG. 23, the two light beams having the mutually different wavelengths are generated with light source chips 39a and 39b and lenses 40a and 40b, the two light beams having the mutually different wavelengths are multiplexed with a polarization beam splitter 41, and the fingertip portion is irradiated with the collimate light through the outgoing window 17. The semiconductor laser is effectively used as the light source chips 39a and 39b from the viewpoints of price, size, and chip lifetime. As to the two wavelengths, the wavelength of the light source chip 39a is set at 1380 nm and the wavelength of the light source chip 39b is set at 1608 nm.

The intensity modulated light beams 1a and 1b from the light source chips 39a and 39b are collimated with the lenses 40a and 40b to adjust the distance between the light source chip 39a and the lens 40a, the material and curvature of the lens 40a, the distance between the light source chip 39b and the lens 40b, and the material and curvature of the lens 40b, which allows the intensity modulated light beams 1a and 1b to be adjusted in the beam diameter suitable to the photoacoustic measurement. In the second example, the two beam diameters are set at 5.0 mm. The scratch-resistant material in which the absorption is not exhibited in the two wavelengths is suitable to the outgoing window 17. For example, the quartz plate, the optical glass plate, and the sapphire plate can be used. A pressure sensitive device in which the piezoelectric material is used is embedded in an edge portion of the outgoing window 17 which is in contact with the living body test region 97, and the pressure sensitive device senses the pressure applied to the outgoing window 17 to start the supply of the electric power to the light source chips 39a and 39b.

In the temperature regulating unit 36, the heater 37 is embedded in the inner wall of the container 21, the current to the heater 37 is adjusted while the difference between the temperature measured by the temperature measurement unit 16 and the temperature setting value of the acoustic matching substance in the inside 22 of the container 21 is monitored. The temperature of the acoustic matching substance is set at 36° C. which is close to the body temperature of the living body. The metal layer (not shown) made of metal (copper or aluminum) having the high heat conductivity is provided in the inner wall of the container 21, the temperature of the acoustic matching substance can efficiently be controlled by bringing the heater 37 and the metal layer into contact with each other.

Third Example

Figure 32:
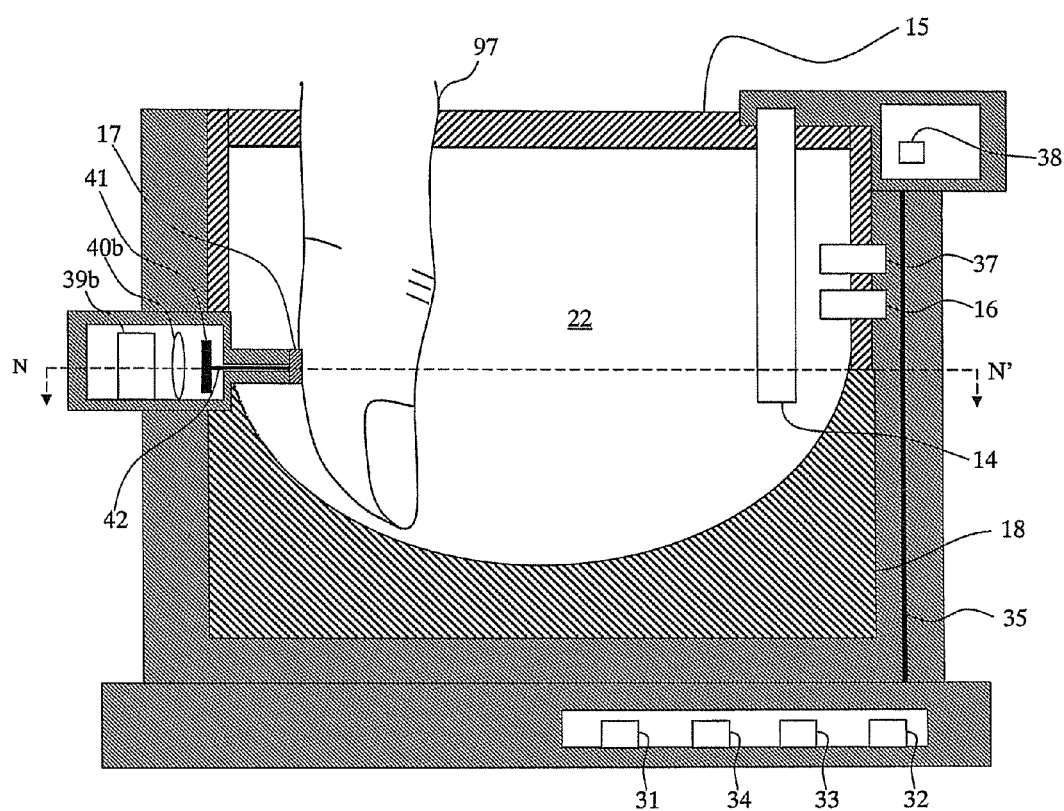
FIG. 32 is a longitudinal sectional view of the blood constituent concentration measuring apparatus.
Figure 33:
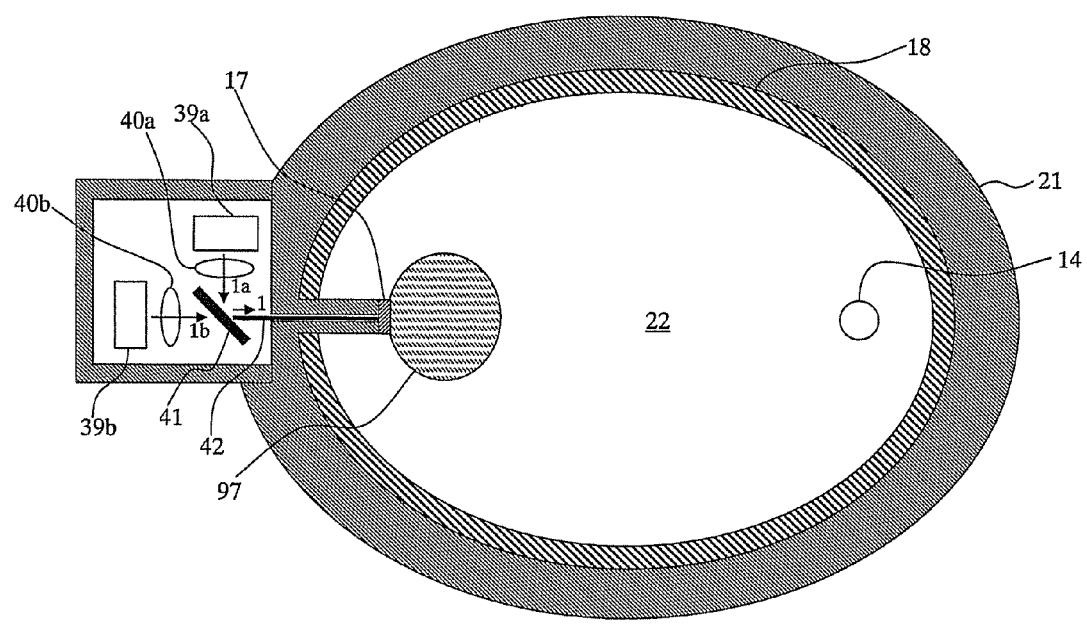
FIG. 33 is a transverse sectional view taken on line N-N' of FIG. 32.

An example of the blood constituent concentration measuring apparatus of the fifth mode shown in FIGS. 27 and 28 will be described with reference to FIGS. 32 and 33. FIG. 32 is a longitudinal sectional view of the blood constituent concentration measuring apparatus, and FIG. 32 shows an example in which the blood constituent concentration measuring apparatus is applied to the finger of the human body. FIG. 33 is a transverse sectional view taken on line N-N' of FIG. 32. The bottom portion of the cylindrical container is formed in elliptic hemisphere having a major axis of 100 mm and a minor axis of 50 mm. The intensity modulated light beams 1a and 1b from the light source chips 39a and 39b are guided to an optical fiber 42 through the lenses 40a and 40b and the beam splitter 41. The intensity modulated light 1 incident to the optical fiber 42 is guided to the outgoing window 17 through the optical fiber 42, and the intensity modulated light 1 is outputted to the inside 22 of the container 21. The living body test region 97 is irradiated with the intensity modulated light 1 outputted from the outgoing window 17.

The lens 40a or 40b is placed at the end face of the optical fiber 42, the irradiation beam diameters of the intensity modulated light beams 1a and 1b are adjusted from the distance between the lenses 40a and 40b, and the beam diameters of the two intensity modulated light beams 1 are set at 5.0 mm. The drive currents of the light source chips 39a and 39b are adjusted such that the power of the irradiation intensity modulated light 1 becomes 4 mW, and the intensity modulation is performed at 200 kHz by the oscillator (not shown). The outgoing window 17 is placed such that the interface between the outgoing window 17 and the water which is of the acoustic matching substance becomes the focal point of the ellipse, namely, the interface between the outgoing window 17 and the living body test region 97 is placed at the focal point of the ellipse during the measurement. A commercially available hydrophone in which the acoustic matching is performed with the water is used as the ultrasonic detection unit 14, and the ultrasonic detection unit 14 is placed at the focal point of the ellipse different from the irradiation portion of the living body test region 97. The needle hydrophone is adopted as the ultrasonic detection unit 14 to finely adjust the position, and the ultrasonic detection unit 14 is placed at the position where the photoacoustic signal becomes the maximum.

The outgoing window 17, the inner wall surface on a horizontal plane, and the bottom surface except for the outgoing window 17 are filled with the reflection material 18 in order to efficiently reflect the photoacoustic signal 3. The stable metal (stainless steel or aluminum), which does not chemically react with the water, is used as the reflection material 18. Other inner surfaces except for above portions are filled with sound absorbing material 15 to decrease the influence multiple reflections.

Fifth Embodiment

Figure 34:
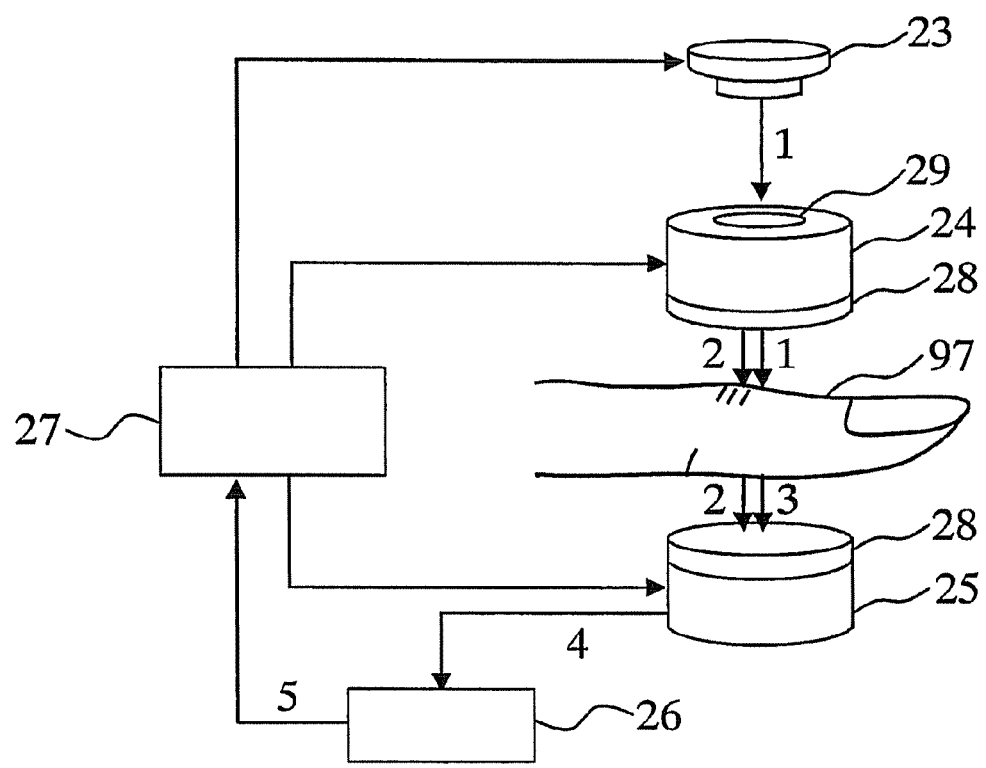
FIG. 34 is a circuit diagram of the blood constituent concentration measuring apparatus according to the embodiment.

FIG. 34 is a circuit diagram of a blood constituent concentration measuring apparatus according to a fifth embodiment. The blood constituent concentration measuring apparatus shown in FIG. 34 includes light generating means for generating the intensity modulated light 1 intensity-modulated at a constant frequency; a excitation light source 23 which is of the light modulation means and light outgoing means; an acoustic wave generator 24 which outputs the acoustic wave 2; and an acoustic wave detector 25 which is of the acoustic wave detection means for detecting the acoustic wave, i.e., photoacoustic signal 3 and the acoustic wave 2, the photoacoustic signal 3 being emitted from the living body test region 97 which is of the test subject irradiated with the intensity modulated light 1, the acoustic wave 2 being transmitted through the living body test region 97 from the acoustic wave generator 24. In FIG. 34, the circuit diagram of a blood constituent concentration measuring apparatus according to the fifth embodiment further includes a control unit 26 which compares the signal intensity of the acoustic wave 2 from the output signal 4 of the acoustic wave 2 detected by the acoustic wave detector 25, the control unit 26 outputting the control signal 5 to control a drive unit 27 such that the intensity of the acoustic wave 2 becomes a particular value; the drive unit 27 which varies the positions of the excitation light source 23, acoustic wave generator 24, and acoustic wave detector 25 by the control signal 5; and acoustic coupling elements 28 which are located in surfaces where acoustic wave generator 24 and acoustic wave detector 25 come into contact with the living body test region 97, the acoustic coupling element 28 having the substantially equal acoustic impedance as the living body test region 97.

FIG. 34 shows the example in which the blood constituent concentration measuring apparatus has a transmission window 29 in a central portion of the acoustic wave generator 24 and the transmission window 29 transmits the intensity modulated light 1 from the excitation light source 23. Preferably, the acoustic wave generator 24 is arranged close to the beam of the intensity modulated light 1 from the excitation light source 23. The reflection/scattering can correctly be examined in the propagation path of the photoacoustic signal 3 by arranging the acoustic wave generator 24 close to the beam of the intensity modulated light 1 from the excitation light source 23. Preferably, the acoustic wave 2 is generated to the living body test region 97 at the position close to the living body test region 97. Because the photoacoustic signal 3 is generated near the cuticle of the living body test region 97 to which the intensity modulated light i is incident, the reflection/scattering can further correctly be examined in the propagation path of the photoacoustic signal 3. The acoustic wave 2 can be causes to propagate efficiently to the living body test region 97 by generating the acoustic wave 2 at the position near the living body test region 97.

The excitation light source 23 shown in FIG. 34 outputs the intensity modulated light 1 which is intensity-modulated at the constant frequency. The excitation light source 23 outputs the light having the absorption wavelength of the measuring object whose concentration is measured. For example, in the case where the measuring object is glucose, the wavelength becomes 1608 nm. The light emitted at a particular frequency from the light source device may be intensity-modulated at a constant frequency using the oscillator, the drive circuit, the 180°-phase shifter, and the like. Examples of the light source device, which emits the light at a particular frequency, include various lasers such as a gas laser, a solid-state laser, and the semiconductor laser and the light generating diode. The blood constituent concentration measuring apparatus may further include a light shielding hood, around at least one part of the optical path of the intensity modulated light 1, the light shielding hood preventing the leakage of the intensity modulated light 1 outside the blood constituent concentration measuring apparatus. The leakage of the intensity modulated light 1 outside the blood constituent concentration measuring apparatus including portions of the living body test region 97 except for the portion to be examined is prevented by further including the light shielding hood. In addition to the fifth embodiment, the light shielding hood can also applied in the first embodiment, the second embodiment, the third embodiment, and the later-mentioned sixth embodiment.

The excitation light source 23 may be fixed to the acoustic wave generator 24 so as to simultaneously operate with the acoustic wave generator 24. For example, the excitation light source 23 may be integrated with the acoustic wave generator 24. Because the excitation light source 23 simultaneously operates with the acoustic wave generator 24, the excitation light source 23 can automatically be moved to the position suitable to the measurement. The fifth embodiment shows the mode in which the excitation light source 23 outputs one light beam. However, the excitation light source 23 can also emit the two light beams having the mutually different wavelengths $\lambda_1$ and $\lambda_2$ and output the intensity modulated light beams having the same frequency and reverse phases. As described in the first embodiment to the fourth embodiment, the two light beams having the mutually different wavelengths in which the frequencies are equal to each other and the phases are reversed to each other are used as the intensity modulated light 1, which allows the influence of the water on the photoacoustic signal to be removed.

The acoustic wave generator 24 shown in FIG. 34 generates and outputs the acoustic wave 2 which is of the ultrasonic wave. The frequency of the ultrasonic wave generated by acoustic wave generator 24 generates the frequency of the photoacoustic signal 3 generated by the living body test region 97. For example, the acoustic wave generator, which generates the acoustic wave having the frequency of about 200 kHz, may be used as acoustic wave generator 24.

Preferably, in the acoustic wave generator 24, the frequency and/or intensity of the outputted acoustic wave 2 is variable. When the frequency of the outputted acoustic wave 2 is variable, the frequency of the photoacoustic signal 3 in which the generated frequency is changed by the change of the living body test region 97 can be outputted from the acoustic wave generator 24. When the intensity of the outputted acoustic wave 2 is variable, the intensity of the acoustic wave 2 outputted from the acoustic wave generator 24 can be decreased and increased according to the intensity of the acoustic wave 2 detected by ultrasonic detector 25, so that the intensity can be compared even if the intensity detected by the acoustic wave detector 25 is small.

Figure 35:
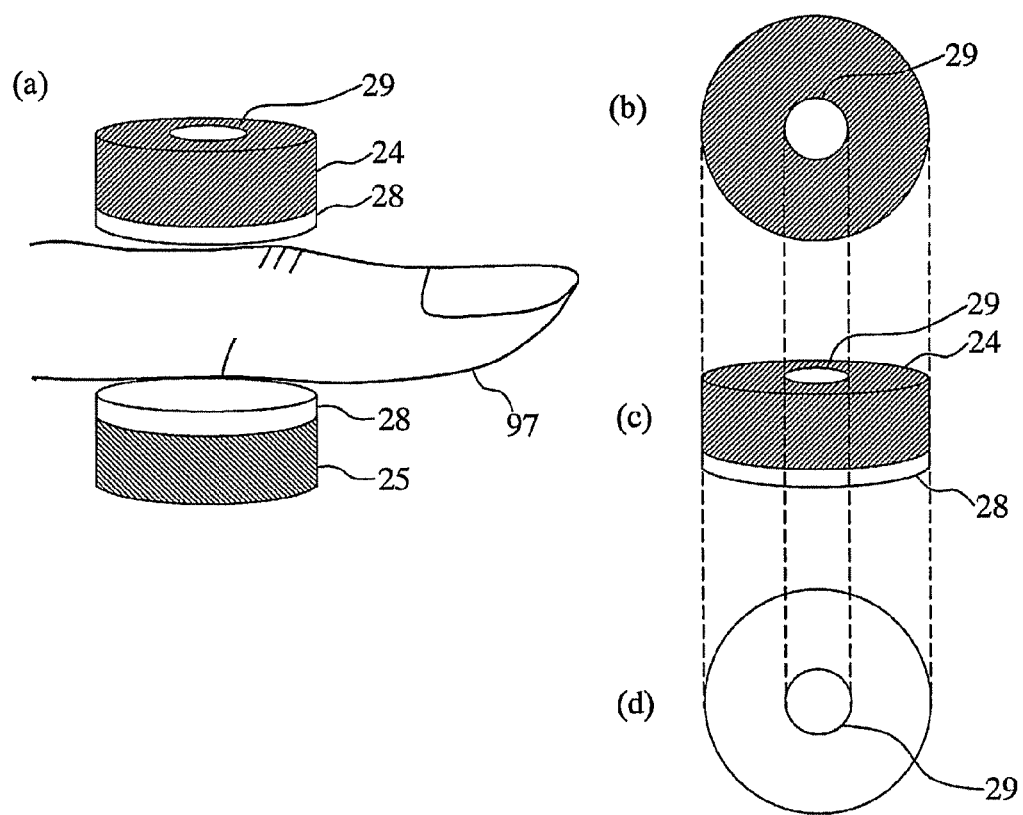
FIG. 35 is a schematic view showing an example of an acoustic wave generator and acoustic wave detection means.

FIG. 35 is a schematic view showing examples of the acoustic wave generator 24 and the acoustic wave detector 25, FIG. 35(a) is an external view, FIG. 35(b) is a top view of the acoustic wave generator, FIG. 35(c) is a perspective view of the acoustic wave generator, and FIG. 35(d) is a bottom view of the acoustic wave generator. FIG. 35(a) shows the state in which the living body test region 97 is clamped by the acoustic wave generator 24 in which the acoustic coupling element 28 is arranged and the acoustic wave detector 25 in which the acoustic coupling element 28 is arranged. As shown in FIGS. 35(b), 35(c), and 35(d), the transmission window 29 which transmits the intensity modulated light beam may be further included in a part of the acoustic wave generator 24. The transmission window 29 may be used as a through hole. A transparent member, which is transparent to the intensity modulated light, may be arranged in the surface which is in contact with the living body test region 97. The acoustic coupling element 28 may be used as the transparent member. Thus, the transmission window 29 is further included, the acoustic wave generator 24 is arranged between the excitation light source and the living body test region 97, and thereby the living body test region 97 can be irradiated from above the acoustic wave generator 24. Accordingly, because the living body test region 97 can be irradiated with the intensity modulated light at the substantially same position as the position where the acoustic wave suitable to the measurement is outputted, the living body test region 97 can be irradiated with the intensity modulated light such that the photoacoustic signal propagates in the propagation path suitable to the measurement. The propagation path suitable to the measurement is confirmed by the acoustic wave.

The acoustic wave detector 25 shown in FIG. 34 detects the acoustic wave 2 and the photoacoustic signal 3 which are of the ultrasonic wave. The acoustic wave detector 25 also includes one which detects the photoacoustic signal 3 to output the electric signals proportional to the acoustic pressures of the acoustic wave 2 and the photoacoustic signal 3 as the output signal 4. Examples of the acoustic wave detector 25 include the acoustic wave detector such as a crystal microphone, a ceramic microphone, and a ceramic ultrasonic wave sensor in which the magneto-striction effect or electro-striction effect is utilized, the acoustic wave detector such as a moving-coil microphone and a ribbon microphone in which electromagnetic induction is utilized, the acoustic wave detector such as a capacitor microphone in which electrostatic effect is utilized, and the acoustic wave detector such as a magneto-striction vibrator in which magneto-striction is utilized. The frequency flat type electro-striction device (ZT) and the acoustic wave detector including the crystal such as PVDF (polyvinylidene fluoride) can be cited as an example of the acoustic wave detector in which the piezoelectric effect is utilized. PZT into which the FET (Field Effect Transistor) amplifier is incorporated may be used as acoustic wave detector 25.

The acoustic coupling element 28 shown in FIG. 34 is a member having the substantially equal acoustic impedance as the living body test region 97. Examples of the acoustic matching substance include rubber, a soft solid such as resin, a liquid, and sol or gel. Preferably, the acoustic coupling element 28 is arranged in the surface in which at least one of the acoustic wave generator 24 and the acoustic wave detector 25 is in contact with living body test region 97, and the reflection/scattering can be decreased at the surface which is in contact with the living body test region by arranging the acoustic coupling element 28.

The drive unit 27 shown in FIG. 34 moves the position at least one of the acoustic wave generator 24 and the acoustic wave detector 25. For example, the excitation light source 23 and the acoustic wave generator 24 may be fixed by a structure such that the optical axis of the excitation light source 23 coincides with the transmission window 29 of the acoustic wave generator 24, and the excitation light source 23 and the acoustic wave generator 24 may be rotated around the living body test region 97 while the positions of the excitation light source 23 and the acoustic wave generator 24 are maintained. The excitation light source 23 and the acoustic wave generator 24 may be moved on the circumference. The distance between the excitation light source 23 and the acoustic wave generator 24 may be varied on the circumference. The excitation light source 23 and the acoustic wave generator 24 may be moved on the surface which is in contact with the living body test region 97. The excitation light source 23 and the acoustic wave generator 24 may three-dimensionally be moved. In FIG. 34, the specific drive mechanism of the drive unit 27 is neglected.

In the drive unit 27, the acoustic wave detector 25 may be fixed while the acoustic wave generator 24 is movable. The acoustic wave generator 24 may be fixed while the acoustic wave detector 25 is movable. Both the acoustic wave generator 24 and the acoustic wave detector 25 may be movable. In the drive unit 27, the excitation light source 23 may be movable. In the drive unit 27, the excitation light source 23 may be moved while simultaneously operating with the acoustic wave generator 24. Because the excitation light source 23 simultaneously operates with the acoustic wave generator 24, the excitation light source 23 can automatically be moved to the position suitable to the measurement. The drive unit 27 may be operated by an instruction from the control unit 26.

The acoustic wave generator 24 is moved with the drive unit 27 by including the above-described drive unit 27, and the influence of the scatterer can be examined in each region in the living body test region 97 using the acoustic wave 2. Therefore, a transmission property of the photoacoustic signal 3 can be estimated in the propagation path of the photoacoustic signal 3. At least one of the irradiation angle and the irradiation position of the intensity modulated light 1 to the living body test region 97 is changed by moving the excitation light source 23 in conjunction with the acoustic wave generator 24, the acoustic wave 2 is monitored in each case such that the acoustic wave 2, which reaches the acoustic wave detector 25 from the acoustic wave generator 24, becomes a particular value, and the influence of the reflected/scattered scatterer on the photoacoustic signal is detected in each propagation path. Therefore, the photoacoustic signal can be detected in the detected optimum arrangement.

The control unit 26 shown in FIG. 34 controls the drive unit 27 such that the intensity of the acoustic wave 2 detected by the acoustic wave detector 25 becomes the particular value. For example, the control unit 26 determines the position where the intensity of the acoustic wave 2 becomes the particular value from the signal intensity of the output signal 4 having the signal intensity which is outputted from the acoustic wave detector 25 and proportional to the acoustic pressure of the acoustic wave 2, and the control unit 26 outputs the control signal 5 to the drive unit 27. The particular value is, the maximum value in the acoustic waves 2 detected by the acoustic wave detector 25. The photoacoustic signal 3 can be detected in the arrangement in which the reflection/scattering become the minimum by setting the acoustic wave 2 at the maximum value. The particular value may be a value which is previously determined before the measurement. When the predetermined value is set at the particular value, the acoustic wave 2 having the constant intensity is outputted, the propagation path is scanned such that the acoustic wave 2 is detected in the predetermined intensity, and the photoacoustic signal 3 is detected in the propagation path. Therefore, the photoacoustic signals 3 having the substantially same influence of reflection/scattering can be detected. Accordingly, the photoacoustic signal 3 can automatically be detected in the detected optimum arrangement.

For example, a comparison circuit which compared two degrees or more of signal intensity, can be used as the comparison of the signal intensity. The output signals 4 to be compared may be electric signals converted into direct-current signals with a smoothing circuit. The drive unit may be controlled by a small oscillation method in which the two consecutively detected degrees of signal intensity are compared to move the drive unit toward the direction having the larger signal intensity.

Either the excitation light source 23 or the acoustic wave detector 25 may be moved by the control signal 5. In the case where the excitation light source 23 and the acoustic wave generator 24 are integrated, the acoustic wave generator 24 may be moved by the control signal 5. The excitation light source 23, the acoustic wave generator 24, and the acoustic wave detector 25 may be moved by the control signal 5. The drive unit 27 is controlled such that the intensity of the acoustic wave 2 detected by the acoustic wave detector 25 becomes the particular value, which allows the photoacoustic signal 3 to be automatically detected in the optimum propagation path.

An operation of the blood constituent concentration measuring apparatus will be described with reference to FIG. 34. The living body test region 97 such as the finger is inserted between the acoustic wave generator 24 and the acoustic wave detector 25, and the drive unit 27 brings the acoustic wave generator 24 and the acoustic wave detector 25 into contact with living body test region 97. Then, the acoustic wave 2 is generated and outputted from the acoustic wave generator 24. The outputted acoustic wave 2 is transmitted through the acoustic coupling element 28 arranged in the acoustic wave generator 24, the living body test region 97, and the acoustic coupling element 28 arranged in the acoustic wave detector 25, and the outputted acoustic wave 2 is detected by the acoustic wave detector 25. The detected acoustic wave 2 is converted into the electric signal proportional to the acoustic pressure, a phase sensitive amplifier (not shown) included in the acoustic wave detector 25 performs the integration and averaging processes to the electric signal, and the output signal 4 is outputted. The control unit 26 obtains the output signal 4 as a reference signal in a first state set by the drive unit 27. Then, the control unit 26 sets a second state in which the output position is changed with respect to the living body test region 97 by the drive unit 27, and the same measurement as the first state is performed. Thus, the control unit 26 obtains the reference signal in each output position. When the acoustic wave 2 is detected predetermined times or in the predetermined range, the operation of the acoustic wave generator 24 is stopped.

The control unit 26 compares the degrees of intensity in each time of the detection of the reference signal to specify the position where the intensity of the particular value is obtained. At this point, it is assumed that the particular value is the maximum value in the acoustic waves 2 detected by the acoustic wave detector 25. The control unit 26 outputs the control signal 5 to the drive unit 27 such that the detection can be performed at the position where the intensity of the particular value is obtained. The drive unit 27 moves the excitation light source 23, the acoustic wave generator 24, and the acoustic wave detector 25 to positions such that the detection can be performed at the position where the intensity of the particular value is obtained. The excitation light source 23 outputs the intensity modulated light 1 from the moved position. The intensity modulated light 1 is transmitted through the transmission window 29, and the living body test region 97 is irradiated with the intensity modulated light 1. The photoacoustic signal 3 generated in the living body test region 97 is detected by the acoustic wave detector 25. Similarly to the acoustic wave 2, the detected photoacoustic signal 3 is outputted as the output signal 4 from the acoustic wave detector 25. The drive unit 27 may change not the output position of the acoustic wave 2 outputted from the acoustic wave generator 24, but the output angle to the living body test region 97. The photoacoustic signal 3 is detected by the above operation, which allows the photoacoustic signal 3 to be detected in the arrangement in which the influences of the reflection/scattering become the minimum.

Another operation of the blood constituent concentration measuring apparatus will further be described with reference to FIG. 34. The living body test region 97 such as the finger is inserted between the acoustic wave generator 24 and the acoustic wave detector 25, and the drive unit 27 brings the acoustic wave generator 24 and the acoustic wave detector 25 into contact with living body test region 97. Then, the acoustic wave 2 is generated and outputted from the acoustic wave generator 24. The acoustic wave 2 is transmitted through the acoustic coupling element 28 arranged in the acoustic wave generator 24, the living body test region 97, and the acoustic coupling element 28 arranged in the acoustic wave detector 25, and the outputted acoustic wave 2 is detected by the acoustic wave detector 25. The detected acoustic wave 2 is converted into the electric signal proportional to the acoustic pressure, the phase sensitive amplifier (not shown) included in the acoustic wave detector 25 performs the integration and averaging processes to the electric signal, and the output signal 4 is outputted. The control unit 26 obtains the output signal 4 as the reference signal in the first state set by the drive unit 27.

Then, the operation of the acoustic wave generator 24 is stopped, and the living body test region 97 is irradiated with the intensity modulated light 1 which is outputted from the excitation light source 23 and transmitted through the transmission window 29. Similarly to the acoustic wave 2, the photoacoustic signal 3 detected by the acoustic wave detector 25 is outputted as the output signal 4 from the acoustic wave detector 25. The output signal 4 from the photoacoustic signal 3 becomes the actual signal in the first state. After the settings of the acoustic wave generator 24 and acoustic wave detector 25 are completed with respect to the living body test region 97, the reference signal and the actual signal are instantly obtained in an electronic manner, so that the position change of the living body test region 97 caused by the body movement is hardly generated.

Then, the control unit 26 sets the second state in which the output angle and the output position are changed with respect to the living body test region 97 by the drive unit 27, and the same measurement as the first state is performed. In this case, only the first and second states are illustrated. However, the measurement may be performed in three or more states. Thus, the measurement is sequentially performed, and the actual signal corresponding to the state in which the reference signal becomes the particular value can be utilized as the measured value. The particular value may be the value which is previously determined before the measurement. The photoacoustic signals 3 having the substantially same influence of reflection/scattering can be detected by utilizing the actual signal corresponding to the state, in which the acoustic wave 2 of the predetermined signal intensity is detected, as the measured value. Therefore, the blood constituent concentration can be measured while the influences of many parameters associated with the change in arrangement of the blood constituent concentration measuring apparatus are removed.

The control method of blood constituent concentration measuring apparatus according to the fifth embodiment sequentially includes an optimum position detection procedure and a photoacoustic signal detection procedure. In the optimum position detection procedure, the acoustic wave generator 24 outputs the acoustic wave 2 from two or more different positions to the living body test region 97 which is of the test subject, and the acoustic wave detector 25 which is of the acoustic wave detection means detects the position where the intensity of the acoustic wave 2 transmitted through the living body test region 97 becomes the particular value. In the photoacoustic signal detection procedure, the light generating means, the light modulation means, and the excitation light source 23 which is of the light outgoing means irradiate the living body test region 97 with the intensity modulated light beams which are intensity-modulated at the constant frequency from the positions where the intensity of the acoustic wave 2 becomes the particular value, and the acoustic wave detector 25 detects the photoacoustic signal 3 emitted from the living body test region 97.

After the influence of the reflected/scattered scatterer on the photoacoustic signal is detected in each propagation path by changing the propagation path of the acoustic wave 2, the living body test region 97 is irradiated with the intensity modulated light 1 to detect the photoacoustic signal 3 such that the photoacoustic signal 3 propagates through the path in which the intensity of the acoustic wave 2 detected by the acoustic wave detector 25 becomes the particular value. Therefore, the photoacoustic signal can be detected in the detected optimum arrangement.

In the optimum position detection procedure, preferably the acoustic wave generator 24 outputs the acoustic wave 2 to the surface of the living body test region 97. Therefore, the generated acoustic wave 2 can efficiently be transmitted to the living body test region 97.

In the photoacoustic signal detection procedure, preferably the excitation light source 23 irradiates the living body test region 97 with the intensity modulated light 1 through the transmission window which is provided in a part of the acoustic wave generator 24 and transparent to the intensity modulated light 1. The excitation light source 23 can irradiate the living body test region 97 with the intensity modulated light 1 from above the acoustic wave generator 24. Accordingly, the living body test region 97 can be irradiated with the intensity modulated light 1 at the substantially same position as the position of the acoustic wave generator 24 where the optimum acoustic wave 2 is detected.

In the light outgoing procedure, as described above, the excitation light source 23 generates the two light beams having the mutually different wavelengths 2 and $\lambda_2$, the excitation light source 23 intensity-modulates the two light beams having the mutually different wavelengths $\lambda_1$ and $\lambda_2$ into the intensity modulated light 1 having the same frequency and reverse phases, and the excitation light source 23 outputs the intensity modulated light 1.

In the optimum position detection procedure, preferably the acoustic wave generator 24 outputs the acoustic wave 2 having the substantially same frequency as the frequency of the intensity modulated light 1. Because the scatterer can be detected with the acoustic wave 2 having the same frequency as the detected photoacoustic signal 3, the influence of the scatterer on the photoacoustic signal 3 can be examined more correctly.

In the optimum position detection procedure, preferably the acoustic wave generator 24 increases and decreases the intensity of the outputted acoustic wave 2 according to the intensity of the acoustic wave 2 detected by the acoustic wave detector 25. Because the intensity of the acoustic wave 2 outputted from the acoustic wave generator 24 is increased or decreased according to the intensity of the acoustic wave 2 detected by the acoustic wave detector 25, the detected intensity can be compared even if the intensity detected by the acoustic wave detector 25 is small.

In the optimum position detection procedure, preferably the acoustic wave generator 24 and the acoustic wave detector 25 are pressed against the living body test region 97 to detect the acoustic wave 2 with the pressuring force in which the pressure can be controlled. Because the pressure at which the acoustic wave generator 24 and the acoustic wave detector 25 are pressed against the living body test region 97 is variable, the pressure at which the acoustic wave generator 24 and the acoustic wave detector 25 come into contact with the living body test region 97 can be maintained at a constant pressure. Therefore, the influence of the pressure pressing the living body test region 97 can be reduced.

The circuit diagram of the blood constituent concentration measuring apparatus shown in FIG. 34 may includes pressing means (not shown) for pressing the acoustic wave generator and the acoustic wave detector against the living body test region with the pressuring force in which the pressure can be controlled. For example, a U-shape arm in which the acoustic wave generator and the acoustic wave detector are fixed to both ends can be used as the pressing means. The arm can change the distance between the acoustic wave generator and the acoustic wave detector to vary the pressure at which the acoustic wave generator and the acoustic wave detector are pressed against the living body test region. Therefore, the pressure at which the acoustic wave generator and the acoustic wave detector come into contact with the living body test region can be maintained at a constant pressure.

In FIG. 34, the living body test region 97 is set at the finger of human body. However, an animal, a bird, and plants such as fruit and vegetable may be used as the object to be measured. The object to be measured includes a pipe through which a liquid flows and the container such as a bottle and a tank in which the liquid, sol or gel is reserved. For example, when the object to be measured is the fruit, the sugar of the fruit can be measured in the noninvasive manner.

As described above, the blood constituent concentration measuring apparatus according to the fifth embodiment detects the arrangement in which the positional relationship between the generation source of the photoacoustic signal and the acoustic wave detector becomes optimum. Therefore, the photoacoustic signal is detected in the optimum arrangement in which the scatterer such as the bone has a little influence on the photoacoustic signal, and the blood constituent concentration can be measured. The photoacoustic signal is detected in the arrangement in which the signal intensity of the detected acoustic wave becomes the predetermined value. Therefore, the blood constituent concentration can be measured while the influences of many parameters associated with the change in arrangement of the blood constituent concentration measuring apparatus are removed.

EXAMPLES

Specific examples in the fifth embodiment will be described below.

First Example

Figure 36:
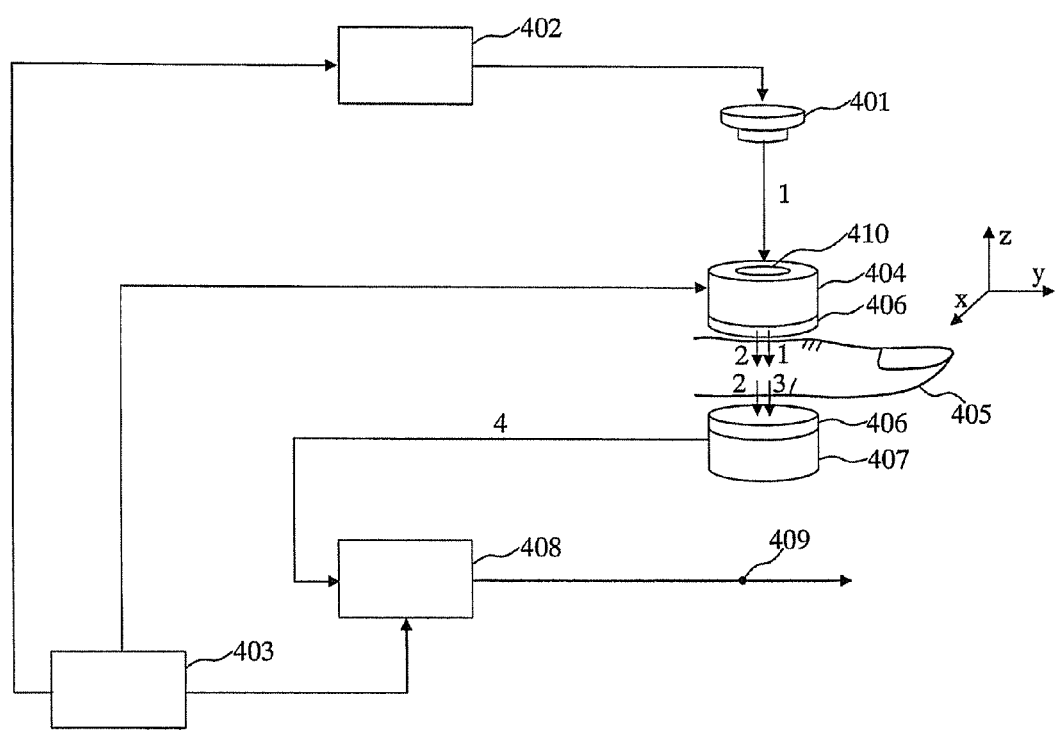
FIG. 36 is a circuit diagram of the blood constituent concentration measuring apparatus according to the embodiment.

A first example of the blood constituent concentration measuring apparatus according to the fifth embodiment of the invention will be described with reference to FIG. 36. FIG. 36 is a circuit diagram of the blood constituent concentration measuring apparatus according to the first example. An acoustic wave generator 404 is connected to an oscillator 403. A hole 410 which is of the outgoing window, is made in the acoustic wave generator 404. The hole 410 is large enough to irradiate the test subject 405 with the intensity modulated light 1 from above the test subject 405. The acoustic wave generator 404 generates the acoustic wave 2 in association with the oscillation frequency of the oscillator 403. The acoustic wave 2 passes through the test subject 405, and an acoustic wave detector 407 detects the acoustic wave 2 through an acoustic coupling element 406, and the acoustic wave detector 407 converts the acoustic wave 2 into the output signal 4 proportional to the acoustic pressure. The waveform of the output signal 4 is observed by a phase sensitive amplifier 408, and the output signal 4 is outputted to an output terminal 409. The phase sensitive amplifier 408 is triggered by the signal synchronized with the frequency of the oscillator 403, and the phase sensitive amplifier 408 can measure the output signal 4 while performing the integration and averaging to the output signal 4. The acoustic wave 2 generated from the acoustic wave generator 404 is detected while the arrangement of the acoustic wave detector 407 and the pressing force against the test subject 405 are changed. The signal intensity of the detected acoustic wave 2 is sequentially measured, and the acoustic wave detector 407 is fixed to the position where the intensity becomes the particular value. The optimum arrangement among the devices is realized while avoiding the influence of the reflection/scattering in the living body.

On the other hand, the oscillator 403 is also connected to a drive power supply 402. The drive power supply 402 supplies the rectangular excitation current associated with the oscillation frequency of the oscillator 403 to a semiconductor laser device 401.

After the arrangement among the devices is calibrated, the semiconductor laser device 401 generates the intensity modulated light 1 while the intensity modulation is performed in the frequency of the oscillator 403. The test subject 405 is irradiated with the intensity modulated light 1 passing through the hole 410 made in the center of the acoustic wave generator 404. The intensity modulated light 1 generates the photoacoustic signal 3 in the test subject 405. The photoacoustic signal 3 is detected through the acoustic coupling element 406 by the acoustic wave detector 407, and the photoacoustic signal 3 is converted into the output signal 4 proportional to the acoustic pressure. The waveform of the output signal 4 is observed by the phase sensitive amplifier 408. The phase sensitive amplifier 408 is triggered by the signal synchronized with the frequency of the oscillator 403, and the phase sensitive amplifier 408 can measure the output signal 4 while performing the integration and averaging to the output signal 4. The measured signal is outputted to the outside from the output terminal 409.

In the above configuration, the acoustic wave generator 404 has the diameter of about 30 mm, the acoustic wave generator 404 has the hole in the center, and the hole has the radius of 10 mm. The acoustic wave generator is brought into close contact with the test subject 405 through the ultrasonic wave gel. The generated acoustic wave 2 is 200 kHz, and the acoustic wave 2 is controlled by the oscillator 403.

The acoustic wave detector 407 is the frequency flat type electrostrictive device (PZT) into which the field effect transistor (FET) amplifier is incorporated. The ultrasonic wave gel is used as the acoustic coupling element 406. In the above configuration, the signal intensity of Vr=1 to 15 mV is obtained as the output signal 4 corresponding to the acoustic wave 2 at the output terminal 409 of the phase sensitive amplifier 408 in which the time constant is set at 0.1 second. Therefore, the optimum arrangement is fixed to the position where Vr=15 mV is detected.

On the other hand, the wavelength of the semiconductor laser device 401 is set at 1608 nm. The wavelength of 1608 nm corresponds to the absorption wavelength of glucose. The modulation frequency in which the intensity modulated light 1 is intensity-modulated is set at 200 kHz, and the output of the intensity modulated light 1 is 5.0 mW.

The light beam diameter with which the test subject 405 is irradiated is set at 2.7 mm such that the Fresnel number becomes 0.1 while the distance between the acoustic wave detector 407 and the position of the test subject 405 irradiated with the beam is set at 10 mm.

In this state of things, the irradiation intensity to the skin with the output light of the semiconductor laser device 401 is 0.22 mW/mm$^2$ in the output light of the semiconductor laser device 401, and the irradiation intensity is in the safe level which is lower than a half of the maximum tolerance. However, preferably the light shielding hood (not shown) is placed at the position where the test subject 405 is arranged such that the light is reflected or scattered from the acoustic coupling element 406 does not leak outside during the measurement or during the test subject 405 is not placed.

The acoustic wave detector 407 is the frequency flat type electrostrictive device (PZT) into which the field effect transistor (FET) amplifier is incorporated. The ultrasonic wave gel is used as the acoustic coupling element 406. In the above configuration, in the case where the test subject 405 is irradiated only with the intensity modulated light 1 outputted from the semiconductor laser device 401, the signal intensity of Vr=20 μV is obtained as the output signal 4 corresponding to the photoacoustic signal 3 at the output terminal 409 of the phase sensitive amplifier 408 in which the time constant is set at 0.1 second.

Thus, before the photoacoustic measurement, the arrangement is calibrated using the acoustic wave 2 generated by the acoustic wave generator 404 as the reference signal, the output signal 4 proportional to the acoustic pressure of the photoacoustic signal 3 is measured by the semiconductor laser device 401, and the photoacoustic signal 3 corresponding to the glucose absorption in the test subject 405 is measured.

Second Example

A second example will be described with reference to FIG. 36. The acoustic wave generator is connected to the oscillator. The hole is made in the acoustic wave generator 404, and the hole is large enough to irradiate the test subject 405 with the excitation light from above the test subject 45.

The acoustic wave generator 404 generates the acoustic wave 2 in association with the oscillation frequency of the oscillator 403. The acoustic wave 2 passes through the test subject 405, and the acoustic wave detector 407 detects the acoustic wave 2 through the acoustic coupling element 406, and the acoustic wave detector 407 converts the acoustic wave 2 into the output signal 4 proportional to the acoustic pressure. The phase sensitive amplifier 408 can measure the waveform of the output signal 4 while performing the integration and averaging to the output signal 4. The acoustic wave 2 generated from the acoustic wave generator 404 is detected while the arrangement of the acoustic wave detector 407 and the pressing force against the test subject 405 are changed. The signal intensity of the detected acoustic wave 2 is sequentially measured, and the acoustic wave detector 407 is fixed to the position where the intensity becomes the particular value. The optimum arrangement among the devices is realized while avoiding the influence of the reflection/scattering in the living body.

On the other hand, the oscillator 403 is also connected to the drive power supply 402. The drive power supply 402 supplies the rectangular excitation current to the semiconductor laser device 401.

After the arrangement among the devices is calibrated, the semiconductor laser device 401 generates the intensity modulated light 1 while the intensity modulation is performed in the frequency of the oscillator 403. The test subject 405 is irradiated with the intensity modulated light 1 passing through the hole 410 made in the center of the acoustic wave generator 404. The intensity modulated light 1 generates the photoacoustic signal 3 in the test subject 405. The photoacoustic signal 3 is detected through the acoustic coupling element 406 by the acoustic wave detector 407, and the photoacoustic signal 3 is converted into the output signal 4 proportional to the acoustic pressure. The waveform of the output signal 4 is observed by the phase sensitive amplifier 408. The phase sensitive amplifier 408 is triggered by the signal synchronized with the frequency of the oscillator 403, and the phase sensitive amplifier 408 can measure the output signal 4 while performing the integration and averaging to the output signal 4. The measured signal is outputted to the outside from the output terminal 409.

In the above configuration, the acoustic wave generator 404 has the diameter of about 30 mm, the acoustic wave generator 404 has the hole in the center, and the hole has the radius of 10 mm. The acoustic wave generator is brought into close contact with the test subject 405 through the ultrasonic wave gel. The generated acoustic wave 2 is 200 kHz, and the acoustic wave 2 is controlled by the oscillator 403.

The acoustic wave detector 407 is the frequency flat type electrostrictive device (PZT) into which the FET (Field Effect Transistor) amplifier is incorporated. The ultrasonic wave gel is used as the acoustic coupling element 406. In the above configuration, the signal intensity of Vr=1 to 15 mV is obtained as the output signal 4 corresponding to the acoustic wave 2 at the output terminal 409 of the phase sensitive amplifier 408 in which the time constant is set at 0.1 second. Therefore, the optimum arrangement is fixed to the position where Vr=15 mV is detected.

On the other hand, the wavelength of the semiconductor laser device 401 is set at 1608 nm. The wavelength of 1608 nm corresponds to the absorption wavelength of glucose. The intensity modulation frequency is set at 200 kHz, and the output is 5.0 mW.

The beam diameter of the intensity modulated light 1 with which the test subject 405 is irradiated is set at 2.7 mm such that the Fresnel number N becomes 0.1 while the distance between the acoustic wave detector 407 and the position of the test subject 405 irradiated with the beam is set at 10 mm.

In this state of things, the irradiation intensity to the skin of the test subject 405 with the output light of the semiconductor laser device 401 is 0.22 mW/mm$^2$, and the irradiation intensity is in the safe level which is lower than a half of the maximum tolerance. However, preferably the light shielding hoods (not shown) is placed at the position where the test subject 405 is arranged such that the light reflected or scattered from the acoustic coupling element 406 does not leak outside during the measurement or during the test subject 405 is not placed.

The acoustic wave detector 407 is the frequency flat type electrostrictive device (PZT) into which the FET (Field Effect Transistor) amplifier is incorporated. The ultrasonic wave gel is used as the acoustic coupling element 406. In the above configuration, in the case where the test subject 405 is irradiated only with the intensity modulated light 1 outputted from the semiconductor laser device 401, the signal intensity of Vr=20 µV is obtained as the output signal 4 corresponding to the photoacoustic signal 3 at the output terminal 409 of the phase sensitive amplifier 408 in which the time constant is set at 0.1 second.

After the above measurement is performed, the measuring apparatus is detached, and the same measurement is performed again. The acoustic wave 2 generated from the acoustic wave generator 404 is detected while the arrangement of the acoustic wave detector 407 and the pressing force against the test subject 405 are changed. The signal intensity of Vr=1 to 15 mV is obtained as the output signal 4 corresponding to the acoustic wave 2 at the output terminal 409 of the phase sensitive amplifier 408 in which the time constant is set at 0.1 second. Therefore, the optimum arrangement is fixed to the position where Vr=15 mV is detected.

When the photoacoustic signal 3 generated by the semiconductor laser device 401 is measured at the fixed position using the phase sensitive amplifier 408, the signal intensity of Vr=20 µV is obtained.

Thus, in performing the re-measurement, the arrangement is calibrated by utilizing the acoustic wave 2 generated by the acoustic wave generator 404 as the reference signal, which allows the measurement to be performed with good reproducibility for the measurement of the photoacoustic signal 3.

Sixth Embodiment

A blood constituent concentration measuring apparatus according to a sixth embodiment includes light generating means for generating two light beams having different wavelengths; light modulation means for electrically intensity-modulating each of the two light beams having the mutually different wavelengths using signals having the same frequency and reverse phases; light outgoing means for multiplexing into one light flex to output the intensity-modulated two light beams having the mutually different wavelengths toward a living body; acoustic wave detection means for detecting an acoustic wave generated in the living body by the outputted light; and enduing means for mounting at least the light outgoing means and the acoustic wave detection means, the enduing means having an annular portion in which the living body is fitted while surrounding the living body. The blood constituent concentration measuring apparatus of the sixth embodiment is characterized in that the light outgoing means and the acoustic wave detection means are arranged inside the annular portion of the enduing means in a portion which is in contact with the living body. The enduing means according to the sixth embodiment can also applied in the blood constituent concentration measuring apparatus according to the first embodiment, the second embodiment, the third embodiment, the fourth embodiment, and the fifth embodiment.

Particularly, in the blood constituent concentration measuring apparatus according to the sixth embodiment, the light generating means effectively sets one of the light wavelengths of the two light beams at the wavelength in which the blood constituent exhibits the characteristic absorption, and the light generating means effectively sets the other light wavelength at the wavelength in which the water exhibits the absorption parallelly equal to that in one of the light wavelengths.

Figure 37:
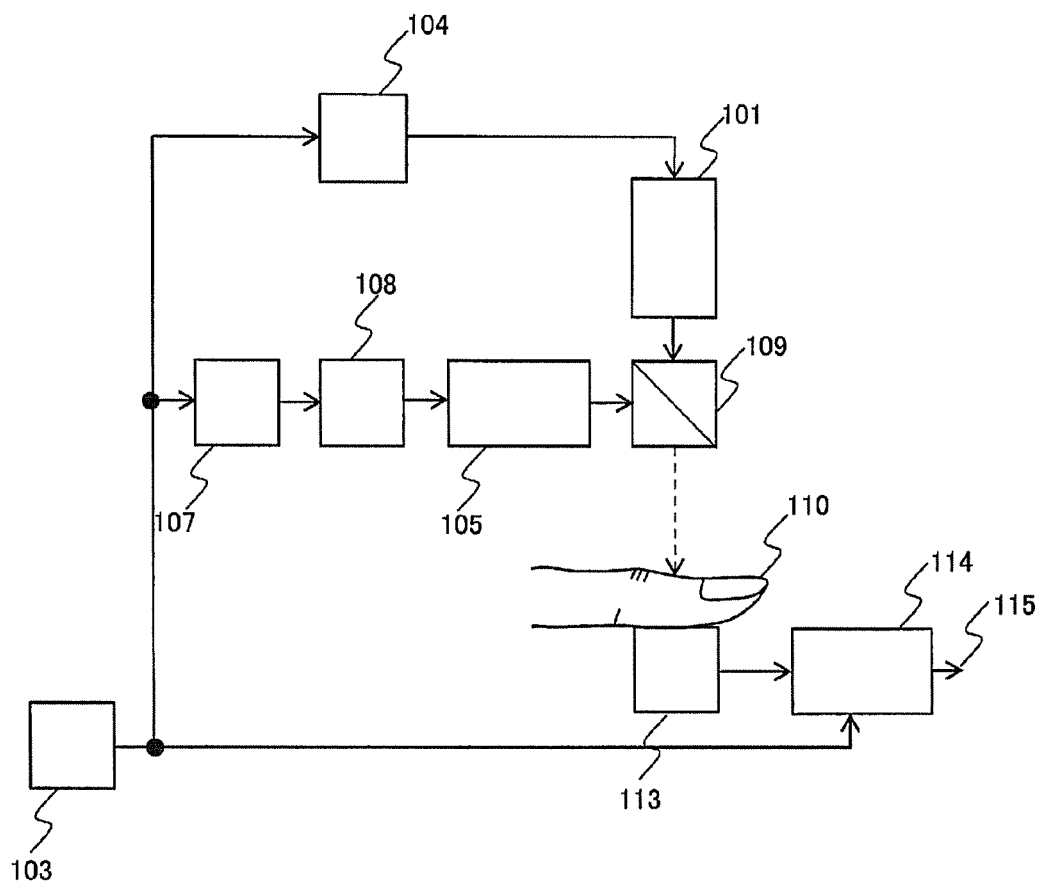
FIG. 37 is an explanatory view showing a configuration of the blood constituent concentration measuring apparatus according to an embodiment.

A basic configuration of a measuring system of the blood constituent concentration measuring apparatus according to the sixth embodiment will be described with reference to FIG. 37. FIG. 37 shows the basic configuration of the measuring system of the blood constituent concentration measuring apparatus according to the sixth embodiment. The components concerning the later-mentioned mounting technique and the components, such as a power supply, which can be realized by the conventional techniques are not shown in FIG. 37.

In FIG. 37, the first light source 101 which is of a part of the light generating means is intensity-modulated in synchronization with the oscillator 103 which is of a part of the light modulation means by the drive circuit 1.04 which is of a part of the light modulation means.

On the other hand, the second light source 105 which is of a part of the light generating means is intensity-modulated in synchronization with the oscillator 103 which is of a part of the light modulation means by the drive circuit 108 which is of a part of the light modulation means. However, the output of the oscillator 103 is supplied to the drive circuit 108 through the 180°-phase-shift circuit 107 which is of a part of the light modulation means. As a result, the second light source 105 is configured so as to be intensity-modulated with the signal whose phase is changed by 180° with respect to the light source 101.

In the wavelengths of the first light source 101 and the second light source 105 shown in FIG. 37, one of the light wavelengths of the two light beams is set at the wavelength in which the blood constituent exhibits the characteristic absorption, and the other light wavelength is set at the wavelength in which the water exhibits the absorption parallelly equal to that in one of the light wavelengths.

By way of example, in the case where the blood constituent of the measuring object is set at glucose, i.e., in the case where the blood sugar level is measured, it is effective that the wavelength ($\lambda_1$) of the first light source 101 is set at 1608 nm and the wavelength ($\lambda_2$) of the second light source 105 is set at 1381 nm. In the case of the longer wavelength band, it is effective that the wavelength ($\lambda_1$) of the first light source 101 is set at 2126 nm and the wavelength ($\lambda_2$) of the second light source 105 is set at 1837 nm or 2294 nm. FIG. 7 shows a relationship between the wavelength ($\lambda_1$) of the first light source 101 and the wavelength ($\lambda_2$) of the second light source 105.

The first light source 101 and the second light source 105 output the light beams having the different wavelengths respectively, the outputted light beams are multiplexed into one light flux by the coupler 109 which is of the light outgoing means, and the multiplexed light is outputted to the living body test region 110. The acoustic waves, i.e., the photoacoustic signals generated in the living body test region 110 by the light beams outputted from the first light source 101 and the second light source 105 are detected by the ultrasonic detector 113 which is of a part of the acoustic wave detection means, and the photoacoustic signals are converted into the electric signals proportional to the acoustic pressures of the photoacoustic signals. The phase sensitive amplifier 114 which is of a part of the acoustic wave detection means synchronized with the oscillator 103 performs the synchronous detection to the electric signal, and the electric signal proportional to the acoustic pressure is outputted to the output terminal 115.

At this point, the intensity of the signal outputted to the output terminal 115 is proportional to a light quantity in which the light beam outputted from each of the first light source 101 and the second light source 105 is absorbed by the constituent in the living body test region 110, so that the signal intensity is proportional to the mount of constituent in the living body test region 110. Accordingly, the blood constituent concentration computation means (mot shown) computes the mount of constituent of the measuring object in the blood of the living body test region 110 from the measured value of the intensity of the signal outputted to the output terminal 115.

In the blood constituent concentration measuring apparatus according to the embodiment, the two light beams having the different wavelengths outputted from the first light source 101 and the second light source 105 are intensity-modulated using the signals having the same period, i.e., the same frequency. Therefore, the blood constituent concentration measuring apparatus according to the sixth embodiment has a feature that the blood constituent concentration measuring apparatus according to the sixth embodiment is not affected by the unevenness of the frequency characteristics of the ultrasonic detector 113. This is the excellent point as compared with the currently existing techniques.

In the blood constituent concentration measuring apparatus according to the sixth embodiment, the light modulation means is effectively formed by light modulation means for performing the modulation at the same frequency as the resonant frequency concerning the detection of the acoustic wave generated in the living body.

Thus, the two light beams having different wavelengths is modulated with the same frequency as the resonant frequency concerning the detection of the acoustic wave generated in the living body, which allows the acoustic wave generated in the living body to be detected with high sensitivity.

On the other hand, the non-linear absorption coefficient dependence existing in the measured value of the photoacoustic signal, which becomes troublesome in the conventional technique, can be solved by performing the measurement using the light beams having the plural wavelengths for giving the equal absorption coefficient in the blood constituent concentration measuring apparatus according to the sixth embodiment. That will be described below.

That is, in the case where background absorption coefficients $\alpha_1^{(b)}$, $\alpha_2^{(b)}$ and molar absorptions $\alpha_1^{(0)}$, $\alpha_2^{(0)}$ of the blood constituent set as the measuring object are already known for light beams having a wavelength $\lambda_1$ and a wavelength $\lambda_2$ respectively, the simultaneous equations including measured values $s_1$ and $s_2$ of the photoacoustic signal in the wavelengths are expressed by the formula (1).

The unknown blood constituent concentration M is determined by solving the formula (1). Where C is a variable coefficient which is hardly controlled or calculated, i.e., C is an unknown multiplier depending on an acoustic coupling state, ultrasonic detector sensitivity, a distance between the light outgoing means and the acoustic wave detection means (hereinafter defined as r), specific heat, a thermal expansion coefficient, sound velocity, the modulation frequency, and the absorption coefficient.

When the difference is generated in C of the first line and the second line of the formula (1), the difference is an amount concerning the irradiation light, i.e., the difference by the absorption coefficient. At this point, when a combination of the wavelength $\lambda_1$ and the wavelength $\lambda_2$ is selected such that the parentheses of the lines of the formula (1), i.e., the absorption coefficients are equal to each other, the absorption coefficients are equal to each other, and C in the first line is equal to C in the second line. However, when the above operation is exactly performed, it is inconvenient because the combination of the wavelength $\lambda_1$ and the wavelength $\lambda_2$ depends on the unknown blood constituent concentration M.

At this point, the background ($\alpha_i^{(b)}$, i=1 and 2) is remarkably larger than a term ($M\alpha_i^{(0)}$) including the blood constituent concentration M in an occupying ratio in the absorption coefficient (parenthesis in each line) of the formula (1). That is, the two light beams having the mutually different wavelength $\lambda_1$ and wavelength $\lambda_2$ may be selected such that the absorption coefficients $\alpha_1^{(b)}$ and $\alpha_2^{(b)}$ of the background are equal to each other. Thus, when C in the first line is equalized to C in the second line, Cs are deleted as an unknown constant, and the blood constituent concentration M of the measuring object is expressed by the following formula (4). In the deformation of the rear stage of the formula (4), quality of $s_1 \cong s_2$ is used.

Referring to the formula (4), in the denominator, the difference in absorption coefficient of the blood constituent of the measuring object emerges in wavelength $\lambda_2$ and wavelength $\lambda_2$. As the difference is increased, the difference signal $s_1-s_2$ of the photoacoustic signal is increased, and the measurement becomes easy. In order to maximize the difference, the wavelength in which the constituent absorption coefficient $\alpha_1^{(0)}$ of the measuring object becomes the maximum is selected as the wavelength $\lambda_1$, and the wavelength in which $\alpha_2^{(0)}=0$, i.e., the constituent of the measuring object does not exhibit the absorption characteristics is selected as the wavelength $\lambda_2$. At this point, in the second wavelength $\lambda_2$, it is necessary that $\alpha_2^{(b)}=\alpha_1^{(b)}$, i.e., the background absorption coefficient is equal to the absorption coefficient of the first wavelength $\lambda_1$.

In the formula (4), the photoacoustic signal $s_1$ emerges only in the form of the difference of $s_1-s_2$ between the photoacoustic signal $s_1$ and the photoacoustic signal $s_2$. For example, when glucose is set at the constituent of the measuring object, as described above, there is only the difference 0.1% or less between the intensity of the photoacoustic signal $s_1$ and the intensity of the photoacoustic signal $s_2$.

However, in the denominator of the formula (4), it is sufficient that the photoacoustic signal $s_2$ has the accuracy of about 5%. Accordingly, the accuracy is easily kept in measuring the difference $s_1-s_2$ between the photoacoustic signal $s_1$ and the photoacoustic signal $s_2$ to divide the measured value by the separately measured photoacoustic signal $s_2$ rather than sequentially separately measuring the photoacoustic signal $s_1$ and the photoacoustic signal $s_2$. Accordingly, in the blood constituent concentration measuring apparatus according to the sixth embodiment, when the light beams having the wavelength $\lambda_1$ and the wavelength $\lambda_2$ are intensity-modulated into the light beams having the reverse phases to irradiate the living body, and the difference signal $s_1-s_2$ of the photoacoustic signals is measured. The difference signal $s_1-s_2$ of the photoacoustic signals is generated in the living body while the photoacoustic signal $s_1$ and the photoacoustic signal $s_2$ are mutually superposed.

As described above, in measuring the blood constituent concentration, using the two light beams having the mutually different particular wavelengths, the measurement is performed not by separately measuring the photoacoustic signals generated in the living body, but by measuring the difference between the photoacoustic signals, one of the photoacoustic signals is measured while the other photoacoustic signal is set to zero, and the measured values are computed by the formula (4). Therefore, the blood constituent concentration can easily be measured.

Figure 38:
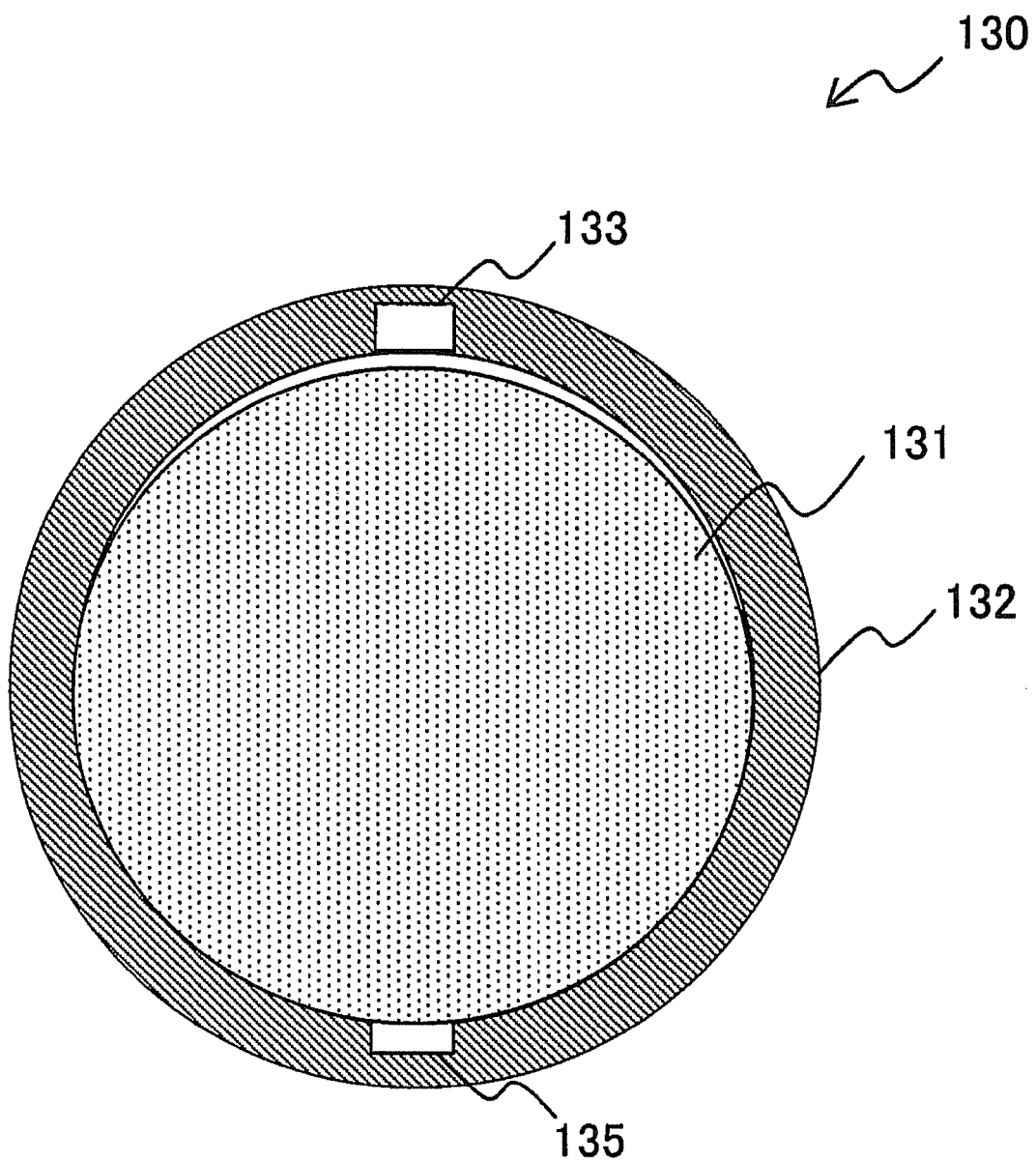
FIG. 38 is an explanatory view showing the structure of an enduing unit of the blood constituent concentration measuring apparatus according to the embodiment.

A mounting structure of the blood constituent concentration measuring apparatus according to the sixth embodiment will be described below. FIG. 38 shows a configuration of an enduing means of the blood constituent concentration measuring apparatus according to the sixth embodiment. In an enduing unit 130 which is of the enduing means shown in FIG. 38, at least a light irradiation unit 133 which is of the light outgoing means and an ultrasonic detection unit 135 which is of the acoustic wave detection means are mounted inside an annular support frame 132 having an annular shape surrounding a living body 131 which is of the test subject. In FIG. 38, the light irradiation unit 133 and the ultrasonic detection unit 135 are mounted in the surface which is in contact with the living body 131 inside the annular support frame 132, and the light irradiation portion of the light irradiation unit 133 and the ultrasonic wave reception portion of the ultrasonic detection unit 135 are mounted while facing each other across the living body 131.

In the enduing unit 130 having the above structure, the living body 131 is securely held, the movement and the change in shape of the living body 131 are effectively minimized, the constant thickness of the living body 131 is maintained between the light irradiation unit 133 and the ultrasonic detection unit 135, the change in shape of the living body 131 is suppressed near the ultrasonic detection unit 135, and the change in reflection of the ultrasonic wave from the living body 131 is decreased near the ultrasonic detection unit 135. Therefore, the blood constituent concentration can correctly be measured.

As described above, the light irradiation unit 133 and the ultrasonic detection unit 135 are arranged at the while substantially facing each other in the annular portion of the enduing unit 130. Therefore, the ultrasonic wave generated in the living body 131 by the light emitted from the light irradiation unit 133 can efficiently be detected by the ultrasonic detection unit 135.

Figure 39:
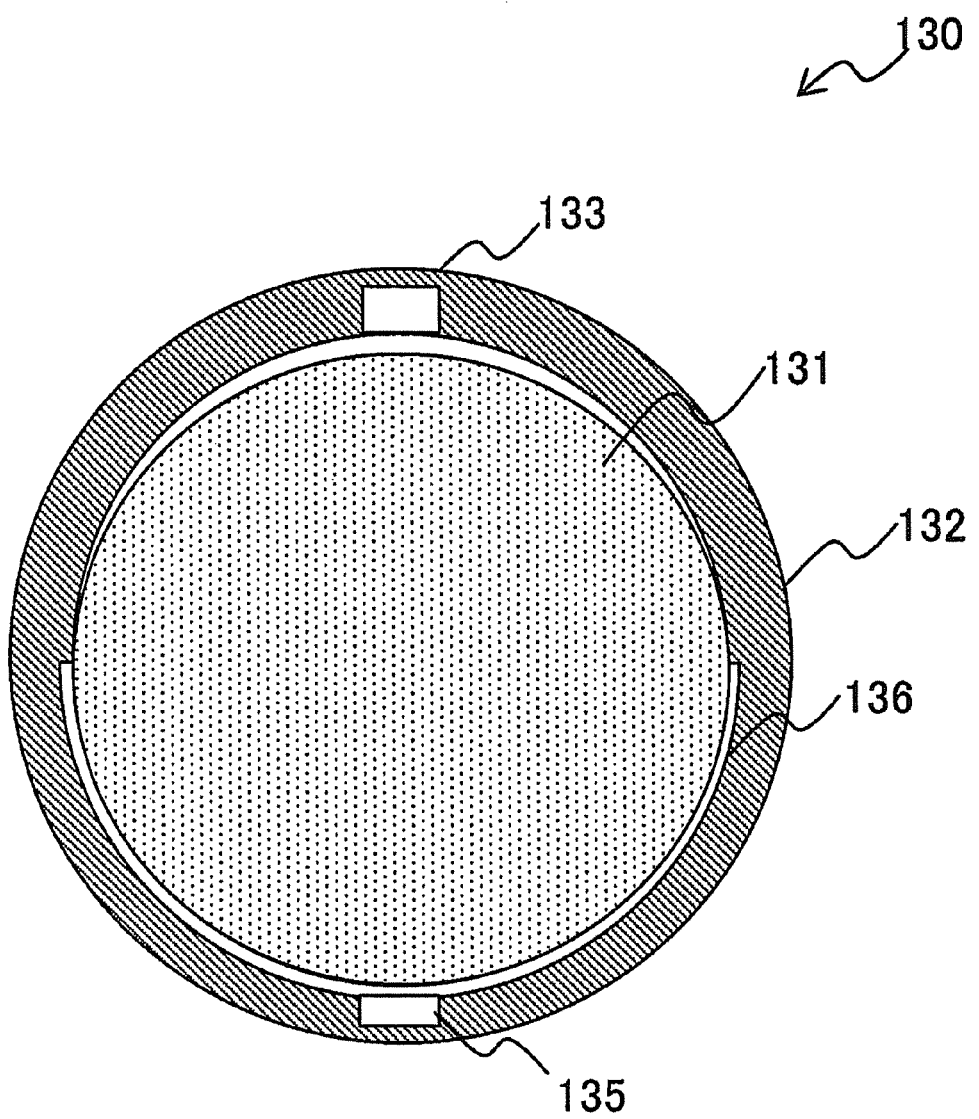
FIG. 39 is an explanatory view showing the structure of an enduing unit of the blood constituent concentration measuring apparatus according to the embodiment.

In the blood constituent concentration measuring apparatus of the sixth embodiment, preferably a cushioning material layer having the acoustic impedance close to that of the living body is arranged at least half around a portion which is in contact with the living body. The portion also includes the point where the acoustic wave detection means is arranged, and the portion is located inside the annular portion of the enduing means. In the configuration of the enduing means in the blood constituent concentration measuring apparatus according to the sixth embodiment, as shown in FIG. 39, the layer made of a cushioning material 136 having the acoustic impedance close to that of the living body is arranged at least half around the portion which is in contact with the living body. The portion also includes the ultrasonic detection unit 135 is arranged, and the portion is located inside the annular portion of the enduing unit 130.

When the acoustic wave is incident to the interface between the mediums having the acoustic impedances $Z_1$ and $Z_2$, generally the incident acoustic wave propagates while divided into a transmitted wave and a reflected wave. A ratio of the reflected wave to the incident wave of the acoustic pressure is called pressure reflectivity. In the case where the acoustic wave is normally incident to the interface, it is known that the pressure reflectivity is expressed by the formula (4).

Because it is known that the acoustic impedance $Z_1$ of the living body 131 is close to that of the water, the acoustic impedance $Z_1$ is about 1.48 MRays (1 MRays=$10^6$ kg/m$^2$·s). On the other hand, air which is normally in contact with the surface of the living body 131, has the acoustic impedance of $4.08\times 104$ MRays, and there is a difference more than three figures between the acoustic impedance values. As a result, the pressure reflectivity exceeds 99.9% when the acoustic wave is normally incident to the surface of the living body 131, and the pressure reflectivity is larger when the acoustic wave is obliquely incident to the surface of the living body 131.

Such reflection can be reduced by utilizing the cushioning material 136 having the acoustic impedance close to that of the living body 131 to perform the acoustic matching. For example, silicone rubber which is not harmful to the living body 131 and is also used in a human body embedded type medical tool typically has the acoustic impedance of 1.24 MR. The pressure reflectivity can be reduced to about 9% at the interface between air and the living body 131 by utilizing the silicone rubber as the cushioning material 136.

In the noninvasive blood constituent concentration measuring apparatus according to the sixth embodiment, the living body 131 is irradiated with the light having the wavelength 1 μm or longer. In this case, because the moisture occupying the large part of the living body 131 exhibits the strong absorption, a sound source is locally formed near the skin surface immediately below the living body 131 of the region irradiated with the light from the light irradiation unit 133, and the generated ultrasonic wave can be regarded as the spherical wave.

As described later, because the light beam diameter of the light irradiation unit 133 is enlarged to about 5 mm, the sound source formed by the irradiation light exhibits a disc shape, and the thickness of the disc depends on the absorption length $\alpha^{-1}$ of the living body 131. In the light irradiation having the wavelength of about 1.6 μm, the thickness of the disc becomes about 1.6 mm. In the light irradiation having the wavelength of about 2.1 μm, the thickness of the disc becomes about 0.4 mm.

Because the sound source exhibits the thin disc shape, directivity is generated in the ultrasonic wave, and the ultrasonic wave generated in the living body 131 propagates in a focused way toward the direction of the ultrasonic detection unit 135. Accordingly, it is effective that the cushioning material 136 is arranged at least half around the portion which is in contact with the living body while including the ultrasonic detection unit 135. The portion is located inside the annular portion of the enduing unit 130.

As described above, the layer made of the cushioning material 136 having the acoustic impedance close to that of the living body 131 is arranged at least half around the portion which is in contact with the living body 131. The portion also includes the ultrasonic detection unit 135 to be arranged, and the portion is located inside the annular portion of the enduing unit 130. Therefore, in the ultrasonic wave generated in the living body 131 by the light emitted from the light irradiation unit 133, the portion of the ultrasonic wave which directly reaches the ultrasonic wave detection unit 135, is efficiently detected by the ultrasonic detection unit 135. Further, the amount of ultrasonic wave which is received by the ultrasonic detection unit 135 as a noise after the multiple reflection is generated at the interface between the living body 131 and the inside of the annular support frame 132 of the enduing unit 130 is decreased. Accordingly, the blood constituent concentration can be measured more correctly.

Figure 40:
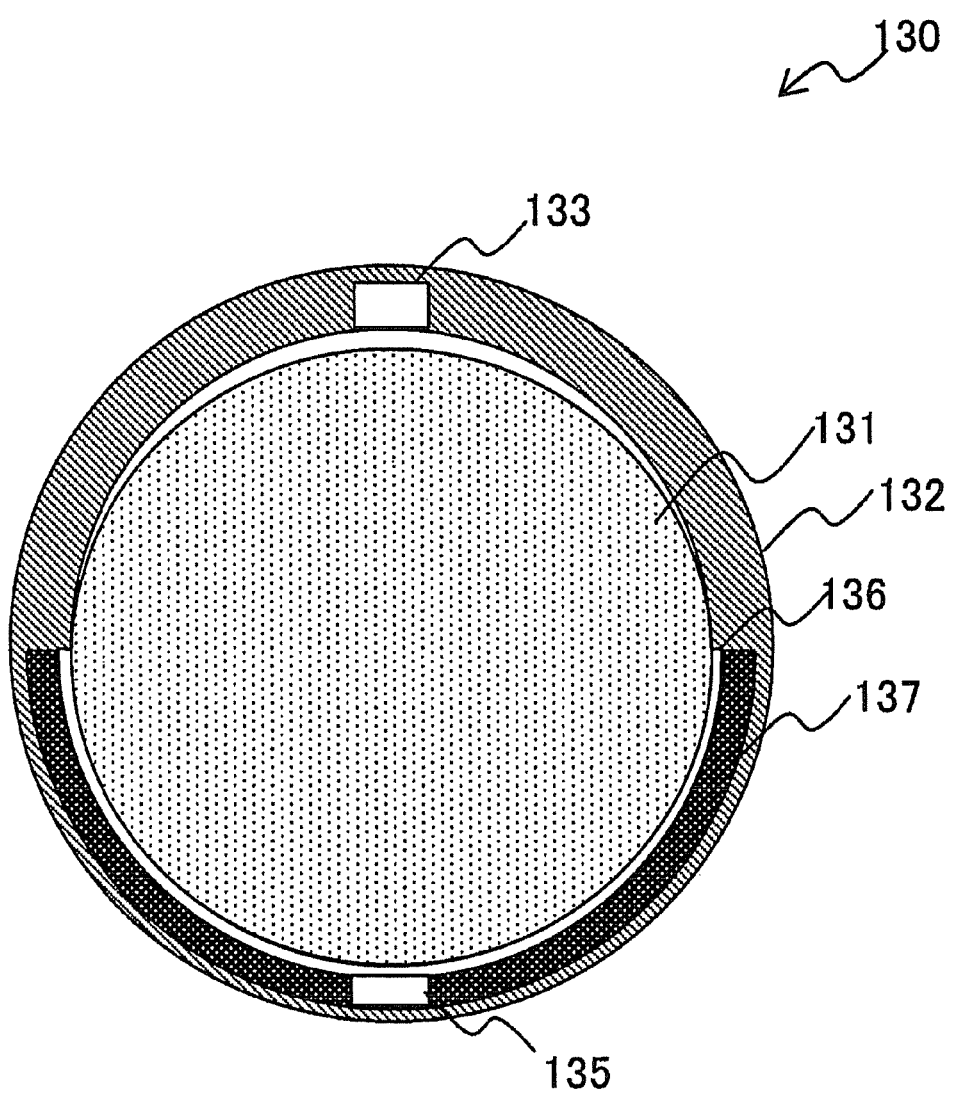
FIG. 40 is an explanatory view showing a structure of an enduing unit of the blood constituent concentration measuring apparatus according to the embodiment.

In the blood constituent concentration measuring apparatus according to the sixth embodiment, the gap between the cushioning material layer and the surface inside the annular portion of the enduing means can be filled with the sound absorbing material. As shown in FIG. 40, in the configuration of the enduing means in the blood constituent concentration measuring apparatus according to the sixth embodiment, the gap between the cushioning material 136 and the surface inside the annular support frame 132 of the annular portion of the enduing unit 130 can be filled with the sound absorbing material 137. The material which well absorbs the ultrasonic wave is used as the sound absorbing material 137. For example, in the case where the silicone rubber is used as the cushioning material 136, assuming that the gap is not filled with the sound absorbing material 137, when the ultrasonic wave traveling in the cushioning material 136 reaches the annular support frame 132 made of metal, the ultrasonic wave is reflected by the surface of the annular support frame 132 because the pressure reflectivity is about 60% between the silicone rubber and the metal. Then, the ultrasonic wave reversely travels in the silicone rubber of the cushioning material 136, and the ultrasonic wave reaches the living body 131 again.

In order to prevent the above reflection, it is effective that the material in which the metal oxide powders (titanium oxide or tungsten oxide) are included in the epoxy resin is used as the sound absorbing material 137.

As described above, the gap between the cushioning material 136 and the surface inside the annular support frame 132 of the annular portion of the enduing unit 130 is filled with the sound absorbing material 137, which reduces the amount of ultrasonic wave, which is detected as the noise by the ultrasonic detection unit 135 after the ultrasonic wave generated in the living body 131 by the light emitted from the light irradiation unit 133 is reflected from the interface between the cushioning material 136 and the annular support frame 132. Therefore, the blood constituent concentration can correctly be measured.

In the blood constituent concentration measuring apparatus according to the sixth embodiment, the light generating means can be formed by the light generating means in which the two light beams having different wavelengths are generated by plural semiconductor laser devices.

As described above, the light generating means generates the two light beams having different wavelengths with the plural semiconductor laser devices, which allows the significant miniaturization and weight reduction to be achieved in the blood constituent concentration measuring apparatus according to the sixth embodiment.

In the blood constituent concentration measuring apparatus according to the sixth embodiment, preferably the light outgoing means includes a beam diameter enlarger which enlarges the light beam diameter generated by the light generating means.

As described above, the light outgoing means includes a beam diameter enlarger which enlarges the light beam diameter generated by the light generating means. Therefore, the light beam outputted to the living body is enlarged, and the relatively strong light can be outputted without affecting the reverse influence on the living body. Accordingly, the blood constituent concentration of the living body can be measured more correctly.

In the blood constituent concentration measuring apparatus according to the sixth embodiment, the enduing means is a ring in which the finger of the human body is fitted, and the enduing means can be formed in the enduing means in which the light outgoing means is arranged on the dorsal side of the finger while the acoustic wave detection means is arranged on the palm side of the finger.

As described above, the enduing means is the ring in which the finger of the human body is fitted, the light outgoing means is arranged on the dorsal side of the finger, and the acoustic wave detection means is arranged on the palm side of the finger. Therefore, the acoustic wave detection means easily comes into contact with the relatively soft skin in the finger, and the acoustic wave detection means can efficiently measure the ultrasonic wave generated in the finger, so that the blood constituent concentration can be measured more correctly. Further, the light outgoing means and the acoustic wave detection means are mounted in the inner surface of the ring, which allows the blood constituent concentration of the human body to be easily and continuously measured without causing difficulties in a daily life.

In the blood constituent concentration measuring apparatus according to the sixth embodiment, the enduing means is a bracelet in which the arm of the human body is fitted, and the enduing means can be formed in the enduing means in which the light outgoing means is arranged on the palm side of the hand while the acoustic wave detection means is arranged on the dorsal side of the hand.

As described above, the enduing means is the bracelet in which the arm of the human body is fitted, the light outgoing means is arranged on the palm side of the hand, and the acoustic wave detection means is arranged on the dorsal side of the hand. Therefore, the acoustic wave detection means easily comes into contact with the relatively soft skin of the arm, and the acoustic wave detection means can efficiently measure the ultrasonic wave generated in the arm, so that the blood constituent concentration can be measured more correctly. Further, the light outgoing means and the acoustic wave detection means are mounted in the inner surface of the bracelet, which allows the constituent concentration of the human body to be easily and blood continuously measured without causing difficulties in a daily life.

EXAMPLES

Specific examples in the sixth embodiment will be described below.

First Example

Figure 41:
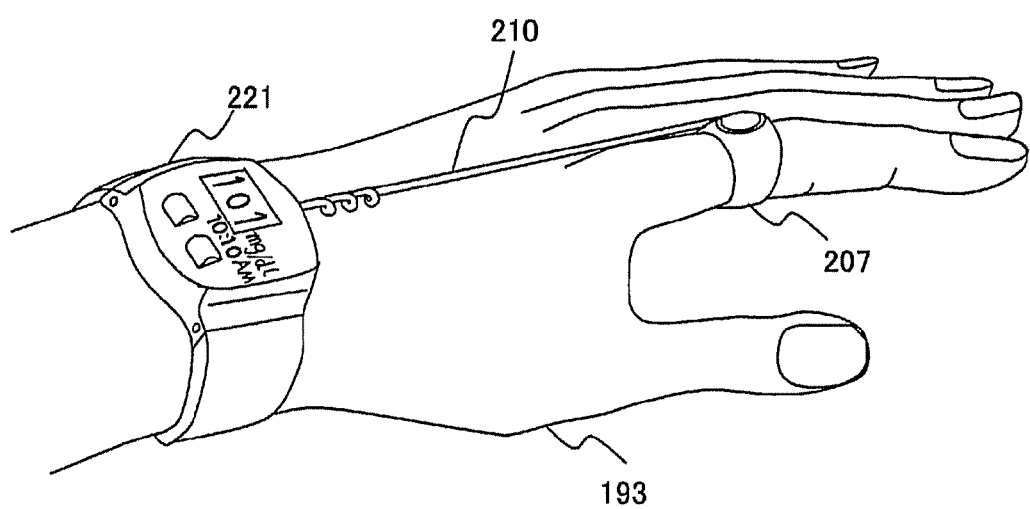
FIG. 41 is an explanatory view of a ring type enduing unit according to the embodiment.

FIG. 41 shows a first example in which the blood constituent concentration measuring apparatus according to the sixth embodiment is applied to the human body to realize the enduing means as the ring.

FIG. 41 shows a first example in which the blood constituent concentration measuring apparatus according to the sixth embodiment is fitted to the hand. In FIG. 41, the light outgoing means and the acoustic wave detection means are embedded in the enduing unit 207 which is of the ring type the enduing means in which the living body 193 which is of the test subject is fitted, and the power supply phase, the phase sensitive amplifier, and the blood constituent concentration detection means are incorporated into a wristwatch type display unit 221. The power supply supplies the electric power to the light outgoing means and the acoustic wave detection means. The phase sensitive amplifier which is of a part of the acoustic wave detection means amplifies the electric signal outputted from the ultrasonic detector which is of a part of the acoustic wave detection means. The enduing unit 207 and the display unit 221 are connected with the connection cable 210.

A display device which plays the measured blood constituent concentration, is provided outside the display unit 221, and at least one button for starting the measurement is also provided. A time measuring function, a function of storing and reading the measurement concentration data, and a communication function of transmitting the stored measured data to the external device are also effective functions.

Desirably the connection cable 210 has stretching properties so as not to block the hand movement, and the connection cable 210 is arranged between the finger extensor tendons in the dorsal of the hand. In FIG. 41, the second finger of the left hand is fitted in the enduing unit 207. However, obviously the enduing unit 207 may be formed such that any finger of the hand can be fitted in.

Figure 42:
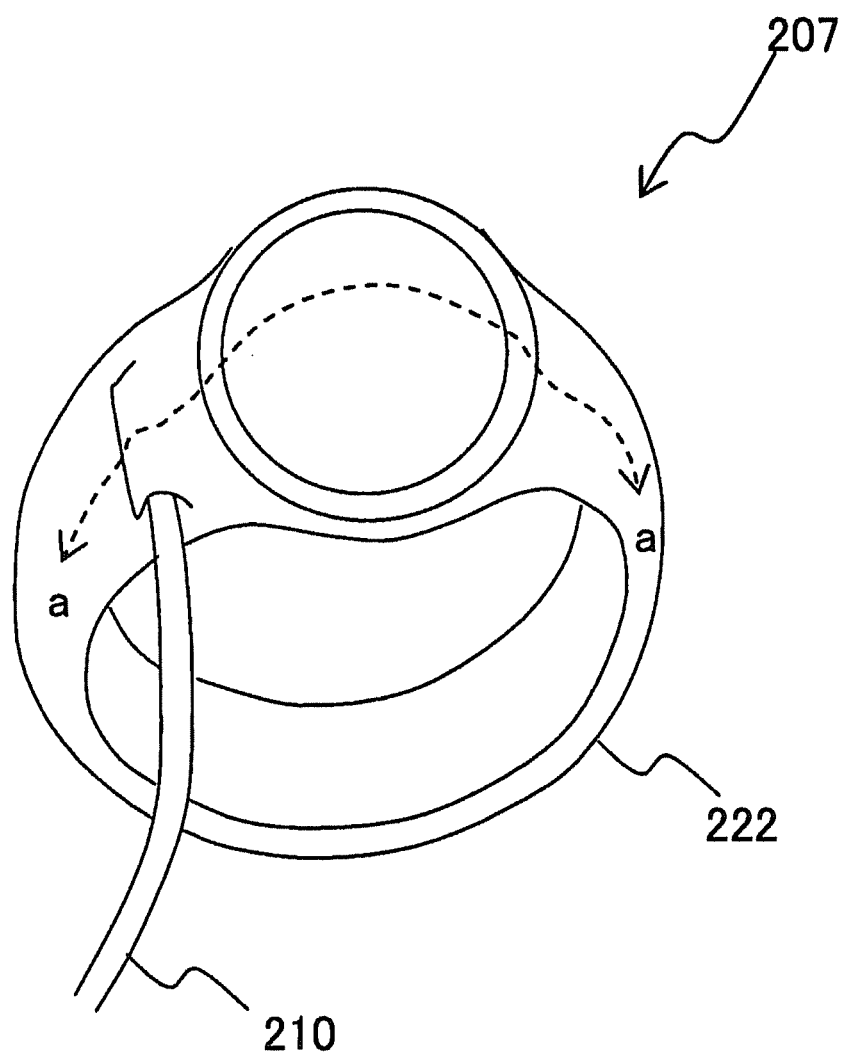
FIG. 42 is an explanatory view showing a detailed structure of the ring type enduing unit according to the embodiment.
Figure 43:
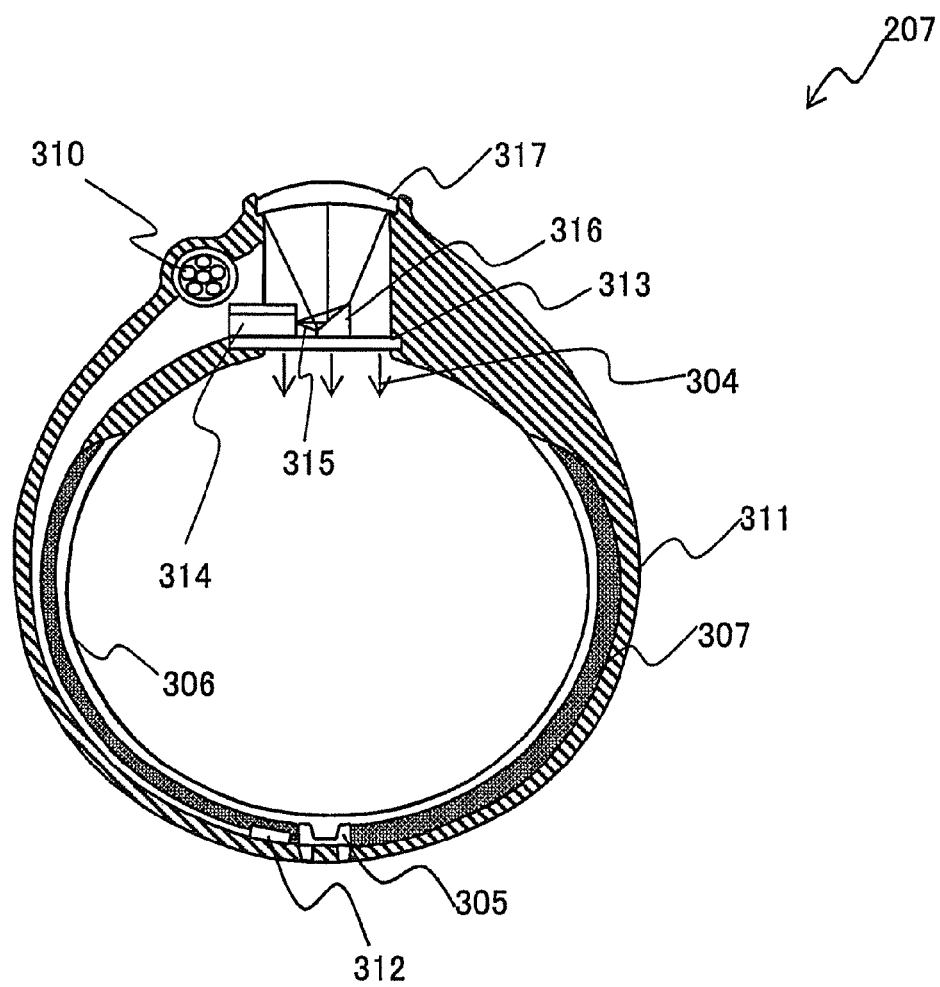
FIG. 43 is an explanatory view showing a cross section of the ring type enduing unit according to the embodiment.

FIG. 42 is a view showing a state in which the ring type enduing unit 207 is detached from the finger, and FIG. 42 shows a state in which the connection cable 210 is placed in a ring frame 222. In order to hold the connection cable 210 between the tendons of the fingers, a lead-out portion of the connection cable 210 is provided in the enduing unit 207 while biased from the top of a bezel of the ring. FIG. 43 show a sectional view taken on broken line a-a of FIG. 42, i.e., the center of the width of the frame 222.

In the section of the enduing unit 207 of FIG. 43, a light source chip 314 which is of a part of the light generating means and an irradiation window 313, a reflecting mirror 316, and a concave mirror 317, which constitute the light outgoing means, are placed in the portion corresponding to the bezel of the ring which is located on the dorsal side (upward direction of FIG. 43) of the finger during the fitting. On the other hand, an ultrasonic detector 305 which is of a part of the acoustic wave detection means is placed in the portion on the palm side (downward direction of FIG. 43) of the finger Because the ultrasonic detector 305 has the high output impedance, from the viewpoint of noise, it is inadvisable that the output is directly guided to the display unit 221 shown in FIG. 41 through the connection cable 310. Therefore, a preamplifier 312 is placed close to the ultrasonic detector 305 which converts the impedance, the preamplifier 312 is connected to the output terminal of the ultrasonic detector 305 to convert the output impedance of the ultrasonic detector 305 into lower level, and the output signal of the preamplifier 312 is supplied to the display unit 221 through the connection cable 210 shown in FIG. 41.

The countermeasures for reflection of the ultrasonic wave are made on both sides of the ultrasonic detector 305 as shown in FIG. 43. That is, the silicone rubber which is of the cushioning material 306, is placed about half around the surface inside the enduing unit 207 while including a directly overhead portion of the ultrasonic detector 305. Additionally the gap between the cushioning material 306 and the frame 311 is filled with the sound absorbing material 307.

The semiconductor laser device may be used as the light source chip 314 which is of the light generating means. In addition to a compact size and a long lifetime, the semiconductor laser has an advantage that the intensity modulation operation necessary to the photoacoustic, method can directly be performed to the device by modulating the injection current.

When the semiconductor laser device is used as the light source chip 314, usually the output beam 315 is a diffuse light flux, and the beam diameter is much smaller than a beam diameter suitable to the photoacoustic method immediately after the light is outputted. Therefore, after the beam diameter is enlarged, it is necessary to obtain the irradiation light 304 to the living body. In the first example, the optical system for enlarging the beam diameter includes the reflecting mirror 316 and the concave mirror 317. That is, the reflecting mirror 316 is placed at a distance of 1.2 mm from the outgoing end face of the light source chip 314 with respect to the output beam 315 having the outgoing total angle of 46° (numerical aperture NA=0.39), and the output beam 315 is reflected toward the concave mirror 317 located above. The concave mirror 317 is maintained while separated away from the reflecting mirror 316 by 4.7 mm. The concave mirror 317 converts the incident light flux from the reflecting mirror 316 into the parallel light flux, and the concave mirror 317 reflects the light toward the direction of the irradiation window 313 (downward of FIG. 43).

In the first example, the focal distance, i.e., ½ of the radius of curvature of the concave mirror 317 is set so as to be equal to the sum of the optical path between the outgoing end face of the light source chip 314 and the reflecting mirror 316 and the optical path between the reflecting mirror 316 and the concave mirror 317, so that the irradiation light 304 having the diameter of 5.0 mm is obtained through the irradiation window 313.

The irradiation window 313 protects the light source chip 314, the reflecting mirror 316, and the concave mirror 317, and the irradiation window 313 also functions as a seat plate with which the light source chip 314 and the reflecting mirror 316 are attached with high accuracy. Because the transparency to the irradiation light 304 and the scratch resistance are required for the material for the irradiation window 313, the sapphire plate is used in the first embodiment.

The backside of the concave mirror 317 is a portion corresponding to the top of the bezel of the ring in the enduing unit 207, and the backside of the concave mirror 317 is the point which plays the central role in the usual use as the ring of the jewelry. In the first example, the backside of the concave mirror 317 can be utilized for the purpose of ornament.

It is necessary that the irradiation window 313 and the concave mirror 317 be fixed to the frame 311 while the relative positions are maintained. Therefore, a notch for alignment of the irradiation window 313 and the concave mirror 317 is provided in the frame 311. The frame 311 also includes a hollow portion (wiring cavity) for electric wiring and a groove to which the sound absorbing material 307 and the cushioning material 306 are bonded. Similarly to the ring base, the frame 311 having the above structure can sufficiently be generated by a die (casting) technique in the jewelry industry.

Figure 44:
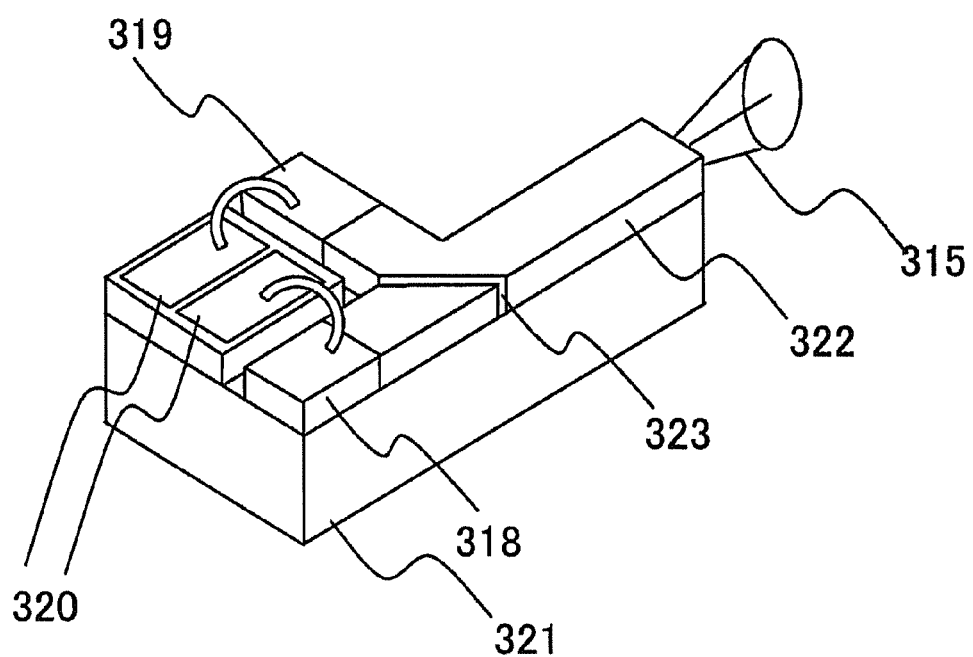
FIG. 44 is an explanatory view of a ring type light generation unit according to the embodiment.

FIG. 44 shows a mounting mode of the light source chip 314. The two semiconductor laser devices having the different wavelengths are used in the first example. Specifically, the semiconductor laser device is formed on a substrate 321 shown in FIG. 44 by a MEMS technique. The substantial size of the light source chip 314 shown in FIG. 44 is 1 mm×1.5 mm×0.6 mm (thickness), and the light source chip 314 has the size which can easily be mounted as the ring type enduing means.

In FIG. 44, the first semiconductor laser 318 is placed at the end face of a principal branch of an optical waveguide 322 made of polyimide fluoride, and the first semiconductor laser 318 outputs the laser oscillation light to the principal branch of the optical waveguide 322. On the other hand, the second semiconductor laser 319 is placed at the end face of a side branch of the optical waveguide 322 made of polyimide fluoride, and the second semiconductor laser 319 outputs the laser oscillation light to the side branch of the optical waveguide 322. The drive currents are supplied to the two semiconductor laser devices through the electrode pads 320 respectively.

A coupler 323 which is of the light outgoing means, is formed at a nodal point of the principal branch and the side branch of the optical waveguide 322. The coupler 323 is the gap where the polyimide fluoride is removed. Based on the multiple interference effect, so-called etalon effect, the coupler 323 exhibits the transmission for the oscillation wavelength of the first semiconductor laser 318, and the coupler 323 exhibits the reflection for the oscillation wavelength of the second semiconductor laser 319.

According to the above configuration, the output light beams having the different wavelengths outputted from the two semiconductor laser device are multiplexed, the light beam propagates in the optical waveguide 322, and the output beam 315 is outputted from the end face at which the semiconductor laser device of the optical waveguide 322 is not placed.

Figure 45:
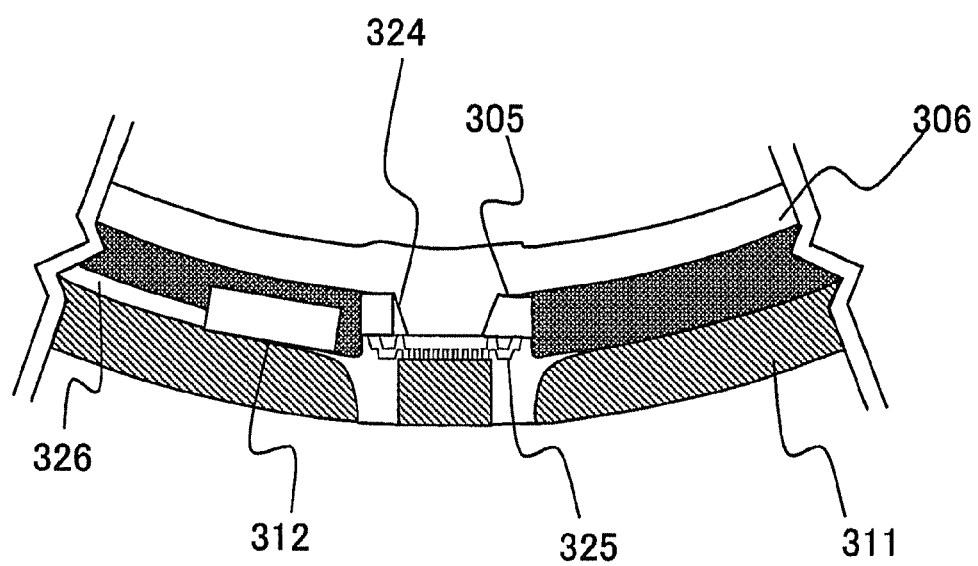
FIG. 45 is an explanatory view showing the cross section of the ring type enduing unit according to the embodiment.

FIG. 45 shows the ring type enduing unit, and FIG. 45 is a sectional view taken on line a-a of FIG. 42. In FIG. 45, the ultrasonic detector 305 and surroundings thereof are shown in an enlarged manner. The well-known piezoelectric ultrasonic wave detection device such as PZT and PVDF (polyvinylidene fluoride) can be used as ultrasonic detector 305. However, because PZT has the high acoustic impedance, it is necessary to add an impedance matching layer. Although PVDF is an advantageous to the acoustic impedance, PVDF has the low output voltage, i.e., the low sensitivity. In the first example, a MEMS type ultrasonic wave detection device generated by the MEMS technique is used instead of PZT or PVDF.

In FIG. 45, an ultrasonic detector 305 is formed by a vibration membrane 324 and a fixed electrode 325.

The cushioning material 306 for acoustic matching is in contact with the vibration membrane 324 in the ultrasonic detector 305. In the MEMS type ultrasonic detector 305, a flow passage is provided in order to release the backpressure on the side of the fixed electrode 325. The flow passage is communicated with the atmospheric pressure through a thin hole made in the frame 311 at the back of the fixed electrode 325. The ultrasonic detector 305 detects the ultrasonic wave by the capacitance change caused by the displacement of the vibration membrane 324 in a flat sheet capacitor formed by the vibration membrane 324 and the fixed electrode 325. Accordingly, in addition to the impedance conversion function, a function of supplying a constant electric charge to the flat sheet capacitor of the ultrasonic detector 305 is added to the preamplifier 312 connected to the ultrasonic detector 305.

The preamplifier 312 and the wiring cavity 326 are placed in the frame 311. The wiring cavity 326 is used for the wiring to the connection cable 310 shown in FIG. 43. The frame 311 is located behind the sound absorbing material 307. This configuration can prevent the preamplifier 312 and the wiring cavity 326 from reflecting the ultrasonic wave.

In FIG. 41, various ideas could be made for the devices, circuits, and connection methods among these devices and circuits, which are incorporated in the ring type enduing unit 207 and display unit 221 without departing from the spirit of the sixth embodiment. For example, an optical fiber (small bending radius is advisable in order to hold the stretching properties of the cable) is included in the connection cable, the light source chip 314 is placed in display unit 221, and only the optical system for enlarging the beam can be left as the light outgoing means of the ring type enduing unit 207.

On the other hand, a battery is incorporated in the ring type enduing unit 207, and all the components concerning the portable type noninvasive blood constituent concentration measuring apparatus including the drive power supply of the light source and the phase sensitive amplifier can be mounted on the ring type enduing unit 207. In this case, the wireless communication of the blood constituent concentration measured value can also be performed between the ring type enduing unit 207 and the display unit 221.

Second Example

Figure 46:
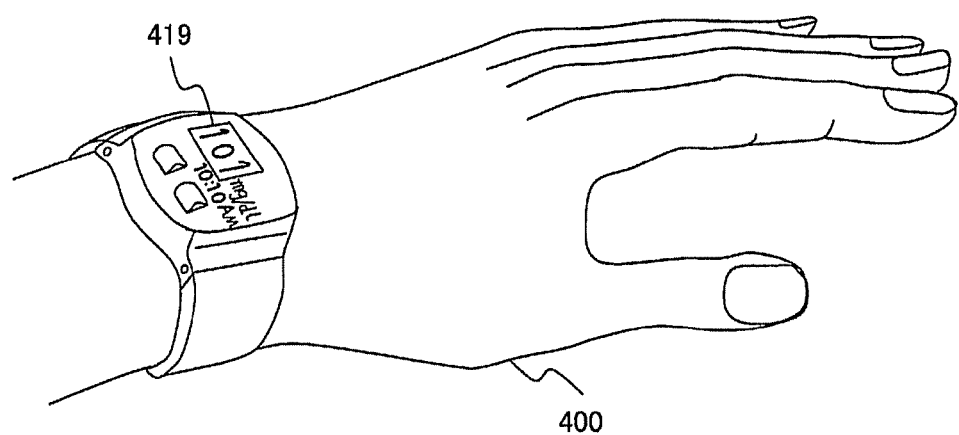
FIG. 46 is an explanatory view of a bracelet type enduing unit according to the embodiment.

FIG. 46 shows a configuration in which the blood constituent concentration measuring apparatus according to the sixth embodiment is applied to the human body and realized as a wrist-fitted bracelet type enduing means.

FIG. 46 shows a state in which the blood constituent concentration measuring apparatus according to the sixth embodiment is fitted to the wrist as the bracelet type enduing means. In the fitting mode in the wrist of the bracelet type enduing means of the blood constituent concentration measuring apparatus shown in FIG. 46, a bracelet type display unit 419 fitted in a living body 400, which is of the test subject, has the configuration in which the wrist-watch type display unit 221 and ring type enduing unit 207 which are described in the first example are integrated.

An ultrasonic detector which is of the acoustic wave detection means, is incorporated into a display unit 419, and the light generating means, the light modulation means, and the light outgoing means are also incorporated in to the display unit 419. The display device which displays the measurement result of the blood constituent concentration, is provided outside the display unit 419, and at least one button for directing the measurement start is also provided. The functions added to the display unit 419 are similar to the first example.

Figure 47:
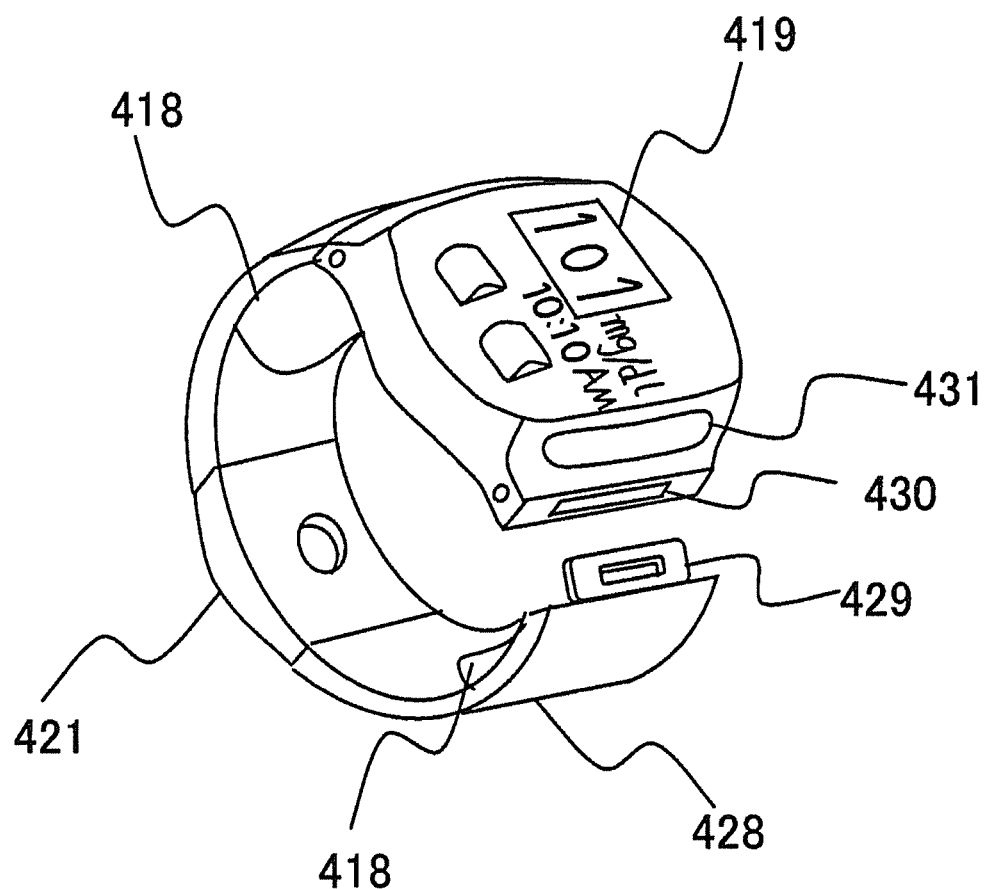
FIG. 47 is an explanatory view of the bracelet type enduing unit according to the embodiment.

FIG. 47 shows a state in which the bracelet type enduing means is detached from the wrist. The bracelet type enduing means includes a display unit 419, a wrist band 428, and light irradiation unit 421 which is of the light outgoing means, and all the components are placed so as to surround the wrist. The bracelet type enduing means has an appearance similar to the usual wristwatch, but bracelet type enduing means differs from the wristwatch in the attachment method. That is, in the case of the usual wristwatch, a buckle and the like for attachment and detachment are placed in overlapping portions of both side bands (referred to as wristwatch band in the wristwatch). On the contrary, in the bracelet type enduing means, the light irradiation unit 421 is placed. Accordingly, another type of an attachment and detachment mechanism is required in the bracelet type enduing means.

In the second example, the bracelet type enduing means is provided with a sheet-belt-like attachment and detachment mechanism including an insertion key 429, an opening 430, and an release button 431 as the attachment and detachment mechanism of the bracelet type enduing means.

In the second example, the ultrasonic detector which is of the acoustic wave detection means, is embedded in the back cover of the display unit 419. Similarly to the first example, PZT, PVDF, and MEMS type ultrasonic wave detection device can be used as the ultrasonic detector.

The cushioning materials 418 are placed in the ultrasonic detector and contact surfaces which is in contact with the living body on the both sides of the ultrasonic detector, and the inside of the cushioning material 418 is filled with the sound absorbing material.

In the second example, the bracelet type enduing means is fitted such that the ultrasonic detector comes into contact with the dorsal side of the wrist while the light irradiation unit 421 comes into contact with the palm side. Because there is irregularity formed by the tendons of long palmer muscle, basilic veins, and the like on the palm side of the wrist, the ultrasonic detector hardly comes into close contact with the skin to obtain the good acoustic coupling on the palm side of the wrist.

Figure 48:
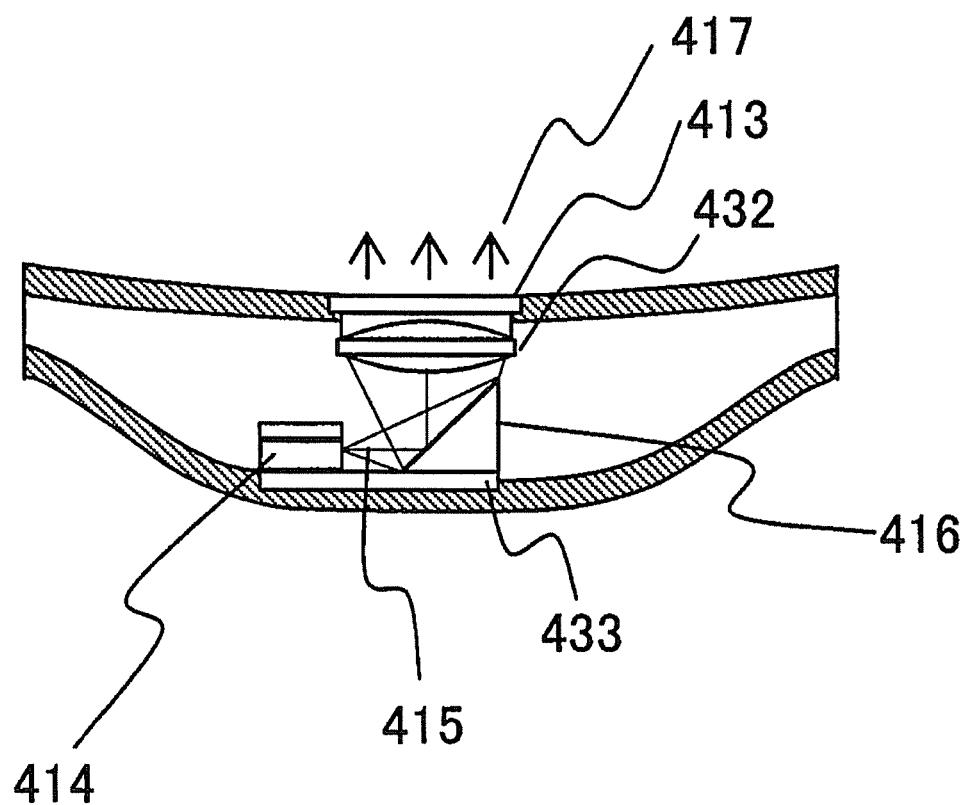
FIG. 48 is an explanatory view showing the cross section of the bracelet type enduing unit according to the embodiment.
Figure 49:
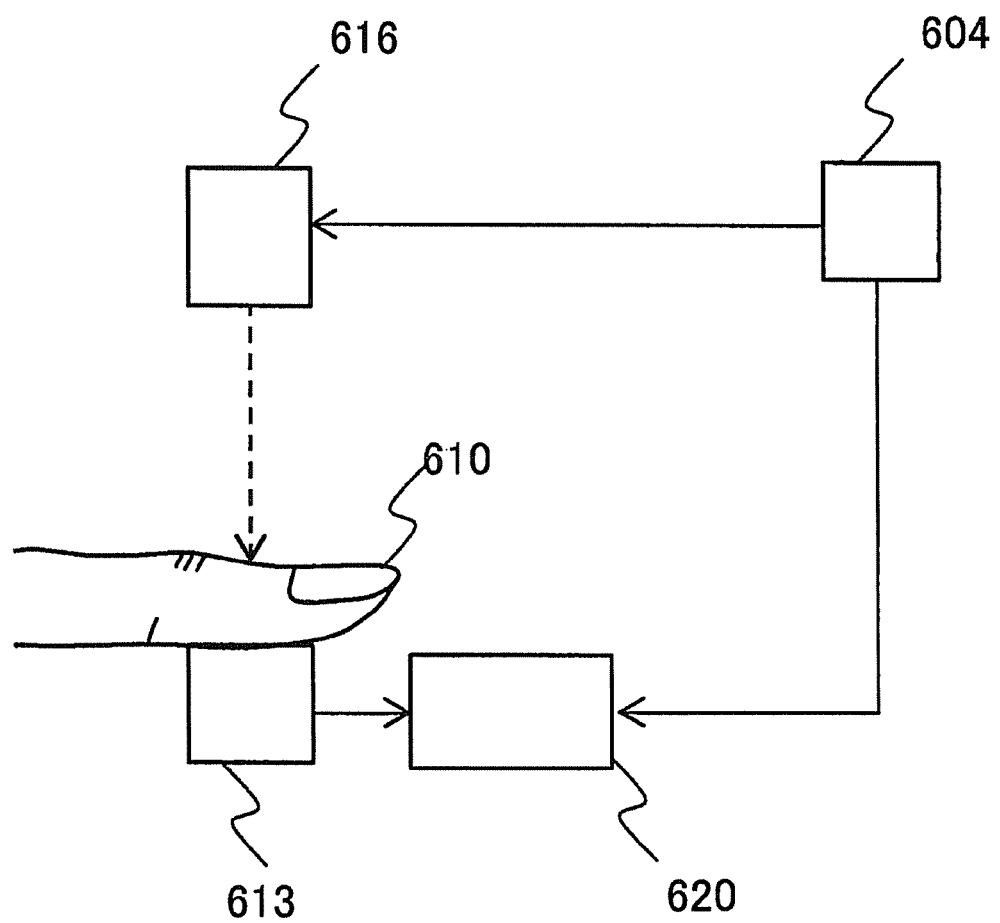
FIG. 49 is an explanatory view showing a configuration example of a conventional blood constituent concentration measuring apparatus.
Figure 50:
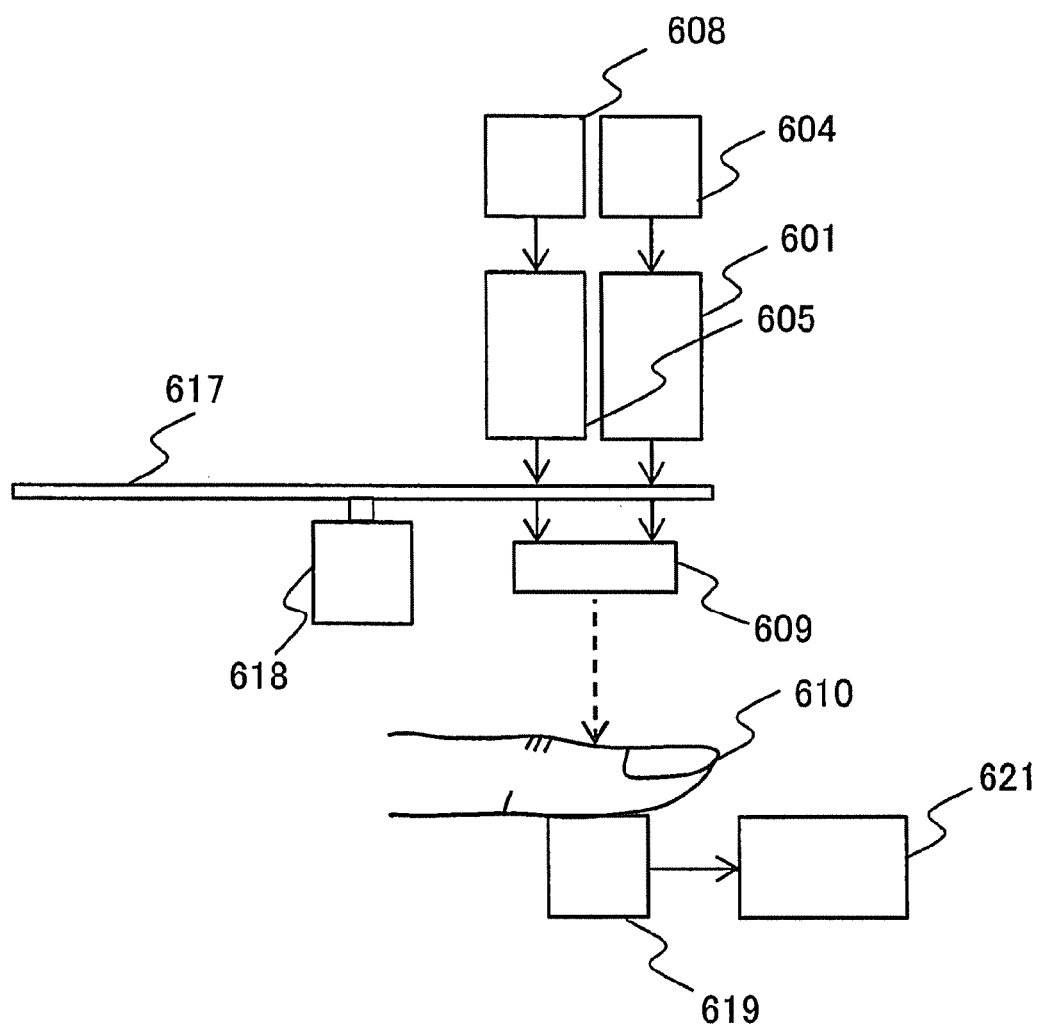
FIG. 50 is an explanatory view showing a configuration example of the conventional blood constituent concentration measuring apparatus.
Figure 51:
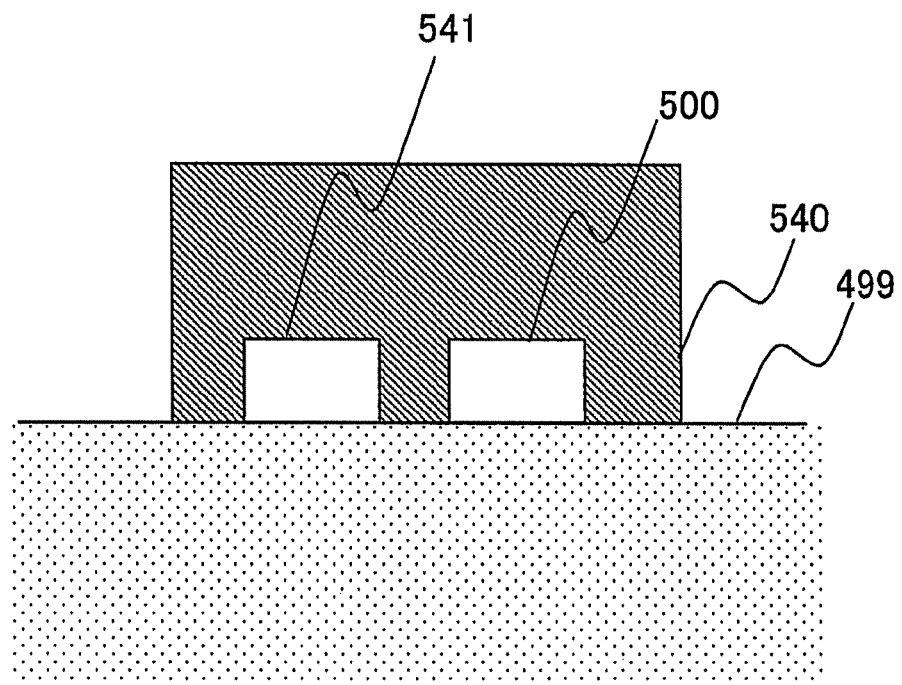
FIG. 51 is an explanatory view of the conventional blood constituent concentration measuring apparatus.
Figure 52:
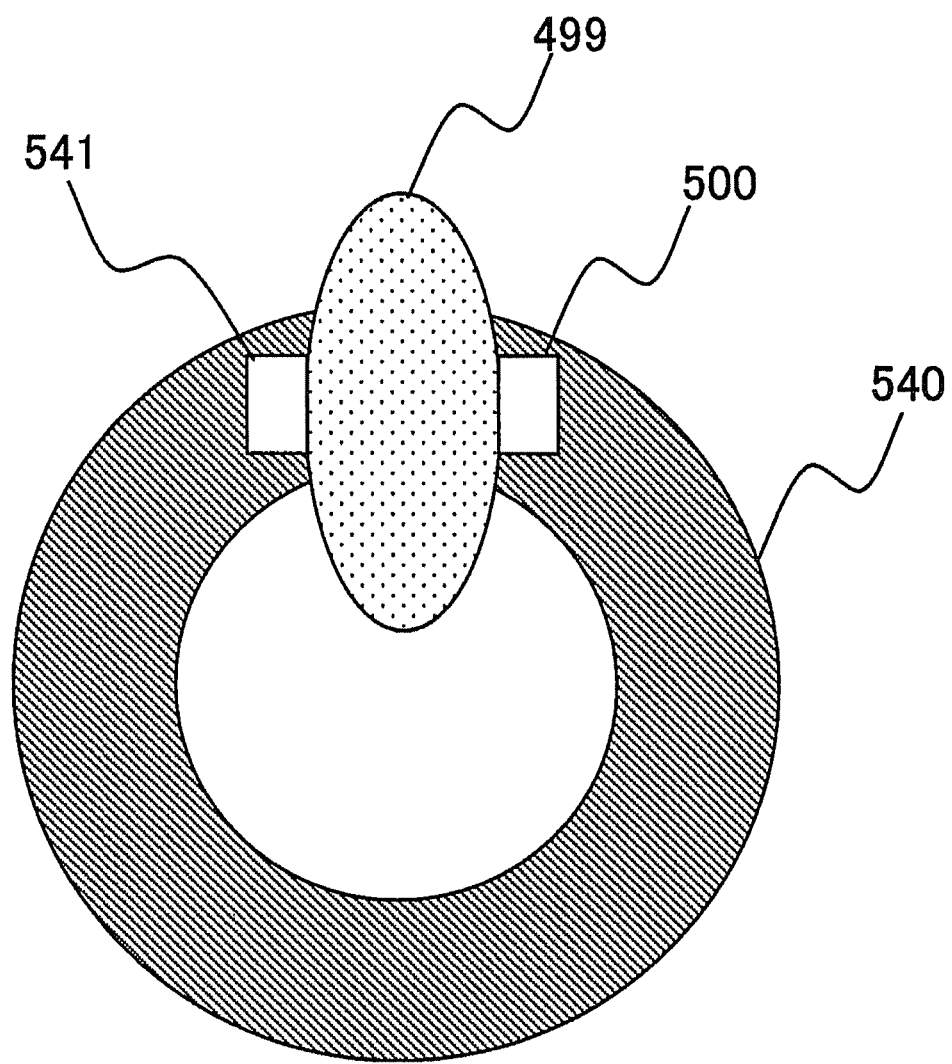
FIG. 52 is an explanatory view of a mounting structure of the conventional blood constituent concentration measuring apparatus.
Figure 53:
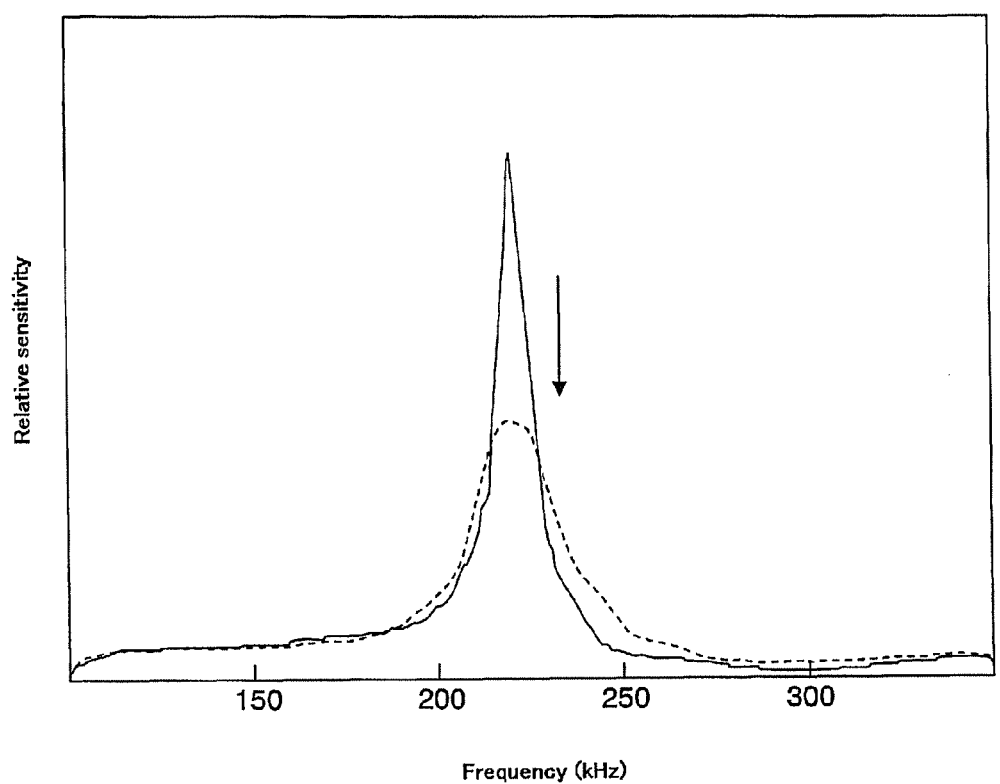
FIG. 53 is an explanatory view showing the sensitivity characteristics of the ultrasonic detector.
Figure 54:
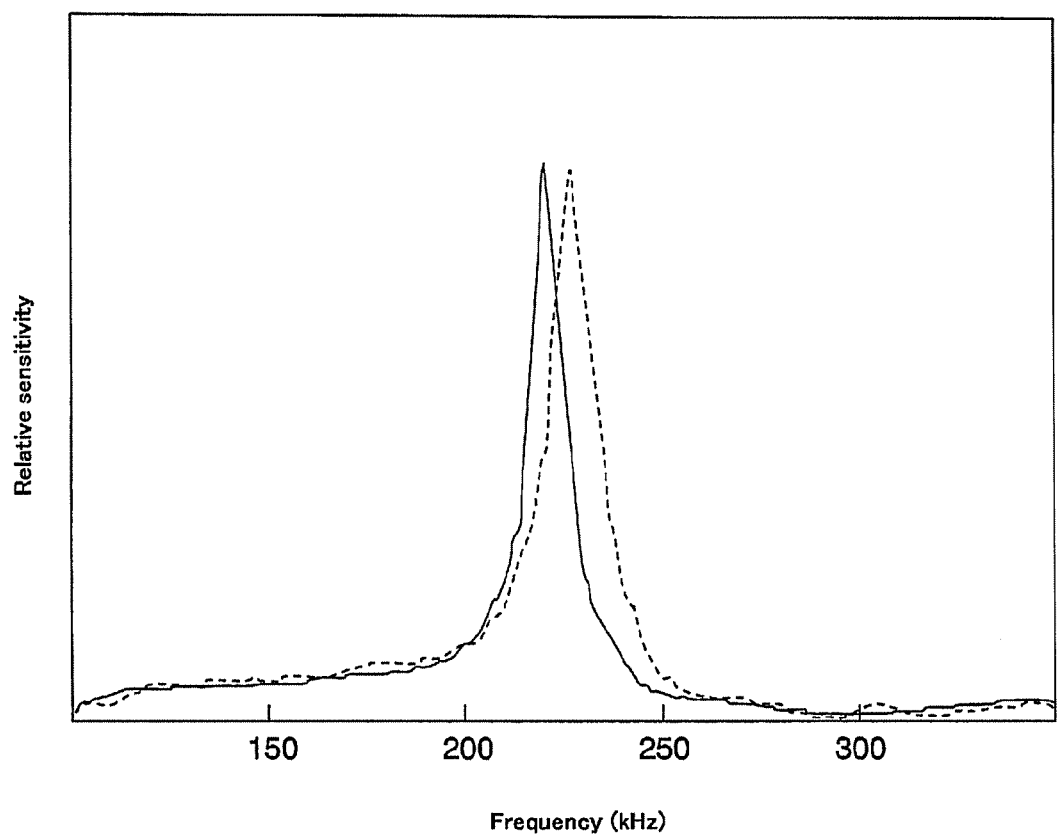
FIG. 54 is an explanatory view showing the sensitivity characteristics of the ultrasonic detector.
Figure 55:
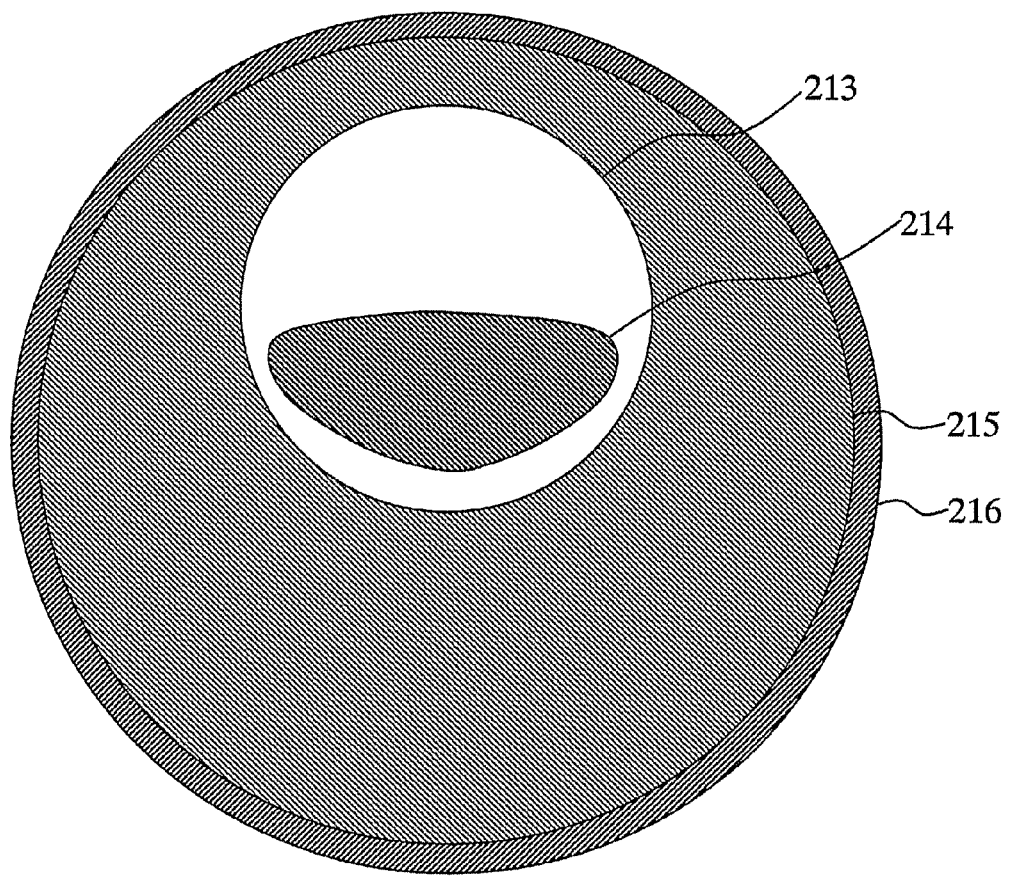
FIG. 55 is a sectional view showing a inner structure of a finger.
Figure 56A:
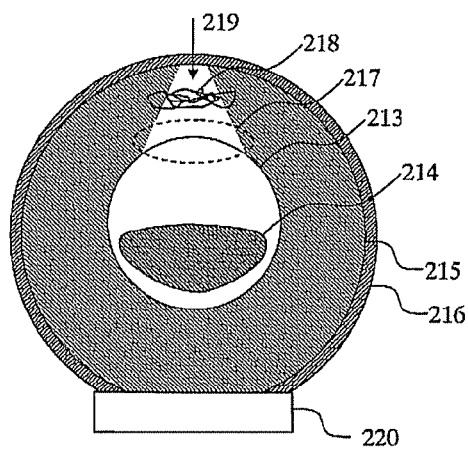
FIG. 56 is a sectional view showing the human finger, FIG. 56(*a*) shows a state in which the photoacoustic signal is scattered by a bone, and FIG. 56(*b*) shows a state in which the photoacoustic signal is attenuated by the bone.
Figure 56B:
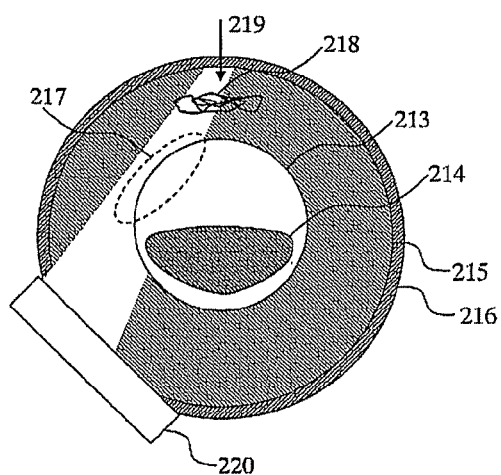

FIG. 48 shows sectional view along the center line from the light irradiation unit 421 toward the wrist band 428. FIG. 48 shows a section of the light irradiation unit 421 of the bracelet type the enduing means shown in FIG. 47. Similarly to the first example, after the beam diameter of the output beam 415 of the light source chip 414 which is of a part of the light generating means, is enlarged, the irradiation light 417 to the living body is obtained.

In the second example, the optical system for enlarging the beam diameter is composed of a reflecting mirror 416 and a lens 432. That is, the reflecting mirror 416 is placed at a distance of 2.7 mm from the outgoing end face of the light source chip 414 with respect to the output beam 415 having the outgoing total angle of 46° (numerical aperture NA=0.39), and the output beam 415 is reflected toward the lens 432. The lens 432 is maintained while separated away from the reflecting mirror 416 by 3.2 mm. The lens 432 converts the incident light flux from the reflecting mirror 416 into the parallel light flux, and the lens 432 irradiates the light toward the direction of the irradiation window 413 (upward of FIG. 48).

In the second example, the focal distance of the lens 432 is set so as to be equal to the sum of the optical path between the outgoing end face of the light source chip 414 and the reflecting mirror 416 and the optical path between the reflecting mirror 416 and the lens 432, so that the irradiation light 417 having the diameter of 5.0 mm is obtained through the irradiation window 413. The irradiation window 413 is provided to protect the components inside the light irradiation unit 421, and it is necessary that the irradiation window 413 is transparent to the irradiation light 417 and scratch resistant. The light source chip 414 and the reflecting mirror 416 are attached to the light sources chassis 433 with high accuracy.

In addition to the above examples, the bracelet type enduing means according to the sixth embodiment can be also applied to an armlet in which a brachium is fitted, an anklet in which an ankle is fitted, and a choker ring in which the neck is fitted (however, only the anklet and the choker ring having the good contact property can be used) without departing from the spirits of the embodiments.

INDUSTRIAL APPLICABILITY

The liquid constituent concentration measuring apparatus and liquid constituent concentration measuring apparatus controlling method according to the embodiments can be applied to the field of measuring the constituent concentration in the liquid, for example, the sugar measurement of the fruit.

The blood constituent concentration measuring apparatus and control method of blood constituent concentration measuring apparatus according to the embodiments can be utilized for daily health control and beauty check. The blood constituent concentration measuring apparatus and control method of blood constituent concentration measuring apparatus according to the embodiments can also be utilized not only for the health control of the living body of the human, but also for the health control of the living body of the animal.

The invention claimed is:

1. A constituent concentration measuring apparatus comprising:
    light generating means for generating light;
    light modulation means for electrically intensity-modulating the light at a constant frequency;
    light outgoing means for outputting the intensity modulated light toward a test subject;
    an acoustic wave generator that outputs an acoustic wave;
    acoustic wave detection means for detecting a photoacoustic signal emitted from the test subject, which is irradiated with the intensity modulated light, as an actual signal, and for detecting an intensity of the acoustic wave output by the acoustic wave generator and transmitted through the test subject as a reference signal;
    drive means for varying a position of at least one of the acoustic wave generator, the light outgoing means, and the acoustic wave detection means; and
    control means for controlling the drive means to detect plural reference signals from a plurality of positions, analyzing the plurality of reference signals to determine an optimum propagation path having minimized reflection/scattering characteristics, and detecting the actual photoacoustic signal from the position corresponding with the optimum propagation path.

2. The constituent concentration measuring apparatus as claimed in claim 1, wherein the control means is further configured for:
    subsequent to detecting the plurality of reference signals and determining the optimum propagation path, controlling the drive means to position at least one of the acoustic wave generator, the light outgoing means, and the acoustic wave detection means such that the photoacoustic signal emitted from the test subject propagates in the optimum propagation path, and causing the light outgoing means to irradiate the test subject with the intensity modulated light for detecting the actual photoacoustic signal.

3. The constituent concentration measuring apparatus as claimed in claim 1, wherein the control means is further configured for:
in addition to the reference signal, detecting a photoacoustic signal for each of the plurality of positions; and
selecting the photoacostic signal corresponding with the optimum propagation path as the actual photoacoustic signal.

4. A constituent concentration measuring apparatus as claimed in claim 1, wherein the light outgoing means is fixed to the acoustic wave generator so as to keep a relative position to the acoustic wave generator.

5. A constituent concentration measuring apparatus as claimed in claim 1, further comprising:
pressing means for pressing the acoustic wave generator and the acoustic wave detection means against the test subject with a pressing force whose pressure can be controlled.

6. A constituent concentration measuring apparatus as claimed in claim 1, wherein the acoustic wave generator is placed in proximity of the intensity modulated light outputted from the light outgoing means.

7. A constituent concentration measuring apparatus as claimed in claim 1, wherein the acoustic wave generator comprises a transmission window that transmits the intensity modulated light.

8. A constituent concentration measuring apparatus as claimed in claim 1, wherein the frequency and/or the intensity of the acoustic wave output by the acoustic wave generator is variable.

9. A constituent concentration measuring apparatus as claimed in claim 1, further comprising:
an acoustic coupling element on a surface of the acoustic wave generator and/or the light outgoing means that is configured to be in contact with the test subject and that has an acoustic impedance substantially equal to that of the test subject.

10. A constituent concentration measuring apparatus as claimed in claim 1, wherein the light outgoing means outputs two light beams set to two wavelengths such that an absorption difference exhibited by a constituent set as a measuring object is larger than an absorption difference exhibited by other constituents.

11. A constituent concentration measuring method comprising:
outputting, from a light source, light that is intensity modulated at a constant frequency toward a test subject;
outputting, from an acoustic wave generator, an acoustic wave toward the test subject;
detecting, with an acoustic wave detector, a photoacoustic signal emitted from the test subject as an actual signal, and an intensity of the acoustic wave output by the acoustic wave generator and transmitted through the test subject as a reference signal;
varying a position of at least one of the acoustic wave generator, the light source, and the acoustic wave detector to detect plural reference signals from a plurality of positions;
analyzing the plurality of reference signals to determine an optimum propagation path having minimized reflection/scattering characteristics; and
detecting the actual photoacoustic signal from the position corresponding with the optimum propagation path.

12. The constituent concentration measuring method as claimed in claim 11, further comprising:
subsequent to detecting the plurality of reference signals and determining the optimum propagation path, moving at least one of the acoustic wave generator, the light source, and the acoustic wave detector such that the photoacoustic signal emitted from the test subject propagates in the optimum propagation path, and causing the light source to irradiate the test subject with the intensity modulated light for detecting the actual photoacoustic signal.

13. The constituent concentration measuring method as claimed in claim 11, further comprising:
in addition to the reference signal, detecting a photoacoustic signal for each of the plurality of positions; and
selecting the photoacostic signal corresponding with the optimum propagation path as the actual photoacoustic signal.

14. A constituent concentration measuring method as claimed in claim 11, further comprising:
fixing the light source to the acoustic wave generator so as to keep a relative position to the acoustic wave generator.

15. A constituent concentration measuring method as claimed in claim 11, further comprising:
pressing the acoustic wave generator and the acoustic wave detector against the test subject with a pressing force whose pressure can be controlled.

16. A constituent concentration measuring method as claimed in claim 11, further comprising:
placing the acoustic wave generator in proximity of the intensity modulated light outputted from the light source.

17. A constituent concentration measuring method as claimed in claim 11, wherein a transmission window that transmits the intensity modulated light is formed in the acoustic wave generator.

18. A constituent concentration measuring method as claimed in claim 11, wherein the frequency and/or the intensity of the acoustic wave is variable.

19. A constituent concentration measuring method as claimed in claim 11, further comprising:
providing an acoustic coupling element on a surface of the acoustic wave generator and/or the light source that is configured to be in contact with the test subject and that has an acoustic impedance substantially equal to that of the test subject.

20. A constituent concentration measuring apparatus as claimed in claim 11, further comprising:
outputting, from the light source, two light beams set to two wavelengths such that an absorption difference exhibited by a constituent set as a measuring object is larger than an absorption difference exhibited by other constituents.

* * * * *